United States Patent
Chupak et al.

(10) Patent No.: US 9,872,852 B2
(45) Date of Patent: Jan. 23, 2018

(54) COMPOUNDS USEFUL AS IMMUNOMODULATORS

(71) Applicant: BRISTOL-MYERS SQUIBB COMPANY, Princeton, NJ (US)

(72) Inventors: Louis S. Chupak, Old Saybrook, CT (US); Xiaofan Zheng, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/915,782

(22) PCT Filed: Sep. 2, 2014

(86) PCT No.: PCT/US2014/053695
§ 371 (c)(1),
(2) Date: Mar. 1, 2016

(87) PCT Pub. No.: WO2015/034820
PCT Pub. Date: Mar. 12, 2015

(65) Prior Publication Data
US 2016/0194307 A1    Jul. 7, 2016

Related U.S. Application Data

(60) Provisional application No. 61/873,398, filed on Sep. 4, 2013.

(51) Int. Cl.
*A61K 31/381* (2006.01)
*A61K 31/396* (2006.01)
(Continued)

(52) U.S. Cl.
CPC .......... *A61K 31/381* (2013.01); *A61K 31/396* (2013.01); *A61K 31/397* (2013.01); *A61K 31/40* (2013.01); *A61K 31/44* (2013.01); *A61K 31/445* (2013.01); *A61K 31/4427* (2013.01); *A61K 31/4523* (2013.01); *A61K 31/496* (2013.01); *A61K 31/5375* (2013.01); *A61K 31/55* (2013.01); *A61K 31/551* (2013.01); *C07C 217/58* (2013.01); *C07C 229/14* (2013.01); *C07C 229/22* (2013.01); *C07C 233/36* (2013.01); *C07C 233/38* (2013.01); *C07C 233/47* (2013.01); *C07C 233/78* (2013.01); *C07C 235/76* (2013.01); *C07C 237/06* (2013.01); *C07C 255/54* (2013.01); *C07C 271/20* (2013.01); *C07C 275/40* (2013.01); *C07C 279/12* (2013.01); *C07C 279/14* (2013.01); *C07C 311/05* (2013.01); *C07D 205/04* (2013.01); *C07D 205/08* (2013.01); *C07D 207/08* (2013.01); *C07D 207/14* (2013.01); *C07D 207/16* (2013.01); *C07D 207/27* (2013.01); *C07D 211/32* (2013.01); *C07D 211/34* (2013.01); *C07D 211/44* (2013.01); *C07D 211/48* (2013.01); *C07D 211/56* (2013.01); *C07D 211/60* (2013.01); *C07D 211/62* (2013.01); *C07D 211/76* (2013.01); *C07D 211/78* (2013.01); *C07D 213/57* (2013.01); *C07D 213/63* (2013.01); *C07D 213/64* (2013.01); *C07D 213/65* (2013.01); *C07D 213/69* (2013.01);
(Continued)

(58) Field of Classification Search
CPC ............ A61K 31/381; A61K 31/31396; A61K 31/397; A61K 31/40; A61K 31/44; A61K 31/4427; A61K 31/445; A61K 31/4523; A61K 31/496; A61K 31/5375; A61K 31/55; A61K 31/557; C07C 217/58; C07C 229/14; C07C 229/22; C07C 233/36; C07C 233/38; C07C 2233/47; C07C 233/78; C07C 237/06; C07C 255/54; C07C 271/20; C07D 405/12; C07D 205/04; C07D 207/08; C07D 211/32; C07D 211/44
USPC .... 514/210.01, 212.01, 218, 231.2, 252, 12, 514/317, 336, 408, 422, 438
See application file for complete search history.

(56) References Cited

U.S. PATENT DOCUMENTS

2005/0119256 A1    6/2005    Endo et al.

FOREIGN PATENT DOCUMENTS

WO     WO 9917777 A1 *  4/1999 ........... C07D 231/12
WO     WO 2004/007439 A1   1/2004
(Continued)

OTHER PUBLICATIONS

Huff et al, "HIV Protease: A novel chemotheratpeutic target for AIDS," J. Medicinal Chemistry (1991), vol. 34(8), pp. 2305-2314.*
(Continued)

*Primary Examiner* — Kathrien Cruz
*Assistant Examiner* — Janet L Coppins
(74) *Attorney, Agent, or Firm* — Pamela A. Mingo

(57) ABSTRACT

Disclosed are compounds of Formula (I): (I). Also disclosed are methods of using such compounds as immunomodulators, and pharmaceutical compositions comprising such compounds. These compounds are useful in treating, preventing, or slowing the progression of virological diseases or disorders and cancer.

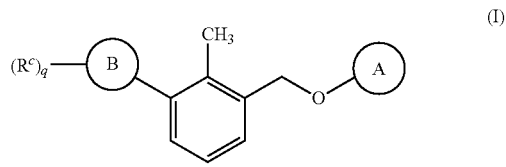

11 Claims, No Drawings

(51) Int. Cl.
*A61K 31/40* (2006.01)
*A61K 31/4427* (2006.01)
*A61K 31/496* (2006.01)
*C07C 217/58* (2006.01)
*C07C 229/22* (2006.01)
*C07C 233/36* (2006.01)
*C07C 235/76* (2006.01)
*C07C 311/05* (2006.01)
*C07D 205/04* (2006.01)
*C07D 207/14* (2006.01)
*C07D 211/32* (2006.01)
*C07D 213/57* (2006.01)
*C07D 213/69* (2006.01)
*C07D 217/02* (2006.01)
*C07D 233/06* (2006.01)
*C07D 249/08* (2006.01)
*C07D 265/30* (2006.01)
*A61K 31/397* (2006.01)
*A61K 31/5375* (2006.01)
*A61K 31/44* (2006.01)
*A61K 31/4523* (2006.01)
*A61K 31/445* (2006.01)
*A61K 31/551* (2006.01)
*A61K 31/55* (2006.01)
*C07D 309/14* (2006.01)
*C07D 311/14* (2006.01)
*C07D 317/50* (2006.01)
*C07D 223/06* (2006.01)
*C07D 319/18* (2006.01)
*C07D 333/20* (2006.01)
*C07D 333/32* (2006.01)
*C07D 333/36* (2006.01)
*C07D 233/61* (2006.01)
*C07D 401/06* (2006.01)
*C07D 401/12* (2006.01)
*C07D 405/12* (2006.01)
*C07D 487/10* (2006.01)
*C07D 205/08* (2006.01)
*C07D 207/08* (2006.01)
*C07D 207/16* (2006.01)
*C07D 207/27* (2006.01)
*C07C 279/12* (2006.01)
*C07D 211/34* (2006.01)
*C07D 211/44* (2006.01)
*C07D 295/12* (2006.01)
*C07D 211/48* (2006.01)
*C07D 211/56* (2006.01)
*C07D 211/60* (2006.01)
*C07D 211/62* (2006.01)
*C07D 295/14* (2006.01)
*C07D 295/18* (2006.01)
*C07D 295/185* (2006.01)
*C07D 211/76* (2006.01)
*C07D 211/78* (2006.01)
*C07D 213/63* (2006.01)
*C07D 213/64* (2006.01)
*C07D 213/65* (2006.01)
*C07C 255/54* (2006.01)
*C07C 271/20* (2006.01)
*C07C 279/14* (2006.01)
*C07C 229/14* (2006.01)
*C07C 233/38* (2006.01)
*C07C 233/47* (2006.01)
*C07C 233/78* (2006.01)
*C07C 237/06* (2006.01)
*C07K 5/083* (2006.01)
*C07C 275/40* (2006.01)
*C07D 217/04* (2006.01)
*C07D 295/13* (2006.01)
*C07D 295/16* (2006.01)
*C07D 311/08* (2006.01)

(52) U.S. Cl.
CPC ......... *C07D 217/02* (2013.01); *C07D 217/04* (2013.01); *C07D 223/06* (2013.01); *C07D 233/61* (2013.01); *C07D 249/08* (2013.01); *C07D 265/30* (2013.01); *C07D 295/12* (2013.01); *C07D 295/13* (2013.01); *C07D 295/14* (2013.01); *C07D 295/16* (2013.01); *C07D 295/18* (2013.01); *C07D 295/185* (2013.01); *C07D 309/14* (2013.01); *C07D 311/08* (2013.01); *C07D 311/14* (2013.01); *C07D 317/50* (2013.01); *C07D 319/18* (2013.01); *C07D 333/20* (2013.01); *C07D 333/32* (2013.01); *C07D 333/36* (2013.01); *C07D 401/06* (2013.01); *C07D 401/12* (2013.01); *C07D 405/12* (2013.01); *C07D 487/10* (2013.01); *C07K 5/0806* (2013.01); *C07K 5/0808* (2013.01); *C07C 2101/02* (2013.01); *C07C 2101/04* (2013.01); *C07C 2101/08* (2013.01); *C07C 2101/14* (2013.01); *C07C 2102/08* (2013.01); *C07C 2102/10* (2013.01)

(56) References Cited

FOREIGN PATENT DOCUMENTS

| | | | |
|---|---|---|---|
| WO | WO 2007/123225 A1 | 11/2007 |
| WO | WO 2009/054423 A1 | 4/2009 |
| WO | WO 2015/160641 A2 | 10/2015 |
| WO | WO 2017/066227 A1 | 4/2017 |

OTHER PUBLICATIONS

NCI online article, "Immunotherapy: Using the Immune System to Treat Cancer," updated online Sep. 14, 2015.*

* cited by examiner

COMPOUNDS USEFUL AS IMMUNOMODULATORS

CROSS-REFERENCE TO RELATED APPLICATIONS

This application claims priority to U.S. Provisional Patent Application No. 61/873,398 filed Sep. 4, 2013, hereby incorporated by reference in its entirety.

The present disclosure generally relates to compounds useful as inhibitors of the PD-1/PD-L1 protein/protein interaction. Provided herein are compounds, compositions comprising such compounds, and methods of their use. The disclosure further pertains to pharmaceutical compositions comprising at least one compound according to the disclosure that are useful for the treatment of various diseases, including cancer and infectious diseases.

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC) (Sharpe et al., Nat. Imm. 2007). When PD-1 expressing T cells contact cells expressing its ligands, functional activities in response to antigenic stimuli, including proliferation, cytokine secretion, and cytotoxicity are reduced. PD-1/PD-Ligand interactions down regulate immune responses during resolution of an infection or tumor, or during the development of self tolerance (Keir M e, Butte M J, Freeman G J, et al. PD-1 and its ligands in tolerance and immunity. Annu. Rev. Immunol. 2008; 26: Epub). Chronic antigen stimulation, such as that which occurs during tumor disease or chronic infections, results in T cells that express elevated levels of PD-1 and are dysfunctional with respect to activity towards the chronic antigen (reviewed in Kim and Ahmed, Curr Opin Imm, 2010). This is termed "T cell exhaustion". B cells also display PD-1/PD-ligand suppression and "exhaustion".

Blockade of the PD-1/PD-L1 ligation using antibodies to PD-L1 has been shown to restore and augment T cell activation in many systems. Patients with advanced cancer benefit from therapy with a monoclonal antibody to PD-L1 (Brahmer et al., New Engl J Med 2012). Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors (Dong H, Chen L. B7-H1 pathway and its role in the Evasion of tumor immunity. J Mol Med. 2003; 81(5):281-287; Dong H, Strome S E, Salamoa D R, et al. Tumor-associated B7-H1 promotes T-cell apoptosis: a potential mechanism of immune evasion. Nat Med. 2002; 8(8):793-800).

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1 (Barber D L, Wherry E J, Masopust D, et al. Restoring function in exhausted CD8 T cells during chronic viral infection. Nature. 2006; 439 (7077):682-687). Humanized mice infected with HIV-1 show enhanced protection against viremia and viral depletion of CD4+ T cells (Palmer et al., J. Immunol 2013). Blockade of PD-1/PD-L1 through monoclonal antibodies to PD-L1 can restore in vitro antigen-specific functionality to T cells from HIV patients (Day, Nature 2006; Petrovas, J. Exp. Med. 2006; Trautman, Nature Med. 2006; D'Souza, J. Immunol. 2007; Zhang, Blood 2007; Kaufmann, Nature Imm. 2007; Kasu, J. Immunol. 2010; Porichis, Blood 2011), HCV patients [Golden-Mason, J. Virol. 2007; Jeung, J. Leuk. Biol. 2007; Urbani, J. Hepatol. 2008; Nakamoto, PLoS Path. 2009; Nakamoto, Gastroenterology 2008] or HBV patients (Boni, J. Virol. 2007; Fisicaro, Gastro. 2010; Fisicaro et al., Gastroenterology, 2012; Boni et al., Gastro., 2012; Penna et al., J. Hep., 2012; Raziorrough, Hepatology 2009; Liang, World J Gastro. 2010; Zhang, Gastro. 2008).

In addition to enhancing immunologic responses to chronic antigens, blockade of the PD-1/PD-L1 pathway has also been shown to enhance responses to vaccination, including therapeutic vaccination in the context of chronic infection (S. J. Ha, S. N. Mueller, E. J. Wherry et al., "Enhancing therapeutic vaccination by blocking PD-1-mediated inhibitory signals during chronic infection," The Journal of Experimental Medicine, vol. 205, no. 3, pp. 543-555, 2008; A. C. Finnefrock, A. Tang, F. Li et al., "PD-1 blockade in rhesus macaques: impact on chronic infection and prophylactic vaccination," The Journal of Immunology, vol. 182, no. 2, pp. 980-987, 2009; M.-Y. Song, S.-H. Park, H. J. Nam, D.-H. Choi, and Y.-C. Sung, "Enhancement of vaccine-induced primary and memory CD8+ t-cell responses by soluble PD-1," The Journal of Immunotherapy, vol. 34, no. 3, pp. 297-306, 2011).

The PD-1 pathway is a key inhibitory molecule in T cell exhaustion that arises from chronic antigen stimulation during chronic infections and tumor disease. Blockade of the PD-1/PD-L1 interaction through targeting the PD-L1 protein has been shown to restore antigen-specific T cell immune functions in vitro and in vivo, including enhanced responses to vaccination in the setting of tumor or chronic infection.

Accordingly, agents that block the interaction of PD-L1 with PD-1 are desired.

Applicants found potent compounds that have activity as inhibitors of the interaction of PD-L1 with PD-1, and thus may be useful for therapeutic administration to enhance immunity in cancer or chronic infection, including therapeutic vaccine. These compounds are provided to be useful as pharmaceuticals with desirable stability, bioavailability, therapeutic index, and toxicity values that are important to their drugability.

The present disclosure provides compounds of Formula (I), which are useful as inhibitors of the PD-1/PD-L1 protein/protein interaction, including salts and prodrugs thereof.

The present disclosure also provides pharmaceutical compositions comprising a compound of Formula (I) and/or a pharmaceutically acceptable salt thereof; and a pharmaceutically acceptable carrier.

The present disclosure also provides a method of treating a disease or disorder associated with the activity of PD-L1 including its interaction with other proteins such as PD-1 and B7-1(CD80), the method comprising administering to a mammalian patient a compound of Formula (I) and/or a pharmaceutically acceptable salt thereof.

The present disclosure also provides processes and intermediates for making the compounds of Formula (I) and/or salts thereof.

The present disclosure also provides a compound of Formula (I) and/or a pharmaceutically acceptable salt thereof, for use in therapy.

The present disclosure also provides the use of the compounds of Formula (I) and/or pharmaceutically acceptable salts thereof, for the manufacture of a medicament for the treatment or prophylaxis of PD-L1 related conditions, such as cancer and infectious diseases.

The compounds of Formula (I) and compositions comprising the compounds of Formula (I) may be used in treating, preventing, or curing various infectious diseases and cancer. Pharmaceutical compositions comprising these compounds are useful in treating, preventing, or slowing the progression of diseases or disorders in a variety of therapeutic areas, such as cancer and infectious diseases.

These and other features of the disclosure will be set forth in expanded form as the disclosure continues.

The first aspect of the present disclosure provides at least one compound of Formula (I):

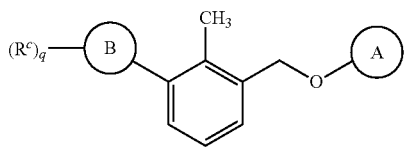
(I)

or salts thereof, wherein:
Ring B is phenyl or thienyl;
Ring A is:

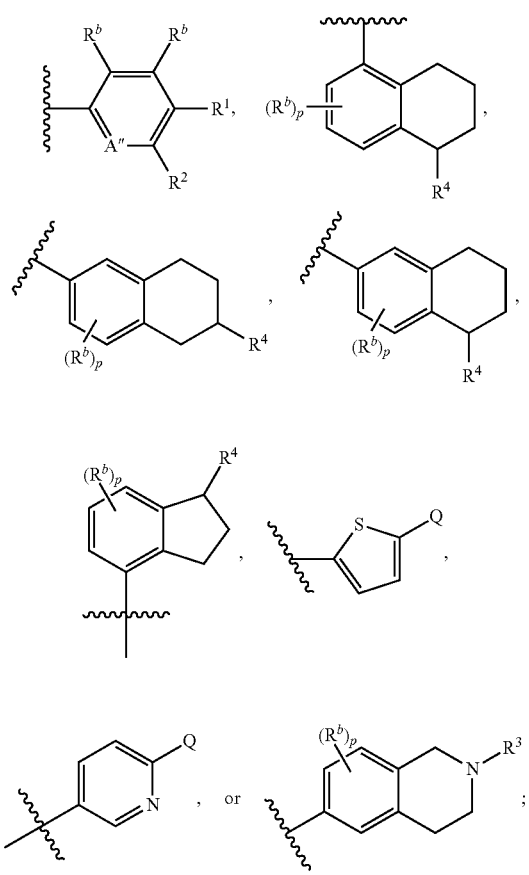

wherein A" is CH or N, and wherein one of $R^1$ and $R^2$ is Q and the other of $R^1$ and $R^2$ is $R^b$;

$R^3$ is H or —$CH_2C(O)OH$;
$R^4$ is —$NHCH_2CH_2NHC(O)CH_3$;
Q is:
(i)

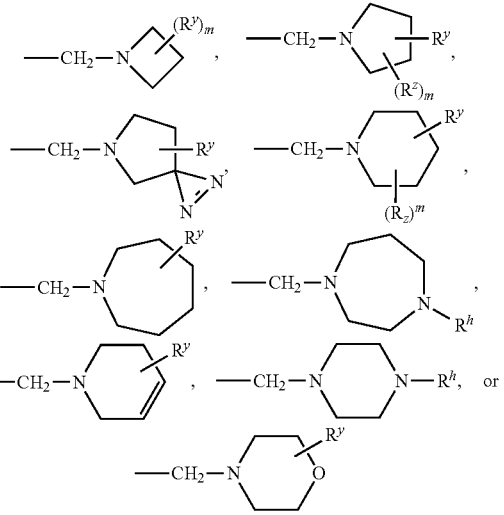

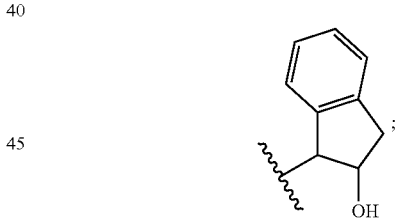

wherein $R^y$ is —OH, —$CH_3$, —$CH_2OH$, —C(O)OH, —$CH_2C(O)OH$, or —C(O)NHCH_2CH_2OH, —C(O)NH_2, —NHC(O)CH_3, and $R^z$ is —OH, —$CH_3$, —$OCH_3$, —OC(O)CH_3, or —$CH_2CH=CH_2$ and $R^h$ is —$CH_3$ or —C(O)CH_3;

(ii) —$CH_2NH$—$R^x$ wherein $R^x$ is cyclobutyl, —($CH_2$)cyclobutyl optionally substituted with two fluorine atoms, cyclopropyl, hydroxycyclopentyl, cyclopentyl, cyclohexyl, hydroxycyclohexyl, hydroxytetrahydrofuranyl, N-methyl piperidinyl, N-ethyl piperidinyl, hydroxytetrahydrothienyl, or

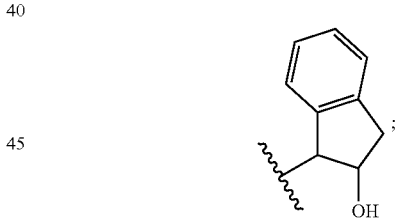

(iii) —$CH_2NR^a$—$CR^aR^a$—($CH_2$)$_n$—$R^x$ wherein $R^x$ is hydrogen, azetidinonyl, cyclohexyl, hydroxyphenyl, pyrrolidinonyl, piperidinonyl, piperazinonyl, morpholinyl, imidazolyl, N-methylimidazolyl, —C(O)(morpholinyl), piperazinyl optionally substituted with a methyl, phenyl, alkoxyphenyl, hydroxyphenyl, pyridinyl, pyrimidinyl, or —C(O)OC(CH_3)_3 group, pyrrolidinyl, pyridinyl, thiomorpholine dioxide, or methyl triazolyl; or (iv) —$CHR^a$—$NR^a$—$CR^aR^a$—($CHR^a$)$_n$—$R^x$ wherein $R^x$ is —OH, —OCH_3, —C(O)OH, —OPh, —CH(CO_2H)—NHC(O)CH_3, —O(CH_2)_2O(CH_2)_2OH, —O(CH_2)_2O(CH_2)_2O(CH_2)_2OH, —O(CH_2)_2O(CH_2)_2O(CH_2)_2O(CH_2)_2O(CH_2)_2CO_2H—O(CH_2)_2O(CH_2)_2O(CH_2)_2O(CH_2)_2O(CH_2)_2O(CH_2)_2CO_2H, —C(O)CH_3, —C(O)NR^aR^a, —C(O)NR^qR^q, —N(CH_3)_2, —NHC(O)CH_3, —NHC(O)Ph, —C(O)NH(CH_2)_2-imidazolyl, NHC(O)OCH_2Ph, —N(CH_3)S(O)_2CH_3, —NHC(O)CH=CH_2, —NHC(O)CH=CHC(O)CH_2CH_3, —NHS(O)_2CH_3, or

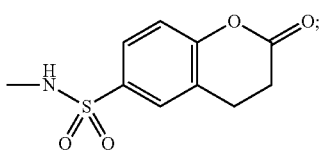 [SMILES: CNS(=O)(=O)c1ccc2c(c1)CCC(=O)O2]

each $R^a$ is independently H, —CH(OH)CH$_3$, OH, —(CH$_2$)$_2$OH, —CH$_2$OH, —(CH$_2$)$_2$NH$_2$, —CH$_2$CH$_3$, or —CH$_3$; or, two $R^a$ groups on the same carbon atom can form a four, five-, or six-membered carbocyclic ring, an N-methylpiperidinyl ring, or a pyranyl ring;

each $R^b$ is independently H, F, Cl, Br, —CF$_3$, —CN, CH$_3$, or —OCH$_3$;

each $R^c$ is independently —OCH$_3$, —OH, —OCH$_2$CH$_3$, —O(CH$_2$)OCH$_3$, —OCH$_2$CH═CH$_2$, —O(CH$_2$)$_2$CH$_3$, —O(CH$_2$)$_2$-morpholinyl, or F;

or two $R^c$ attached to adjacent carbon atoms form —O—(CH$_2$)$_v$—O—, wherein v is 1 or 2;

each $R^q$ is selected from hydrogen, —CH$_2$C(O)NHCH$_2$CO$_2$H, —(CH$_2$)C(O)NHCH(CO$_2$H)CH$_2$CH(CH$_3$)$_2$, —CH(Bn)—C(O)NHCH(CO$_2$H)(CH$_2$)$_3$NHC(NH)NH$_2$;

m is zero or 1;
n is zero, 1, 2, or 3;
each p is independently zero or 1; and
q is zero, 1, or 2.

In a first embodiment of the first aspect Ring A is:

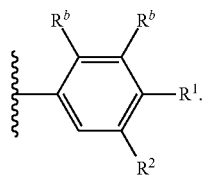

In a second embodiment the present disclosure provides a compound of formula (I), or salts thereof, wherein Ring A is:

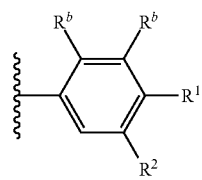

and Q is

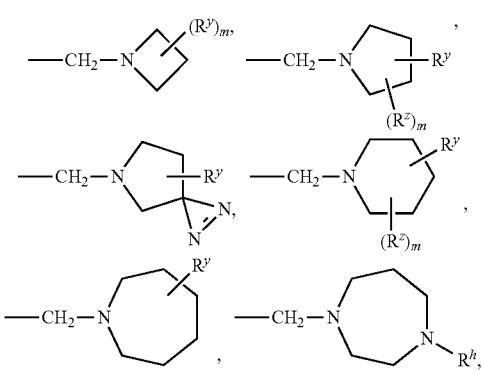

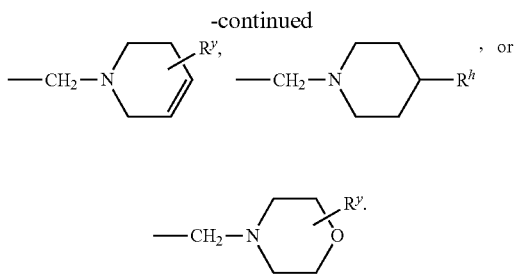

In a third embodiment the present disclosure provides a compound of formula (I), or salts thereof, wherein Ring A is:

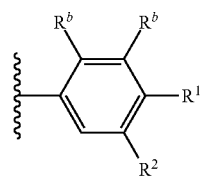

and Q is —CH$_2$NH—R$^x$ wherein R$^x$ is cyclobutyl, —(CH$_2$) cyclobutyl optionally substituted with two fluorine atoms, cyclopropyl, hydroxycyclopentyl, cyclopentyl, cyclohexyl, hydroxycyclohexyl, hydroxytetrahydrofuranyl, N-methyl piperidinyl, N-ethyl piperidinyl, hydroxytetrahydrothienyl, or

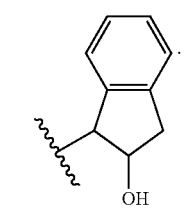

In a fourth embodiment of the first aspect the present disclosure provides a compound of formula (I), or salts thereof, wherein Ring A is:

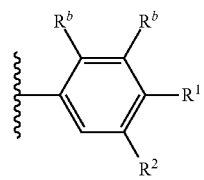

and Q is —CH$_2$NR$^a$—CR$^a$R$^a$—(CH$_2$)$_n$—R$^x$ wherein R$^x$ is hydrogen, azetidinonyl, cyclohexyl, hydroxyphenyl, pyrrolidinonyl, piperidinonyl, piperazinonyl, morpholinyl, imidazolyl, N-methylimidazolyl, —C(O)(morpholinyl), piperazinyl optionally substituted with a methyl, phenyl, alkoxyphenyl, hydroxyphenyl, pyridinyl, pyrimidinyl, or —C(O)OC(CH$_3$)$_3$ group, pyrrolidinyl, pyridinyl, thiomorpholine dioxide, or methyl triazolyl.

In a fifth embodiment of the first aspect the present disclosure provides a compound of formula (I), or salts thereof, wherein Ring A is:

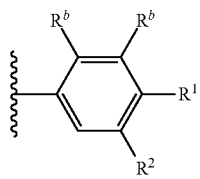

and Q is —CHR$^a$—NR$^a$—CR$^a$R$^a$—(CHR$^a$)$_n$—R$^x$ wherein R$^x$ is —OH, —OCH$_3$, —C(O)OH, —OPh, —CH(CO$_2$H)—NHC(O)CH$_3$, —O(CH$_2$)$_2$O(CH$_2$)$_2$OH, —O(CH$_2$)$_2$O(CH$_2$)$_2$O(CH$_2$)$_2$OH, —O(CH$_2$)$_2$O(CH$_2$)$_2$O(CH$_2$)$_2$O(CH$_2$)$_2$CO$_2$H—O(CH$_2$)$_2$O(CH$_2$)$_2$O(CH$_2$)$_2$O(CH$_2$)$_2$O(CH$_2$)$_2$O(CH$_2$)$_2$CO$_2$H, —C(O)CH$_3$, —C(O)NR$^a$R$^a$, —C(O)NR$^a$R$^a$, —N(CH$_3$)$_2$, —NHC(O)CH$_3$, —NHC(O)Ph, —C(O)NH(CH$_2$)$_2$-imidazolyl, NHC(O)OCH$_2$Ph, —N(CH$_3$)S(O)$_2$CH$_3$, —NHC(O)CH=CH$_2$, —NHC(O)CH=CHC(O)CH$_2$CH$_3$, —NHS(O)$_2$CH$_3$, or

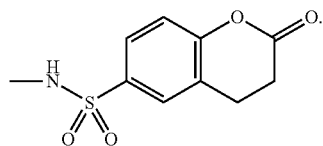 [SMILES: CNS(=O)(=O)c1ccc2c(c1)CCC(=O)O2]

In a sixth embodiment of the first aspect the present disclosure provides a compound of formula (I) or salts thereof wherein Ring A is:

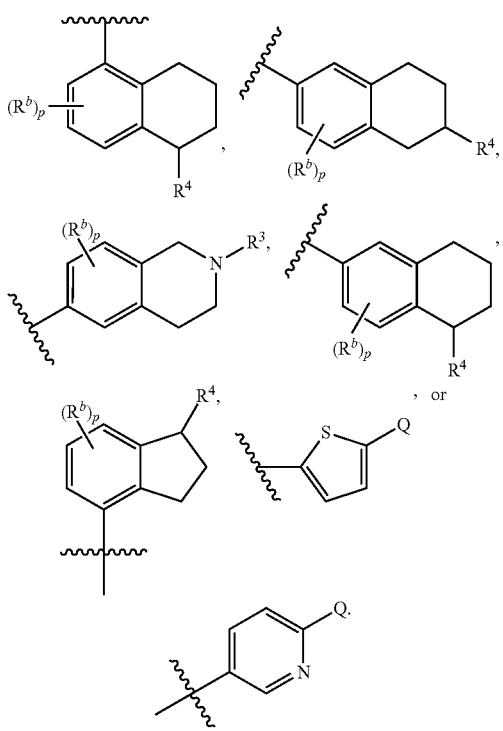

In a second aspect the present disclosure provides a pharmaceutical composition comprising a compound of formula (I) or a pharmaceutically acceptable salt thereof, and a pharmaceutically acceptable carrier.

In a third aspect the present disclosure provides a method of treating a disease or disorder associated with the inhibition of the PD-1/PD-L1 interaction, the method comprising administering to a mammalian patient a compound of formula (I) or a pharmaceutically acceptable salt thereof. In a first embodiment of the third aspect said disease or disorder is a virological infection or cancer.

In another aspect the present disclosure provides a compound of formula (II)

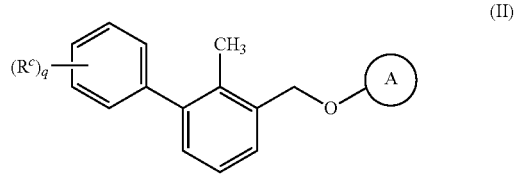

or salts thereof, wherein:
Ring A is:

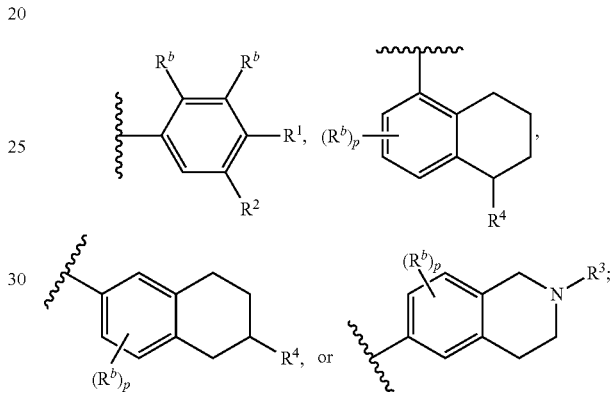

one of R$^1$ and R$^2$ is Q and the other of R$^1$ and R$^2$ is R$^b$;
R$^3$ is H or —CH$_2$C(O)OH;
R$^4$ is —NHCH$_2$CH$_2$NHC(O)CH$_3$;
Q is:
(i)

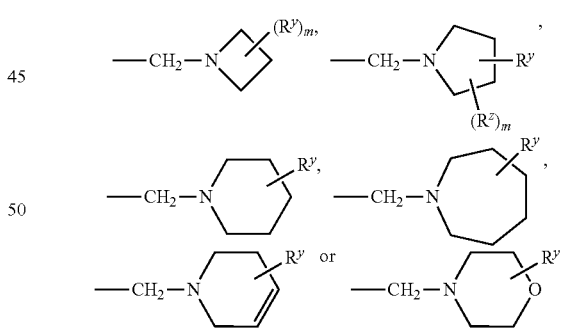

wherein R$^y$ is —CH$_2$OH, —C(O)OH, —CH$_2$C(O)OH, or —C(O)NHCH$_2$CH$_2$OH, and R$^z$ is —OH, —CH$_3$, —OCH$_3$, —OC(O)CH$_3$, or —CH$_2$CH=CH$_2$;

(ii) —CH$_2$NH—R$^x$ wherein R$^x$ is cyclobutyl, hydroxycyclohexyl, N-methyl piperidinyl, or N-ethyl piperidinyl;

(iii) —CH$_2$NR$^a$—CR$^a$R$^a$—(CH$_2$)$_n$—R$^x$ wherein R$^x$ is pyrrolidinonyl, piperidinonyl, piperazinonyl, morpholinyl, —C(O)(morpholinyl), N-methyl piperazinyl, or methyl triazolyl; or (iv) —CHR$^a$—NR$^a$—CR$^a$R$^a$—(CH$_2$)$_n$—R$^x$ wherein R$^x$ is —OH, —C(O)OH, —C(O)CH$_3$, —C(O)NR$^a$R$^a$, —NHC(O)CH$_3$, or —NHS(O)$_2$CH$_3$;

each $R^a$ is independently H or —CH$_3$;
each $R^b$ is independently H, F, Cl, Br, —CH$_3$, or —OCH$_3$;
each $R^c$ is independently —OCH$_3$ or F;
or two $R^c$ attached to adjacent carbon atoms form —O—CH$_2$—O—;
m is zero or 1;
n is zero, 1, or 2;
each p is independently zero or 1; and
q is zero, 1, or 2.

One embodiment provides compounds of Formula (II) wherein Ring A is

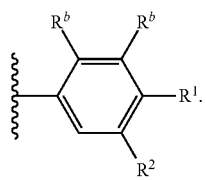

The compounds of this embodiment have the structure of Formula (III):

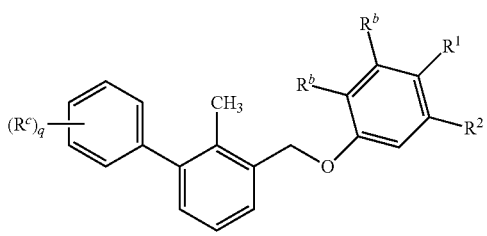

(III)

wherein $R^1$, $R^2$, $R^b$, $R^c$, and q are defined in the first aspect. Included in this embodiment are the compounds of Formula (IIIA) in which $R^1$ is Q and $R^2$ is $R^b$:

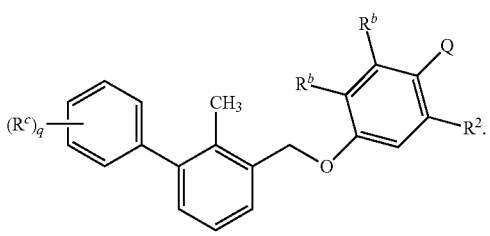

(IIIA)

Also included in this embodiment are the compounds of Formula (IIIB) in which $R^1$ is $R^b$; and $R^2$ is Q:

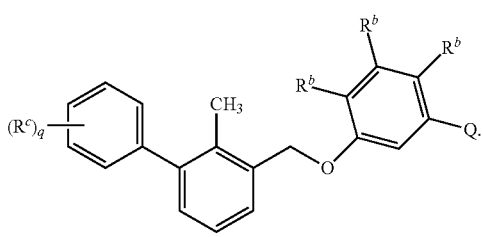

(IIIB)

One embodiment provides compounds of Formula (III) in which Q is:

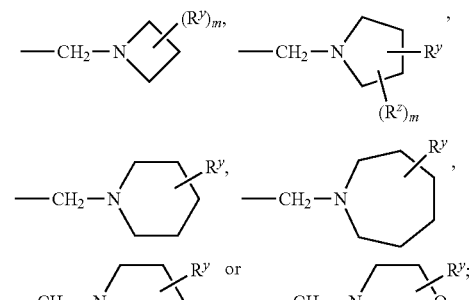

and wherein $R^1$, $R^2$, $R^b$, $R^c$, $R^y$, $R^z$, m, and q are defined in the first aspect. Included in this embodiment are the compounds of Formula (IIIA) and the compounds of Formula (IIIB). Also included in this embodiment are compounds in which m is zero. Additionally, included in this embodiment are compounds in which m is zero and q is zero.

One embodiment provides compounds of Formula (III) in which Q is:

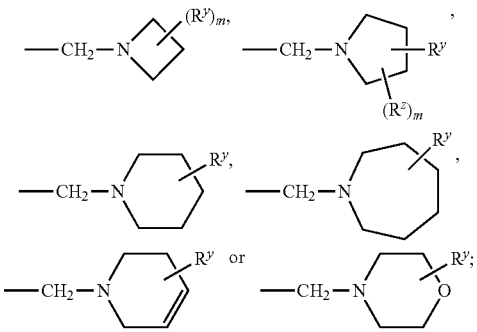

$R^y$ is —C(O)OH or —CH$_2$C(O)OH; and $R^1$, $R^2$, $R^b$, $R^c$, $R^z$, m, and q are defined in the first aspect. Included in this embodiment are compounds in which m is zero. Also included in this embodiment are compounds in which m is zero and q is zero.

One embodiment provides compounds of Formula (III) in which m is zero; and $R^1$, $R^2$, $R^b$, $R^c$, and q are defined in the first aspect. Included in this embodiment are compounds in which Q is

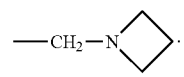

One embodiment provides compounds of Formula (III) in which m is 1; and $R^1$, $R^2$, $R^b$, $R^c$, and q are defined in the first aspect.

One embodiment provides compounds of Formula (III) in which Q is:

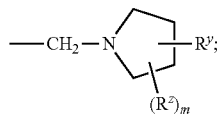

R$^y$ is —CH$_2$OH or —C(O)OH; R$^z$ is —OH, —CH$_3$, —OCH$_3$, —OC(O)CH$_3$, or —CH$_2$CH=CH$_2$; and R$^1$, R$^2$, R$^b$, R$^c$, m, and q are defined in the first aspect. Included in this embodiment are compounds of Formula II in which Q is:

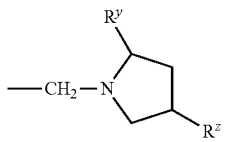

and R$^z$ is —OH, —CH$_3$, —OCH$_3$, or —OC(O)CH$_3$. Also included in this embodiment are compounds in which p is zero and Q is:

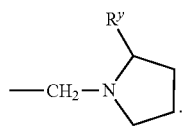

One embodiment provides compounds of Formula (III) in which Q is:

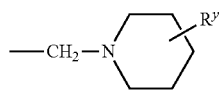

and R$^y$ is —C(O)OH, —CH$_2$C(O)OH, or —C(O)NHCH$_2$CH$_2$OH; and R$^1$, R$^2$, R$^b$, R$^c$, R$^y$, and q are defined in the first aspect. Included in this embodiment are compounds in which R$^y$ is —C(O)OH.

One embodiment provides compounds of Formula (III) in which Q is:

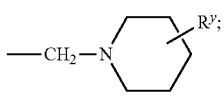

R$^y$ is —C(O)OH or —CH$_2$C(O)OH; and R$^1$, R$^2$, R$^b$, R$^c$, R$^y$, and q are defined in the first aspect. Included in this embodiment are compounds of Formula III in which Q is:

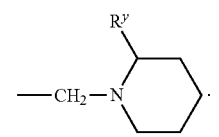

One embodiment provides compounds of Formula (III) in which R$^y$ is —C(O)OH and Q is:

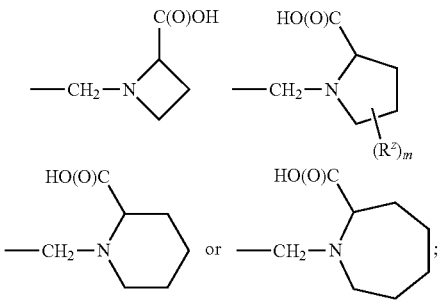

and R$^1$, R$^2$, R$^b$, R$^c$, R$^z$, m, and q are defined in the first aspect.

One embodiment provides compounds of Formula (III) in which Q is:

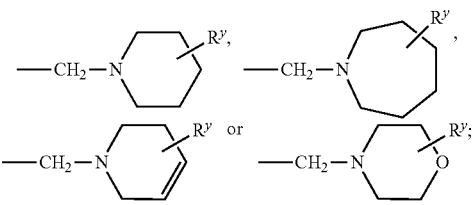

R$^y$ is —C(O)OH; and R$^1$, R$^2$, R$^b$, R$^c$, and q are defined in the first aspect.

One embodiment provides compounds of Formula (III) in which Q is: —CH$_2$NH—R$^x$; and R$^x$ is cyclobutyl, hydroxycyclohexyl, N-methyl piperidinyl, or N-ethyl piperidinyl; and wherein R$^1$, R$^2$, R$^b$, R$^c$, m, and q are defined in the first aspect. Included in this embodiment are the compounds of Formula (IIA) and the compounds of Formula (IIB).

One embodiment provides compounds of Formula (III) in which Q is: —CH$_2$NR$^a$—CR$^a$R$^a$—(CH$_2$)$_n$—R$^x$; R$^x$ is pyrrolidinonyl, piperidinonyl, piperazinonyl, morpholinyl, —C(O)(morpholinyl), N-methyl piperazinyl, or methyl triazolyl; and R$^1$, R$^2$, R$^a$, R$^b$, R$^c$, n, p, and q are defined in the first aspect. Included in this embodiment are the compounds of Formula (IIIA) and the compounds of Formula (IIIB). Additionally, included in this embodiment are compounds or Formula (III) in which n is 1 or 2.

One embodiment provides compounds of Formula (III) in which Q is —CH$_2$NHCH$_2$(pyrrolidinonyl), —CH$_2$NHCH$_2$CH$_2$(pyrrolidinonyl), —CH$_2$NHCH$_2$CH$_2$CH$_2$(pyrrolidinonyl), —CH$_2$NHCH$_2$CH$_2$(piperidinonyl), —CH$_2$NHCH$_2$CH$_2$(morpholinyl), —CH$_2$NHCH$_2$C(O)(morpholinyl), —CH$_2$NHCH$_2$CH$_2$(N-methyl piperazinyl), —CH$_2$NHCH$_2$CH$_2$(piperazinonyl), or —CH$_2$NHCH(CH$_3$)(methyl triazolyl); and R$^1$, R$^2$, R$^a$, R$^b$, R$^c$, n, p, and q are defined in the first aspect.

One embodiment provides compounds of Formula (III) in which Q is: —CH$_2$NH—CH$_2$—R$^x$; R$^x$ is pyrrolidinonyl; and R$^1$, R$^2$, R$^b$, R$^c$, and q are defined in the first aspect. Included in this embodiment are compounds in which q is zero.

One embodiment provides compounds of Formula (III) in which Q is: —CH$_2$NR$^a$—CR$^a$R$^a$—(CH$_2$)$_n$—R$^x$; R$^x$ is pyrrolidinonyl or piperidinonyl; n is 1 or 2; and R$^1$, R$^2$, R$^a$, R$^b$, R$^c$, and p are defined in the first aspect. Included in this embodiment are compounds in which q is zero.

One embodiment provides compounds of Formula (IIIa) in which Q is: —CH$_2$NR$^a$—CR$^a$R$^a$—(CH$_2$)$_n$—R$^x$; and R$^x$ is pyrrolidinonyl, piperidinonyl, piperazinonyl, morpholinyl, —C(O)(morpholinyl), N-methyl piperazinyl, or methyl triazolyl; and $R^1$, $R^2$, $R^a$, $R^b$, $R^c$, p, and q are defined in the first aspect.

One embodiment provides compounds of Formula (IIIb) in which Q is: —$CH_2NR^a$—$CR^aR^a$—$(CH_2)_n$—$R^x$; $R^x$; and $R^x$ is pyrrolidinonyl, piperidinonyl, piperazinonyl, morpholinyl, —C(O)(morpholinyl), N-methyl piperazinyl, or methyl triazolyl; and $R^1$, $R^2$, $R^a$, $R^b$, $R^c$, and q are defined in the first aspect.

One embodiment provides compounds of Formula (III) in which Q is: —$CHR^a$—$NR^a$—$CR^aR^a$—$(CH_2)$—$R^x$ and $R^x$ is —OH, —C(O)OH, —C(O)$CH_3$, —C(O)$NR^aR^a$, —NHC(O)$CH_3$, or —NHS(O)$_2CH_3$; and $R^1$, $R^2$, $R^a$, $R^b$, R, n, and q are defined in the first aspect. Included in this embodiment are compounds in which Q is —$CH_2$—NH—$CH_2$—$(CH_2)_n$—C(O)$NR^aR^a$ and n is zero or 1. Also included in this embodiment are compounds in which Q is: —$CH_2$—$NR^a$—$CR^aR^a$—$(CH_2)_n$—$R^x$; $R^x$ is —OH, —C(O)OH, —NHC(O)$CH_3$, or —NHS(O)$_2CH_3$.

One embodiment provides compounds of Formula (III) in which Q is: —$CH_2N(CH_3)CH_2C(O)OH$, —$CH_2N(CH_3)CH(CH_3)C(O)OH$, —$CH_2NHCH(CH_3)C(O)OH$, —$CH_2NHC(CH_3)_2C(O)OH$, —$CH_2NHCH(CH_3)CH_2C(O)OH$, —$CH_2NHCH_2CH_2C(O)CH_3$, —$CH_2NHCH_2CH_2C(O)NH_2$, —$CH_2NHCH_2C(O)N(CH_3)_2$, —$CH_2NHCH_2CH_2NHC(O)CH_3$, —$CH_2NHCH_2CH_2CH_2NHC(O)CH_3$, —$CH(CH_3)NHCH_2CH_2NHC(O)CH_3$, or —$CH_2NHCH_2CH_2N(CH_3)S(O)_2CH_3$; and $R^1$, $R^2$, $R^a$, $R^b$, $R^c$, n, and q are defined in the first aspect.

One embodiment provides compounds of Formula (IIIA) wherein each $R^b$ is H. Included in this embodiment are compounds of Formula (IIIA-1) having the structure:

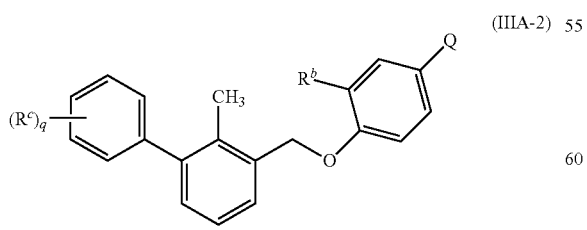

(IIA-1)

wherein Q, $R^c$, and q are defined in the first aspect.

One embodiment provides compounds of Formula (IIIA) wherein $R^2$ is H. Included in this embodiment are compounds of Formula (IIIA-2) having the structure:

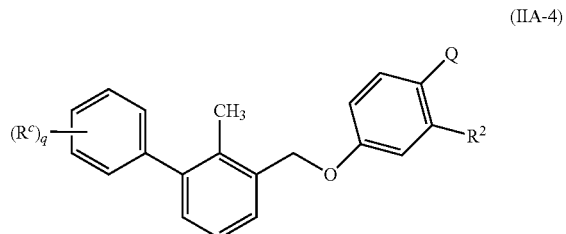

(IIIA-2)

wherein Q, $R^b$, $R^c$, and q are defined in the first aspect. Also included in this embodiment are compounds of Formula (IIIA-3) having the structure:

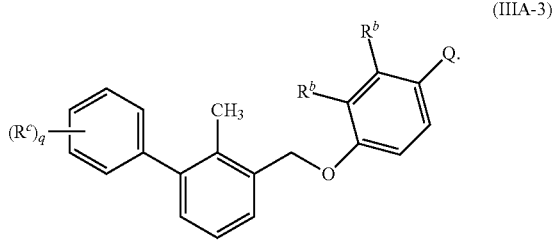

(IIIA-3)

Examples of this embodiment include compounds in which $R^b$ is F, Cl, Br, or —$CH_3$.

One embodiment provides compounds of Formula (IIIA) wherein $R^2$ is $R^b$ and having the structure of Formula (IIIA-4):

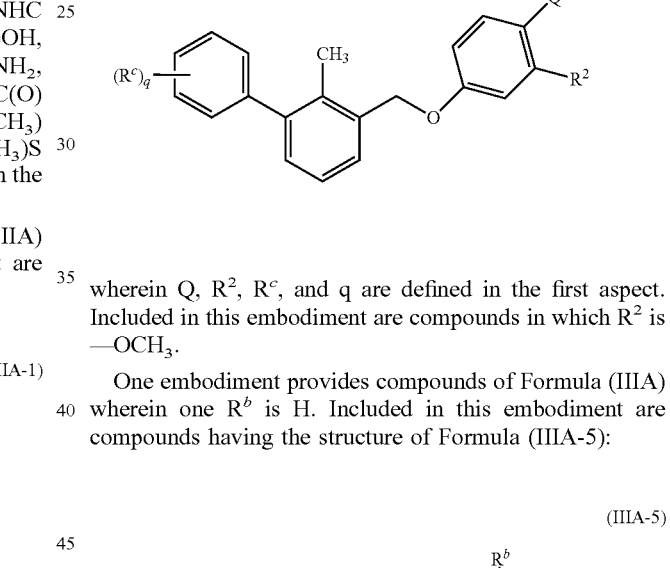

(IIA-4)

wherein Q, $R^2$, $R^c$, and q are defined in the first aspect. Included in this embodiment are compounds in which $R^2$ is —$OCH_3$.

One embodiment provides compounds of Formula (IIIA) wherein one $R^b$ is H. Included in this embodiment are compounds having the structure of Formula (IIIA-5):

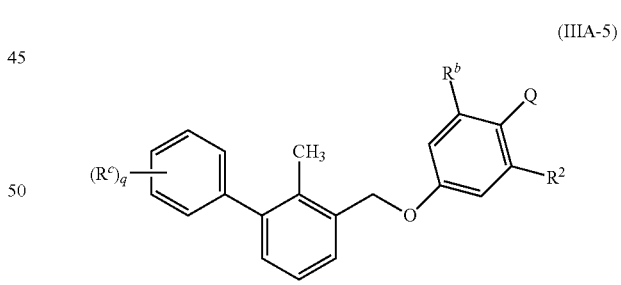

(IIIA-5)

wherein Q, $R^2$, $R^b$, $R^c$, and q are defined in the first aspect. Examples of compounds of Formula (IIIA-5) include compounds in which (i) $R^2$ is —$OCH_3$; (ii) $R^2$ is —$CH_3$ or —$OCH_3$; (iii) $R^b$ is —$CH_3$ and $R^2$ is —$CH_3$; (iv) $R^b$ is —$OCH_3$ and $R^2$ is —$OCH_3$; and (v) $R^b$ is —$CH_3$ or —$OCH_3$ and $R^2$ is —$CH_3$ or —$OCH_3$.

One embodiment provides compounds of Formula (IIIA) wherein each $R^2$ is H. The compounds of this embodiment have the structure of Formula (IIIA-6):

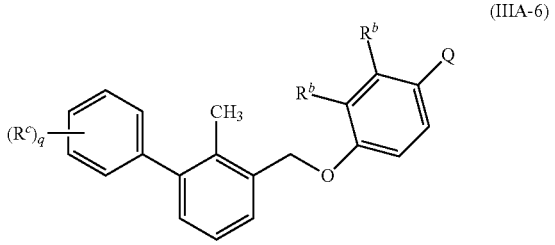

(IIIA-6)

wherein Q, $R^b$, $R^c$, and q are defined in the first aspect. Included in this embodiment are compounds in which each $R^b$ is independently —$CH_3$ or —$OCH_3$.

One embodiment provides compounds of Formula (IIIA) wherein each $R^2$ is H. The compounds of this embodiment have the structure of Formula (IIIA-7):

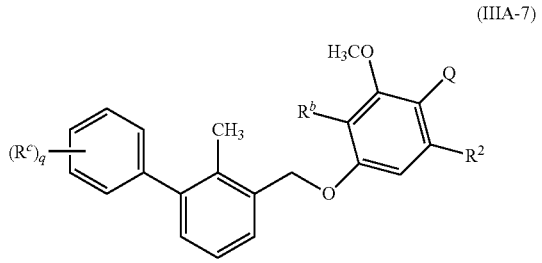

(IIIA-7)

wherein Q, $R^2$, $R^b$, $R^c$, and q are defined in the first aspect. Included in this embodiment are compounds in which each $R^b$ is Br and $R^2$ is —$OCH_3$.

One embodiment provides compounds of Formula (III) in which p is 1. Included in this embodiment are compounds of Formula (II-1) having the structure:

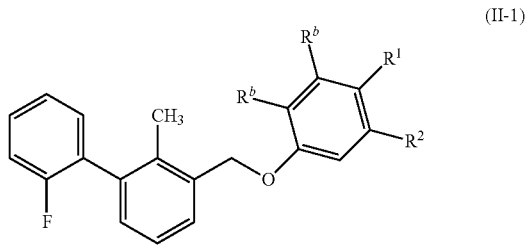

(II-1)

wherein $R^1$, $R^2$, and $R^b$ are defined in the first aspect.

One embodiment provides compounds of Formula (IIIA) in which q is 2 and the two $R^c$ are attached to adjacent carbon atoms to form —O—$CH_2$—O—. Included in this embodiment are compounds of Formula (IIIA-8) having the structure:

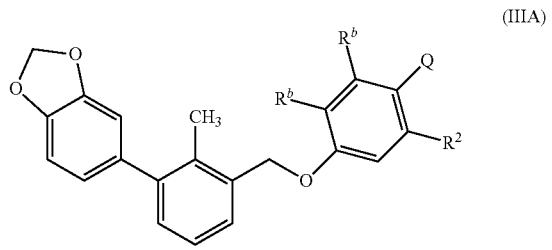

(IIIA)

wherein Q, $R^2$, and $R^b$ are defined in the first aspect.

One embodiment provides a compound of Formula (IIIA) selected from (S)-1-(2,6-dimethoxy-4-((2-methylbiphenyl-3-yl)methoxy)benzyl)piperidine-2-carboxylic acid (1); 1-(4-((2'-fluoro-2-methylbiphenyl-3-yl)methoxy)benzyl)azetidine (3); N-{2-[({3-bromo-2,6-dimethoxy-4-[(2-methyl-3-phenylphenyl)methoxy]phenyl}methyl)amino]ethyl}acetamide (4); ({2,6-dimethoxy-4-[(2-methyl-3-phenylphenyl)methoxy]phenyl}methyl)[2-methyl-1-(4-methylpiperazin-1-yl)propan-2-yl]amine (5); N-{2-[({2,6-dimethoxy-4-[(2-methyl-3-phenylphenyl)methoxy]phenyl}methyl)amino]ethyl}-N-methylmethanesulfonamide (6); 1-({3-bromo-4-[(2-methyl-3-phenylphenyl)methoxy]phenyl}methyl)piperidine-2-carboxylic acid (7); 2-[({2,6-dimethoxy-4-[(2-methyl-3-phenylphenyl)methoxy]phenyl}methyl)amino]-1-(morpholin-4-yl)ethan-1-one (8); ({2,6-dimethoxy-4-[(2-methyl-3-phenylphenyl)methoxy]phenyl}methyl)[2-(4-methylpiperazin-1-yl)ethyl]amine (9); 1-{2-[({2,6-dimethoxy-4-[(2-methyl-3-phenylphenyl)methoxy]phenyl}methyl)amino]ethyl}piperidin-2-one (10); 1-{3-[({2,6-dimethoxy-4-[(2-methyl-3-phenylphenyl)methoxy]phenyl}methyl)amino]propyl}pyrrolidin-2-one (11); 4-{2-[({2,6-dimethoxy-4-[(2-methyl-3-phenylphenyl)methoxy]phenyl}methyl)amino]ethyl}piperazin-2-one (12); ({2,6-dimethoxy-4-[(2-methyl-3-phenylphenyl)methoxy]phenyl}methyl)[2-(morpholin-4-yl)ethyl]amine (13); 1-({2,6-dimethoxy-4-[(2-methyl-3-phenylphenyl)methoxy]phenyl}methyl)piperidine-2-carboxylic acid (14); N-({2,6-dimethoxy-4-[(2-methyl-3-phenylphenyl)methoxy]phenyl}methyl)-1-ethylpiperidin-3-amine (16); 1-{2-[({2,6-dimethoxy-4-[(2-methyl-3-phenylphenyl)methoxy]phenyl}methyl)amino]ethyl}pyrrolidin-2-one (17); (2S,4R)-4-(acetyloxy)-1-({3-methyl-4-[(2-methyl-3-phenylphenyl)methoxy]phenyl}methyl) pyrrolidine-2-carboxylic acid (18); N-(2-hydroxyethyl)-1-({3-methyl-4-[(2-methyl-3-phenylphenyl)methoxy]phenyl}methyl) piperidine-4-carboxamide (19); ({2,6-dimethoxy-4-[(2-methyl-3-phenylphenyl)methoxy]phenyl}methyl)[1-(5-methyl-4H-1,2,4-triazol-3-yl)ethyl]amine (20); N-{2-[({3-bromo-4-[(2-methyl-3-phenylphenyl)methoxy]phenyl}methyl)amino]ethyl}acetamide (21); (2S,4R)-1-({3-chloro-4-[(2-methyl-3-phenylphenyl) methoxy]phenyl}methyl)-4-methoxypyrrolidine-2-carboxylic acid (22); N-{3-[({2,6-dimethoxy-4-[(2-methyl-3-phenylphenyl) methoxy]phenyl}methyl)amino]propyl}acetamide (23); (1R,2R)-2-[({2,6-dimethoxy-4-[(2-methyl-3-phenylphenyl) methoxy]phenyl}methyl)amino]cyclohexan-1-ol (24); N-({2,6-dimethoxy-4-[(2-methyl-3-phenylphenyl)methoxy] phenyl}methyl)-1-methylpiperidin-3-amine (25); (2S)-1-({2-methoxy-3-methyl-4-[(2-methyl-3-phenylphenyl) methoxy]phenyl}methyl)piperidine-2-carboxylic acid (26); (2S)-1-({3-methyl-4-[(2-methyl-3-phenylphenyl)methoxy] phenyl}methyl)-2-(prop-2-en-1-yl)pyrrolidine-2-carboxylic acid (27); 3-[({3-bromo-4-[(2-methyl-3-phenylphenyl) methoxy]phenyl}methyl)amino]propanamide (28); 4-({3-chloro-4-[(2-methyl-3-phenylphenyl)methoxy] phenyl}methyl)morpholine-3-carboxylic acid (30); 3-[({2,6-dimethoxy-4-[(2-methyl-3-phenylphenyl)methoxy] phenyl}methyl)amino]butanoic acid (31); 1-({3-chloro-4-[(2-methyl-3-phenylphenyl)methoxy]phenyl}methyl) piperidine-4-carboxylic acid (32); (2R)-1-({3-chloro-4-[(2-methyl-3-phenylphenyl) methoxy]phenyl}methyl)piperidine-2-carboxylic acid (33); (2S)-1-({3-chloro-4-[(2-methyl-3-phenylphenyl)methoxy]phenyl}methyl) piperidine-2-carboxylic acid (34); 2-[({2,6-dimethoxy-4-[(2-methyl-3-phenylphenyl)methoxy]phenyl}methyl) amino]-N,N-dimethylacetamide (35); N-{2-[({2,6- dimethoxy-4-[(2-methyl-3-phenylphenyl)methoxy]phenyl}methyl)amino]ethyl}acetamide (36); 1-({2-methoxy-4-[(2-methyl-3-phenylphenyl)methoxy]phenyl}methyl)piperidine-2-carboxylic acid (37); (2S,4R)-4-methoxy-1-({3-methyl-4-[(2-methyl-3-phenylphenyl)methoxy]phenyl}methyl) pyrrolidine-2-carboxylic acid (39); 1-({2,6-dimethyl-4-[(2-methyl-3-phenylphenyl)methoxy]phenyl}methyl)piperidine-2-carboxylic acid (40); 1-({3-methyl-4-[(2-methyl-3-phenylphenyl)methoxy]phenyl}methyl)azepane-2-carboxylic acid (41); 2-[1-({3-methyl-4-[(2-methyl-3-phenylphenyl)methoxy]phenyl}methyl)piperidin-2-yl]acetic acid (42); 1-{3-[({3-methyl-4-[(2-methyl-3-phenylphenyl)methoxy]phenyl}methyl)amino]propyl}pyrrolidin-2-one (43); N-{2-[(1-{3-chloro-4-[(2-methyl-3-phenylphenyl)methoxy]phenyl}ethyl)amino]ethyl}acetamide (44); 2-[({2,6-dimethoxy-4-[(2-methyl-3-phenylphenyl)methoxy]phenyl}methyl)(methyl)amino]acetic acid (45); 3-[({2,6-dimethoxy-4-[(2-methyl-3-phenylphenyl)methoxy]phenyl}methyl)amino]propanamide (46); (2S)-2-[({2,6-dimethoxy-4-[(2-methyl-3-phenylphenyl)methoxy]phenyl}methyl)amino]propanoic acid (47); 1-({3-fluoro-4-[(2-methyl-3-phenylphenyl)methoxy]phenyl}methyl)piperidine-2-carboxylic acid (49); (2R,4R)-4-hydroxy-1-({3-methyl-4-[(2-methyl-3-phenylphenyl)methoxy]phenyl}methyl)pyrrolidine-2-carboxylic acid (50); (2R,4S)-4-hydroxy-1-({3-methyl-4-[(2-methyl-3-phenylphenyl)methoxy]phenyl}methyl) pyrrolidine-2-carboxylic acid (51); 1-({3-methyl-4-[(2-methyl-3-phenylphenyl)methoxy]phenyl}methyl)piperidine-2-carboxylic acid (52); 1-({3-methyl-4-[(2-methyl-3-phenylphenyl)methoxy]phenyl}methyl)piperidine-3-carboxylic acid (53); (3R)-1-({3-methyl-4-[(2-methyl-3-phenylphenyl)methoxy]phenyl}methyl)piperidine-3-carboxylic acid (54); (2R,4R)-4-methyl-1-({3-methyl-4-[(2-methyl-3-phenylphenyl)methoxy]phenyl}methyl)pyrrolidine-2-carboxylic acid (55); (2S)-1-({3-methyl-4-[(2-methyl-3-phenylphenyl)methoxy]phenyl}methyl)piperidine-2-carboxylic acid (56); 1-({3-methyl-4-[(2-methyl-3-phenylphenyl)methoxy]phenyl}methyl)piperidine-4-carboxylic acid (57); (2R)-1-({3-methyl-4-[(2-methyl-3-phenylphenyl)methoxy]phenyl}methyl)piperidine-2-carboxylic acid (58); 1-({3-methyl-4-[(2-methyl-3-phenylphenyl)methoxy]phenyl}methyl)-1,2,5,6-tetrahydropyridine-3-carboxylic acid (63); 2-[({3-chloro-4-[(2-methyl-3-phenylphenyl)methoxy]phenyl}methyl)amino]-2-methylpropanoic acid (64); N-{2-[({3-chloro-4-[(2-methyl-3-phenylphenyl)methoxy]phenyl}methyl)amino]ethyl}acetamide (65); 1-({3-bromo-4-[(2-methyl-3-phenylphenyl)methoxy]phenyl}methyl)azetidine (66); N-{2-[({2-methoxy-4-[(2-methyl-3-phenylphenyl)methoxy]phenyl}methyl)amino]ethyl}acetamide (67); N-({2,6-dimethoxy-4-[(2-methyl-3-phenylphenyl)methoxy]phenyl}methyl)cyclobutanamine (68); N-{2-[({2,6-dimethyl-4-[(2-methyl-3-phenylphenyl)methoxy]phenyl}methyl)amino]ethyl}acetamide (69); N-{2-[(1-{3-methyl-4-[(2-methyl-3-phenylphenyl)methoxy]phenyl}ethyl)amino]ethyl}acetamide (70); (2S)-1-({3-methyl-4-[(2-methyl-3-phenylphenyl)methoxy]phenyl}methyl)pyrrolidine-2-carboxylic acid (71); 1-({3-methyl-4-[(2-methyl-3-phenylphenyl)methoxy]phenyl}methyl)pyrrolidine-2-carboxylic acid (72); (1R,2R)-2-[({3-methyl-4-[(2-methyl-3-phenylphenyl)methoxy]phenyl}methyl)amino]cyclohexan-1-ol (73); 1-({4-[(2-methyl-3-phenylphenyl)methoxy]phenyl}methyl)piperidine-2-carboxylic acid (74); (2R)-1-({3-methyl-4-[(2-methyl-3-phenylphenyl)methoxy]phenyl}methyl)pyrrolidine-2-carboxylic acid (75); 5-{[({3-methyl-4-[(2-methyl-3-phenylphenyl)methoxy]phenyl}methyl)amino]methyl}pyrrolidin-2-one (76); (2S)-2-[({3-chloro-4-[(2-methyl-3-phenylphenyl)methoxy]phenyl}methyl)amino]propanoic acid (77); (2R)-2-[({3-chloro-4-[(2-methyl-3-phenylphenyl)methoxy]phenyl}methyl)amino]propanoic acid (78); N-{2-[({3-fluoro-4-[(2-methyl-3-phenylphenyl)methoxy]phenyl}methyl)amino]ethyl}acetamide (79); (2S)-2-[({2-methoxy-4-[(2-methyl-3-phenylphenyl)methoxy]phenyl}methyl)amino]propanoic acid (80); 3-[({2-methoxy-4-[(2-methyl-3-phenylphenyl)methoxy]phenyl}methyl)amino]propanamide (82); 1-({2,6-dimethoxy-4-[(2-methyl-3-phenylphenyl)methoxy]phenyl}methyl)azetidine (83); 3-[({3-methyl-4-[(2-methyl-3-phenylphenyl)methoxy]phenyl}methyl)amino]butanoic acid (84); (2R)-2-[methyl({3-methyl-4-[(2-methyl-3-phenylphenyl)methoxy]phenyl}methyl)amino]propanoic acid (85); 3-[({2,6-dimethyl-4-[(2-methyl-3-phenylphenyl)methoxy]phenyl}methyl)amino]propanamide (86); N-{2-[({3-methyl-4-[(2-methyl-3-phenylphenyl)methoxy]phenyl}methyl)amino]ethyl}acetamide (87); N-{2-[({4-methyl-3-[(2-methyl-3-phenylphenyl)methoxy]phenyl}methyl)amino]ethyl}acetamide (88); (2S)-1-({3-methyl-4-[(2-methyl-3-phenylphenyl) methoxy]phenyl}methyl)azetidine-2-carboxylic acid (90); 5-{[({4-[(2-methyl-3-phenylphenyl)methoxy]phenyl}methyl)amino]methyl}pyrrolidin-2-one (91); 5-{[({4-[(2-methyl-3-phenylphenyl)methoxy]phenyl}methyl)amino]methyl}pyrrolidin-2-one (92); (2S)-2-[({3-methyl-4-[(2-methyl-3-phenylphenyl)methoxy]phenyl}methyl)amino]propanoic acid (93); 2-[methyl({3-methyl-4-[(2-methyl-3-phenylphenyl)methoxy]phenyl}methyl)amino]acetic acid (94); 3-[({3-methyl-4-[(2-methyl-3-phenylphenyl)methoxy]phenyl}methyl)amino]propanamide (95); (2R)-2-[({3-methyl-4-[(2-methyl-3-phenylphenyl)methoxy]phenyl}methyl)amino]propanoic acid (96); 1-({3-chloro-4-[(2-methyl-3-phenylphenyl)methoxy]phenyl}methyl)azetidine (97); 1-({2-methoxy-4-[(2-methyl-3-phenylphenyl)methoxy]phenyl}methyl)azetidine (98); 1-({3-methyl-4-[(2-methyl-3-phenylphenyl)methoxy]phenyl}methyl)azetidine (99); 1-({3-methyl-4-[(2-methyl-3-phenylphenyl)methoxy]phenyl}methyl)azetidine (100); 2-[({3-methyl-4-[(2-methyl-3-phenylphenyl)methoxy]phenyl}methyl)amino]ethan-1-ol (102); 2-[({2,6-dimethoxy-4-[(2-methyl-3-phenylphenyl)methoxy]phenyl}methyl)amino]ethan-1-ol (103); (2S)-2-[({3-bromo-4-[(2-methyl-3-phenylphenyl)methoxy]phenyl}methyl)amino]propanoic acid (104); (2R)-2-[({2,6-dimethoxy-4-[(2-methyl-3-phenylphenyl) methoxy]phenyl}methyl)amino]propanoic acid (105); (2R)-2-{[(2,6-dimethoxy-4-{[3-(3-methoxyphenyl)-2-methylphenyl]methoxy}phenyl)methyl]amino}propanoic acid (106); (2R)-2-{[(4-{[3-(3-fluoro-5-methoxyphenyl)-2-methylphenyl]methoxy}-2,6-dimethoxyphenyl)methyl]amino}propanoic acid (107); (2R)-2-{[(4-{[3-(2H-1,3-benzodioxol-5-yl)-2-methylphenyl]methoxy}-2,6-dimethoxyphenyl)methyl]amino}propanoic acid (108); and a salt thereof.

One embodiment provides a compound of Formula (III-B) selected from 2-[methyl({3-[(2-methyl-3-phenylphenyl)methoxy]phenyl}methyl)amino]acetic acid (15); 3-[({3-[(2-methyl-3-phenylphenyl)methoxy]phenyl}methyl)amino]propanamide (29); 1-({3-[(2-methyl-3-phenylphenyl)methoxy]phenyl}methyl)azetidine (38); 1-({3-[(2-methyl-3-phenylphenyl)methoxy]phenyl}methyl)piperidine-2-carboxylic acid (48); (2S)-1-({4-methyl-3-[(2-methyl-3-phenylphenyl)methoxy]phenyl}methyl)piperidine-2-carboxylic acid (59); 1-{3-[({3-[(2-methyl-3-phenylphenyl)methoxy]phenyl}methyl)amino]propyl}pyrrolidin-2-one (60); (2S)-2-[({3-[(2-methyl-3-phenylphenyl)methoxy]phenyl}methyl)amino]propanoic acid (81); [(2S)-1-({3-methyl-4-[(2-methyl-3-phenylphenyl)methoxy]phenyl}methyl)pyrrolidin-2-yl]methanol (89); and a salt thereof.

One embodiment provides compounds of Formula (II) wherein Ring A is:

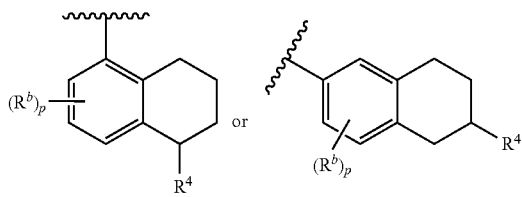

wherein $R^4$, $R^b$, $R^c$, p, and q are defined in the first aspect. Included in this embodiment are the compounds of Formula (IVA) in which Ring A is

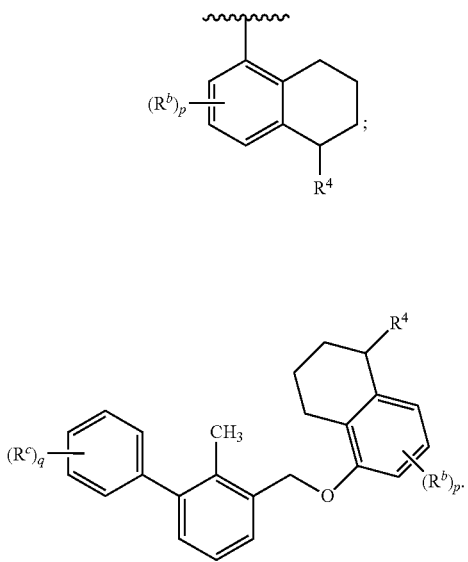

(IVA)

Also included in this embodiment are the compounds of Formula (IVB) in which Ring A is

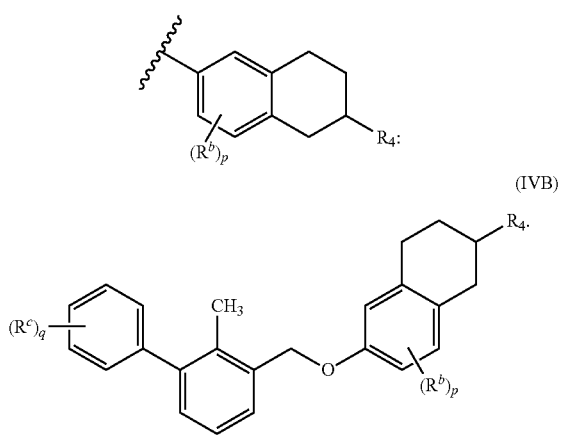

(IVB)

One embodiment provides compounds of Formula (IVA) and Formula (IVB) in which q is zero.

One embodiment provides compounds of Formula (IVA) and Formula (IVB) in which p is zero.

One embodiment provides compounds of Formula (IVA) and Formula (IVB) in which p is zero and q is zero.

One embodiment provides a compound selected from N-[2-({5-[(2-methyl-3-phenylphenyl)methoxy]-1,2,3,4-tetrahydronaphthalen-1-yl}amino)ethyl]acetamide (61); N-[2-({6-[(2-methyl-3-phenylphenyl)methoxy]-1,2,3,4-tetrahydronaphthalen-1-yl}amino)ethyl]acetamide (62); and a salt thereof.

One embodiment provides compounds of Formula (II) wherein Ring A is:

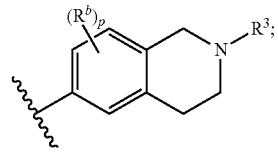

wherein $R^3$, $R^b$, $R^c$, and p are defined in the first aspect. The compounds of this embodiment have the structure of Formula (V):

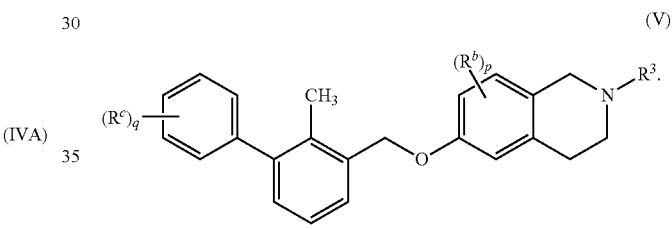

(V)

One embodiment provides compounds of Formula (V) in which q is zero.

One embodiment provides compounds of Formula (V) in which p is zero.

One embodiment provides compounds of Formula (V) in which p is zero and q is zero.

One embodiment provides a compound selected from 2-(6-((2-methyl-[1,1'-biphenyl]-3-yl)methoxy)-3,4-dihydroisoquinolin-2(1H)-yl)acetic acid (2); 6-[(2-methyl-3-phenylphenyl)methoxy]-1,2,3,4-tetrahydroisoquinoline (101); and a salt thereof.

One embodiment provides a compound selected from the exemplified examples within the scope of the first aspect and salts thereof.

One embodiment provides a compound selected from any subset list of compounds within the scope of any of the above embodiments.

One embodiment provides a composition comprising at least one of the compounds of the present disclosure or salts thereof.

One embodiment provides a pharmaceutical composition comprising: a pharmaceutically acceptable carrier; and at least one of the compounds of the present disclosure or salts thereof.

One embodiment provides a pharmaceutical composition comprising; a pharmaceutically acceptable carrier; and a therapeutically effective amount of at least one of the compounds of the present disclosure or salts thereof.

One embodiment provides a process for making a compound of the present disclosure or salts thereof.

One embodiment provides an intermediate for making a compound of the present disclosure or salts thereof.

The present disclosure may be embodied in other specific forms without departing from the spirit or essential attributes thereof. This disclosure encompasses all combinations of the aspects and/or embodiments of the disclosure noted herein. It is understood that any and all embodiments of the present disclosure may be taken in conjunction with any other embodiment or embodiments to describe additional embodiments. It is also to be understood that each individual element of the embodiments is meant to be combined with any and all other elements from any embodiment to describe an additional embodiment.

The features and advantages of the disclosure may be more readily understood by those of ordinary skill in the art upon reading the following detailed description. It is to be appreciated that certain features of the disclosure that are, for clarity reasons, described above and below in the context of separate embodiments, may also be combined to form a single embodiment. Conversely, various features of the disclosure that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compound(s) or salts thereof" refers to at least one compound, at least one salt of the compounds, or a combination thereof. For example, compounds of Formula (I) or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

Listed below are definitions of various terms used to describe the present disclosure. These definitions apply to the terms as they are used throughout the specification (unless they are otherwise limited in specific instances) either individually or as part of a larger group. The definitions set forth herein take precedence over definitions set forth in any patent, patent application, and/or patent application publication incorporated herein by reference.

Throughout the specification, groups and substituents thereof may be chosen by one skilled in the field to provide stable moieties and compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this disclosure. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the disclosure. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the compounds of Formula (I) are also within the scope of the present disclosure. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present disclosure.

"Stable compound" and "stable structure" are meant to indicate a compound that is sufficiently robust to survive isolation to a useful degree of purity from a reaction mixture, and formulation into an efficacious therapeutic agent. The present disclosure is intended to embody stable compounds.

"Therapeutically effective amount" is intended to include an amount of a compound of the present disclosure alone or an amount of the combination of compounds claimed or an amount of a compound of the present disclosure in combination with other active ingredients effective to act as an inhibitor of PD-1, or effective to treat or prevent cancer or chronic infection, such as hepatitis B and hepatitis C.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present disclosure are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Compounds in accordance with Formula (I) and/or pharmaceutically acceptable salts thereof can be administered by any means suitable for the condition to be treated, which can depend on the need for site-specific treatment or quantity of Formula (I) compound to be delivered. Also embraced within this disclosure is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present disclosure may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the disclosure can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present disclosure include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this disclosure include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this disclosure can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this disclosure depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this disclosure are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this disclosure comprise at least one compound of Formula (I) and/or at least one pharmaceutically acceptable salt thereof, and optionally an additional agent selected from any pharmaceutically acceptable carrier, adjuvant, and vehicle. Alternate compositions of this disclosure comprise a compound of the Formula (I) described herein, or a prodrug thereof, and a pharmaceutically acceptable carrier, adjuvant, or vehicle.

The compounds of the disclosure inhibit the PD-1/PDL-1 protein/protein interaction, resulting in a PD-1 blockade. The blockade of PD-1 can enhance the immune response to cancerous cells and infectious diseases in mammals, including humans. In one aspect, the present disclosure relates to treatment of a subject in vivo using a compound of Formula (I) or a salt thereof such that growth of cancerous tumors is inhibited. A compound of Formula (I) or a salt thereof may be used alone to inhibit the growth of cancerous tumors. Alternatively, a compound of Formula (I) or a salt thereof may be used in conjunction with other immunogenic agents or standard cancer treatments, as described below.

In one embodiment, the disclosure provides a method of inhibiting growth of tumor cells in a subject, comprising administering to the subject a therapeutically effective amount of a compound of Formula (I) or a salt thereof.

In one embodiment, a method is provided for treating cancer comprising administering to a patient in need thereof, a therapeutically effective amount of a compound of Formula (I) or a salt thereof. Examples of cancers include those whose growth may be inhibited using compounds of the disclosure include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al. (2005) Int. Immunol. 17:133-144).

Optionally, the compounds of Formula (I) or salts thereof can be combined with another immunogenic agent, such as cancerous cells, purified tumor antigens (including recombinant proteins, peptides, and carbohydrate molecules), cells, and cells transfected with genes encoding immune stimulating cytokines (He et al (2004) J. Immunol. 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. In humans, some tumors have been shown to be immunogenic such as melanomas. It is anticipated that by raising the threshold of T cell activation by PD-1 blockade, tumor responses are expected to be activated in the host.

The PD-1 blockade can be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogenenic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci. U.S.A. 90: 3539-43).

The study of gene expression and large scale gene expression patterns in various tumors has led to the definition of so called tumor specific antigens (Rosenberg, S A (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269:1585-1588; Tamura, Y. et al. (1997) Science 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with PD-1 blockade to activate more potent anti-tumor responses.

PD-1 blockade may also be combined with standard cancer treatments. PD-1 blockade may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is a compound of this disclosure in combination with dacarbazine for the treatment of melanoma. Another example of such a combination is a compound of this disclosure in combination with interleukin-2 (IL-2) for the treatment of melanoma. The scientific rationale behind the combined use of PD-1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-1 blockade through cell death are radiation, surgery, and hormone deprivation. Each of these protocols creates a source of tumor antigen in the host. Angiogenesis inhibitors may also be combined with PD-1 blockade. Inhibition of angiogenesis leads to tumor cell death which may feed tumor antigen into host antigen presentation pathways.

The compounds of this disclosure can also be used in combination with bispecific macrocyclic peptides that target Fc alpha or Fc gamma receptor-expressing effectors cells to tumor cells (see, e.g., U.S. Pat. Nos. 5,922,845 and 5,837, 243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of PD-1 blockade. Alternatively, antigen may be delivered directly to DCs by the use of bispecific macrocyclic peptides which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Macrocyclic peptides to each of these entities may be used in combination with the compounds of this disclosure to counteract the effects of the immunosuppressive agent and favor tumor immune responses by the host.

Macrocyclic peptides that activate host immune responsiveness can be used in combination with anti-PD-1. These include molecules on the surface of dendritic cells which activate DC function and antigen presentation. Anti-CD40 macrocyclic peptides are able to substitute effectively for T cell helper activity (Ridge, J. et al. (1998) Nature 393: 474-478) and can be used in conjunction with PD-1 macrocyclic peptides (Ito, N. et al. (2000) Immunobiology 201 (5) 527-40). Activating macrocyclic peptides to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-1 blockade can be used to increase the effectiveness of the donor engrafted tumor specific T cells. Other methods of the disclosure are used to treat patients who have been exposed to particular toxins or pathogens. Accordingly, another aspect of the disclosure provides a method of treating an infectious disease in a subject comprising administering to the subject a therapeutically effective amount of a compound of Formula (I) or salts thereof. Similar to its application to tumors as discussed above, the compound of Formula (I) or salts thereof can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, & C), Influenza, Herpes, *Giardia*, Malaria, *Leishmania*, *Staphylococcus aureus*, *Pseudomonas Aeruginosa*. PD-1 blockade is particularly useful against established infections by agents such as HIV that present altered antigens over the course of the infections. These novel epitopes are recognized as foreign at the time of administration, thus provoking a strong T cell response that is not dampened by negative signals through PD-1.

Some examples of pathogenic viruses causing infections treatable by methods of the disclosure include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include chlamydia, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Some examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*. In all of the above methods, PD-1 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2:1121-1123).

The compounds of this disclosure may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al. (1999) Proc. Natl. Acad. Sci. U.S.A. 96: 2982-2987); autoimmune prostatitis evoked by TRAMP tumor cell vaccines (Hurwitz, A. (2000) supra), melanoma peptide antigen vaccination and vitiligo observed in human clinical trials (Rosenberg, S A and White, D E (1996) J. Immunother Emphasis Tumor Immunol 19 (1): 81-4).

Therefore, it is possible to consider using anti-PD-1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., (1999) Nature 400: 173-177).

Other self proteins may also be used as targets such as IgE for the treatment of allergy and asthma, and TNF.alpha. for rheumatoid arthritis. Finally, antibody responses to various hormones may be induced by the use of a compound of Formula (I) or salts thereof. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-1 antibody can be used for induction of therapeutic autoimmune responses to treat patients having an inappropriate accumulation of other self-antigens, such as amyloid deposits, including A.beta. in Alzheimer's disease, cytokines such as TNF.alpha., and IgE. The compounds of this disclosure may be used to stimulate antigen-specific immune responses by coadministration of a compound of Formula (I) or salts thereof with an antigen of interest (e.g., a vaccine). Accordingly, in another aspect the disclosure provides a method of enhancing an immune response to an antigen in a subject, comprising administering to the subject: (i) the antigen; and (ii) a compound of Formula (I) or salts thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

As previously described, the compounds of the disclosure can be co-administered with one or more other therapeutic agents, e.g., a cytotoxic agent, a radiotoxic agent or an immunosuppressive agent. The compounds of the disclosure can be administered before, after or concurrently with the other therapeutic agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of a compound of Formula (I) or salts thereof, with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present disclosure are kits comprising a compound of Formula (I) or salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

The above other therapeutic agents, when employed in combination with the compounds of the present disclosure, may be used, for example, in those amounts indicated in the Physicians' Desk Reference (PDR) or as otherwise determined by one of ordinary skill in the art. In the methods of the present disclosure, such other therapeutic agent(s) may be administered prior to, simultaneously with, or following the administration of the inventive compounds.

In one embodiment, the compounds of Formula (I) inhibit the PD-1/PD-L1 interaction with $IC_{50}$ values of 10 μM or less, for example, from 0.01 to 10 μM, as measured by the PD-1/PD-L1 Homogenous Time-Resolved Fluorescence (HTRF) binding assay. Preferably, the compounds of Formula (I) inhibit the PD-1/PD-L1 interaction with $IC_{50}$ values of 1 μM or less, for example, from 0.01 to 1 μM.

EXAMPLES

The disclosure is further defined in the following Examples. It should be understood that the Examples are given by way of illustration only. From the above discussion and the Examples, one skilled in the art can ascertain the essential characteristics of the disclosure, and without departing from the spirit and scope thereof, can make various changes and modifications to adapt the disclosure to various uses and conditions. As a result, the disclosure is not limited by the illustrative examples set forth hereinbelow, but rather is defined by the claims appended hereto.

ABBREVIATIONS

Ac acetyl
anhyd. anhydrous
aq. aqueous
Bn benzyl
Bu butyl
CV Column Volumes
Et ethyl
h, hr or hrs hour(s)
HPLC high pressure liquid chromatography
LC liquid chromatography
M molar
mM millimolar
Me methyl
MHz megahertz
min. minute(s)
mins minute(s)
$M^{+1}$ $(M+H)^{+}$
MS mass spectrometry
n or N normal
nM nanomolar
Ph phenyl
Ret Time or RT retention time
sat. saturated
SFC supercritical fluid chromatography Example 1

(S)-1-(2,6-dimethoxy-4-((2-methylbiphenyl-3-yl)methoxy)benzyl)piperidine-2-carboxylic acid

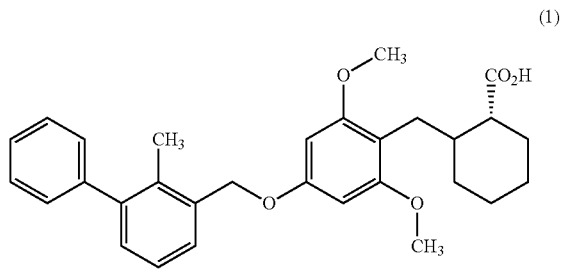 [SMILES: COc1cc(OCc2cccc(-c3ccccc3)c2C)cc(OC)c1CC1CCCC[C@H]1C(=O)O]

Intermediate 1A: (2-methylbiphenyl-3-yl)methanol

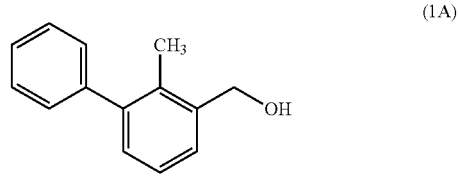

A mixture of (3-bromo-2-methylphenyl)methanol (2.071 g, 10.3 mmol), phenylboronic acid (2.51 g, 20.60 mmol) and [1,1'-bis(diphenylphosphino)ferrocene]dichloropalladium (II) dichloromethane complex (0.084 g, 0.103 mmol) in toluene (15.45 ml) and ethanol (5.15 ml) was placed under argon. To this solution was added sodium bicarbonate, 2M (15.45 ml, 30.9 mmol) and the mixture was heated at 80° C. for 30 min. The reaction mixture was diluted with 20 mL ethyl acetate and 5 mL water. The organic portion was concentrated by rotatory evaporation. The crude product was chromatographed on silica gel eluting with 0-40% ethyl acetate in hexane to afford 2 g of an off-white solid. $^1$H NMR (400 MHz, CHLOROFORM-d) δ 7.47-7.29 (m, 7H), 7.23 (s, 1H), 4.80 (d, J=5.6 Hz, 2H), 2.27 (s, 3H), 1.63-1.59 (m, 1H).

Intermediate 1B: 2,6-dimethoxy-4-((2-methylbiphenyl-3-yl)methoxy)benzaldehyde

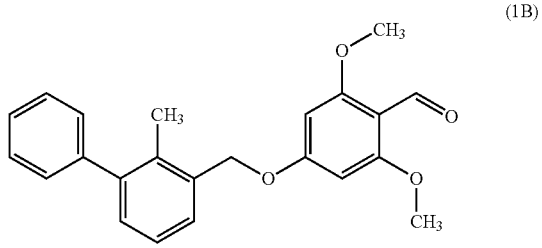 [SMILES: COc1cc(OCc2cccc(-c3ccccc3)c2C)cc(OC)c1C=O]

(1B)

Diisopropyl azodicarboxylate (2.158 mL, 11.10 mmol) in THF (50 mL) was added dropwise to a cooled (0° C.) solution of 4-hydroxy-2,6-dimethoxybenzaldehyde (1.838 g, 10.09 mmol), triphenylphosphine (2.91 g, 11.10 mmol) and 2-methyl-[1,1'-biphenyl]-3-yl)methanol (2 g, 10.09 mmol) in dry THF (50 mL). The resulting yellow solution was allowed to slowly warm to room temperature with stirring overnight. 1H NMR (500 MHz, CHLOROFORM-d) δ 10.40 (s, 1H), 7.48-7.42 (m, 3H), 7.40 (d, J=7.6 Hz, 1H), 7.36-7.30 (m, 4H), 6.23 (s, 2H), 5.19 (s, 2H), 3.94-3.89 (m, 6H), 2.30 (s, 3H). Rf=0.55 1:1 ethyl acetate:hexanes.

Example 1

A solution of 2,6-dimethoxy-4-((2-methylbiphenyl-3-yl)methoxy)benzaldehyde (20 mg, 0.055 mmol), (S)-piperidine-2-carboxylic acid and sodium triacetoxy borohydride (35.1 mg, 0.166 mmol) in dichloromethane (4 mL) was stirred at 85° C. for 45 min. The crude material was purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 25-65% B over 20 minutes, then a 5-minute hold at 100% B; Flow: 20 mL/min. Fractions containing the desired product were combined and dried via centrifugal evaporation. The yield of the product was 20.3 mg, and its estimated purity by LCMS analysis was 99%. LC/MS Method A: 2.8 min., M$^{+1}$: 476.3, M$^{-1}$: 474.4, Exact Mass: 475.2. $^1$H NMR (500 MHz, DMSO-d$_6$) δ 7.55-7.15 (m, 8H), 6.43 (s, 2H), 5.20 (s, 2H), 4.12 (s, 2H), 3.80 (s, 6H), 3.20-3.04 (m, 3H), 3.22-3.02 (m, 3H), 2.65 (br. s., 1H), 2.22 (s, 3H), 1.82 (br. s., 2H), 1.57 (br. s., 2H), 1.40 (d, J=6.7 Hz, 2H).

Examples 6, 7, 9-15, 17, 18, 21, 24-26, 32, 36, 37, 46-48, 69, 84, 103, 105, 111, 163-190, 195, 196, 233-244 and 246-284 in the table were prepared from Intermediate 1B, 2,6-dimethoxy-4-((2-methylbiphenyl-3-yl)methoxy)benzaldehyde, and an appropriate amine according to the general synthetic process described for Example 1.

Example 2

2-(6-((2-methyl-[1,1'-biphenyl]-3-yl)methoxy)-3,4-dihydroisoquinolin-2(1H)-yl)acetic acid

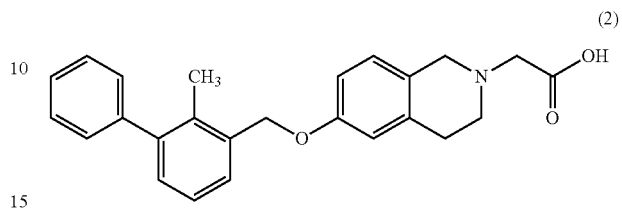

(2)

Intermediate 2A: tert-butyl 6-hydroxy-3,4-dihydroisoquinoline-2(1H)-carboxylate

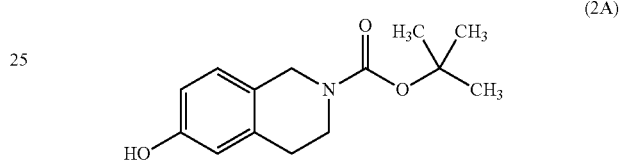

(2A)

A solution of 1,2,3,4-tetrahydroisoquinolin-6-ol HCl (1 g, 5.39 mmol) and BOC$_2$O (2.251 ml, 9.70 mmol) in saturated aqueous sodium bicarbonate solution (10 mL) and chloroform (10 mL) was stirred at room temperature overnight. The aqueous portion was neutralized with concentrated HCl and extracted with ethyl acetate. The combined organic portions were washed with 0.1 N HCl, dried over MgSO$_4$, filtered and concentrated to give 1.6 g of a yellow oil. The oil was chromatographed on silica gel with 0-60% ethyl acetate in hexanes to provide 0.58 g of product. $^1$H NMR (400 MHz, CHLOROFORM-d) δ 6.99 (d, J=8.3 Hz, 1H), 6.70 (dd, J=8.3, 2.5 Hz, 1H), 6.64 (d, J=2.5 Hz, 1H), 4.52 (s, 2H), 3.64 (t, J=5.9 Hz, 2H), 2.80 (t, J=5.9 Hz, 2H), 1.62-1.46 (m, 13H).

Intermediate 2B: tert-butyl 6-((2-methyl-[1,1'-biphenyl]-3-yl)methoxy)-3,4-dihydroisoquinoline-2(1H)-carboxylate

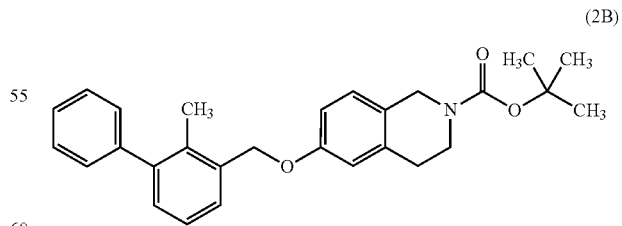

(2B)

A solution of diisopropyl azodicarboxylate (0.503 mL, 2.59 mmol) in THF (11.800 mL) was added dropwise to a cooled (0° C.) solution of tert-butyl 6-hydroxy-3,4-dihydroisoquinoline-2(1H)-carboxylate (586 mg, 2.351 mmol), triphenylphosphine (678 mg, 2.59 mmol) and (2-methyl-[1, 1'-biphenyl]-3-yl)methanol (513 mg, 2.59 mmol) in dry THF (11.800 mL). The resulting yellow solution was allowed to slowly warm to room temperature and stirred overnight. Excess solvent was removed and the residue purified via chromatography with 0-35% ethyl acetate in hexane on a silica gel column. ¹H NMR (400 MHz, CHLOROFORM-d) δ 7.48-7.42 (m, 3H), 7.41-7.33 (m, 3H), 7.30-7.26 (m, 2H), 7.07 (d, J=8.3 Hz, 1H), 6.90 (dd, J=8.3, 2.7 Hz, 1H), 6.83 (d, J=2.4 Hz, 1H), 5.09 (s, 2H), 4.55 (s, 2H), 3.66 (t, J=5.6 Hz, 2H), 2.85 (t, J=5.7 Hz, 2H), 2.69 (br. s., 2H), 2.27 (s, 3H), 1.52 (s, 9H).

Intermediate 2C: 6-((2-methyl-[1,1'-biphenyl]-3-yl) methoxy)-1,2,3,4-tetrahydroisoquinoline HCl

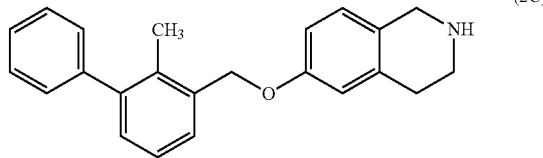

(2C)

The compound, tert-butyl 6-((2-methyl-[1,1'-biphenyl]-3-yl)methoxy)-3,4-dihydroisoquinoline-2(1H)-carboxylate (580 mg, 1.350 mmol), was dissolved in excess 2N HCl in diethyl ether, 3 mL, at room temperature. The solution was allowed to sit overnight. A yellow precipitate was collected, washed once with ether and dried under house vacuum overnight to afford a yellow solid (425 mg). ¹H NMR (500 MHz, DMSO-d₆) δ 7.49-7.42 (m, 3H), 7.41-7.36 (m, 1H), 7.32 (d, J=7.6 Hz, 2H), 7.28 (t, J=7.6 Hz, 1H), 7.19 (d, J=7.6 Hz, 1H), 6.98 (d, J=8.5 Hz, 1H), 6.88-6.77 (m, 2H), 5.10 (s, 2H), 3.04-2.98 (m, 2H), 2.74 (t, J=5.6 Hz, 2H), 2.19 (s, 3H), 1.90 (s, 2H). Intermediate 2C is Example 101.

Example 2

A mixture was prepared by combining potassium carbonate (0.055 g, 0.400 mmol) and 6-((2-methyl-[1,1'-biphenyl]-3-yl)methoxy)-1,2,3,4-tetrahydroisoquinoline (0.066 g, 0.2 mmol) in acetonitrile (2.000 ml). Methyl 2-bromoacetate was filtered through a small plug of potassium carbonate to remove any hydrogen bromide. The methyl 2-bromoacetate (0.034 g, 0.220 mmol) was added to the mixture. The resulting mixture was stirred for 3 hours. The extent of reaction was determined to be about 20%. The mixture was heated to 35° C. for 1 hour. The remaining starting material was consumed. The material was used without further purification.

Half of the unpurified material was diluted with 2 mL methanol and 1 mL 1N sodium hydroxide. The mixture was stirred at room temperature overnight. LCMS showed that the starting material was consumed and product was present. The solvents were removed using a rotovap. The solid material was dissolved in DMF. An insoluble portion remained. The resulting mixture was filtered. The crude material was purified via preparative LC/MS with the following conditions: Column: Waters Xbridge C18, 19×200 mm, 5-μm particles; Mobile Phase A: water with 20-mM ammonium acetate; Mobile Phase B: 95:5 acetonitrile:water with 20-mM ammonium acetate; Gradient: 15-100% B over 20 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 97%. LC/MS Method M: 2.8 min., M⁺¹: 388.2, M⁻¹: 386.1, Exact Mass: 387.2. ¹H NMR (500 MHz, DMSO-d₆) δ 7.49-7.43 (m, 3H), 7.41-7.36 (m, 1H), 7.32 (d, J=7.3 Hz, 2H), 7.28 (t, J=7.5 Hz, 1H), 7.19 (d, J=7.3 Hz, 1H), 7.00 (d, J=9.2 Hz, 1H), 6.85 (s, 2H), 5.11 (s, 2H), 3.72 (s, 2H), 3.30 (s, 2H), 2.85 (dd, J=10.8, 4.4 Hz, 4H), 2.19 (s, 3H).

Example 3

2-[({3-methyl-4-[(2-methyl-3-phenylphenyl) methoxy]phenyl}methyl)amino]ethan-1-ol

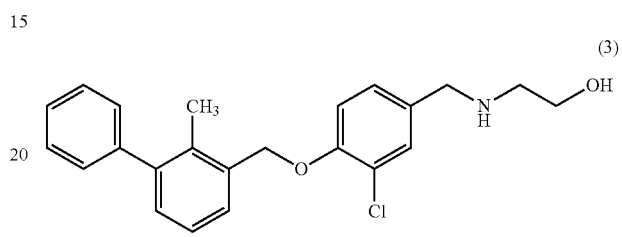

(3)

Intermediate 3A: 3-chloro-4-((2-methylbiphenyl-3-yl)methoxy)benzaldehyde

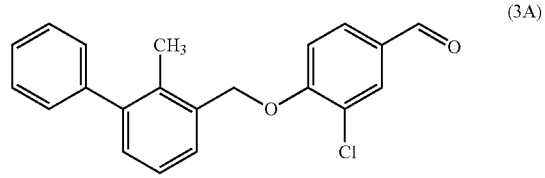 [SMILES: Cc1c(COc2ccc(C=O)cc2Cl)cccc1-c1ccccc1]

(3A)

Diisopropyl azodicarboxylate (1.01 g, 5 mmol) in THF (30 mL) was added dropwise to a cooled (0° C.) solution of 4-hydroxy-3-chlorobenzaldehyde (0.782 g, 5 mmol), triphenylphosphine (1.3 g, 4.99 mmol) and intermediate 1A, 2-methyl-[1,1'-biphenyl]-3-yl)methanol (0.90 g, 4.54 mmol) in dry THF (30 mL). The resulting yellow solution was allowed to slowly warm to room temperature with stirring overnight. Solvent was removed by rotary evaporator. The residue was purified on a 40 g silica gel column with 10:1 Hexane:Ethyl acetate. Isolated 0.97 g of the desired product as white solid. ¹H NMR (400 MHz, CHLOROFORM-d) δ 9.90 (s, 1H), 7.98 (d, J=2.0 Hz, 1H), 7.81 (dd, J=8.6, 2.0 Hz, 1H), 7.53-7.49 (m, 1H), 7.49-7.43 (m, 2H), 7.39 (d, J=7.1 Hz, 1H), 7.36-7.29 (m, 4H), 7.20 (d, J=8.3 Hz, 1H), 5.30 (s, 2H), 2.30 (s, 3H).

Example 3

The solution of 3-chloro-4-((2-methyl-[1,1'-biphenyl]-3-yl)methoxy)benzaldehyde (20 mg, 0.059 mmol) and 2-aminoethanol (3.99 mg, 0.065 mmol) in dichloromethane (5 mL) was stirred at room temperature for 1 hour. The solvent was removed and toluene (3 mL) was added and removed with rotary evaporator. To the residue was added dichloromethane (5 mL) and sodium triacetoxyborohydride (37.8 mg, 0.178 mmol). The resulting light yellow mixture was stirred at room temperature overnight. The solvent was removed and the residue was dissolved in methanol for purification. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 100%. LC/MS Method A: 2.7 min., M$^{+1}$: 382.4 Exact Mass: 381.2. $^1$H NMR (500 MHz, DMSO-d$_6$) δ 7.51 (d, J=7.6 Hz, 1H), 7.49-7.44 (m, 2H), 7.42 (s, 1H), 7.41-7.36 (m, 1H), 7.34-7.28 (m, 3H), 7.27 (s, 2H), 7.21 (d, J=7.6 Hz, 1H), 5.23 (s, 2H), 3.65 (s, 2H), 3.46 (t, J=5.8 Hz, 2H), 2.55 (t, J=5.8 Hz, 2H), 2.23 (s, 3H), 1.90 (s, 1H, acetate).

Examples 23, 31, 33-35, 65, 66, 78, 79, 98, 115, 116, 117 and 197 were prepared according to the general procedure described in Example 3 except an appropriate, commercially available amine was used for reductive amination instead of piperidine-2-carboxylic acid.

Examples 162 was prepared according to the general procedure described in Example 3 except (S)-5-(tert-butoxycarbonyl)-1,2,5-triazaspiro[2.4]hept-1-ene-6-carboxylic acid (Van Der Meijden, B. Robinson, J. A. *ARKIVOC*, 2011, vi, 130-136) was used for reductive amination instead of piperidine-2-carboxylic acid.

Examples 102 was prepared according to the general process described in Example 3 except that 4-hydroxy-3-methylbenzaldehyde was use in the first step instead of 4-hydroxy-3-chlorobenzaldehyde.

Example 4

1-(4-((3'-methoxy-2-methylbiphenyl-3-yl)methoxy)benzyl)azetidine (4)

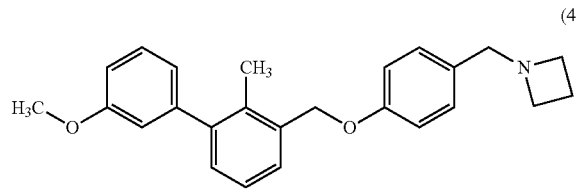 [SMILES: COc1cccc(-c2cccc(COc3ccc(CN4CCC4)cc3)c2C)c1]

Intermediate 4A:
4-(3-bromo-2-methylbenzyloxy)benzaldehyde (4A)

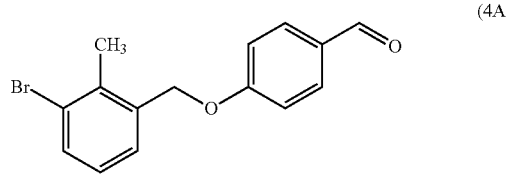 [SMILES: Cc1c(Br)cccc1COc1ccc(C=O)cc1]

A solution of diisopropyl azodicarboxylate (4.25 mL, 21.88 mmol) in THF (100 mL) was added to a cooled (0° C.) solution of 4-hydroxybenzaldehyde (2.67 g, 21.88 mmol), triphenylphosphine (5.74 g, 21.88 mmol) and (3-bromo-2-methylphenyl) methanol (4.0 g, 19.89 mmol) in dry THF (100 mL). The resulting yellow solution was allowed to slowly warm to room temperature and stirred overnight. The solvent was removed by rotary evaporation. The residue was purified by silica gel chromatography eluting with 0-100% ethyl acetate in hexanes to give 4.9 grams of the title compound (81%). $^1$H NMR (500 MHz, CHLOROFORM-d) δ 9.93 (s, 1H), 7.92-7.85 (m, 2H), 7.61 (dd, J=8.0, 0.9 Hz, 1H), 7.38 (d, J=7.6 Hz, 1H), 7.15-7.07 (m, 3H), 5.17 (s, 2H), 2.48 (s, 3H).

Intermediate 4B:
1-(4-(3-bromo-2-methylbenzyloxy)benzyl)azetidine (4B)

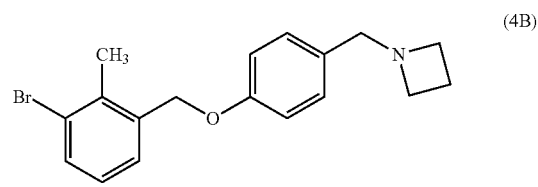 [SMILES: Cc1c(Br)cccc1COc1ccc(CN2CCC2)cc1]

A solution of tetramethyl ammonium triacetoxyborohydride (345 mg, 1.311 mmol) and azetidine hydrochloride salt (123 mg, 1.311 mmol) in dichloromethane (12 mL) was added to a solution of 4-((3-bromo-2-methylbenzyl)oxy)benzaldehyde (200 mg, 0.655 mmol) in dichloromethane (12 mL). The reaction mixture was stirred at room temperature overnight. The reaction was quenched by the addition of saturated sodium bicarbonate. The organic layer, was washed with saturated, aqueous sodium chloride and dried (Na$_2$SO$_4$). The crude residue was then purified by preparative HPLC using a methanol-H$_2$O-TFA buffer system. Fractions were collected and concentrated using a speed-vac overnight to give 102 mg of a white solid. Analytical LC/MS was used to determine the final purity: Column: Phenomenex Luna 2.0×30 mm, Mobile Phase A: 10:90 methanol:water with 0.1% trifluoroacetic acid; Mobile Phase B: 90:10 methanol:water with 10.1% trifluoroacetic acid; Gradient: 0% B, 0-100% B over 2 minutes; Flow: 1.0 mL/min. Retention time: 1.8 minutes, M$^{+1}$: 348.

Example 4

A solution of 1-(4-((3-bromo-2-methylbenzyl)oxy)benzyl)azetidine (330 mg, 880 mol) in dioxane (22 mL) was prepared. Next, a solution of cesium carbonate (568 mg, 1.8 mmol) in water (4.4 mL) was prepared. To 3-methoxyphenylboronic acid in a 2 mL microwave vials was added 1 mL of the (S)-2-((4-((3-bromo-2-methylbenzyl)oxy)benzyl)amino)propanoic acid solution, 200 μL of the cesium carbonate solution and 1,1'-bis(diphenylphosphino)ferrocenepalladium(II) dichloride, dichloromethane (3.56 mg, 4.33 μmol). The vial was capped and heated on a Biotage Initiator (400 W) microwave for 10 min at 140° C. with 20 seconds of stirring and using a fixed hold time. The contents were transferred to 6-mL PL-Thiol SPE cartridges (conditioned with methanol). The reaction vial was rinsed with 500 μL methanol each and the rinses were transferred to SPE cartridges. The product eluted with 4 mL methanol each collecting into 16×100 mm culture tubes. Sample was dried in a Zymark tabletop dryer at 35° C. for 3 hours. Next, 1 mL DMF was added to each vial and purified by reverse phase HPLC: Column: Waters Xbridge C18, 19×200 mm, 5-μm particles; Mobile Phase A: water with 20-mM ammonium acetate; Mobile Phase B: 95:5 acetonitrile:water with 20-mM ammonium acetate; Gradient: 15-100% B over 20 minutes, then a 5-minute hold at 100% B; Flow: 20 mL/min. Fractions containing the desired product were combined and dried via centrifugal evaporation. LC/MS Method M: 3.9 min., M$^{+1}$: 374.4, Exact Mass: 373.2. $^1$H NMR (500 MHz, DMSO-d$_6$) δ 7.44 (d, J=7.0 Hz, 1H), 7.36 (t, J=7.5 Hz, 1H), 7.26 (t, J=7.5 Hz, 1H), 7.20 (d, J=5.5 Hz, 3H), 6.99 (d, J=8.2 Hz, 2H), 6.95 (d, J=8.5 Hz, 1H), 6.87 (d, J=7.9 Hz, 1H), 6.84 (br. s., 1H), 5.11 (s, 2H), 3.79 (s, 3H), 3.49 (br. s., 2H), 3.14 (t, J=6.9 Hz, 4H), 2.19 (s, 3H), 2.02-1.95 (m, 2H).

Examples 75, 92, and 93 were prepared according to the general procedure described in Example 4 except the appropriate amine was substituted for azetidine in the reductive amination step and an appropriate boronic acid was used in the palladium catalyzed coupling step.

Example 5

N-{2-[({3-bromo-2,6-dimethoxy-4-[(2-methyl-3-phenylphenyl)methoxy]phenyl}methyl)amino]ethyl}acetamide

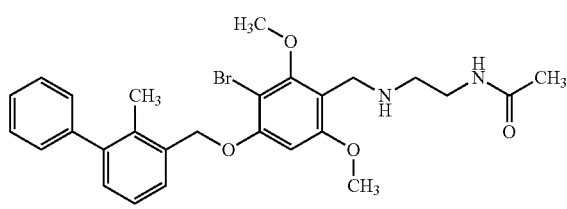

(5)

Example 5 was prepared by bromination of Example 37: To a solution of potassium bromide (26.5 mg, 0.223 mmol) and bromine (14.25 mg, 0.089 mmol) in water was added N-(2-((2,6-dimethoxy-4-((2-methyl-[1,1'-biphenyl]-3-yl) methoxy)benzyl)amino)ethyl)acetamide (20 mg, 0.045 mmol) at 0° C. The mixture was stirred at 0° C. for 2 hr and a yellow precipitate was formed. Water was added and the yellow precipitate was collected (19 mg). The crude material was purified via preparative LC/MS with the following conditions: Column: Waters Xbridge C18, 19×200 mm, 5-µm particles; Mobile Phase A: water with 20-mM ammonium acetate; Mobile Phase B: 95:5 acetonitrile:water with 20-mM ammonium acetate; Gradient: 30-70% B over 10 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 100%. $^1$H NMR (500 MHz, DMSO-d$_6$) δ 7.81 (br. s., 1H), 7.58 (d, J=7.6 Hz, 1H), 7.51-7.44 (m, 2H), 7.40 (d, J=7.0 Hz, 1H), 7.34-7.29 (m, 3H), 7.23 (d, J=7.6 Hz, 1H), 6.83 (s, 1H), 5.29 (s, 2H), 3.88 (s, 3H), 3.77 (s, 3H), 3.71 (s, 2H), 3.14 (d, J=6.1 Hz, 2H), 2.58 (t, J=6.0 Hz, 2H), 2.26 (s, 3H), 1.79 (s, 3H).

Examples 8, 22, 29, 67 and 104 were prepared according to the general procedure described in Example 1 except 3-bromo-4-hydroxybenzaldehyde was used instead of 4-hydroxy-2,6-dimethoxybenzaldehyde and an appropriate amine was used for reductive amination instead of piperidine-2-carboxylic acid.

Examples 16, 30, 39, 49, 61 and 82 were prepared according to the general procedure described in Example 1 except 3-hydroxybenzaldehyde was used instead of 4-hydroxy-2,6-dimethoxybenzaldehyde and an appropriate amine was used for reductive amination instead of piperidine-2-carboxylic acid.

Examples 60 and 89 were prepared according to the general procedure described in Example 1 except 3-hydroxy-4-methylbenzaldehyde was used instead of 4-hydroxy-2,6-dimethoxybenzaldehyde and an appropriate amine was used for reductive amination instead of piperidine-2-carboxylic acid.

Examples 19, 20, 28, 40, 42-44, 51-59, 64, 72-74, 76, 77, 85, 86, 88, 90, 91, 94-97, 100 and 110 were prepared according to the general procedure described in Example 1 except 4-hydroxy-3-methylbenzaldehyde was used instead of 4-hydroxy-2,6-dimethoxybenzaldehyde and an appropriate amine was used for reductive amination instead of piperidine-2-carboxylic acid.

Example 27 was prepared according to the general procedure described in Example 1 except 4-hydroxy-2-methoxy-3-methylbenzaldehyde was used instead of 4-hydroxy-2,6-dimethoxybenzaldehyde.

Examples 38, 68, 81, 83 and 99 were prepared according to the general procedure described in Example 1 except 4-hydroxy-2-methoxybenzaldehyde was used instead of 4-hydroxy-2,6-dimethoxybenzaldehyde and an appropriate amine was used for reductive amination instead of piperidine-2-carboxylic acid.

Examples 41, 70 and 87 were prepared according to the general procedure described in Example 1 except 4-hydroxy-2,6-dimethylbenzaldehyde was used instead of 4-hydroxy-2,6-dimethoxybenzaldehyde and an appropriate amine was used for reductive amination instead of piperidine-2-carboxylic acid.

Examples 50 and 80 were prepared according to the general procedure described in Example 1 except 3-fluoro-4-hydroxybenzaldehyde was used instead of 4-hydroxy-2,6-dimethoxybenzaldehyde and an appropriate amine was used for reductive amination instead of piperidine-2-carboxylic acid.

Examples 106, 107, and 108 were prepared according to the general procedure described in Example 4 except 4-hydroxy-2,6-dimethoxybenzaldehyde was used instead of 4-hydroxybenzaldehyde, alanine was substituted for azetidine in the reductive amination step and an appropriate boronic acid was used in the palladium catalyzed coupling step.

Example 45

N-{2-[(1-{3-chloro-4-[(2-methyl-3-phenylphenyl)methoxy]phenyl}ethyl)amino]ethyl}acetamide

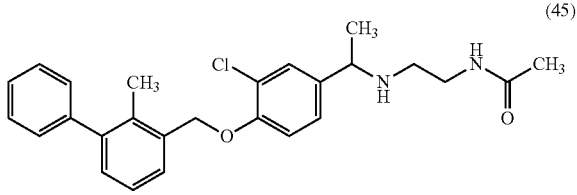 [SMILES: CC(=O)NCCNC(C)c1ccc(OCc2cccc(-c3ccccc3)c2C)c(Cl)c1]

(45)

Intermediate 45A: 1-(3-chloro-4-((2-methylbiphenyl-3-yl)methoxy)phenyl)ethanone

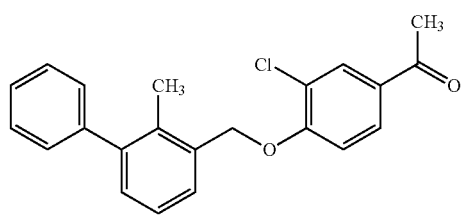

(45A)

Intermediate 45A was prepared from 1-(3-chloro-4-hydroxyphenyl)ethanone and Intermediate 1A according to the general procedure described to prepare Intermediate 1B.

Example 45

To a solution of 1-(3-chloro-4-((2-methyl-[1,1'-biphenyl]-3-yl)methoxy)phenyl) ethanone (20 mg, 0.057 mmol) in THF (2 mL) was added N-acetylethylenediamine (12.94 mg, 0.114 mmol) and tetra-tert-butyl orthotitanate (0.050 mL, 0.143 mmol). The resulting white mixture was heated at 85° C. in a microwave for 1 hour. Additional tetra-tert-butyl orthotitanate (0.050 mL, 0.143 mmol) was added and heated at 100° C. for 1 hour. Sodium borohydride (6.47 mg, 0.171 mmol) was added followed by ethanol (2 mL). The mixture was stirred at room temperature for 2 hrs. The crude material was purified via preparative LC/MS with the following conditions: Column: Waters Xbridge C18, 19×200 mm, 5-μm particles; Mobile Phase A: water with 20-mM ammonium acetate; Mobile Phase B: 95:5 acetonitrile:water with 20-mM ammonium acetate; Gradient: 10-100% B over 20 minutes, then a 5-minute hold at 100% B; Flow: 20 mL/min. Fractions containing the desired product were combined and dried via centrifugal evaporation. The yield of the product was 12.6 mg, and its estimated purity by LCMS analysis was 98%. $^1$H NMR (500 MHz, DMSO-$d_6$) δ 7.77 (br. s., 1H), 7.51 (d, J=7.3 Hz, 1H), 7.49-7.43 (m, 2H), 7.43-7.35 (m, 2H), 7.35-7.24 (m, 5H), 7.21 (d, J=7.6 Hz, 1H), 5.22 (s, 2H), 3.66 (d, J=6.4 Hz, 1H), 3.14-2.99 (m, 2H), 2.42-2.28 (m, 2H), 2.23 (s, 3H), 1.77 (s, 3H), 1.26-1.18 (m, 3H).

Example 71 was prepared according to the general procedure described in Example 45 except 1-(4-hydroxy-3-methylphenyl)ethanone was used instead of 1-(3-chloro-4-hydroxyphenyl)ethanone.

Example 62 was prepared according to the general procedure described in Example 45 except 5-hydroxy-3,4-dihydronaphthalen-1(2H)-one was used instead of 1-(3-chloro-4-hydroxyphenyl)ethanone.

Example 63 was prepared according to the general procedure described in Example 45 except 6-hydroxy-3,4-dihydronaphthalen-1(2H)-one was used instead of 1-(3-chloro-4-hydroxyphenyl)ethanone.

Example 109 was prepared according to the general procedure described in Example 45 except 1-amino-2,3-dihydro-1H-inden-4-ol was used instead of 1-(3-chloro-4-hydroxyphenyl)ethanone.

Example 112

(2S)-1-[(4-{[3-(2,3-dihydro-1,4-benzodioxin-6-yl)-2-methylphenyl]methoxy}-3-(trifluoromethyl)phenyl)methyl]piperidine-2-carboxylic acid

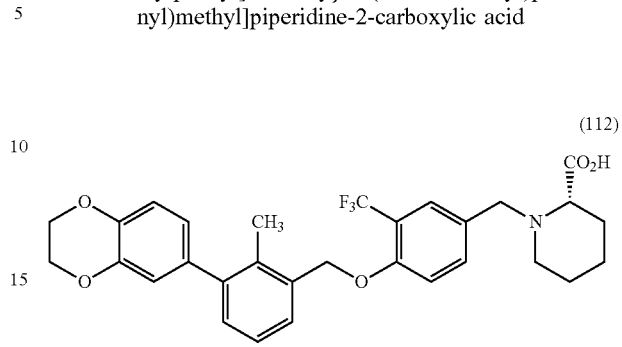

(112)

Intermediate 112A: (3-(2,3-dihydrobenzo[b][1,4]dioxin-6-yl)-2-methylphenyl)methanol

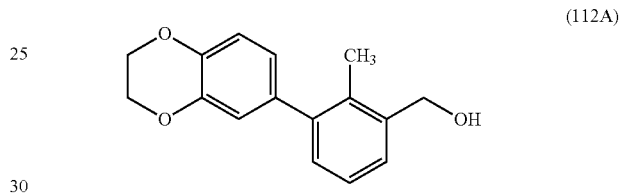

(112A)

(2,3-dihydrobenzo[b][1,4]dioxin-6-yl)boronic acid (0.537 g, 2.98 mmol), (3-bromo-2-methylphenyl)methanol (0.5 g, 2.487 mmol) and 2nd Generation XPhos precatalyst (0.059 g, 0.075 mmol) was covered with THF (24 ml) and degassed. Potassium phosphate, tribasic (12.43 ml, 6.22 mmol) added as an 0.5 M aqueous solution. The reaction was stirred at room temperature sealed under argon overnight. The solvent was removed by rotary evaporation. The residue was purified using 3:1 hexanes:ethyl acetate on a 24 g silica gel column. The fractions containing the desired product provided 0.59 g of the title compound as a colorless oil. $^1$H NMR (400 MHz, CHLOROFORM-d) δ 7.39 (d, J=7.3 Hz, 1H), 7.25 (t, J=7.6 Hz, 1H), 7.22-7.18 (m, 1H), 6.92 (d, J=8.1 Hz, 1H), 6.83 (d, J=1.7 Hz, 1H), 6.78 (dd, J=8.2, 1.8 Hz, 1H), 4.79 (d, J=5.9 Hz, 2H), 4.33 (s, 4H), 2.28 (s, 3H).

Intermediate 112B: 4-((3-(2,3-dihydrobenzo[b][1,4]dioxin-6-yl)-2-methylbenzyl)oxy)-3-(trifluoromethyl)benzaldehyde

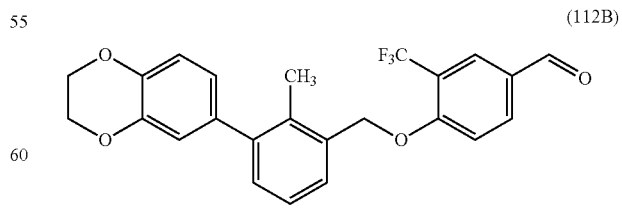

(112B)

Combined 4-hydroxy-3-(trifluoromethyl)benzaldehyde (35.9 mg, 0.189 mmol), triphenylphosphine (49.5 mg, 0.189 mmol) and (3-(2,3-dihydrobenzo[b][1,4]dioxin-6-yl)-2-methylphenyl)methanol (44 mg, 0.172 mmol) in dry THF (1 ml). Cooled to 0° C. Diisopropyl azodicarboxylate (0.037 ml, 0.189 mmol) in THF (1 ml) was added dropwise. The resulting yellow solution was allowed to slowly warm to room temperature while stirring overnight. Solvent was removed by rotary evaporator. The crude residue was purified with 5:1 hexanes:ethyl acetate on a 24 g silica gel column. Combined fractions to afford 0.046 g of the desired product as light yellow solid.

Example 112

A DMF (1.5 mL) solution of 4-((3-(2,3-dihydrobenzo[b][1,4]dioxin-6-yl)-2-methylbenzyl)oxy)-3-(trifluoromethyl)benzaldehyde (15 mg, 0.035 mmol) was stirred (S)-piperidine-2-carboxylic acid (13.57 mg, 0.105 mmol) at room temperature for 1 hour. Sodium cyanoborohydride (6.60 mg, 0.105 mmol) and 3 drops of acetic acid (2.004 µl, 0.035 mmol) were added. The reaction was stirred at room temperature overnight. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation. The yield of the product was 14.3 mg, and its estimated purity by LCMS analysis was 100%. $^1$H NMR (500 MHz, DMSO-$d_6$) δ 7.67-7.55 (m, 2H), 7.52-7.37 (m, 2H), 7.27 (t, J=7.5 Hz, 1H), 7.18 (d, J=7.3 Hz, 1H), 6.93 (d, J=8.1 Hz, 1H), 6.79-6.73 (m, 2H), 5.28 (s, 2H), 4.29 (s, 4H), 3.87 (d, J=13.2 Hz, 1H), 3.51 (d, J=13.6 Hz, 3H), 2.86 (br. s., 1H), 2.26-2.22 (m, 1H), 2.21 (s, 3H), 1.80 (br. s., 1H), 1.70 (d, J=9.2 Hz, 1H), 1.50 (d, J=18.7 Hz, 3H), 1.37 (br. s., 1H).

Example 113 were prepared according to the general procedure described in Example 112 except N-(2-aminoethyl)acetamide was used for reductive amination instead of piperidine-2-carboxylic acid.

Example 114 were prepared according to the general procedure described in Example 112 except (S)-4-amino-3-hydroxybutanoic acid was used for reductive amination instead of piperidine-2-carboxylic acid.

Example 118

2-[({5-[(2-methyl-3-phenylphenyl)methoxy]thiophen-2-yl}methyl)amino]ethan-1-ol

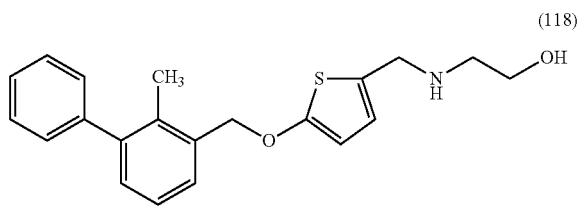 [SMILES: Cc1c(COc2ccc(CNCCO)s2)cccc1-c1ccccc1]

(118)

In a 8 mL clear vial, (2-methyl-[1,1'-biphenyl]-3-yl)methanol (50 mg, 0.252 mmol), cesium carbonate (123 mg, 0.378 mmol), 2-(Di-t-butylphosphino)-3-methoxy-6-methyl-2'-4'-6'-tri-i-propyl-1,1'-biphenyl (7.09 mg, 0.015 mmol), 4A molecular sieves (50 mg) and toluene (0.4 mL) were combined. The reaction mixture was degassed with argon gas. 5-chlorothiophene-2-carbaldehyde (55.5 mg, 0.378 mmol, Cole, Andrew G.; Letourneau, Jeffrey John; Ho, Koc-Kan WO 2010059922 A1) and allylpalladium(ii) chloride dimer (2.77 mg, 7.57 µmol) were added. Then reaction mixture was heated at 90° C. for 24 hrs. The reaction mixture was diluted with ethylacetate, filtered through celite and concentrated. The residue was purified using a gradient of 0 to 15% ethylacetate in petroleum ether on a 4 gm silica gel column. The fractions containing the product were combined and concentration to give the desired aldehyde (0.039 g). Example 118 was prepared from this aldehyde and 2-amino ethanol according to the reductive amination conditions as described for Example 1.

Example 119

2-[({5-[(2-methyl-3-phenylphenyl)methoxy]pyridin-2-yl}methyl)amino]ethan-1-ol

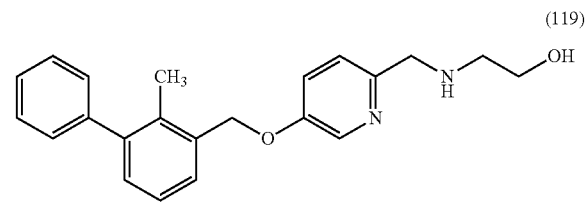 [SMILES: Cc1c(COc2ccc(CNCCO)nc2)cccc1-c1ccccc1]

(119)

Intermediate 119A: 2-methyl-5-((2-methyl-[1,1'-biphenyl]-3-yl)methoxy)pyridine

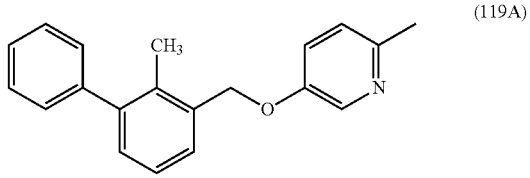 [SMILES: Cc1ccc(OCc2cccc(-c3ccccc3)c2C)cn1]

(119A)

To a solution of 6-methylpyridin-3-ol (0.209 g, 1.915 mmol) and cesium carbonate (1.248 g, 3.83 mmol) in DMF (5 mL) was added 3-(bromomethyl)-2-methyl-1,1'-biphenyl (0.5 g, 1.915 mmol) and the reaction mixture was stirred at room temperature for 3 hours. TLC analysis with 40% ethyl acetate in petroleum ether showed that the starting material was consumed. The reaction mixture was quenched with water (50 ml) and extracted with ethyl acetate (2×50 ml). The combined organic extracts were washed with water (50 ml), saturated, aqueous sodium chloride (50 ml), dried over sodium sulphate and concentrated to give a crude residue (500 mg). The crude residue was purified with a gradient of 25-30% ethyl acetate in petroleum ether on a 12 gram silica gel column to proved the desired compound (0.365 g, 65%). $^1$H NMR (400 MHz, DMSO-$d_6$) δ 8.25 (s, 1H), 7.50-7.30 (m, 5H), 7.30-7.25 (m, 3H), 7.18 (d, J=7.6 Hz, 2H), 5.19 (s, 2H), 2.40 (s, 3H), 2.19 (s, 3H).

Intermediate 119B: 2-methyl-5-((2-methyl-[1,1'-biphenyl]3-yl)methoxy)pyridine 1-oxide

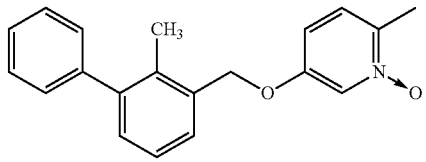

(119B)

To a solution of 2-methyl-5-((2-methyl-[1,1'-biphenyl]-3-yl)methoxy)pyridine (365 mg, 1.261 mmol) and sodium bicarbonate (318 mg, 3.78 mmol) in chloroform (8 mL) at 0° C. was added m-chloroperbenzoic acid (435 mg, 2.52 mmol). The reaction was allowed to warm to room temperature and then stirred at room temperature for 3 h during which time the reaction became a thick emulsion. TLC analysis with 50% ethyl acetate in petroleum ether showed that the starting material was consumed. To the reaction mixture water (20 ml) was added and extracted with dichloromethane (3×30 ml). The combined organic portions were washed with 10% sodium bicarbonate (40 ml), water (40 ml), saturated, aqueous sodium chloride (30 ml), dried over sodium sulphate and concentrated to get the crude which was used without purification. $^1$H NMR (400 MHz, DMSO-$d_6$) δ 8.23 (s, 1H), 7.45 (m, 3H), 7.34 (d, J=8.4 Hz, 2H), 7.29 (m, 3H), 7.20 (d, J=7.2 Hz, 1H), 7.20 (dd, J=8.8, 2.4 Hz, 1H), 5.20 (s, 2H), 2.28 (s, 3H), 2.19 (s, 3H).

Intermediate 119C: (5-((2-methyl-[1,1'-biphenyl]-3-yl)methoxy)pyridin-2-yl)methanol

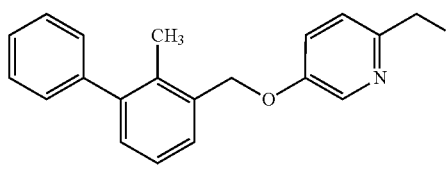

(119C)

A solution of 2-methyl-5-((2-methyl-[1,1'-biphenyl]-3-yl) methoxy)pyridine 1-oxide (0.38 g, 1.244 mmol) in acetic anhydride (3 ml, 31.8 mmol) was heated to 100° C. for 30 minutes. TLC analysis with 50% Ethyl acetate in petroleum ether showed that the starting material was consumed to provide a higher rf compound consistent with the intermediate acetate. The reaction mixture was diluted with ethyl acetate (50 ml) and washed with saturated sodium bicarbonate solution (30 ml), water (30 ml), saturated, aqueous sodium chloride (30 ml), dried over sodium sulphate and concentrated to give the crude acetate (380 mg). The crude acetate (380 mg) was dissolved in methanol (20 mL) and potassium carbonate (0.602 g, 4.36 mmol) was added. The reaction mixture was stirred at room temperature overnight. TLC analysis with 50% ethyl acetate in petroleum ether showed that the acetate was consumed to provide a lower rf compound. The solvent was concentrated and the residue was dissolved in EtOAc (30 ml), washed with water (20 ml), saturated, aqueous sodium chloride (20 ml), dried over sodium sulphate and concentrated. The crude residue was purified with a gradient of 30% EtOAc in petroleum ether on a 4 gram silica gel column to isolate the desired product. $^1$H NMR (300 MHz, DMSO-$d_6$) δ 8.30 (s, 1H), 7.15-7.60 (m, 10H), 5.30 (t, J=7.6 Hz, 1H), 5.22 (s, 2H), 4.50 (d, J=7.6 Hz, 2H), 2.20 (s, 3H).

Intermediate 119D: 5-((2-methyl-[1,1'-biphenyl]-3-yl)methoxy)picolinaldehyde

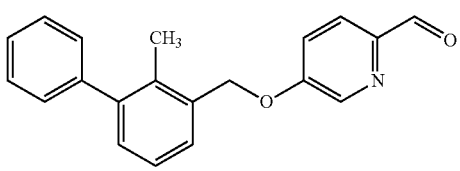

(119D)

To a solution of (5-((2-methyl-[1,1'-biphenyl]-3-yl) methoxy)pyridin-2-yl)methanol (190 mg, 0.622 mmol) in methanol (5 mL) at RT was added manganese dioxide (541 mg, 6.22 mmol) and the reaction mixture was stirred at room temperature for 4 hours. TLC analysis with 30% ethyl acetate in petroleum ether showed that the starting material was consumed. The reaction mixture was filtered through celite and the bed was washed with dichloromethane (50 ml). The filtrate was concentrated to give the crude product. The product (0.13 g, 67%) was isolated chromatography on a 4 gram silica gel column using 10-12% ethyl acetate in petroleum ether. $^1$H NMR (400 MHz, DMSO-$d_6$) δ 9.90 (s, 1H, CHO), 8.6 (s, 1H), 7.97 (d, J=8.8 Hz, 1H), 7.74 (dd, J=8.4, 2.8 Hz, 1H), 7.50-7.40 (m, 3H), 7.39 (m, 1H), 7.36 (m, 3H), 7.23 (dd, J=7.6, 1.2 Hz, 1H), 5.38 (s, 2H), 2.21 (s, 3H).

Example 119 was prepared from intermediate 119D, 5-((2-methyl-[1,1'-biphenyl]-3-yl)methoxy) picolinaldehyde, and 2-amino ethanol according to the reductive amination conditions as described for Example 1.

Example 120 was prepared from intermediate 119D, 5-((2-methyl-[1,1'-biphenyl]-3-yl)methoxy) picolinaldehyde, and (1-aminocyclopentyl)methanol according to the reductive amination conditions as described for Example 1.

Example 121 was prepared from intermediate 119D, 5-((2-methyl-[1,1'-biphenyl]-3-yl)methoxy) picolinaldehyde, and methyl amine according to the reductive amination conditions as described for Example 1.

Example 122 was prepared from intermediate 119D, 5-((2-methyl-[1,1'-biphenyl]-3-yl)methoxy) picolinaldehyde, and 5-(aminomethyl)pyrrolidin-2-one according to the reductive amination conditions as described for Example 1.

Examples 123-161 and 295

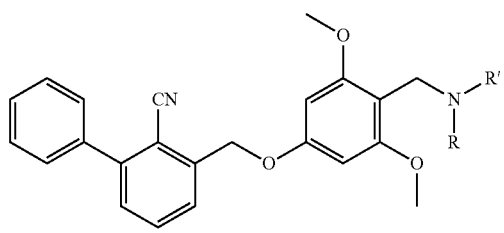

Intermediate 123A: 2-chloro-6-(hydroxymethyl)benzonitrile

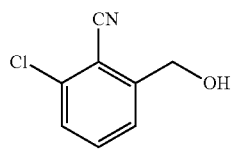

(123A)

To a 1000 ml single neck round-bottom flask was charged ethyl 3-chloro-2-cyanobenzoate (8.0 g, 38.2 mmol, Dean, David Kenneth; Munoz-Muriedas, Jorge; Sime, Mairi; Steadman, Jon Graham Anthony; Thewlis, Rachel Elizabeth Anne; Trani, Giancarlo; Walter, Daryl Simon WO 2010125102 A1) and tetrahydrofuran (390 mL). The mixture was stirred until a clear solution was obtained. The solution was cooled to −40° C. and lithium borohydride (1.663 g, 76 mmol) was added portion wise over 15 minutes. After all the lithium borohydride was added, the reaction was slowly brought to room temperature and stirred overnight. TLC analysis with 4:6 ethyl acetate:petroleum ether showed that the starting material was consumed. Saturated aqueous ammonium chloride was charged to a 2000 ml multineck round-bottom flask and cooled to −5° C. (inner temperature). Added crude reaction slowly over 15 minutes. After addition was complete the temperature was maintained at −5° C. for 20 minutes. The reaction was diluted with dichloromethane (500 ml) and the layers were separated. The aqueous layer was extracted with dichloromethane (1×300 ml) and the combined organic portions were washed with 1.5 N aqueous hydrochloric acid (1×50 ml), saturated, aqueous sodium chloride (1×50 ml) and dried over sodium sulfate. The solvent was removed under reduced pressure to give a yellow solid (7.0 g). The crude material was dissolved in minimum amount of dichloromethane and cooled in ice bath. Petroleum ether was added until white solid formed. The solid was collected by filtration, washed with petroleum ether and dried under vacuum to give the title compound (3.5 g). $^1$H NMR (300 MHz, CDCl$_3$) δ 7.55 (m, J=2.6 Hz, 2H), 4.99 (s, 2H), 2.14 (bs, 1H, OH).

Intermediate 123B: 3-(hydroxymethyl)-[1,1'-biphenyl]-2-carbonitrile

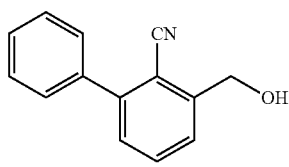

(123B)

To the solution of 2-chloro-6-(hydroxymethyl)benzonitrile, 123A, (2 g, 11.93 mmol) in THF (80 mL), was added phenylboronic acid (2.183 g, 17.90 mmol) and 2nd generation Xphos precatalyst (0.263 g, 0.334 mmol, CAS Number 1310584-14-5). Nitrogen was bubbled into the reaction for 5 minutes to purge oxygen. The reaction mixture was cooled to 0° C. and cold 0.5M potassium phosphate tribasic (47.9 mL, 23.94 mmol) in water was added into the reaction mixture and nitrogen purging was continued for 5 minutes. The reaction was stirred overnight at room temperature. TLC analysis with 1:1 ethyl acetate:petroleum ether showed that starting material was consumed. The reaction was diluted with 75 mL dichloromethane and the layers separated. The aqueous layer was extracted with 15 mL dichloromethane. The combined organic portions were washed with 20 mL saturated, aqueous sodium chloride solution, dried over sodium sulfate and evaporated under vacuum at 40° C. to give the crude product. The residue was purified on a 120 gram silica gel column using petroleum ether and ethyl acetate as eluent. The product was eluted at 10% ethyl acetate in petroleum ether. The collected fractions were evaporated to get the product as an off-white solid (1.82 g) $^1$H NMR (400 MHz, CDCl$_3$) δ 7.60-7.70 (m, 2H), 7.40-7.55 (m, 6H), 4.99 (d, J=6.0 Hz, 2H), 2.13 (t, J=6.0, 1H, OH).

Intermediate 123C: 3-((4-formyl-3,5-dimethoxyphenoxy)methyl)-[1,1'-biphenyl]-2-carbonitrile

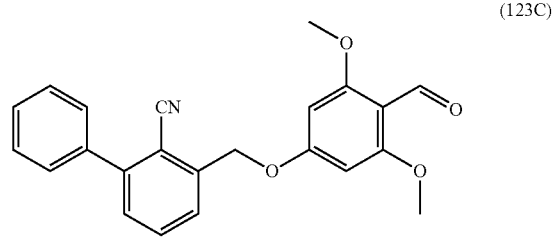 [SMILES: COc1cc(OCc2cccc(-c3ccccc3)c2C#N)cc(OC)c1C=O]

(123C)

To a solution of 3-(hydroxymethyl)-[1,1'-biphenyl]-2-carbonitrile, 123B, (300 mg, 1.434 mmol) in tetrahydrofuran (10 mL) was added 4-hydroxy-2,6-dimethoxybenzaldehyde (261 mg, 1.434 mmol) and triphenylphosphine (489 mg, 1.864 mmol) under a nitrogen atmosphere. The reaction mixture appeared brown and cloudy. Cooled to 0° C. and then added a solution of diisopropyl azodicarboxylate (0.367 mL, 1.864 mmol) in 1 ml THF. Stirred the reaction overnight at room temperature. TLC analysis showed no product formation. Added tetrahydrofuran (10 mL), triphenylphosphine (489 mg, 1.864 mmol) and diisopropyl azodicarboxylate (0.367 mL, 1.864 mmol) at room temperature. The reaction mixture became clear solution. Stirred for 3 hours at room temperature. The solvent was evaporated under vacuum and the residue was purified by on a 40 gram silica gel column using petroleum ether and ethyl acetate as eluent. The product was eluted at 40%-45% ethyl acetate. The product was eluted as mixture along with the polar triphenyl phosphine oxide impurity. The collected fractions were evaporated to get the compound as an off white solid (500 mg). The 500 mg compound was slurried in 5 ml isopropyl alcohol and stirred for 30 minutes. The solids were collected by filtration, washed with 2.5 ml isopropyl alcohol and dried for 2 hours under vacuum to give the title compound (180 mg). $^1$H NMR (400 MHz, DMSO-d$_6$) δ 10.23 (s, 1H, CHO), 7.80 (m, 2H), 7.65 (dd, J=1.2, 7.6 Hz, 1H), 7.60 (m, 5H), 6.44 (s, 2H), 5.45 (s, 2H), 3.84 (s, 6H).

Examples 123-161 and 295 were prepared from intermediate 123C 3-((4-formyl-3,5-dimethoxyphenoxy)methyl)-[1,1'-biphenyl]-2-carbonitrile according to the reductive amination conditions as described for Example 1 using the appropriate amine to obtain the desired product.

Example 190

N1-(2,6-dimethoxy-4-((2-methyl-[1,1'-biphenyl]-3-yl)methoxy)benzyl)-N1-methylethane-1,2-diamine

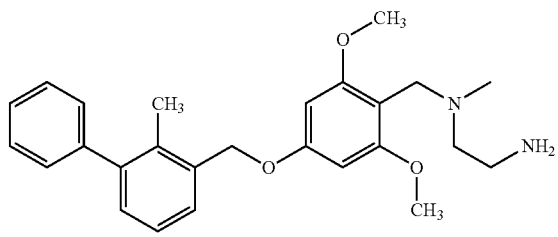

(190)

Intermediate 190A: tert-butyl (2-((2,6-dimethoxy-4-((2-methyl-[1,1'-biphenyl]-3-yl)methoxy)benzyl)(methyl)amino)ethyl)carbamate

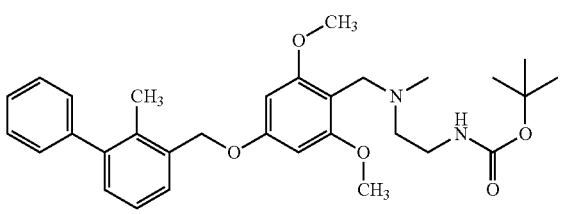

(190A)

Combined tert-butyl (2-(methylamino)ethyl)carbamate (0.348 g, 2.000 mmol), sodium triacetoxyborohydride (0.636 g, 3.00 mmol) and 2,6-dimethoxy-4-((2-methyl-[1,1'-biphenyl]-3-yl)methoxy)benzaldehyde (0.362 g, 1 mmol) in DMF (5 ml). Stirred at room temperature overnight. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-90% B over 15 minutes, then a 5-minute hold at 100% B; Flow: 20 mL/min. Fractions containing the desired product were combined and dried via centrifugal evaporation. The yield of the product was 600 mg, and its estimated purity by LCMS analysis was 100%. LC\MS Method A: 2.2 minutes, $M^{+1}$=521.6, EM=520.3. LC\MS Method M: 3.1 minutes, $M^{+1}$=521.6, EM=520.3. $^1$H NMR (500 MHz, DMSO-$d_6$) δ 7.52-7.44 (m, 3H), 7.41-7.37 (m, 1H), 7.35-7.28 (m, 3H), 7.21 (d, J=7.0 Hz, 1H), 6.45-6.25 (m, 3H), 5.17 (s, 2H), 3.82-3.73 (m, 6H), 3.41 (br. s., 2H), 3.06 (d, J=5.8 Hz, 2H), 2.38 (br. s., 2H), 2.28-2.18 (m, 3H), 2.07 (s, 3H), 1.43-1.34 (m, 9H).

Example 191

Dissolved Intermediate 191A tert-butyl (2-((2,6-dimethoxy-4-((2-methyl-[1,1'-biphenyl]-3-yl)methoxy)benzyl)(methyl)amino)ethyl)carbamate (0.6 g, 1.15 mmol) in 5 mL of 0.5N hydrochloric acid in diethyl ether. Stirred at room temperature for 1 hour. Diluted with ether and bubbled nitrogen through reaction for 10 minutes. The solvent was removed by rotary evaporation. The residue was place under vacuum overnight.

Chromatographed by reverse phase HPLC using the following conditions. Start % B=5 to Final % B=100, Gradient time=10 minutes, Flow Rate=40 mL/minute, Wavelength=220 nm, Solvent A=10% methanol, 90% water with 0.1% TFA, Solvent B=90% methanol, 10% water with 0.1% TFA, Column=Phenomenex-Luna 30×50 mm S10.

The major peak at 8.6 minutes was consistent with desired product. Fractions containing the desired product were combined and dried via centrifugal evaporation to the title compound as the bis trifluoro acetic acid salt (0.61 g, 82%). $^1$H NMR (400 MHz, CHLOROFORM-d) δ 7.47-7.41 (m, 3H), 7.38 (d, J=7.1 Hz, 1H), 7.33 (d, J=6.8 Hz, 2H), 7.30 (d, J=3.2 Hz, 1H), 6.28 (s, 2H), 5.48 (br. s., 4H), 5.12 (s, 2H), 4.29 (q, J=13.0 Hz, 2H), 3.92-3.77 (m, 6H), 3.70-3.39 (m, 5H), 2.86-2.73 (m, 3H), 2.29 (s, 3H). $^1$H NMR (500 MHz, DMSO-$d_6$) δ 7.52-7.44 (m, 3H), 7.42-7.37 (m, 1H), 7.35-7.27 (m, 3H), 7.22 (d, J=7.6 Hz, 1H), 6.38 (s, 2H), 5.17 (s, 2H), 3.77 (s, 6H), 3.40 (s, 2H), 2.74 (br. s., 2H), 2.45-2.38 (m, 2H), 2.25-2.19 (m, 3H), 2.07 (s, 3H).

Example 191

1-(2-((2,6-dimethoxy-4-((2-methyl-[1,1'-biphenyl]-3-yl)methoxy)benzyl)(methyl)amino)ethyl)-3-phenylurea

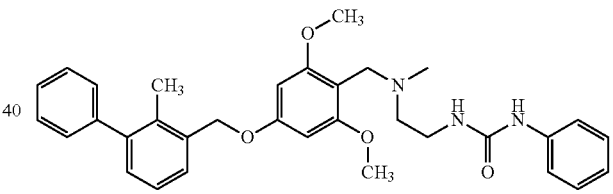

(191)

Charged isocyanatobenzene (0.012 g, 0.100 mmol) in dichloromethane (0.5 mL) to a 5 mL reaction vial. Added a solution of Example 190, N1-(2,6-dimethoxy-4-((2-methyl-[1,1'-biphenyl]-3-yl)methoxy)benzyl)-N1-methylethane-1,2-diamine, 2 TFA (0.032 g, 0.05 mmol) and Hunig's Base (0.027 mL, 0.155 mmol) in dichloromethane (0.5 mL). Stirred at room temperature overnight. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 7-minute hold at 100% B; Flow: 20 mL/min. Fractions containing the desired product were combined and dried via centrifugal evaporation. The yield of the product was 5.9 mg, and its estimated purity by LCMS analysis was 99%. $^1$H NMR (500 MHz, DMSO-$d_6$) δ 8.82 (br. s., 1H), 7.55-7.45 (m, 3H), 7.39 (d, J=7.3 Hz, 3H), 7.37-7.28 (m, 3H), 7.25-7.16 (m, 3H), 6.88 (t, J=7.2 Hz, 1H), 6.38 (s, 2H), 6.05 (br. s., 1H), 5.18 (s, 2H), 3.76 (s, 6H), 3.47 (br. s., 2H), 3.23 (d, J=5.2 Hz, 2H), 2.48-2.42 (m, 2H), 2.24 (s, 3H), 2.13 (s, 3H).

Example 192

N-{2-[({2,6-dimethoxy-4-[(2-methyl-3-phenylphenyl)methoxy]phenyl}methyl)(methyl)amino]ethyl}-2-oxo-2H-chromene-6-sulfonamide

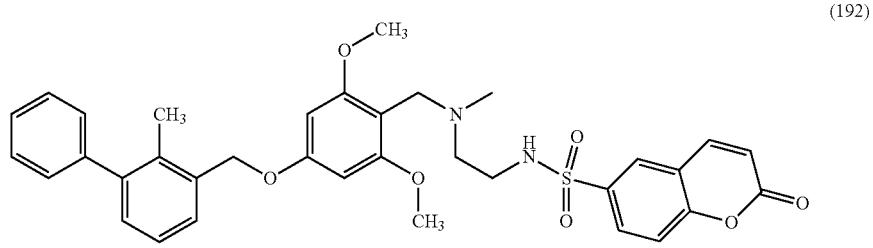 [SMILES: COc1cc(OCc2cccc(-c3ccccc3)c2C)cc(OC)c1CN(C)CCNS(=O)(=O)c1ccc2oc(=O)ccc2c1]

(192)

Charged 2-oxo-2H-chromene-6-sulfonyl chloride (0.024 g, 0.100 mmol) to a 5 mL reaction vial. Added a solution of Example 190, N1-(2,6-dimethoxy-4-((2-methyl-[1,1'-biphenyl]-3-yl)methoxy)benzyl)-N1-methylethane-1,2-diamine, 2 TFA (0.032 g, 0.05 mmol) and Hunig's Base (0.027 mL, 0.155 mmol) in dichloromethane (0.5 mL). Stirred at room temperature 30 minutes. Reaction check by LCMS showed mostly desired product. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 19.3 mg, and its estimated purity by LCMS analysis was 97%. $^1$H NMR (500 MHz, DMSO-d$_6$) δ 8.25 (s, 1H), 8.20 (d, J=9.8 Hz, 1H), 7.97 (d, J=8.2 Hz, 1H), 7.60 (d, J=8.5 Hz, 1H), 7.53-7.45 (m, 3H), 7.43-7.37 (m, 1H), 7.36-7.27 (m, 3H), 7.22 (d, J=7.3 Hz, 1H), 6.63 (d, J=9.8 Hz, 1H), 6.36 (s, 2H), 5.17 (s, 2H), 3.73 (s, 6H), 3.36 (s, 2H), 2.91 (t, J=6.7 Hz, 2H), 2.35 (t, J=6.9 Hz, 2H), 2.23 (s, 3H), 1.99 (s, 3H).

Example 193

N-{2-[({2,6-dimethoxy-4-[(2-methyl-3-phenylphenyl)methoxy]phenyl}methyl)(methyl)amino]ethyl}prop-2-enamide

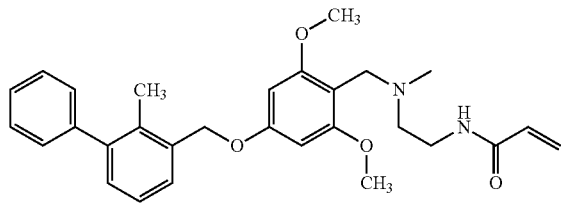

(193)

Example 190, N1-(2,6-dimethoxy-4-((2-methyl-[1,1'-biphenyl]-3-yl)methoxy)benzyl)-N1-methylethane-1,2-diamine (0.021 g, 0.05 mmol), was combined with Hunig's Base (0.026 mL, 0.150 mmol) and acryloyl chloride (0.014 g, 0.150 mmol) in Dichloromethane (1 mL). After 1 hour, LC/MS showed desired product. Added methanol and removed solvent under a stream of air. Redissolved in methanol and filtered. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. The yield of the product was 19.2 mg, and its estimated purity by LCMS analysis was 98%. $^1$H NMR (500 MHz, DMSO-d$_6$) δ 7.91-7.86 (m, 1H), 7.47 (s, 3H), 7.42-7.37 (m, 1H), 7.33 (d, J=7.9 Hz, 3H), 7.24-7.19 (m, 1H), 6.37 (s, 2H), 6.27-6.16 (m, 1H), 6.13-5.97 (m, 1H), 5.61-5.52 (m, 1H), 5.17 (s, 2H), 3.75 (s, 6H), 3.30-3.22 (m, 2H), 2.44-2.37 (m, 2H), 2.23 (s, 3H), 2.10 (s, 3H).

Example 194

Ethyl (2E)-3-({2-[({2,6-dimethoxy-4-[(2-methyl-3-phenylphenyl)methoxy]phenyl}methyl)(methyl)amino]ethyl}carbamoyl)prop-2-enoate

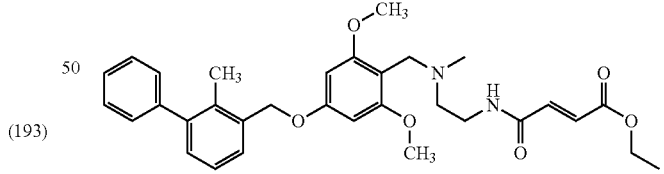

(194)

Combined Example 190 N1-(2,6-dimethoxy-4-((2-methyl-[1,1'-biphenyl]-3-yl)methoxy)benzyl)-N1-methylethane-1,2-diamine (0.021 g, 0.05 mmol), Hunig's Base (0.026 mL, 0.150 mmol) and (E)-ethyl 4-chloro-4-oxobut-2-enoate (0.024 g, 0.150 mmol) in dichloromethane (1 mL). After 30 minutes, reaction check by LC/MS showed desired product. Added methanol and removed solvent under a stream of air. Redissolved in methanol and filtered. The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 20 minutes, then a 5-minute hold at 100% B; Flow: 20 mL/min. Fractions containing the desired product were combined and dried via centrifugal evaporation. The yield of the product was 17.8 mg, and its estimated purity by LCMS analysis was 97%. $^1$H NMR (500 MHz, DMSO-$d_6$) δ 8.40 (br. s., 1H), 7.52-7.45 (m, 3H), 7.42-7.37 (m, 1H), 7.35-7.27 (m, 3H), 7.21 (d, J=7.3 Hz, 1H), 7.02 (d, J=15.3 Hz, 1H), 6.56 (d, J=15.6 Hz, 1H), 6.37 (s, 2H), 5.16 (s, 2H), 4.18 (q, J=7.2 Hz, 2H), 3.75 (s, 6H), 3.30 (d, J=5.8 Hz, 2H), 2.43 (t, J=6.6 Hz, 2H), 2.23 (s, 3H), 2.12 (s, 3H), 1.24 (t, J=7.0 Hz, 3H).

Example 198

N-{2-[({3-cyano-4-[(2-methyl-3-phenylphenyl) methoxy]phenyl}methyl)amino]ethyl}acetamide

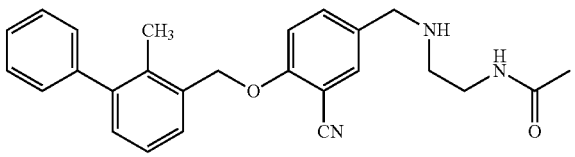

(198)

Intermediate 198A: 3-bromo-4-((2-methyl-[1,1'-biphenyl]-3-yl)methoxy)benzaldehyde

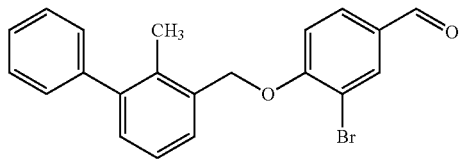

(198A)

To a cooled (0° C.) solution of 3-bromo-4-hydroxybenzaldehyde (101 mg, 0.5 mmol), triphenylphosphine (146 mg, 0.555 mmol) and (2-methyl-[1,1'-biphenyl]-3-yl)methanol (100 mg, 0.504 mmol) in dry THF (3 mL) was added dropwise of diisopropyl azodicarboxylate (0.108 mL, 0.555 mmol) in THF (3 mL). The resulting yellow solution was allowed to slowly warm to room temperature while stirring overnight. Excess solvent was evaporated by rotary evaporation. The crude residue was dissolved in methanol and purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 30-100% B over 20 minutes, then a 4-minute hold at 100% B; Flow: 20 mL/min. Fractions containing the desired product were combined and dried via centrifugal evaporation. The yield of the product was 106.9 mg, and its estimated purity by LCMS analysis was 100%. LC/MS Method A: 3.1 minutes, M$^{+1}$=381.0, EM=380.0.

Example 198

Combined copper(i) cyanide (18 mg, 0.201 mmol) and 3-bromo-4-((2-methyl-[1,1'-biphenyl]-3-yl)methoxy)benz-aldehyde (50 mg, 0.131 mmol) in DMF (1311 µl) under argon. Sealed and heated at 120° C. for 72 hours. Filtered and combined the solution directly with sodium triacetoxyhydroborate (84 mg, 0.394 mmol) and N-(2-aminoethyl) acetamide (26.8 mg, 0.263 mmol) in DMF (657 µl). Stirred at room temperature overnight and filtered through a 0.45 m PVDF Whatman syringe filter. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 20 minutes, then a 5-minute hold at 100% B; Flow: 20 mL/min. Fractions containing the desired product were combined and dried via centrifugal evaporation. The yield of the product was 16.1 mg, and its estimated purity by LCMS analysis was 91%. $^1$H NMR (500 MHz, DMSO-$d_6$) δ 7.80 (br. s., 1H), 7.69 (s, 1H), 7.63 (d, J=8.4 Hz, 1H), 7.53-7.44 (m, 3H), 7.42-7.36 (m, 2H), 7.34-7.28 (m, 3H), 7.23 (d, J=7.7 Hz, 1H), 5.33 (s, 2H), 3.66 (s, 2H), 3.38 (d, J=11.7 Hz, 2H), 3.18-3.06 (m, 2H), 2.23 (s, 3H), 1.79 (s, 3H).

Example 199

N-(2-((4-((3-(2,3-dihydrobenzo[b][1,4]dioxin-6-yl)-2-methylbenzyl)oxy)-2,5-difluorobenzyl)amino) ethyl)acetamide

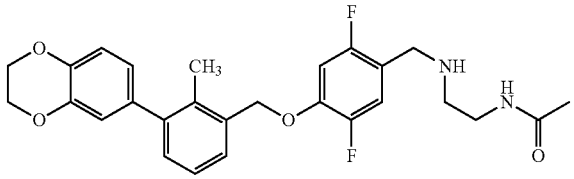

(199)

Intermediate 199A 4-((3-(2,3-dihydrobenzo[b][1,4] dioxin-6-yl)-2-methylbenzyl)oxy)-2,5-difluorobenz-aldehyde

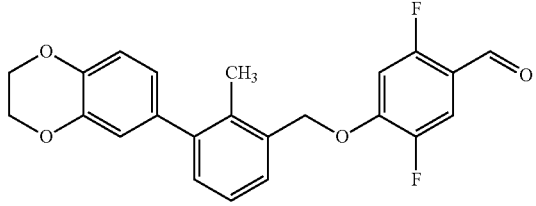

(199A)

Combined 2,5-difluoro-4-hydroxybenzaldehyde (204 mg, 1.288 mmol), triphenylphosphine (338 mg, 1.288 mmol) and (3-(2,3-dihydrobenzo[b][1,4]dioxin-6-yl)-2-methylphenyl)methanol (300 mg, 1.171 mmol) in dry THF (5853 µl) and cooled on an ice/water bath. Added diisopropyl azodicarboxylate (250 µl, 1.288 mmol) in THF (5853 µl) dropwise. The resulting yellow solution was allowed to slowly warm to room temperature with stirring over the weekend. The major peak did not have the product mass by LCMS.

Excess solvent was evaporated by rotary evaporator. Chromatographed on a 40 g silica gel column with 0-30% ethyl acetate in hexanes over 20 column volumes to give 340 mg of a white solid. In CDCl$_3$ some of the aromatic peaks were missing and most likely hidden by residual chloroform. NMR in DMSO confirmed the structure. $^1$H NMR (400 MHz, DMSO-d$_6$) δ 10.09 (d, J=2.2 Hz, 1H), 7.66 (dd, J=10.9, 6.5 Hz, 1H), 7.57 (dd, J=12.2, 6.6 Hz, 1H), 7.45 (d, J=7.3 Hz, 1H), 7.32-7.25 (m, 1H), 7.24-7.19 (m, 1H), 6.93 (d, J=8.1 Hz, 1H), 6.79 (s, 1H), 6.78-6.74 (m, 1H), 5.37 (s, 2H), 4.29 (s, 4H), 2.22 (s, 3H).

Example 199

A mixture of N-(2-aminoethyl)acetamide (12.37 mg, 0.121 mmol) and 4-((3-(2,3-dihydrobenzo[b][1,4]dioxin-6-yl)-2-methylbenzyl)oxy)-2,5-difluorobenzaldehyde (40 mg, 0.101 mmol) were combined in dichloroethane (505 µl). The solids did not dissolve. Sodium triacetoxyborohydride (42.8 mg, 0.202 mmol) was added and the mixture stirred at room temperature overnight. Most solids had dissolved. LCMS suggested 1:1:5:2 mixture of product:imine:starting material:dialkylation. Added 10 equivalents of N-(2-aminoethyl)acetamide (100 mg, 1 mmol) and sodium cyano borohydride and stirred for 2 hours. LCMS showed only desired product: The crude material was purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-80% B over 15 minutes, then a 5-minute hold at 100% B; Flow: 20 mL/min. Fractions containing the desired product were combined and dried via centrifugal evaporation. The yield of the product was 29.6 mg, and its estimated purity by LCMS analysis was 96%. $^1$H NMR (500 MHz, DMSO-d$_6$) δ 7.79 (br. s., 1H), 7.42 (d, J=7.7 Hz, 1H), 7.36-7.23 (m, 3H), 7.19 (d, J=7.0 Hz, 1H), 6.93 (d, J=8.1 Hz, 1H), 6.78 (s, 1H), 6.76 (d, J=8.1 Hz, 1H), 5.21 (s, 2H), 4.29 (s, 4H), 3.12 (q, J=6.1 Hz, 2H), 2.21 (s, 3H), 1.92 (br. s., 2H), 1.82-1.74 (m, 3H). 2 missing hydrogens are assumed to be under the DMSO or water peaks.

Example 200 was prepared from intermediate 199A, 4-((3-(2,3-dihydrobenzo[b][1,4]dioxin-6-yl)-2-methylbenzyl)oxy)-2,5-difluorobenzaldehyde, and (S)-4-amino-3-hydroxybutanoic acid according to the reductive amination conditions as described for Example 1.

Example 201 was prepared from intermediate 199A, 4-((3-(2,3-dihydrobenzo[b][1,4]dioxin-6-yl)-2-methylbenzyl)oxy)-2,5-difluorobenzaldehyde, and (S)-piperidine-2-carboxylic acid according to the reductive amination conditions as described for Example 1.

Example 202

N-{2-[({2-methoxy-6-[(2-methyl-3-phenylphenyl)methoxy]pyridin-3-yl}methyl)amino]ethyl}acetamide (202)

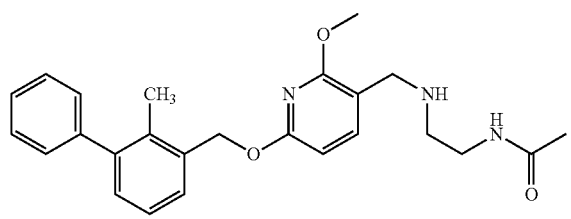

Intermediate 202A: 2-methoxy-6-((2-methyl-[1,1'-biphenyl]-3-yl)methoxy) nicotinaldehyde (202A)

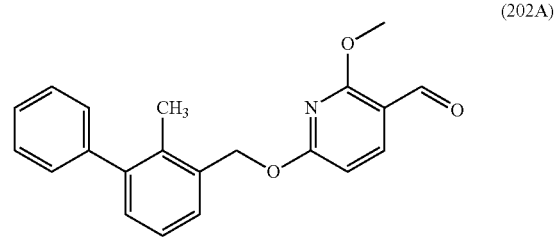 [SMILES: COc1nc(OCc2cccc(-c3ccccc3)c2C)ccc1C=O]

Cesium carbonate (223 mg, 0.683 mmol), palladium(ii) acetate (7.67 mg, 0.034 mmol), 2-di-tert-butylphosphino-2',4',6'-triisopropylbiphenyl(t-butyl Xphos) (29 mg, 0.068 mmol), 6-chloro-2-methoxynicotinaldehyde (58.6 mg, 0.341 mmol), and (2-methyl-[1,1'-biphenyl]-3-yl)methanol (88 mg, 0.444 mmol) were combined in a 25 mL round-bottom flask equipped with a stir bar. Toluene (2 mL) was added and the mixture purged with a stream of argon for 5 minutes. The reaction was sealed and heated at 80° C. overnight. LC/MS showed 11 peaks of similar intensities. Peaks at 4 minutes had an M+1 of 334 consistent with desired product. The soluble portion of the crude reaction was charged to a 25 g silica gel column with dichloromethane. Chromatographed with 0-60% ethyl acetate in hexanes. A fraction containing at least 2 compounds tested positive for an aldehyde using 2,4 dinitrophenyl hydrazine stain. This aldehyde-positive fraction was isolated and used without further purification.

Example 202

Combined sodium cyanoborohydride (20 mg, 0.318 mmol), N-(2-aminoethyl)acetamide (25 mg, 0.245 mmol), and crude 2-methoxy-6-((2-methyl-[1,1'-biphenyl]-3-yl)methoxy)nicotinaldehyde (20 mg, 0.060 mmol) in DMF (2 mL) and acetic acid (0.100 mL) at 1:00 pm. Stirred at room temperature overnight. LC/MS showed product: 3.5 minutes, M+1=420.3, EM=419.2. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 15 minutes, then a 5-minute hold at 100% B; Flow: 20 mL/min. Fractions containing the desired product were combined and dried via centrifugal evaporation. The yield of the product was 11.0 mg, and its estimated purity by LCMS analysis was 96%. $^1$H NMR (600 MHz, DMSO-d$_6$) δ 7.80 (br. s., 1H), 7.62 (d, J=8.1 Hz, 1H), 7.48-7.43 (m, 3H), 7.41-7.36 (m, 1H), 7.31 (d, J=7.3 Hz, 2H), 7.26 (t, J=7.5 Hz, 1H), 7.18 (d, J=7.7 Hz, 1H), 6.42 (d, J=7.7 Hz, 1H), 5.41 (s, 2H), 3.89 (s, 3H), 3.58 (s, 1H), 3.18-3.05 (m, 2H), 2.22 (s, 3H), 1.82-1.72 (m, 3H). The methylenes of the diamino acetamide were assumed to be under the DMSO peak at 2.5 ppm.

Examples 203 Through 226

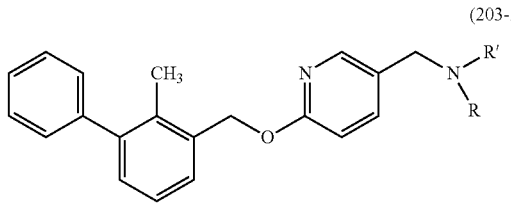

Intermediate 203A: 5-bromo-2-((2-methyl-[1,1'-biphenyl]-3-yl)methoxy)pyridine

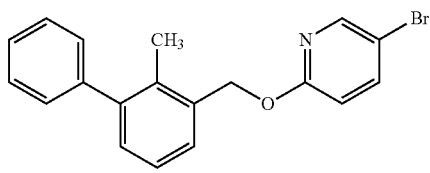

A mixture of 2,5-dibromopyridine (5 g, 21.11 mmol), (2-methyl-[1,1'-biphenyl]-3-yl)methanol (5.44 g, 27.4 mmol), dibenzo-18-crown-6 (0.380 g, 1.055 mmol), potassium hydroxide (2.84 g, 50.7 mmol) and toluene (50 mL) was stirred at reflux with a Dean-Stark trap (pre-filled with toluene). After 1.5 hours, the heat was removed. TLC analysis showed that starting material was consumed. LC/MS consistent with crude desired product. The solvents were removed under reduced pressure by rotary evaporation. Water (50 mL) was added and the product extracted into dichloroethane (3×50 mL). The combined organic portion was dried over magnesium sulfate and filtered. The solvents were removed under reduced pressure by rotary evaporation to give 9.7 grams of a yellow oil. LC/MS was consistent with crude desired product. The yellow oil became an off-white solid on standing. Chromatographed on a 330 g silica gel column with 0-20% ethyl acetate in hexanes to give the product (6.3 g, 84%). $^1$H NMR (400 MHz, DMSO-$d_6$) δ 8.34 (dd, J=2.8, 0.5 Hz, 1H), 7.95 (dd, J=8.8, 2.5 Hz, 1H), 7.50-7.43 (m, 3H), 7.42-7.37 (m, 1H), 7.34-7.31 (m, 2H), 7.28 (t, J=7.5 Hz, 1H), 7.23-7.18 (m, 1H), 6.95 (dd, J=8.8, 0.5 Hz, 1H), 5.41 (s, 2H), 2.20 (s, 3H).

Intermediate 203B: 6-((2-methyl-[1,1'-biphenyl]-3-yl)methoxy)nicotinaldehyde

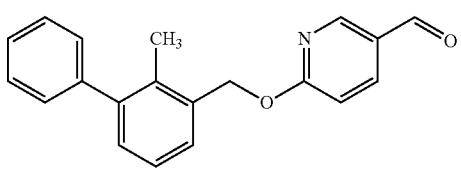

N-butyllithium (1.140 mL, 2.96 mmol) (2.6M in toluene) was added to a THF (10 mL) solution of 5-bromo-2-((2-methyl-[1,1'-biphenyl]-3-yl)methoxy)pyridine (1.0 g, 2.82 mmol) at −78° C. The reaction was stirred for 1 hr before adding DMF (0.437 mL, 5.65 mmol). After 30 minutes, the reaction was warmed to room temperature. LC/MS was consistent with the presence of the desired product. The reaction was poured into 20 mL of 5% aqueous sodium bicarbonate and extracted with diethyl ether (3×20 mL). The combined organics were dried over magnesium sulphate and filtered. The solvents were removed under reduced pressure by rotary evaporation to provide 840 mg of a yellow solid. This compound was used without further purification. $^1$H NMR (400 MHz, DMSO-$d_6$) δ 9.99 (s, 1H), 8.81 (d, J=2.4 Hz, 1H), 8.16 (dd, J=8.6, 2.4 Hz, 1H), 7.53-7.16 (m, 8H), 7.09 (d, J=8.6 Hz, 1H), 5.55 (s, 2H), 2.24-2.16 (m, 3H).

Examples 203-226 were prepared from Intermediate 203B 6-((2-methyl-[1,1'-biphenyl]-3-yl)methoxy)nicotinaldehyde according to the reductive amination conditions as described for Example 1 using the appropriate amine to obtain the desired product.

Example 227

(2R)-2-{[(4-{[3-(3-fluoro-5-methoxyphenyl)-2-methylphenyl]methoxy}-2,6-dimethoxyphenyl)methyl]amino}propanoic acid

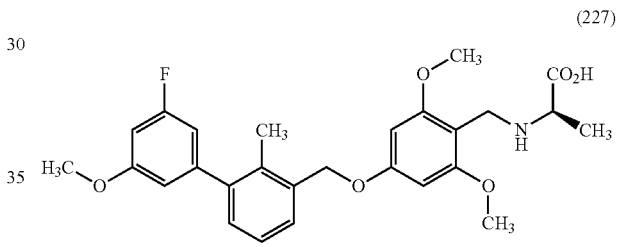

Intermediate 227A: (R)-methyl 2-((4-((3-bromo-2-methylbenzyl)oxy)-2,6-dimethoxybenzyl)amino)propanoate

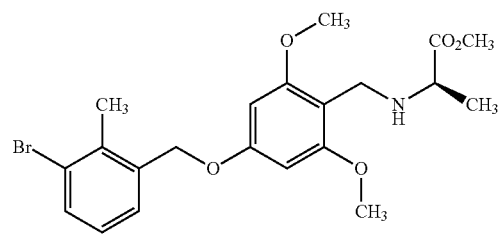

A solution of 4-((3-bromo-2-methylbenzyl)oxy)-2,6-dimethoxybenzaldehyde (1.15 g, 3.15 mmol) in dichloroethane (50 mL) was combined with D-alanine methyl ester hydrochloride (1.319 g, 9.45 mmol) and sodium triacetoxyborohydride (2.002 g, 9.45 mmol). The reaction was heated at 85° C. for 3 hours. The crude was concentrated, redissolved in ethyl acetate and washed with water, brine and dried over magnesium sulfate. The solvent was removed and the crude product was used directly in the next step without purification.

Intermediate 227B: 5-bromo-2-((2-methyl-[1,1'-biphenyl]-3-yl)methoxy)pyridine

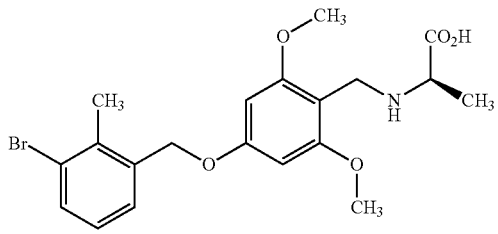

(227B)

Aqueous sodium hydroxide (1N) (3.15 mL, 3.15 mmol) was added to a THF (20 mL) and methanol (20 mL) solution of intermediate 227A (R)-methyl 2-((4-((3-bromo-2-methylbenzyl)oxy)-2,6-dimethoxybenzyl)amino)propanoate (1.425 g, 3.15 mmol). The mixture was stirred at room temperature overnight. The solvent was removed to afford a light yellow solid. Purified by preparative HPLC to afford reddish, light-brown solid (1.2 g).

Example 227

Intermediate 227B, (S)-2-(((3'-bromo-3,5-dimethoxy-2'-methyl-[1,1'-biphenyl]-4-yl)methyl)amino)propanoic acid (714 mg, 1.8 mmol) was dissolved in dioxane (35 mL). Cesium carbonate (1.7 gm, 5.3 mmol) was dissolved in water (3.5 mL). (3-Fluoro-5-methoxyphenyl)boronic acid (18 mg, 0.1 mmol) was weighed into 0.5-2 mL microwave vial. (S)-2-(((3'-bromo-3,5-dimethoxy-2'-methyl-[1,1'-biphenyl]-4-yl)methyl)amino)propanoic acid solution (1 mL, 0.052 mmol), 100 µL of the cesium carbonate solution and 1,1'-bis(diphenylphosphino)ferrocene-palladium(II)dichloride dichloromethane complex (4.25 mg, 0.0052 mmol). The reaction was heated in a Biotage Initiator™ (400 W) microwave for 15 minutes at 150° C. with 20 seconds of prestirring and using a fixed hold time. Transferred contents to 6 mL MP-Thiol SPE cartridges (conditioned with methanol). Rinsed reaction vials 2×500 µL methanol, transferring rinses to the SPE cartridge. Eluted products with 4 mL methanol. Samples were blown down in the Zymark tabletop dryer at 40° C. for 1 hour. Added 1 mL DMF to each vial. Transferred contents to 16×48 mm threaded vials. Rinsed culture tubes with 500 µL DMF each. The crude material was purified via preparative LC/MS with the following conditions: Column: XBridge C18, 19×mm, 5-µm particles; Mobile Phase A: 5:95 methanol:water with 10-mM ammonium acetate; Mobile Phase B: 95:5 methanol:water with 10-mM ammonium acetate; Gradient: 10-100% B over 18 minutes, then a 7-minute hold at 100% B; Flow: 20 mL/min. Fractions containing the desired product were combined and dried via centrifugal evaporation. The yield of the product was 8.1 mg, and its estimated purity by LCMS analysis was 100%. $^1$H NMR (500 MHz, DMSO-$d_6$) δ 7.52 (d, J=7.9 Hz, 1H), 7.29 (d, J=7.3 Hz, 1H), 7.24 (d, J=7.9 Hz, 1H), 6.86 (d, J=11.3 Hz, 1H), 6.76-6.68 (m, 2H), 6.44 (s, 2H), 5.20 (s, 2H), 3.97 (br. s., 2H), 3.82 (d, J=3.7 Hz, 9H), 3.05 (d, J=6.7 Hz, 1H), 2.23 (s, 3H), 1.27 (d, J=6.7 Hz, 3H).

Example 228, (2R)-2-{[(4-{[3-(2H-1,3-benzodioxol-5-yl)-2-methylphenyl]methoxy}-2,6-dimethoxyphenyl)methyl]amino}propanoic acid, was prepared from Intermediate 227B, (S)-2-(((3'-bromo-3,5-dimethoxy-2'-methyl-[1,1'-biphenyl]-4-yl)methyl)amino)propanoic acid and benzo[d][1,3]dioxol-5-ylboronic acid using the same reaction conditions employed for the synthesis of Example 227.

Example 229

3-[3-(4-{[(2-hydroxyethyl)amino]methyl}-3,5-dimethoxyphenoxymethyl)-2-methylphenyl]phenol

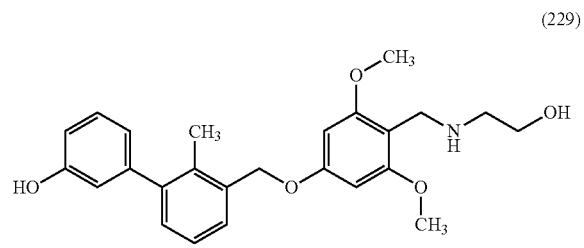 [SMILES: COc1cc(OCc2cccc(-c3cccc(O)c3)c2C)cc(OC)c1CNCCO]

(229)

Intermediate 229A: 4-((3-bromo-2-methylbenzyl)oxy)-2,6-dimethoxybenzaldehyde

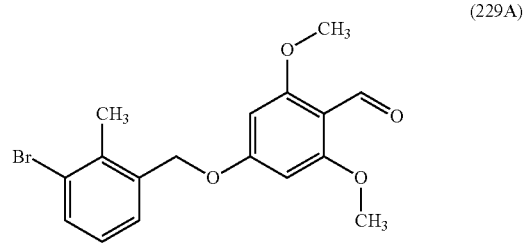 [SMILES: COc1cc(OCc2cccc(Br)c2C)cc(OC)c1C=O]

(229A)

A solution of 4-hydroxy-2,6-dimethoxybenzaldehyde (3.99 g, 21.88 mmol), triphenylphosphine (6 g, 22.88 mmol) and (3-bromo-2-methylphenyl)methanol (4 g, 19.89 mmol) in dry THF (50 mL) was cooled in an ice bath. Diisopropyl azodicarboxylate (4.25 mL, 21.88 mmol) in THF (50 mL) was added dropwise. The resulting yellow solution was allowed to slowly warm to room temperature with stirring overnight. Excess solvent was removed by rotary evaporator. The crude product was purified by chromatography on a 360 g silica gel cartridge eluting with ethyl acetate in hexanes. Fractions containing the desired product were combined and the solvent removed under vacuum to give the title compound (4.0 g, 55%). $^1$H NMR (400 MHz, CHLOROFORM-d) δ 10.39 (s, 1H), 7.62 (d, J=8.0 Hz, 1H), 7.37 (d, J=7.3 Hz, 1H), 7.12 (t, J=7.8 Hz, 1H), 6.18 (s, 2H), 5.13 (s, 2H), 3.91 (s, 6H), 2.49 (s, 3H).

Example 229

A solution of 4-((3-bromo-2-methylbenzyl)oxy)-2,6-dimethoxybenzaldehyde (310 mg, 850 µmol) in DCE (8.5 mL) was prepared. Separately, a solution of 2-aminoethanol (77 uL, 1.3 mmol) in DCE (7.5 mL) was prepared. A 0.5 mL aliquot of each solution was charged to a reaction vial. Acetic acid (2.86 µl, 50.0 µmol) was added to the vial, capped and allowed to shake at 40° C. for 1 hr. The solvent was removed in a Zymark tabletop dryer at 40° C. for 1 hour. Toluene (0.5 mL) was added and the solvent was removed in a Zymark tabletop dryer at 40° C. for 1 hour. A solution of tetramethylammonium triacetoxyborohydride (672 mg, 2.6 mmol) in DCE (17 mL) was prepared and 1 mL was added to the reaction. The reaction was capped and allowed to shake at room temperature overnight. The contents were transferred to a 6-mL PL-SO3H SPE cartridge (conditioned with methanol). The reaction vial was rinsed with 500 μL methanol and the rinse transferred to the SPE cartridge. The cartridge was washed with 4 mL methanol. The product was eluted with 4 mL 1N ammonia in methanol The solvent was removed in a Zymark tabletop dryer at 35° C. for 1 hour. The residue was dissolved in dioxane (1 mL) and transferred to a vial containing (3-hydroxyphenyl)boronic acid (13.8 mg, 0.1 mmol). A solution (0.1 mL) of the cesium carbonate (831 mg, 2.6 mmol) in water (1.7 mL) and solid 1,1'-bis(diphenylphosphino)ferrocene-palladium(II)dichloride dichloromethane complex (4.08 mg, 0.005 mmol) were added. The reaction was heated overnight at 100° C. with stirring. The reaction contents were transferred to a 6-mL PL-Thiol SPE cartridges (conditioned with methanol). The reaction vial was rinsed with methanol (0.5 mL) and the rinse added to the SPE cartridges. The product was eluted with 4 mL methanol. The solvent was removed in a Zymark tabletop dryer at 35° C. for 2 hour. The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 15 minutes, then a 5-minute hold at 100% B; Flow: 20 mL/min. Fractions containing the desired product were combined and dried via centrifugal evaporation. The yield of the product was 2.4 mg, and its estimated purity by LCMS analysis was 96%. $^1$H NMR (500 MHz, DMSO-$d_6$) δ 7.47 (d, J=7.3 Hz, 1H), 7.30-7.22 (m, 2H), 7.18 (d, J=7.3 Hz, 1H), 6.78 (d, J=8.2 Hz, 1H), 6.71 (d, J=7.3 Hz, 1H), 6.68 (br. s., 1H), 6.38 (s, 2H), 5.16 (s, 2H), 3.91 (s, 1H), 3.78 (s, 6H), 3.67 (br. s., 2H), 3.47-3.43 (m, 2H), 2.56-2.53 (m, 2H), 2.22 (s, 3H).

Examples 230, 231, 232 and 245 were prepared from 4-((3-bromo-2-methylbenzyl)oxy)-2,6-dimethoxybenzaldehyde and 2-aminoethanol using the same procedure outlined for Example 229 except the appropriate boronic acid was substituted for (3-hydroxyphenyl)boronic acid to obtain the desired product.

Examples 285, 286, 287 and 289 were prepared from 4-((3-bromo-2-methylbenzyl)oxy)-2,6-dimethoxybenzaldehyde and N-(2-aminoethyl)acetamide using the same procedure outlined for Example 229 except the appropriate boronic acid was substituted for (3-hydroxyphenyl)boronic acid to obtain the desired product.

Examples 288, 290, 291, 292, 293 and 294 were prepared from 4-((3-bromo-2-methylbenzyl)oxy)-2,6-dimethoxybenzaldehyde and 2-methyl-1-(4-methylpiperazin-1-yl)propan-2-amine using the same procedure outlined for Example 229 except the appropriate boronic acid was substituted for (3-hydroxyphenyl)boronic acid to obtain the desired product.

Example 296

(3S)-3-hydroxy-4-[({5-[(2-methyl-3-phenylphenyl)methoxy]pyridin-2-yl}methyl)amino]butanoic acid

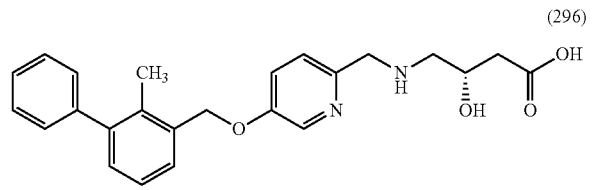 [SMILES: Cc1c(COc2ccc(CNC[C@@H](O)CC(=O)O)nc2)cccc1-c1ccccc1]

(296)

(S)-4-amino-3-hydroxybutanoic acid (35.7 mg, 300 μmol) and 5-((2-methyl-[1,1'-biphenyl]-3-yl)methoxy)picolinaldehyde (30.3 mg, 100 μmol) were dissolved in a mixture of DMF (0.5 mL) and acetic acid (5.72 μl, 100 μmol). The reaction was stirred at 40° C. for 1 hour and a solution of sodium cyanoborohydride (18.85 mg, 300 μmol) in DMF (0.5 mL) was added. Stirred at room temperature overnight. The reaction was diluted with 500 μL MeOH. The solvent was removed in a Zymark tabletop dryer at 35° C. for 1 hour. The residue was redissolved in 1 mL DMF and filtered using syringe filter. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 9.1 mg, and its estimated purity by LCMS analysis was 94%. $^1$H NMR (500 MHz, DMSO-$d_6$) δ 8.33 (d, J=2.6 Hz, 1H), 7.50 (d, J=8.8 Hz, 1H), 7.46 (t, J=7.5 Hz, 3H), 7.41-7.36 (m, 2H), 7.32 (d, J=7.3 Hz, 2H), 7.29 (t, J=7.7 Hz, 1H), 7.21 (d, J=7.7 Hz, 1H), 5.22 (s, 2H), 3.89-3.83 (m, 1H), 3.78 (br. s., 2H), 3.45 (br. s., 3H), 2.28 (dd, J=15.0, 5.1 Hz, 1H), 2.21 (s, 3H), 2.17-2.09 (m, 1H).

Example 297

N-(2-{[(3-chloro-4-{[2-methyl-3-(thiophen-3-yl)phenyl]methoxy}phenyl)methyl]amino}ethyl)acetamide

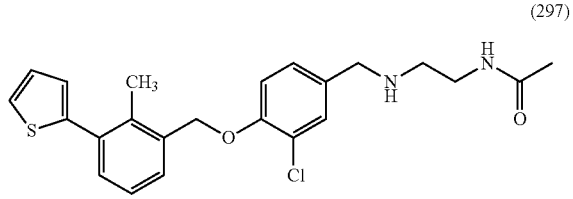 [SMILES: CC(=O)NCCNCc1ccc(OCc2cccc(-c3cccs3)c2C)c(Cl)c1]

(297)

Intermediate 297A: (2-methyl-3-(4,4,5,5-tetramethyl-1,3,2-dioxaborolan-2-yl)phenyl)methanol

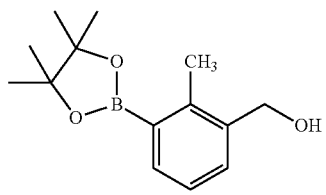

(297A)

Dioxane (200 mL) was charged to a 500 mL round-bottom flask and nitrogen was bubbled through for 10 minutes. (3-bromo-2-methylphenyl)methanol (9.0 g, 44.8 mmol) was added and nitrogen was bubbled through for 10 minutes. Potassium acetate (13.18 g, 134 mmol) was added and nitrogen was bubbled through for 10 minutes. Bis(pinacolato)diboron (18.19 g, 71.6 mmol) was added and nitrogen was bubbled through for 10 minutes. PdCl$_2$(dppf)-

CH$_2$Cl$_2$ (4.75 g, 5.82 mmol) was added and nitrogen was bubbled through for 10 minutes. The reaction was heated at 80° C. overnight.

The reaction was diluted with ethyl acetate (200 ml), filtered through a celite bed and the bed washed with ethyl acetate. The combined organic portions were concentrated under vacuum to provide a black pasty residue. This crude residue was adsorbed onto silica gel and chromatographed on a 120 g silica gel column using acetone in petroleum ether. The product eluted at 5.0% acetone. Fractions containing the product were combined and the solvent was removed under vacuum. An off-white solid was obtained. The solid was stirred with petroleum ether and filtered under vacuum to remove boron impurities. The title compound (8.7 g, 77%) was pure by NMR analysis. $^1$H NMR (500 MHz, DMSO-d$_6$) δ 7.33 (dd, J=0.9, 7.5 Hz, 1H), 7.45 (d, J=6.9 Hz, 1H), 7.22 (t, J=7.5 Hz, 1H), 4.73 (d, J=3.0 Hz, 2H), 2.58 (s, 3H), 1.58 (br. s., 1H, OH), 1.37 (s, 12H).

Intermediate 297B: 3-chloro-4-((2-methyl-3-(4,4,5,5-tetramethyl-1,3,2-dioxaborolan-2-yl)benzyl)oxy)benzaldehyde

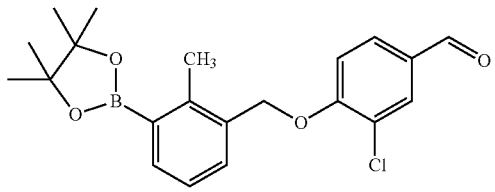

(297B)

A solution of 3-chloro-4-hydroxybenzaldehyde (126 mg, 0.806 mmol), triphenylphosphine (233 mg, 0.887 mmol) and (2-methyl-3-(4,4,5,5-tetramethyl-1,3,2-dioxaborolan-2-yl)phenyl)methanol (200 mg, 0.806 mmol) in dry THF (5 mL) was cooled in an ice bath. Diisopropyl azodicarboxylate (0.172 mL, 0.887 mmol) in THF (5 mL) was added dropwise. The resulting yellow solution was allowed to slowly warm to room temperature while stirring overnight. The solvent was removed and the residue was purified on a 24 g silica column with 2:1 hexanes:ethyl acetate. Collected fractions to afford the desired product (0.305 g, 98%). $^1$H NMR (400 MHz, CHLOROFORM-d) δ 9.86 (s, 1H), 7.94 (d, J=2.0 Hz, 1H), 7.81 (dd, J=7.5, 1.1 Hz, 1H), 7.75 (dd, J=8.4, 2.1 Hz, 1H), 7.55 (d, J=7.5 Hz, 1H), 7.25 (t, J=7.6 Hz, 1H), 7.12 (d, J=8.6 Hz, 1H), 5.24 (s, 2H), 2.61 (s, 3H), 1.39 (s, 12H).

Example 297

A solution of (3-((2-chloro-4-formylphenoxy)methyl)-2-methylphenyl)boronic acid (352 mg, 1.2 mmol) in dioxane (16 mL) was degassed with nitrogen. Tripotassium phosphate (613 mg, 2.9 mmol) was dissolved in water (4 mL) and degassed with nitrogen. A reaction vial was charged with 2-bromothiophene (23.6 mg, 0.144 mmol), 1 mL of the (3-((2-chloro-4-formylphenoxy)methyl)-2-methylphenyl) boronic acid solution, 250 μL of the tripotassium phosphate solution and solid 2nd generation Xphos precatalyst (2.84 mg, 3.61 μmol, CAS Number 1310584-14-5). The vial was sealed and allowed to shake at room temperature overnight. The reaction mixture was transferred to 6 mL PL-Thiol SPE cartridge (conditioned with methanol). The reaction vial was rinsed with 500 μL methanol and the rinse transferred to the SPE cartridges. The intermediate product was eluted with 4 mL methanol and solvent removed in a Zymark tabletop dryer at 40° C. for 3 hours. The intermediate was used without further purification.

A solution of N-(2-aminoethyl)acetamide (336 μL, 3.5 mmol) in DCE (8.0 mL) was prepared and 500 μL of the N-(2-aminoethyl)acetamide solution was added to the dried aldehyde intermediate. Acetic acid (4.14 μl, 0.072 mmol) was added and the sealed reaction was allowed to stir at 40° C. for 1 hour. The solvent was removed in a Zymark tabletop dryer at 40° C. for 2 hours. Toluene (500 μL) was added and solvent removed in a Zymark tabletop dryer at 40° C. for 1 hour. Tetramethylammonium triacetoxyborohydride (1.4 gm, 5.2 mmol) was dissolved in DCE (16 mL) and 1.0 mL of this solution was added to the reaction. The reaction was sealed allowed to shake at room temperature overnight. LCMS consistent mostly with imine intermediate. The solvent was removed in a Zymark tabletop dryer at 40° C. for 3 hours. A solution of N-(2-aminoethyl)acetamide (336 μL, 3.5 mmol) in DMF (8.0 mL) was prepared and 500 μL was added to the reaction. Acetic acid (4.14 μl, 0.072 mmol) was added. The sealed reaction was allowed to shake at room temp for 1 hr. Sodium cyanoborohydride (327 mg, 5.2 mmol) was dissolved in DMF (8.0 mL) and 500 μL was added to the reaction. The sealed reaction was allowed to shake at room temperature overnight. The reaction contents were transferred to 6-mL PL-SO3H SPE cartridge conditioned with methanol. The reaction vial was rinsed with 500 μL methanol and the rinse was transferred to the SPE cartridge. The cartridge was rinsed with 4 mL methanol. The product was eluted with 4 mL 1N ammonia in methanol. The solvent was removed in a Zymark tabletop dryer at 40° C. for 2 hours and the residue dissolved in DMF (1 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 97%. $^1$H NMR (500 MHz, DMSO-d$_6$) δ 7.64 (d, J=5.1 Hz, 1H), 7.55 (s, 1H), 7.52 (d, J=7.3 Hz, 1H), 7.40-7.34 (m, 3H), 7.33-7.27 (m, 1H), 7.20-7.16 (m, 1H), 7.14 (d, J=3.3 Hz, 1H), 5.28 (s, 2H), 3.92 (br. s., 2H), 3.25 (d, J=6.2 Hz, 2H), 2.77 (br. s., 2H), 2.36 (s, 3H), 1.82 (s, 3H).

HPLC Methods

Method A: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Method M: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method AA: Ascentis Express C18, 4.6×50 mm, 2.7 μm column; 4 ml/min flow; 4 min gradient from 0% B to 100%

B; A=5% ACN-95% H2O 10 mM NH4OAc, B=95% ACN-5% H2O 10 mM NH4OAc UV detection at 220 nm; and a column heater set at 45° C.

Method AT: Ascentis Express C18, 2.1×50 mm, 2.7 μm column; 1.1 ml/min flow; 3 min gradient from 0% B to 100% B; A=5% ACN-95% H2O 0.1% TFA, B=95% ACN-5% H2O 0.1% TFA UV detection at 220 nm; and a column heater set at 50° C.

Method A50: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Method M50: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

| Ex. No. | Structure | Name | HPLC Retention Time (minutes) (Method) | ESI-MS m/z MH+ | ESI-MS m/z MH− |
|---|---|---|---|---|---|
| 5 | 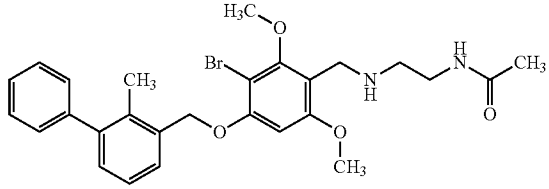 [SMILES: COc1cc(OCc2cccc(-c3ccccc3)c2C)c(Br)c(OC)c1CNCCNC(C)=O] | N-{2-[({3-bromo-2,6-dimethoxy-4-[(2-methyl-3-phenylphenyl)methoxy]phenyl[methyl)amino]ethyl}acetamide | 2.8 A | 529.2 | — |
| 6 | 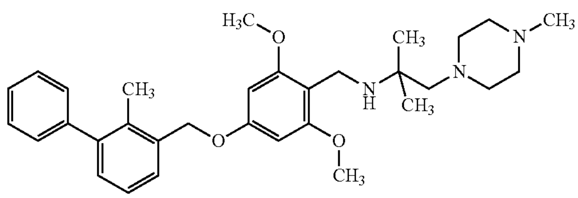 [SMILES: COc1cc(OCc2cccc(-c3ccccc3)c2C)cc(OC)c1CNC(C)(C)CN1CCN(C)CC1] | ({2,6-dimethoxy-4-[(2-methyl-3-phenylphenyl)methoxy]phenyl}methyl)[2-methyl-1-(4-methylpiperazin-1-yl)propan-2-yl] amine | 4.16 M | 518.5 | — |
| 7 | 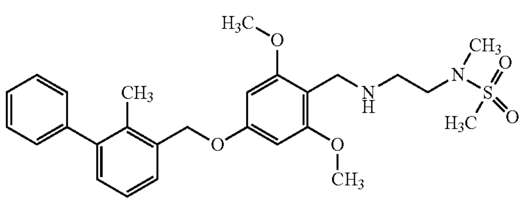 [SMILES: COc1cc(OCc2cccc(-c3ccccc3)c2C)cc(OC)c1CNCCN(C)S(C)(=O)=O] | N-{2-[({2,6-dimethoxy-4-[(2-methyl-3-phenylphenyl)methoxy]phenyl}methyl)amino]ethyl}-N-methylmethanesulfonamide | 2.91 A | 499.3 | — |
| 8 | 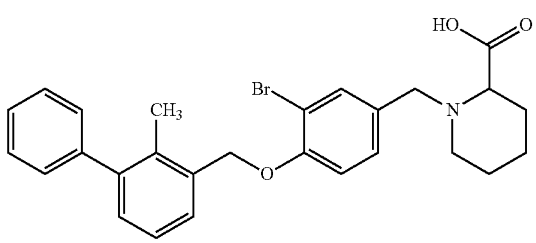 [SMILES: Cc1c(COc2ccc(CN3CCCCC3C(=O)O)cc2Br)cccc1-c1ccccc1] | 1-({3-bromo-4-[(2-methyl-3-phenylphenyl)methoxy]phenyl}methyl)piperidine-2-carboxylic acid | 4.15 M | 494.4 | — |
| 9 | 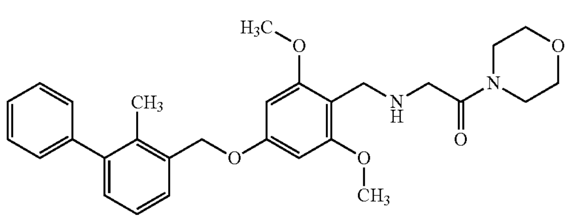 [SMILES: COc1cc(OCc2cccc(-c3ccccc3)c2C)cc(OC)c1CNCC(=O)N1CCOCC1] | 2-[({2,6-dimethoxy-4-[(2-methyl-3-phenylphenyl)methoxy]phenyl}methyl)amino]-1-(morpholin-4-yl)ethan-1-one | 2.9 A | 491.4 | — |
| 10 | 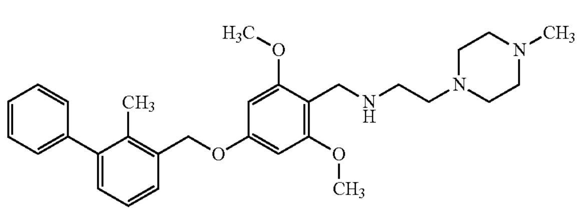 [SMILES: COc1cc(OCc2cccc(-c3ccccc3)c2C)cc(OC)c1CNCCN1CCN(C)CC1] | ({2,6-dimethoxy-4-[(2-methyl-3-phenylphenyl)methoxy]phenyl}methyl)[2-(4-methylpiperazin-1-yl)ethyl] amine | 4.1 M | 490.5 | — |

-continued

| Ex. No. | Structure | Name | HPLC Retention Time (minutes) (Method) | ESI-MS m/z MH+ | ESI-MS m/z MH− |
|---|---|---|---|---|---|
| 11 | 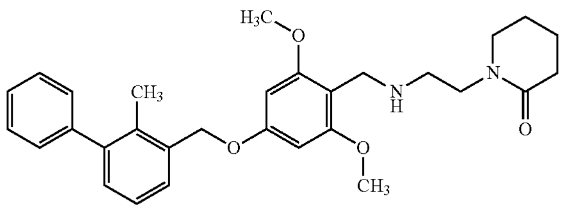 [SMILES: COc1cc(OCc2cccc(-c3ccccc3)c2C)cc(OC)c1CNCCN1CCCCC1=O] | 1-{2-[({2,6-dimethoxy-4-[(2-methyl-3-phenylphenyl)methoxy]phenyl}methyl)amino]ethyl}piperidin-2-one | 4.1 M | 489.4 | — |
| 12 | 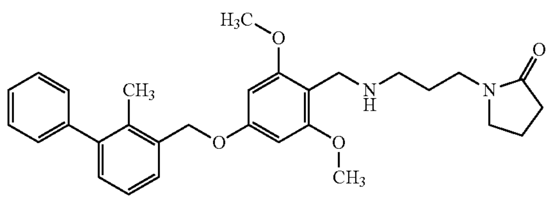 [SMILES: COc1cc(OCc2cccc(-c3ccccc3)c2C)cc(OC)c1CNCCCN1CCCC1=O] | 1-{3-[({2,6-dimethoxy-4-[(2-methyl-3-phenylphenyl)methoxy]phenyl}methyl)amino]propyl}pyrrolidin-2-one | 4.0 M | 489.4 | — |
| 13 | 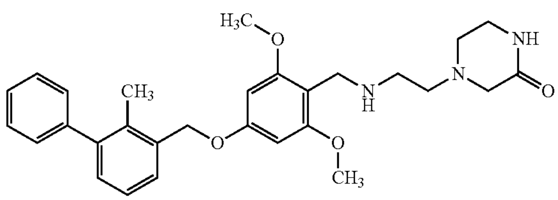 [SMILES: COc1cc(OCc2cccc(-c3ccccc3)c2C)cc(OC)c1CNCCN1CCNC(=O)C1] | 4-{2-[({2,6-dimethoxy-4-[(2-3-phenylphenyl)methyl-methoxy]phenyl}methyl)amino]ethyl}piperazin-2-one | 4.0 M | 489.4 | — |
| 14 | 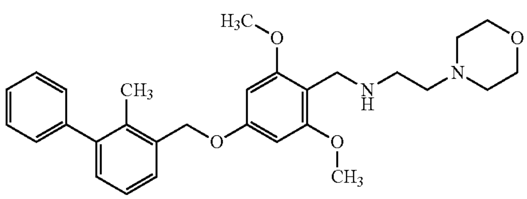 [SMILES: COc1cc(OCc2cccc(-c3ccccc3)c2C)cc(OC)c1CNCCN1CCOCC1] | 1-({2,6-dimethoxy-4-[(2-methyl-3-phenylphenyl)methoxy]phenyl}methyl)(2-(morpholin-4-yl)ethyl]amine | 4.0 M | 477.3 | — |
| 15 | 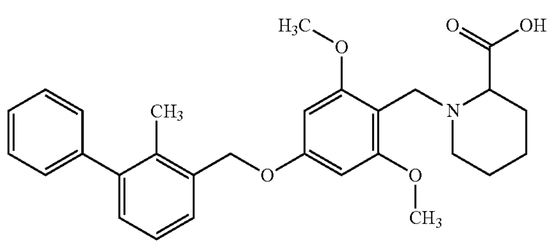 [SMILES: COc1cc(OCc2cccc(-c3ccccc3)c2C)cc(OC)c1CN1CCCCC1C(=O)O] | 1-({2,6-dimethoxy-4-[(2-methyl-3-phenylphenyl)methoxy]phenyl}methyl)piperidine-2-carboxylic acid | 4.2 M | 476.5 | — |
| 16 | 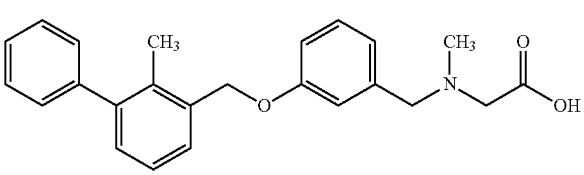 [SMILES: Cc1c(COc2cccc(CN(C)CC(=O)O)c2)cccc1-c1ccccc1] | 2-[methyl({3-[(2-methyl-3-phenylphenyl)methoxy]phenyl}methyl)amino]acetic acid | 4.2 M | 476.5 | — |
| 17 | 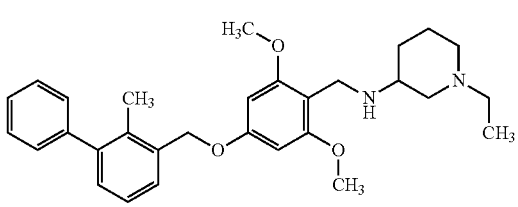 [SMILES: CCN1CCCC(NCc2c(OC)cc(OCc3cccc(-c4ccccc4)c3C)cc2OC)C1] | N-({2,6-dimethoxy-4-[(2-methyl-3-phenylphenyl)methoxy]phenyl}methyl)-1-ethylpiperidin-3-amine | 4.3 M | 475.5 | — |

| Ex. No. | Structure | Name | HPLC Retention Time (minutes) (Method) | ESI-MS m/z MH+ | ESI-MS m/z MH− |
|---|---|---|---|---|---|
| 18 | 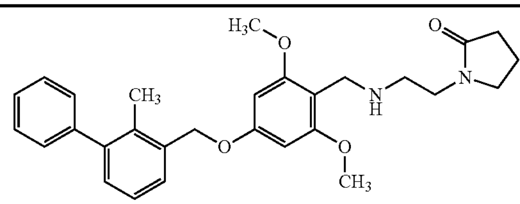 | 1-{2-[({2,6-dimethoxy-4-[(2-methyl-3-phenylphenyl)methoxy]phenyl}methyl)amino]ethyl}pyrrolidin-2-one | 4.1 M | 475.4 | — |
| 19 | 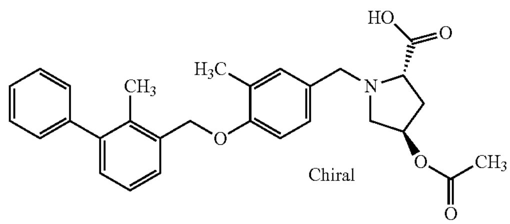 [SMILES: CC(=O)O[C@@H]1C[C@@H](C(=O)O)N(Cc2ccc(OCc3cccc(-c4ccccc4)c3C)c(C)c2)C1] | (2S,4R)-4-(acetyloxy)-1-({3-methyl-4-[(2-methyl-3-phenylphenyl)methoxy]phenyl}methyl)pyrrolidine-2-carboxylic acid | 4.1 M | 474.3 | — |
| 20 | 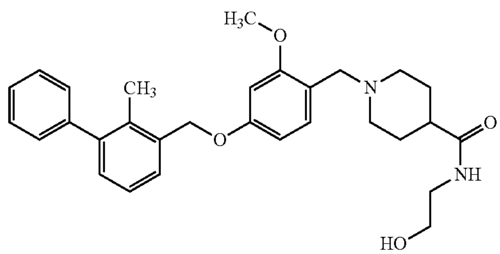 [SMILES: COc1cc(OCc2cccc(-c3ccccc3)c2C)ccc1CN1CCC(C(=O)NCCO)CC1] | N-(2-hydroxyethyl)-1-({3-methyl-4-[(2-methyl-3-phenylphenyl)methoxy]phenyl}methyl)piperidine-4-carboxamide | 4.2 M | 473.5 | — |
| 21 | 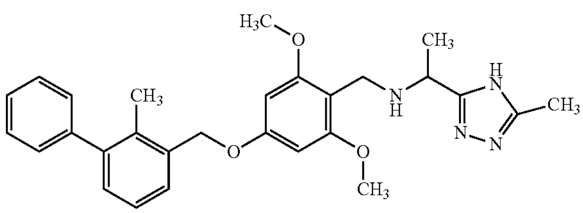 [SMILES: COc1cc(OCc2cccc(-c3ccccc3)c2C)cc(OC)c1CNC(C)c1nnc(C)[nH]1] | ({2,6-dimethoxy-4-[(2-methyl-3-phenylphenyl)methoxy]phenyl}methyl)[1-(5-methyl-4H-1,2,4-triazol-3-yl)ethyl] amine | 2.7 A | 473.4 | — |
| 22 | 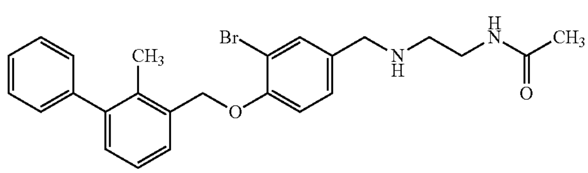 [SMILES: CC(=O)NCCNCc1ccc(OCc2cccc(-c3ccccc3)c2C)c(Br)c1] | N-{2-[({3-bromo-4-[(2-methyl-3-phenylphenyl)methoxy]phenyl}methyl)amino]ethyl}acetamide | 2.8 A | 467.4 | — |
| 23 | 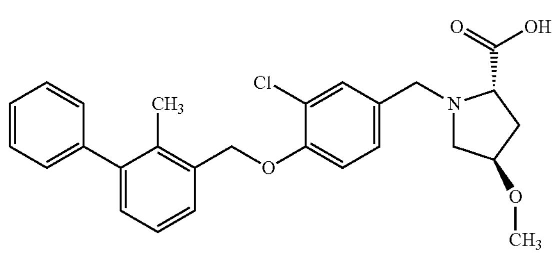 [SMILES: CO[C@@H]1C[C@@H](C(=O)O)N(Cc2ccc(OCc3cccc(-c4ccccc4)c3C)c(Cl)c2)C1] | (2S,4R)-1-({3-chloro-4-[(2-methyl-3-phenylphenyl)methoxy]phenyl}methyl)-4-methoxypyrrolidine-2-carboxylic acid | 2.7 A | 466.4 | 464.4 |
| 24 | 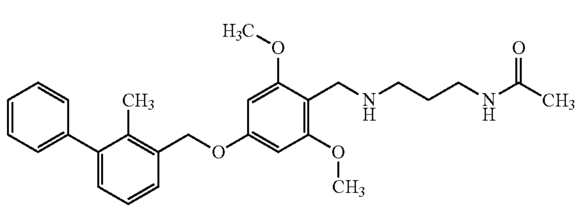 [SMILES: COc1cc(OCc2cccc(-c3ccccc3)c2C)cc(OC)c1CNCCCNC(C)=O] | N-{3-[({2,6-dimethoxy-4-[(2-methyl-3-phenylphenyl)methoxy]phenyl}methyl)amino]propyl}acetamide | 4.0 M | 463.5 | — |

-continued

| Ex. No. | Structure | Name | HPLC Retention Time (minutes) (Method) | ESI-MS m/z MH+ | ESI-MS m/z MH− |
|---|---|---|---|---|---|
| 25 | 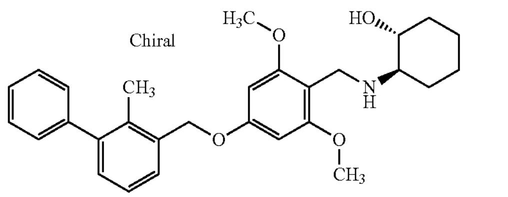 [SMILES: COc1cc(OCc2cccc(-c3ccccc3)c2C)cc(OC)c1CN[C@@H]1CCCC[C@H]1O] | (1R,2R)-2-[({2,6-dimethoxy-4-[(2-methyl-3-phenylphenyl)methoxy]phenyl}methyl)amino]cyclohexan-1-ol | 4.2 M | 462.4 | — |
| 26 | 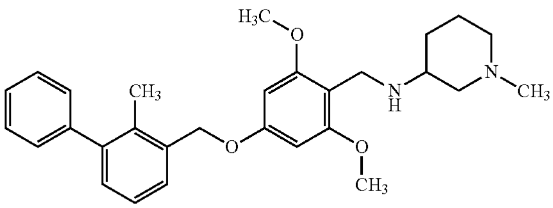 [SMILES: COc1cc(OCc2cccc(-c3ccccc3)c2C)cc(OC)c1CNC1CCCN(C)C1] | N-({2,6-dimethoxy-4-[(2-methyl-3-phenylphenyl)methoxy]phenyl}methyl)-1-methylpiperidin-3-amine | 4.1 M | 461.6 | — |
| 27 | 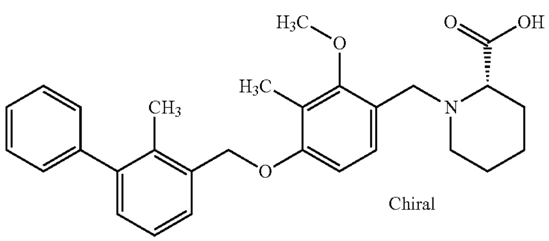 [SMILES: COc1c(CN2CCCC[C@H]2C(=O)O)ccc(OCc2cccc(-c3ccccc3)c2C)c1C] | (2S)-1-({2-methoxy-3-methyl-4-[(2-methyl-3-phenylphenyl)methoxy]phenyl}methyl)piperidine-2-carboxylic acid | 2.7 A | 460.3 | 458.4 |
| 28 | 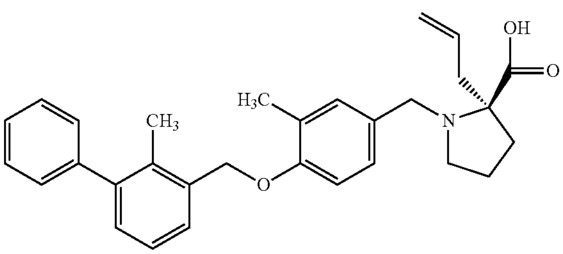 [SMILES: C=CC[C@]1(C(=O)O)CCCN1Cc1ccc(OCc2cccc(-c3ccccc3)c2C)c(C)c1] | (2S)-1-({3-methyl-4-[(2-methyl-3-phenylphenyl)methoxy]phenyl}methyl)-2-(prop-2-en-1-yl)pyrrolidine-2-carboxylic acid | 4.3 M | 456.4 | — |
| 29 | 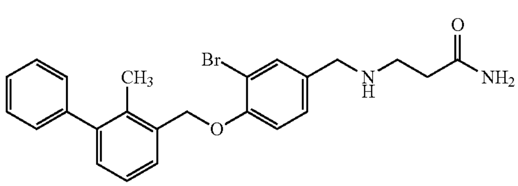 [SMILES: Cc1c(COc2ccc(CNCCC(N)=O)cc2Br)cccc1-c1ccccc1] | 3-[({3-bromo-4-[(2-methyl-3-phenylphenyl)methoxy]phenyl}methyl)amino]propanamide | 2.7 A | 453.4 | — |
| 30 | 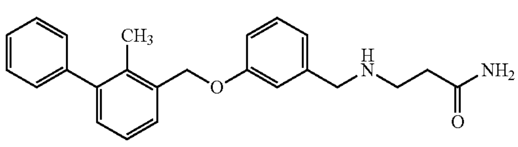 [SMILES: Cc1c(COc2cccc(CNCCC(N)=O)c2)cccc1-c1ccccc1] | 3-[({3-[(2-methyl-3-phenylphenyl)methoxy]phenyl}methyl)amino]propanamide | 4.1 M | 452.4 | — |
| 31 | 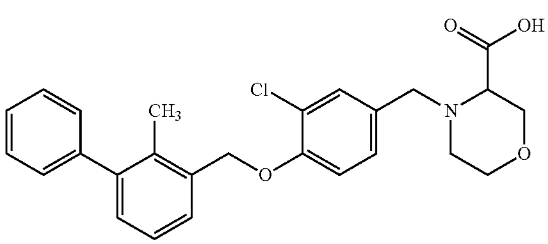 [SMILES: Cc1c(COc2ccc(CN3CCOCC3C(=O)O)cc2Cl)cccc1-c1ccccc1] | 4-({3-chloro-4-[(2-methyl-3-phenylphenyl)methoxy]phenyl}methyl)morpholine-3-carboxylic acid | 4.2 M | 452.7 | 450.6 |

| Ex. No. | Structure | Name | HPLC Retention Time (minutes) (Method) | ESI-MS m/z MH+ | ESI-MS m/z MH− |
|---|---|---|---|---|---|
| 32 | 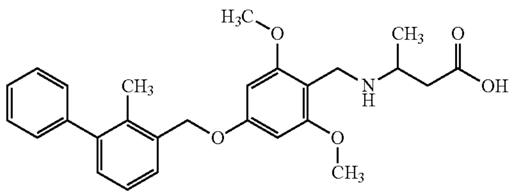 [SMILES: COc1cc(OCc2cccc(-c3ccccc3)c2C)cc(OC)c1CNC(C)CC(=O)O] | 3-[({2,6-dimethoxy-4-[(2-methyl-3-phenylphenyl)methoxy]phenyl}methyl)amino]butanoic acid | 4.0 M | 450.2 | — |
| 33 | 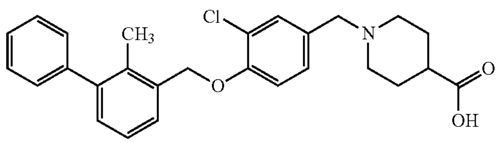 [SMILES: Cc1c(COc2ccc(CN3CCC(C(=O)O)CC3)cc2Cl)cccc1-c1ccccc1] | 1-({3-chloro-4-[(2-methyl-3-phenylphenyl)methoxy]phenyl}methyl)piperidine-4-carboxylic acid | 4.1 M | 450.3 | 448.3 |
| 34 | 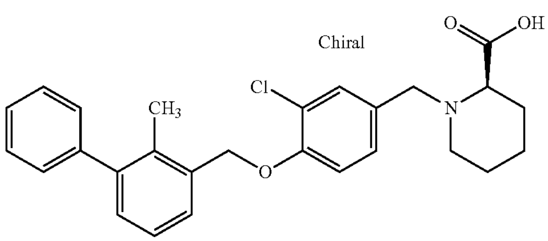 [SMILES: Cc1c(COc2ccc(CN3CCCC[C@@H]3C(=O)O)cc2Cl)cccc1-c1ccccc1] | (2R)-1-({3-chloro-4-[(2-methyl-3-phenylphenyl)methoxy]phenyl}methyl)piperidine-2-carboxylic acid | 4.1 M | 450.4 | 448.5 |
| 35 | 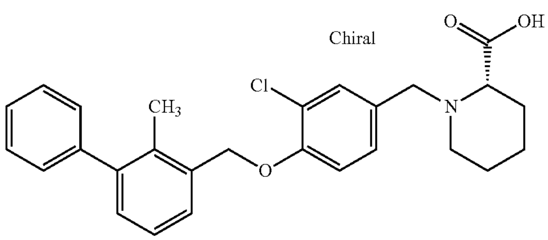 [SMILES: Cc1c(COc2ccc(CN3CCCC[C@H]3C(=O)O)cc2Cl)cccc1-c1ccccc1] | (2S)-1-({3-chloro-4-[(2-methyl-3-phenylphenyl)methoxy]phenyl}methyl)piperidine-2-carboxylic acid | 4.1 M | 450.4 | 448.5 |
| 36 | 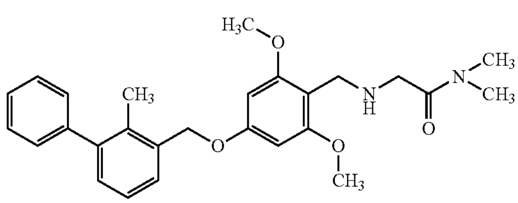 [SMILES: COc1cc(OCc2cccc(-c3ccccc3)c2C)cc(OC)c1CNCC(=O)N(C)C] | 2-[({2,6-dimethoxy-4-[(2-methyl-3-phenylphenyl)methoxy]phenyl}methyl)amino]-N,N-dimethylacetamide | 4.1 M | 449.4 | — |
| 37 | 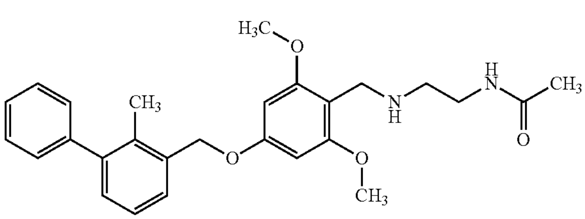 [SMILES: COc1cc(OCc2cccc(-c3ccccc3)c2C)cc(OC)c1CNCCNC(C)=O] | N-{2-[({2,6-dimethoxy-4-[(2-methyl-3-phenylphenyl)methoxy]phenyl}methyl)amino]ethyl}acetamide | 2.7 A | 449.0 | — |
| 38 | 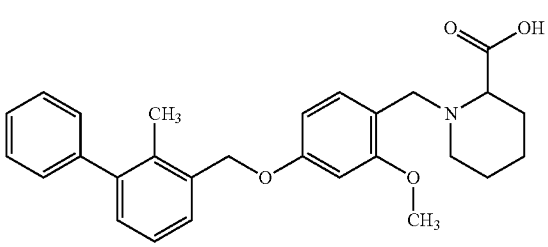 [SMILES: COc1cc(OCc2cccc(-c3ccccc3)c2C)ccc1CN1CCCCC1C(=O)O] | 1-({2-methoxy-4-[(2-methyl-3-phenylphenyl)methoxy]phenyl}methyl)piperidine-2-carboxylic acid | 4.1 M | 446.5 | — |

-continued

| Ex. No. | Structure | Name | HPLC Retention Time (minutes) (Method) | ESI-MS m/z MH+ | ESI-MS m/z MH− |
|---|---|---|---|---|---|
| 39 | 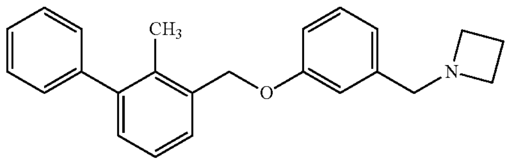 [SMILES: Cc1c(COc2cccc(CN3CCC3)c2)cccc1-c1ccccc1] | 1-({3-[(2-methyl-3-phenylphenyl)methoxy]phenyl}methyl)azetidine | 4.1 M | 446.5 | — |
| 40 | Chiral | (2S,4R)-4-methoxy-1-({3-methyl-4-[(2-methyl-3-phenylphenyl)methoxy]phenyl}methyl)pyrrolidine-2-carboxylic acid | −2.7 A | 446.4 | 444.5 |
| 41 | 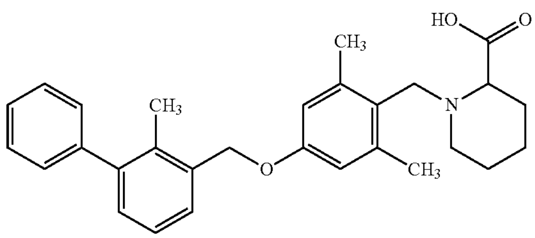 [SMILES: Cc1cc(OCc2cccc(-c3ccccc3)c2C)cc(C)c1CN1CCCCC1C(=O)O] | 1-({2,6-dimethyl-4-[(2-methyl-3-phenylphenyl)methoxy]phenyl}methyl)piperidine-2-carboxylic acid | 4.2 M | 444.6 | — |
| 42 | 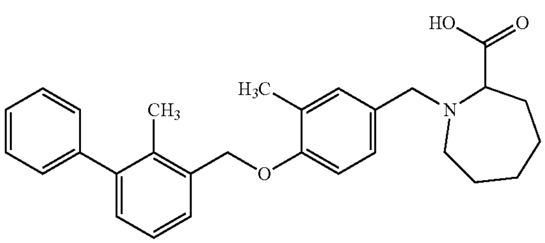 [SMILES: Cc1cc(CN2CCCCCC2C(=O)O)ccc1OCc1cccc(-c2ccccc2)c1C] | 1-({3-methyl-4-[(2-methyl-3-phenylphenyl)methoxy]phenyl}methyl)azepane-2-carboxylic acid | 4.2 M | 444.4 | — |
| 43 | 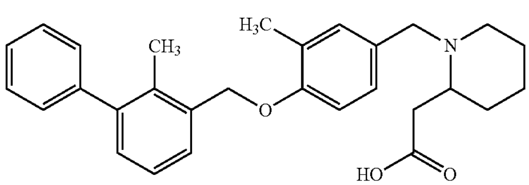 [SMILES: Cc1cc(CN2CCCCC2CC(=O)O)ccc1OCc1cccc(-c2ccccc2)c1C] | 2-[1-({3-methyl-4-[(2-methyl-3-phenylphenyl)methoxy]phenyl}methyl)piperidin-2-yl]acetic acid | 4.1 M | 444.4 | — |
| 44 | 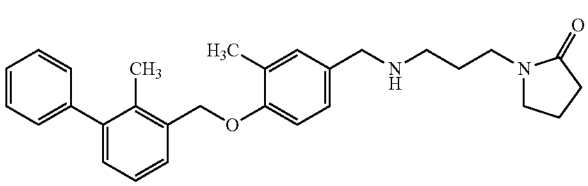 [SMILES: Cc1cc(CNCCCN2CCCC2=O)ccc1OCc1cccc(-c2ccccc2)c1C] | 1-{3-[({3-methyl-4-[(2-methyl-3-phenylphenyl)methoxy]phenyl}methyl)amino]propyl}pyrrolidin-2-one | 4.1 M | 443.3 | — |
| 45 | 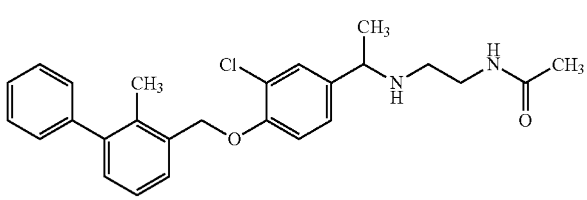 [SMILES: CC(=O)NCCNC(C)c1ccc(OCc2cccc(-c3ccccc3)c2C)c(Cl)c1] | N-{2-[(1-{3-chloro-4-[(2-methyl-3-phenylphenyl)methoxy]phenyl}ethyl)amino]ethyl}acetamide | 2.7 A | 427.2 | — |

-continued

| Ex. No. | Structure | Name | HPLC Retention Time (minutes) (Method) | ESI-MS m/z MH+ | ESI-MS m/z MH− |
|---|---|---|---|---|---|
| 46 | 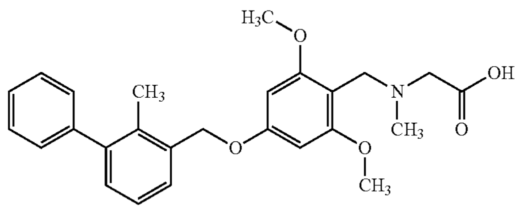 [SMILES: COc1cc(OCc2cccc(-c3ccccc3)c2C)cc(OC)c1CN(C)CC(=O)O] | 2-[({2,6-dimethoxy-4-[(2-methyl-3-phenylphenyl)methoxy]phenyl}methyl)(methyl)amino]acetic acid | 2.6 A | 436.4 | — |
| 47 | 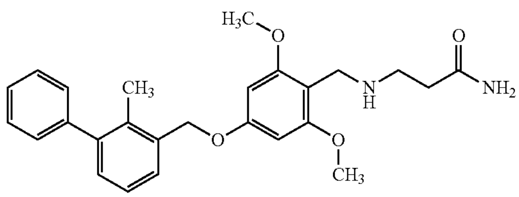 [SMILES: COc1cc(OCc2cccc(-c3ccccc3)c2C)cc(OC)c1CNCCC(N)=O] | 3-[({2,6-dimethoxy-4-[(2-methyl-3-phenylphenyl)methoxy]phenyl}methyl)amino]propanamide | 2.7 A | 435.4 | — |
| 48 | 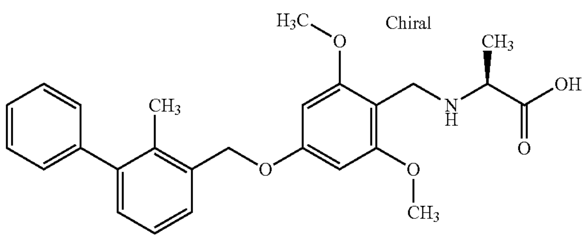 [SMILES: COc1cc(OCc2cccc(-c3ccccc3)c2C)cc(OC)c1CN[C@@H](C)C(=O)O] | (2S)-2-[({2,6-dimethoxy-4-[(2-methyl-3-phenylphenyl)methoxy]phenyl}methyl)amino]propanoic acid | 4.1 M | 434.5 | — |
| 49 | 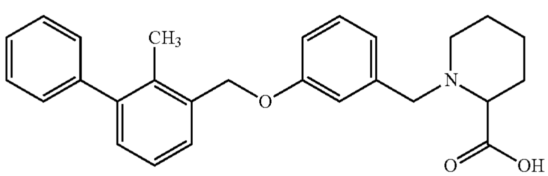 [SMILES: Cc1c(COc2cccc(CN3CCCCC3C(=O)O)c2)cccc1-c1ccccc1] | 1-({3-[(2-methyl-3-phenylphenyl)methoxy]phenyl}methyl)piperidine-2-carboxylic acid | 4.1 M | 434.5 | — |
| 50 | 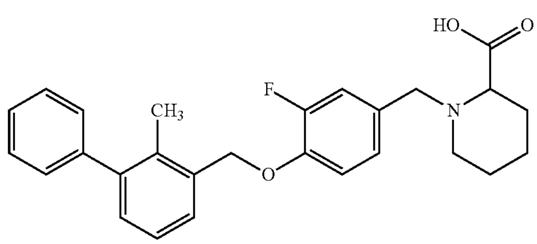 [SMILES: Cc1c(COc2ccc(CN3CCCCC3C(=O)O)cc2F)cccc1-c1ccccc1] | 1-({3-fluoro-4-[(2-methyl-3-phenylphenyl)methoxy]phenyl}methyl)piperidine-2-carboxylic acid | 4.0 M | 434.4 | — |
| 51 | 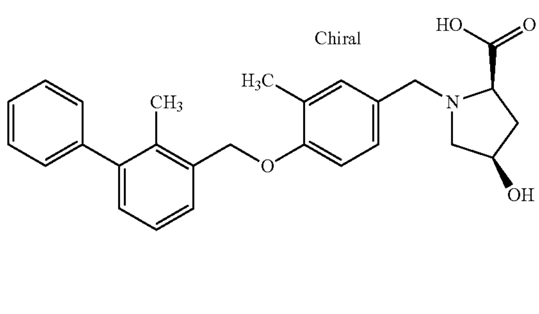 [SMILES: Cc1cc(CN2C[C@H](O)C[C@@H]2C(=O)O)ccc1OCc1cccc(-c2ccccc2)c1C] | (2R,4R)-4-hydroxy-1-({3-methyl-4-[(2-methyl-3-phenylphenyl)methoxy]phenyl}methyl)pyrrolidine-2-carboxylic acid | 4.0 M | 432.3 | — |

-continued

| Ex. No. | Structure | Name | HPLC Retention Time (minutes) (Method) | ESI-MS m/z MH+ | ESI-MS m/z MH− |
|---|---|---|---|---|---|
| 52 | 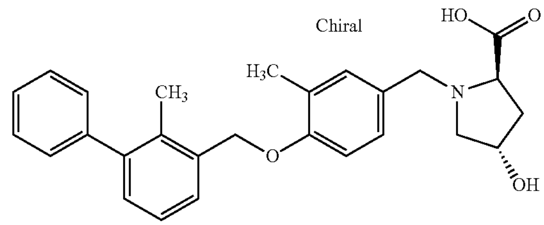 [SMILES: Cc1cc(CN2C[C@@H](O)C[C@@H]2C(=O)O)ccc1OCc1cccc(-c2ccccc2)c1C] | (2R,4S)-4-hydroxy-1-({3-methyl-4-[(2-methyl-3-phenylphenyl)methoxy]phenyl}methyl)pyrrolidine-2-carboxylic acid | 4.0 M | 432.3 | — |
| 53 | 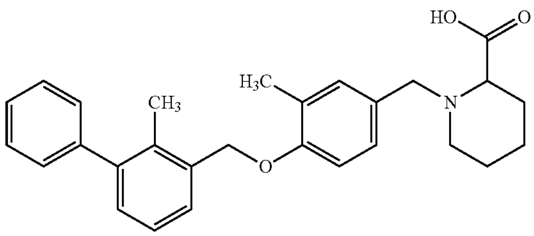 | 1-({3-methyl-4-[(2-methyl-3-phenylphenyl)methoxy]phenyl}methyl)piperidine-2-carboxylic acid | 4.2 M | 430.4 | — |
| 54 | 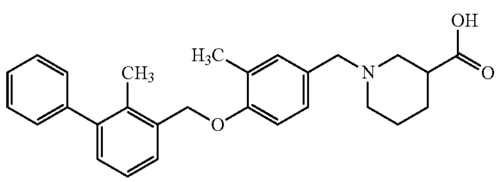 [SMILES: Cc1cc(CN2CCCC(C(=O)O)C2)ccc1OCc1cccc(-c2ccccc2)c1C] | 1-({3-methyl-4-[(2-methyl-3-phenylphenyl)methoxy]phenyl}methyl)piperidine-3-carboxylic acid | 4.1 M | 430.4 | — |
| 55 | 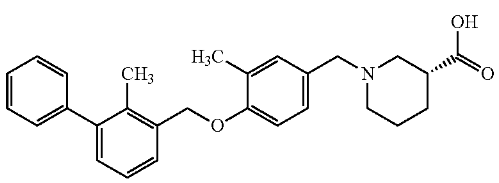 [SMILES: Cc1cc(CN2CCC[C@@H](C(=O)O)C2)ccc1OCc1cccc(-c2ccccc2)c1C] | (3R)-1-({3-methyl-4-[(2-methyl-3-phenylphenyl)methoxy]phenyl[methyl)piperidine-3-carboxylic acid | 4.1 M | 430.4 | — |
| 56 | 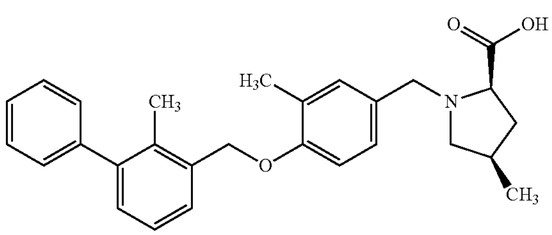 [SMILES: Cc1cc(CN2C[C@H](C)C[C@@H]2C(=O)O)ccc1OCc1cccc(-c2ccccc2)c1C] | (2R,4R)-4-methyl-1-({3-methyl-4-[(2-methyl-3-phenylphenyl)methoxy]phenyl}methyl)pyrrolidine-2-carboxylic acid | 4.2 M | 430.4 | — |
| 57 | 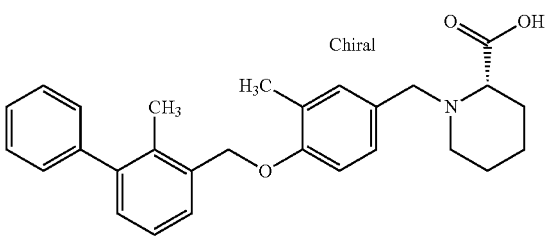 [SMILES: Cc1cc(CN2CCCC[C@H]2C(=O)O)ccc1OCc1cccc(-c2ccccc2)c1C] | (2S)-1-({3-methyl-4-[(2-methyl-3-phenylphenyl)methoxy]phenyl}methyl)piperidine-2-carboxylic acid | 2.7 A | 430.4 | 428.5 |
| 58 | 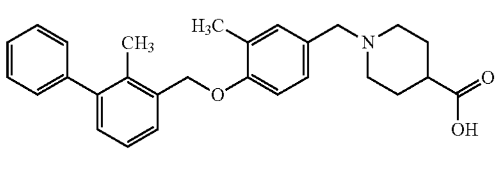 [SMILES: Cc1cc(CN2CCC(C(=O)O)CC2)ccc1OCc1cccc(-c2ccccc2)c1C] | 1-({3-methyl-4-[(2-methyl-3-phenylphenyl)methoxy]phenyl}methyl)piperidine-4-carboxylic acid | 2.7 A | 430.4 | 428.5 |

-continued

| Ex. No. | Name | HPLC Retention Time (minutes) (Method) | ESI-MS m/z MH+ | ESI-MS m/z MH− |
|---|---|---|---|---|
| 59 | (2R)-1-({3-methyl-4-[(2-methyl-3-phenylphenyl)methoxy]phenyl}methyl)piperidine-2-carboxylic acid | 2.7 A | 430.4 | 428.5 |
| 60 | (2S)-1-({4-methyl-3-[(2-methyl-3-phenylphenyl)methoxy)phenyl}methyl)piperidine-2-carboxylic acid | 2.7 A | 430.4 | 428.5 |
| 61 | 1-{3-[({3-[(2-methyl-3-phenylphenyl)methoxy]phenyl}methyl)amino]propyl}pyrrolidin-2-one | 4.1 M | 429.5 | — |
| 62 | N-[2-({5-[(2-methyl-3-phenylphenyl)methoxy]-1,2,3,4-tetrahydronaphthalen-1-yl}amino)ethyl]acetamide | 2.9 A | 429.4 | — |
| 63 | N-[2-({6-[(2-methyl-3-phenylphenyl)methoxy]-1,2,3,4-tetrahydronaphthalen-1-yl}amino)ethyl]acetamide | 2.9 A | 429.4 | — |
| 64 | 1-({3-methyl-4-[(2-methyl-3-phenylphenyl)methoxy)phenyl}methyl)-1,2,5,6-tetrahydropyridine-3-carboxylic acid | 4.1 M | 428.4 | — |
| 65 | 2-[({3-chloro-4-[(2-methyl-3-phenylphenyl)methoxy]phenyl}methyl)amino]-2-methylpropanoic acid | 2.7 A | 424.3 | 422.3 |

-continued

| Ex. No. | Structure | Name | HPLC Retention Time (minutes) (Method) | ESI-MS m/z MH+ | ESI-MS m/z MH− |
|---|---|---|---|---|---|
| 66 | 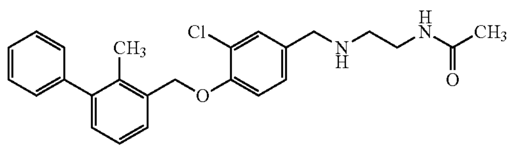 [SMILES: CC(=O)NCCNCc1ccc(OCc2cccc(-c3ccccc3)c2C)c(Cl)c1] | N-{2-[({3-chloro-4-[(2-methyl-3-phenylphenyl)methoxy]phenyl}methyl)amino]ethyl}acetamide | 4.2 M | 423.4 | 421.0 |
| 67 | 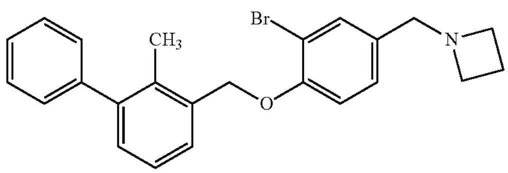 | 1-({3-bromo-4-[(2-methyl-3-phenylphenyl)methoxy]phenyl}methyl)azetidine | 4.4 M | 422.4 | — |
| 68 | 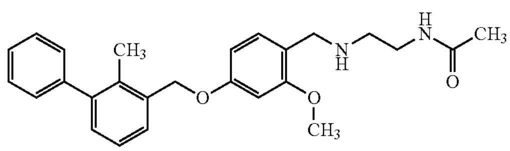 [SMILES: COc1cc(OCc2cccc(-c3ccccc3)c2C)ccc1CNCCNC(C)=O] | N-{2-[({2-methoxy-4-[(2-methyl-3-phenylphenyl)methoxy]phenyl}methyl)amino]ethyl}acetamide | 4.0 M | 419.5 | — |
| 69 | 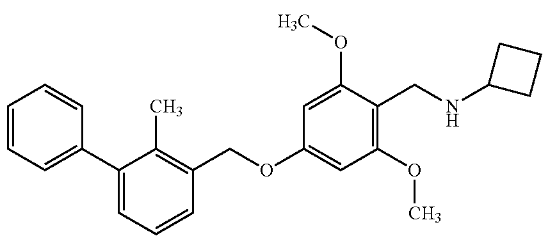 [SMILES: COc1cc(OCc2cccc(-c3ccccc3)c2C)cc(OC)c1CNC1CCC1] | N-({2,6-dimethoxy-4-[(2-methyl-3-phenylphenyl)methoxy]phenyl}methyl)cyclobutanamine | 4.1 M | 418.2 | — |
| 70 | 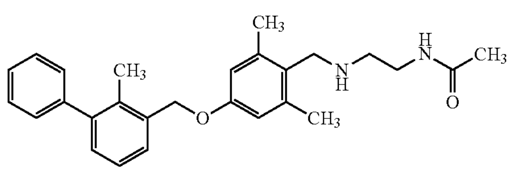 [SMILES: CC(=O)NCCNCc1c(C)cc(OCc2cccc(-c3ccccc3)c2C)cc1C] | N-{2-[({2,6-dimethyl-4-[(2-methyl-3-phenylphenyl)methoxy]phenyl}methyl)amino]ethyl}acetamide | 2.8 A | 417.5 | — |
| 71 | 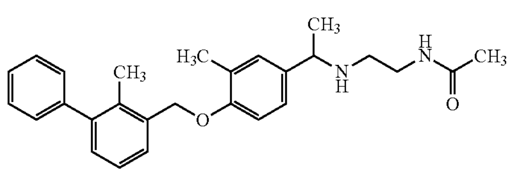 [SMILES: CC(=O)NCCNC(C)c1ccc(OCc2cccc(-c3ccccc3)c2C)c(C)c1] | N-{2-[(1-{3-methyl-4-[(2-methyl-3-phenylphenyl)methoxy]phenyl}ethyl)amino]ethyl}acetamide | 2.7 A | 417.3 | — |
| 72 | 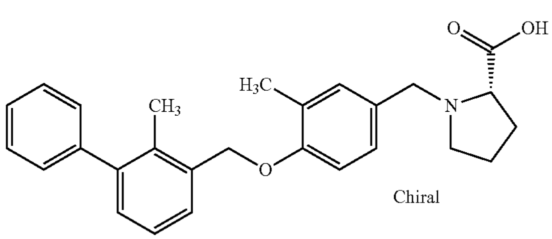 [SMILES: Cc1cc(CN2CCC[C@H]2C(=O)O)ccc1OCc1cccc(-c2ccccc2)c1C] | (2S)-1-({3-methyl-4-[(2-methyl-3-phenylphenyl)methoxy]phenyl}methyl)pyrrolidine-2-carboxylic acid | 4.0 M | 416.4 | — |

| Ex. No. | Structure | Name | HPLC Retention Time (minutes) (Method) | ESI-MS m/z MH+ | ESI-MS m/z MH− |
|---|---|---|---|---|---|
| 73 | 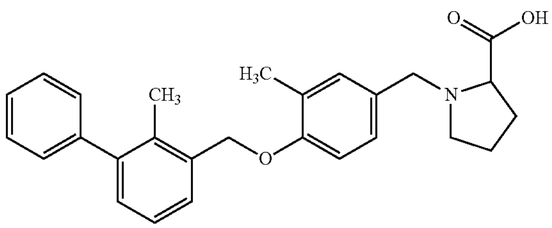 [SMILES: Cc1cc(CN2CCCC2C(=O)O)ccc1OCc1cccc(-c2ccccc2)c1C] | 1-({3-methyl-4-[(2-methyl-3-phenylphenyl)methoxy)phenyl}methyl)pyrrolidine-2-carboxylic acid | 4.0 M | 416.4 | — |
| 74 | 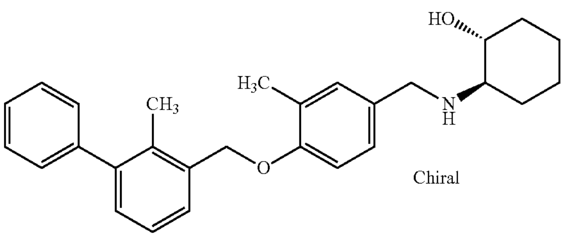 [SMILES: Cc1cc(CN[C@@H]2CCCC[C@H]2O)ccc1OCc1cccc(-c2ccccc2)c1C] | (1R,2R)-2-[({3-methyl-4-[(2-methyl-3-phenylphenyl)methoxy]phenyl}methyl)amino]cyclohexan-1-ol | 4.2 M | 416.4 | — |
| 75 | 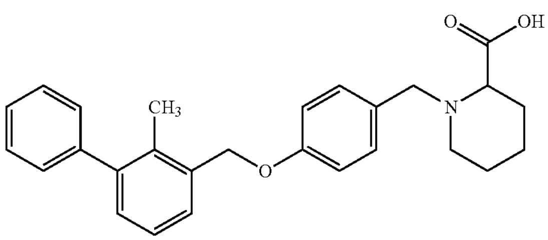 [SMILES: Cc1c(COc2ccc(CN3CCCCC3C(=O)O)cc2)cccc1-c1ccccc1] | 1-({4-[(2-methyl-3-phenylphenyl)methoxy]phenyl}methyl)piperidine-2-carboxylic acid | 4.2 M | 416.4 | — |
| 76 | 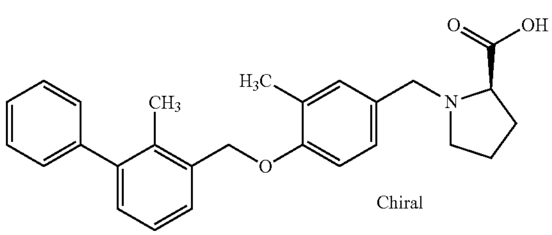 [SMILES: Cc1cc(CN2CCC[C@@H]2C(=O)O)ccc1OCc1cccc(-c2ccccc2)c1C] | (2R)-1-({3-methyl-4-[(2-methyl-3-phenylphenyl)methoxy]phenyl}methyl)pyrrolidine-2-carboxylic acid | 4.1 M | 416.3 | — |
| 77 | 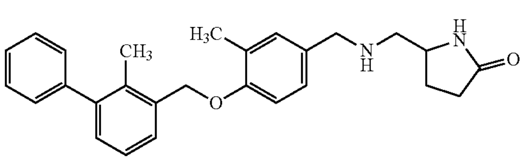 [SMILES: Cc1cc(CNCC2CCC(=O)N2)ccc1OCc1cccc(-c2ccccc2)c1C] | 5-{[({3-methyl-4-[(2-methyl-3-phenylphenyl)methoxy]phenyl}methyl)amino]methyl}pyrrolidin-2-one | 4.3 M | 415.3 | — |
| 78 | 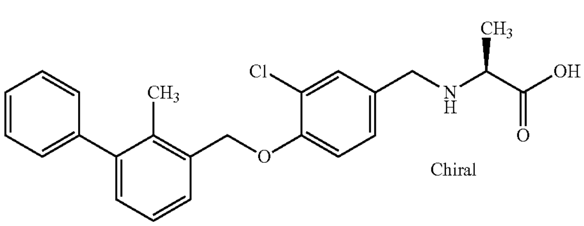 [SMILES: Cc1c(COc2ccc(CN[C@@H](C)C(=O)O)cc2Cl)cccc1-c1ccccc1] | (2S)-2-[({3-chloro-4-[(2-methyl-3-phenylphenyl)methoxy]phenyl}methyl)amino]propanoic acid | 4.1 M | 410.2 | — |

-continued

| Ex. No. | Name | HPLC Retention Time (minutes) (Method) | ESI-MS m/z MH+ | ESI-MS m/z MH− |
|---|---|---|---|---|
| 79 | (2R)-2-[({3-chloro-4-[(2-methyl-3-phenylphenyl)methoxy]phenyl}methyl)amino]propanoic acid | 2.6 | 410.3 | 408.4 |
| 80 | N-{2-[({3-fluoro-4-[(2-methyl-3-phenylphenyl)methoxy]phenyl}methyl)amino]ethyl}acetamide | 3.68 M | 407.5 | — |
| 81 | (2S)-2-[({2-methoxy-4-[(2-methyl-3-phenylphenyl)methoxy]phenyl}methyl)amino]propanoic acid | 4.0 M | 406.4 | — |
| 82 | (2S)-2-[({3-[(2-methyl-3-phenylphenyl)methoxy]phenyl}methyl)amino]propanoic acid | 4.0 M | 406.4 | — |
| 83 | 3-[({2-methoxy-4-[(2-methyl-3-phenylphenyl)methoxy]phenyl}methyl)amino]propanamide | 2.6 A | 405.5 | — |
| 84 | 1-({2,6-dimethoxy-4-[(2-methyl-3-phenylphenyl)methoxy]phenyl}methyl) azetidine | 2.8 A | 404.5 | — |
| 85 | 3-[({3-methyl-4-[(2-methyl-3-phenylphenyl)methoxy]phenyl}methyl)amino]butanoic acid | 4.0 M | 404.3 | — |

-continued

| Ex. No. | Structure | Name | HPLC Retention Time (minutes) (Method) | ESI-MS m/z MH+ | ESI-MS m/z MH− |
|---|---|---|---|---|---|
| 86 | 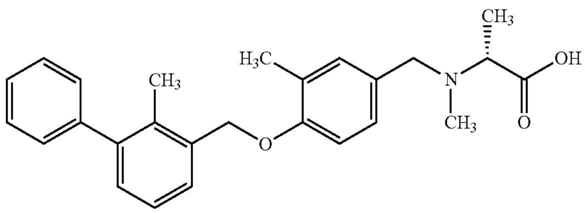 [SMILES: Cc1cc(CN(C)[C@H](C)C(=O)O)ccc1OCc1cccc(-c2ccccc2)c1C] | (2R)-2-[methyl({3-methyl-4-[(2-methyl-3-phenylphenyl)methoxy]phenyl}methyl)amino]propanoic acid | 4.1 M | 404.3 | — |
| 87 | 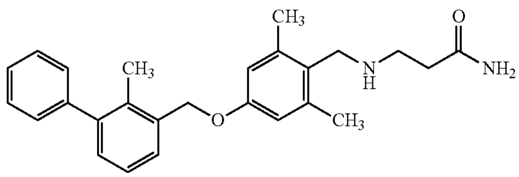 [SMILES: Cc1cc(OCc2cccc(-c3ccccc3)c2C)cc(C)c1CNCCC(N)=O] | 3-[({2,6-dimethyl-4-[(2-methyl-3-phenylphenyl)methoxy]phenyl}methyl)amino]propanamide | 2.7 A | 403.5 | — |
| 88 | 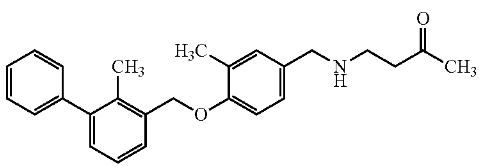 [SMILES: CC(=O)CCNCc1ccc(OCc2cccc(-c3ccccc3)c2C)c(C)c1] | N-{2-[({3-methyl-4-[(2-methyl-3-phenylphenyl)methoxy]phenyl}methyl)amino]ethyl}acetamide | 2.7 A | 403.5 | — |
| 89 | 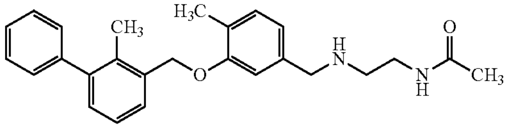 [SMILES: CC(=O)NCCNCc1ccc(C)c(OCc2cccc(-c3ccccc3)c2C)c1] | N-{2-[({4-methyl-3-[(2-methyl-3-phenylphenyl)methoxy]phenyl}methyl)amino]ethyl}acetamide | 2.8 A | 403.4 | — |
| 90 | 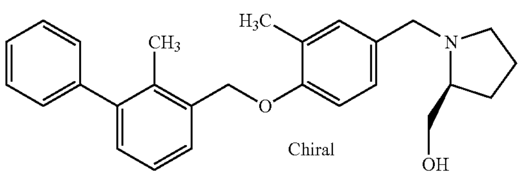 [SMILES: Cc1cc(CN2CCC[C@H]2CO)ccc1OCc1cccc(-c2ccccc2)c1C] | [(2S)-1-({3-methyl-4-[(2-methyl-3-phenylphenyl)methoxy]phenyl}methyl) pyrrolidin-2-yl]methanol | 4.2 M | 402.4 | — |
| 91 | 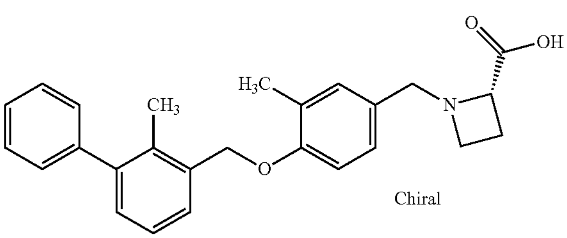 [SMILES: Cc1cc(CN2CC[C@H]2C(=O)O)ccc1OCc1cccc(-c2ccccc2)c1C] | (2S)-1-({3-methyl-4-[(2-methyl-3-phenylphenyl)methoxy]phenyl}methyl)azetidine-2-carboxylic acid | 4.0 M | 402.3 | — |
| 92 | 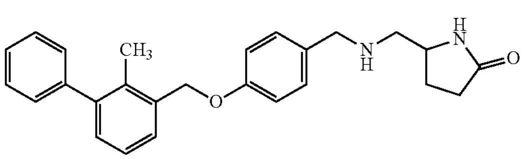 [SMILES: Cc1c(COc2ccc(CNCC3CCC(=O)N3)cc2)cccc1-c1ccccc1] | 5-{[({4-[(2-methyl-3-phenylphenyl)methoxy]phenyl}methyl)amino]methyl}pyrrolidin-2-one | 4.1 M | 401.5 | — |
| 93 | 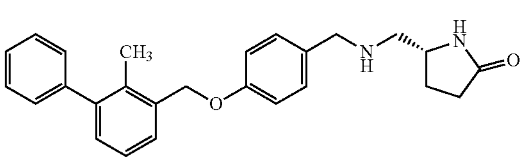 [SMILES: Cc1c(COc2ccc(CNC[C@H]3CCC(=O)N3)cc2)cccc1-c1ccccc1] | 5-{[({4-[(2-methyl-3-phenylphenyl)methoxy]phenyl}methyl)amino]methyl}pyrrolidin-2-one | 4.1 M | 401.5 | 399.5 |

-continued

| Ex. No. | Structure | Name | HPLC Retention Time (minutes) (Method) | ESI-MS m/z MH+ | ESI-MS m/z MH− |
|---|---|---|---|---|---|
| 94 | 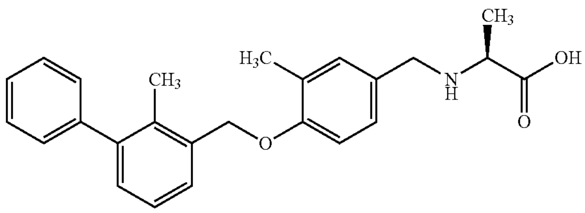 | (2S)-2-[({3-methyl-4-[(2-methyl-3-phenylphenyl)methoxy) phenyl}methyl)amino] propanoic acid | 4.1 M | 390.4 | — |
| 95 | 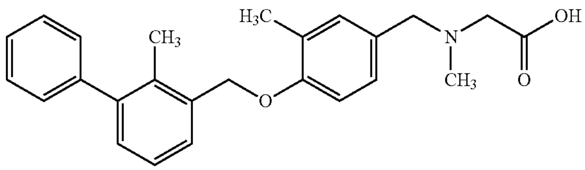 [SMILES: Cc1cc(CN(C)CC(=O)O)ccc1OCc1cccc(-c2ccccc2)c1C] | 2-[methyl({3-methyl-4-[(2-methyl-3-phenylphenyl) methoxy]phenyl}methyl)amino] acetic acid | 4.0 M | 390.3 | — |
| 96 | 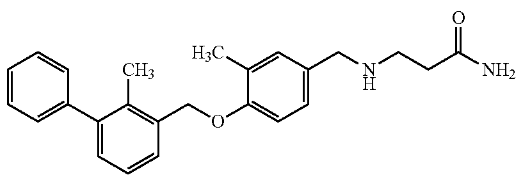 [SMILES: Cc1cc(CNCCC(N)=O)ccc1OCc1cccc(-c2ccccc2)c1C] | 3-[({3-methyl-4-[(2-methyl-3-phenylphenyl)methoxy]phenyl} methyl)amino] propanamide | 4.1 M | 389.4 | — |
| 97 | 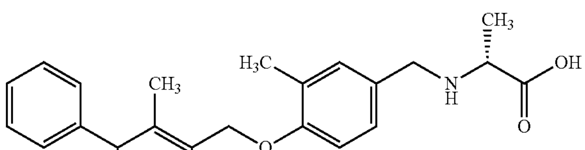 | (2R)-2-[({3-methyl-4-[(2-methyl-3-phenylphenyl) methoxy]phenyl}methyl)amino] propanoic acid | 4.1 M | 390.4 | — |
| 98 | 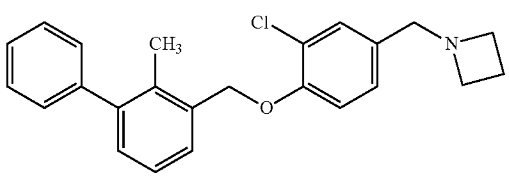 [SMILES: Cc1c(COc2ccc(CN3CCC3)cc2Cl)cccc1-c1ccccc1] | 1-({3-chloro-4-[(2-methyl-3-phenylphenyl)methoxy)phenyl} methyl)azetidine | 4.3 M | 378.3 | — |
| 99 | 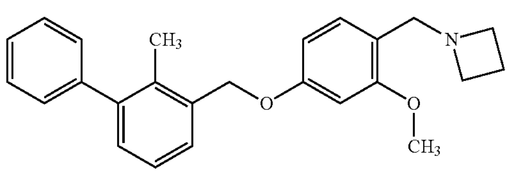 [SMILES: COc1cc(OCc2cccc(-c3ccccc3)c2C)ccc1CN1CCC1] | 1-({2-methoxy-4-[(2-methyl-3-phenylphenyl)methoxy]phenyl} methyl)azetidine | 2.7 A | 374.5 | — |
| 100 | 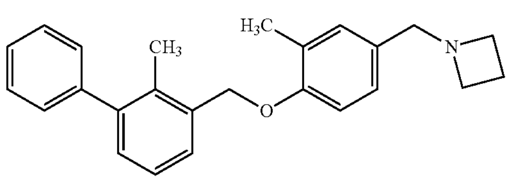 | 1-({3-methyl-4-[(2-methyl-3-phenylphenyl)methoxy]phenyl} methyl)azetidine | 2.8 A | 358.4 | — |
| 101 | 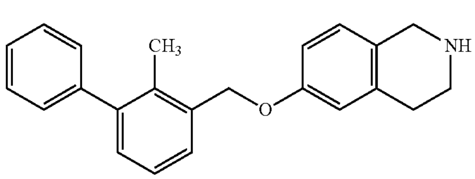 [SMILES: Cc1c(COc2ccc3c(c2)CCNC3)cccc1-c1ccccc1] | 6-[(2-methyl-3-phenylphenyl) methoxy]-1,2,3,4-tetrahydroisoquinoline | 2.6 A | 330.0 | 328 |

-continued

| Ex. No. | Structure | Name | HPLC Retention Time (minutes) (Method) | ESI-MS m/z MH+ | ESI-MS m/z MH− |
|---|---|---|---|---|---|
| 102 | 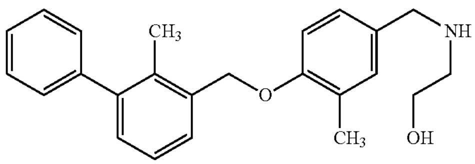 [SMILES: Cc1cc(CNCCO)ccc1OCc1cccc(-c2ccccc2)c1C] | 2-[({3-methyl-4-[(2-methyl-3-phenylphenyl)methoxy)phenyl}methyl)amino]ethan-1-ol | 2.8 A | 362.2 | 360.2 |
| 103 | 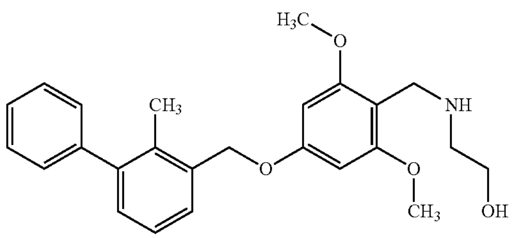 [SMILES: COc1cc(OCc2cccc(-c3ccccc3)c2C)cc(OC)c1CNCCO] | 2-[({2,6-dimethoxy-4-[(2-methyl-3-phenylphenyl)methoxy]phenyl}methyl)amino]ethan-1-ol | 2.7 A | 408.2 | 406.2 |
| 104 | 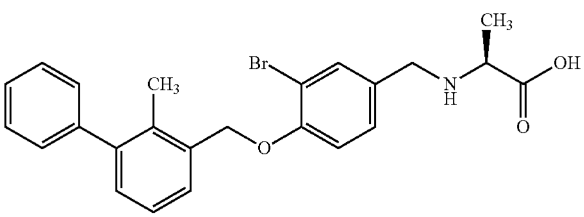 [SMILES: Cc1c(COc2ccc(CN[C@@H](C)C(=O)O)cc2Br)cccc1-c1ccccc1] | (2S)-2-[({3-bromo-4-[(2-methyl-3-phenylphenyl)methoxy]phenyl}methyl)amino]propanoic acid | 4.1 M | — | 452.4 |
| 105 | 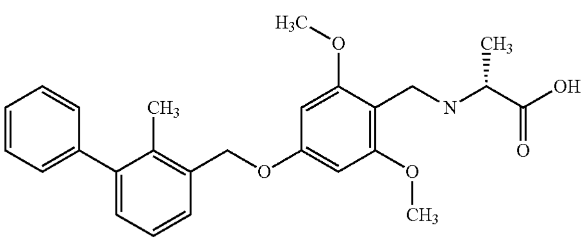 [SMILES: COc1cc(OCc2cccc(-c3ccccc3)c2C)cc(OC)c1CN[C@H](C)C(=O)O] | (2R)-2-[({2,6-dimethoxy-4-[(2-methyl-3-phenylphenyl)methoxy]phenyl}methyl)amino]propanoic acid | 2.7 A | 436.2 | 434.2 |
| 106 | 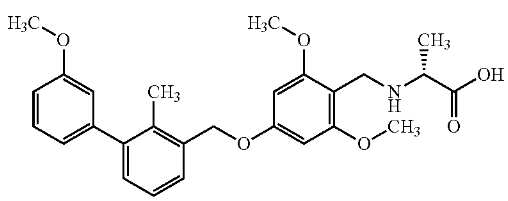 [SMILES: COc1cccc(-c2cccc(COc3cc(OC)c(CN[C@H](C)C(=O)O)c(OC)c3)c2C)c1] | (2R)-2-{[(2,6-dimethoxy-4-{[3-(3-methoxyphenyl)-2-methylphenyl]methoxy}phenyl)methyl]amino}propanoic acid | 2.7 A | 931.4 | — |
| 107 | 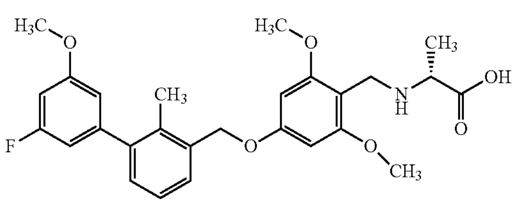 [SMILES: COc1cc(F)cc(-c2cccc(COc3cc(OC)c(CN[C@H](C)C(=O)O)c(OC)c3)c2C)c1] | (2R)-2-{[(4-{[3-(3-fluoro-5-methoxyphenyl)-2-methylphenyl]methoxy}-2,6-dimethoxyphenyl)methyl]amino}propanoic acid | 2.5 A | 484.5 | — |
| 108 | 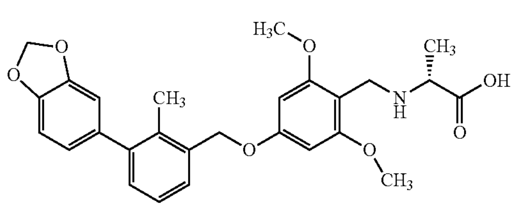 [SMILES: COc1cc(OCc2cccc(-c3ccc4c(c3)OCO4)c2C)cc(OC)c1CN[C@H](C)C(=O)O] | (2R)-2-{[(4-{[3-(2H-1,3-benzodioxol-5-yl)-2-methylphenyl]methoxy}-2,6-dimethoxyphenyl)methyl]amino}propanoic acid | 2.4 A | 502.4 | — |

-continued

| Ex. No. | Structure | Name | HPLC Retention Time (minutes) (Method) | ESI-MS m/z MH+ | ESI-MS m/z MH− |
|---|---|---|---|---|---|
| 109 | 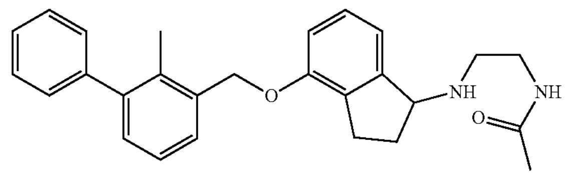 [SMILES: CC(=O)NCCNC1CCc2c(OCc3cccc(-c4ccccc4)c3C)cccc21] | N-[2-({4-[(2-methyl-3-phenylphenyl)methoxy]-2,3-dihydro-1H-inden-1-yl}amino)ethyl]acetamide | 2.6 A | 415.3 | — |
| 110 | 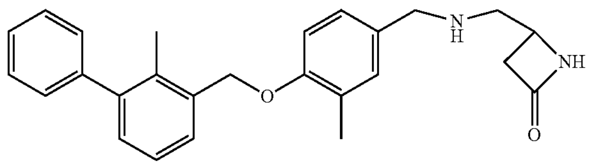 [SMILES: Cc1cc(CNCC2CC(=O)N2)ccc1OCc1cccc(-c2ccccc2)c1C] | 4-{[({3-methyl-4-[(2-methyl-3-phenylphenyl)methoxy]phenyl}methyl)amino)methyl]azetidin-2-one | 3.0 A | — | 399.4 |
| 111 | 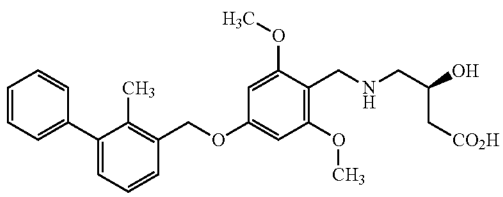 [SMILES: COc1cc(OCc2cccc(-c3ccccc3)c2C)cc(OC)c1CNC[C@@H](O)CC(=O)O] | (3S)-4-[({2,6-dimethoxy-4-[(2-methyl-3-phenylphenyl)methoxy]phenyl}methyl)amino]-3-hydroxybutanoic acid | 2.0 A | 466.4 | 464.4 |
| 112 | 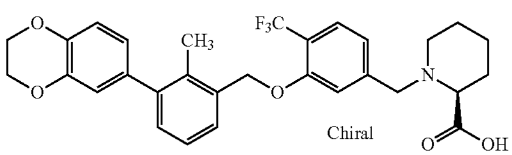 [SMILES: Cc1c(COc2cc(CN3CCCC[C@H]3C(=O)O)ccc2C(F)(F)F)cccc1-c1ccc2c(c1)OCCO2] | (2S)-1-[(4-{[3-(2,3-dihydro-1,4-benzodioxin-6-yl)-2-methylphenyl]methoxy}-3-(trifluoromethyl)phenyl)methyl]piperidine-2-carboxylic acid | 1.8 A | 542.4 | 540.4 |
| 113 | 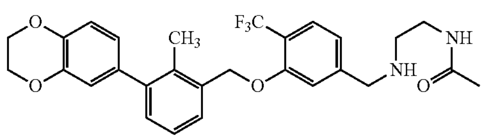 [SMILES: CC(=O)NCCNCc1ccc(C(F)(F)F)c(OCc2cccc(-c3ccc4c(c3)OCCO4)c2C)c1] | N-(2-{[(4-{[3-(2,3-dihydro-1,4-benzodioxin-6-yl)-2-methylphenyl]methoxy}-3-(trifluoromethyl)phenyl)methyl]amino}ethyl)acetamide | 1.9 A | 515.3 | — |
| 114 | 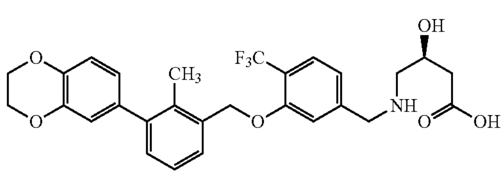 [SMILES: Cc1c(COc2cc(CNC[C@@H](O)CC(=O)O)ccc2C(F)(F)F)cccc1-c1ccc2c(c1)OCCO2] | (3S)-4-{[(4-{[3-(2,3-dihydro-1,4-benzodioxin-6-yl)-2-methylphenyl]methoxy}-3-(trifluoromethyl)phenyl)methyl]amino}-3-hydroxybutanoic acid | 2.0 A | 532.3 | 530.3 |
| 115 | 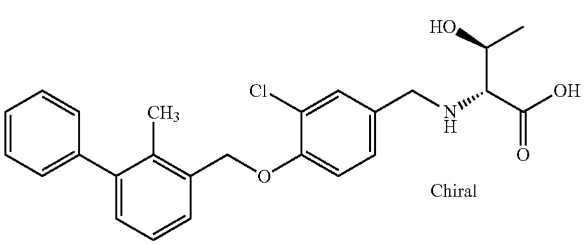 [SMILES: Cc1c(COc2ccc(CN[C@@H](C(=O)O)[C@H](C)O)cc2Cl)cccc1-c1ccccc1] | (2R,3S)-2-[({3-chloro-4-[(2-methyl-3-phenylphenyl)methoxy]phenyl}methyl)amino]-3-hydroxybutanoic acid | 1.8 A | 440.3 | 438.3 |
| 116 | 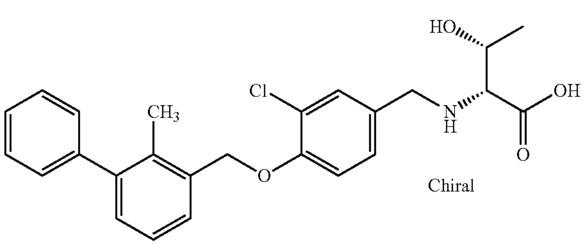 [SMILES: Cc1c(COc2ccc(CN[C@@H](C(=O)O)[C@@H](C)O)cc2Cl)cccc1-c1ccccc1] | (2R,3R)-2-[({3-chloro-4-[(2-methyl-3-phenylphenyl)methoxy]phenyl}methyl)amino]-3-hydroxybutanoic acid | 1.7 A | 440.2 | 438.2 |

-continued

| Ex. No. | Structure | Name | HPLC Retention Time (minutes) (Method) | ESI-MS m/z MH+ | ESI-MS m/z MH− |
|---|---|---|---|---|---|
| 117 | 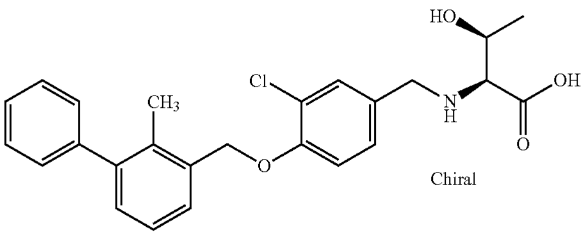 [SMILES: Cc1c(COc2ccc(CN[C@H](C(=O)O)[C@H](C)O)cc2Cl)cccc1-c1ccccc1] | (2S,3S)-2-[({3-chloro-4-[(2-methyl-3-phenylphenyl)methoxy]phenyl}methyl)amino]-3-hydroxybutanoic acid | 1.8 A | 440.2 | 438.3 |
| 118 | 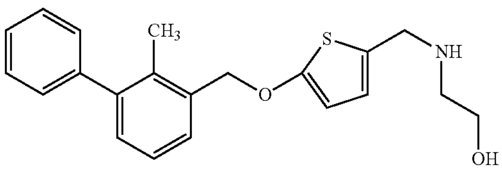 [SMILES: Cc1c(COc2ccc(CNCCO)s2)cccc1-c1ccccc1] | 2-[({5-[(2-methyl-3-phenylphenyl)methoxy]thiophen-2-yl}methyl)amino]ethan-1-ol | 2.4 AA | 354.2 | — |
| 119 | 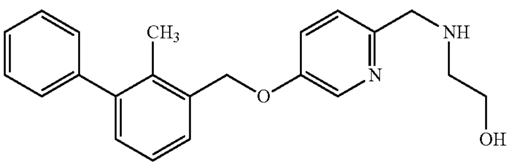 [SMILES: Cc1c(COc2ccc(CNCCO)nc2)cccc1-c1ccccc1] | 2-[({5-[(2-methyl-3-phenylphenyl)methoxy]pyridin-2-yl}methyl)amino]ethan-1-ol | 1.5 AA | 349.0 | |
| 120 | 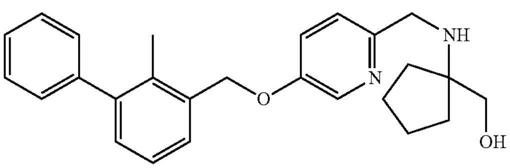 [SMILES: Cc1c(COc2ccc(CNC3(CO)CCCC3)nc2)cccc1-c1ccccc1] | {1-[({5-[(2-methyl-3-phenylphenyl)methoxy]pyridin-2-yl}methyl)amino]cyclopentyl}methanol | 1.7 AA | 403.2 | |
| 121 | 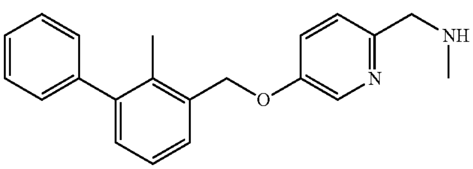 [SMILES: CNCc1ccc(OCc2cccc(-c3ccccc3)c2C)cn1] | methyl({5-[(2-methyl-3-phenylphenyl)methoxy]pyridin-2-yl}methyl)amine | 1.5 AA | 319.0 | |
| 122 | 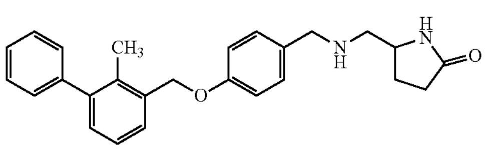 [SMILES: Cc1c(COc2ccc(CNCC3CCC(=O)N3)cc2)cccc1-c1ccccc1] | 5-{[({5-[(2-methyl-3-phenylphenyl)methoxy]pyridin-2-yl}methyl)amino]methyl}pyrrolidin-2-one | 1.6 AA | 402.2 | |
| 123 | 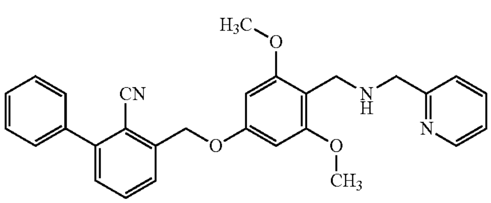 [SMILES: COc1cc(OCc2cccc(-c3ccccc3)c2C#N)cc(OC)c1CNCc1ccccn1] | 2-(3,5-dimethoxy-4-{[(pyridin-2-ylmethyl)amino]methyl}phenoxymethyl)-6-phenylbenzonitrile | 1.5 AT | 466.0 | |
| 124 | 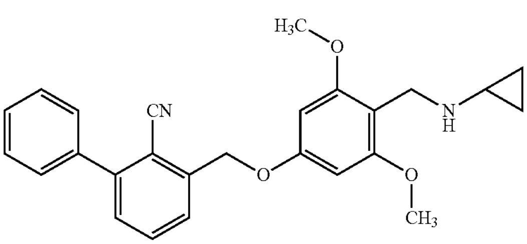 [SMILES: COc1cc(OCc2cccc(-c3ccccc3)c2C#N)cc(OC)c1CNC1CC1] | 2-{4-[(cyclopropylamino)methyl]-3,5-dimethoxyphenoxymethyl}-6-phenylbenzonitrile | 1.5 AT | 415.0 | |

-continued

| Ex. No. | Structure | Name | HPLC Retention Time (minutes) (Method) | ESI-MS m/z MH+ | ESI-MS m/z MH− |
|---|---|---|---|---|---|
| 125 | 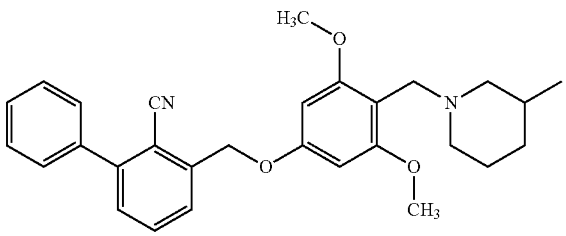 [SMILES: COc1cc(OCc2cccc(-c3ccccc3)c2C#N)cc(OC)c1CN1CCCC(C)C1] | 2-(3,5-dimethoxy-4-[(3-methylpiperidin-1-yl)methyl]phenoxymethyl}-6-phenylbenzonitrile | 1.7 AT | 457.2 | |
| 126 | 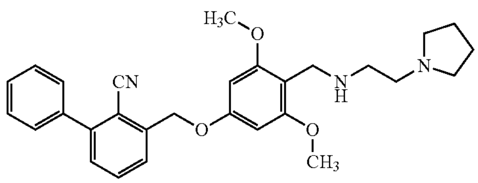 [SMILES: COc1cc(OCc2cccc(-c3ccccc3)c2C#N)cc(OC)c1CNCCN1CCCC1] | 2-[3,5-dimethoxy-4-({[2-(pyrrolidin-1-yl)ethyl]amino}methyl)phenoxymethyl]-6-phenylbenzonitrile | 1.2 AT | 472.2 | |
| 127 | 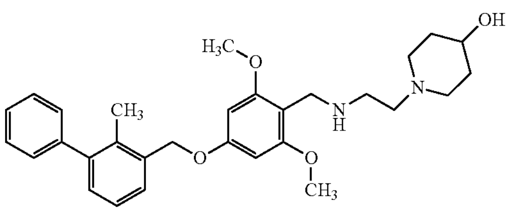 [SMILES: COc1cc(OCc2cccc(-c3ccccc3)c2C)cc(OC)c1CNCCN1CCC(O)CC1] | 2-{4-[(4-hydroxypiperidin-1-yl)methyl]-3,5-dimethoxyphenoxymethyl}-6-phenylbenzonitrile | 1.4 AT | 459.2 | |
| 128 | 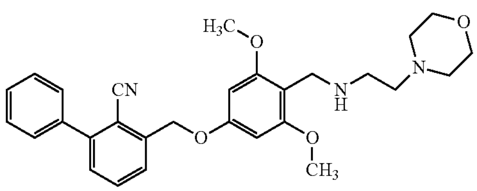 [SMILES: COc1cc(OCc2cccc(-c3ccccc3)c2C#N)cc(OC)c1CNCCN1CCOCC1] | 2-[3,5-dimethoxy-4-(morpholin-4-ylmethyl)phenoxymethyl]-6-phenylbenzonitrile | 1.4 AT | 445.2 | |
| 129 | 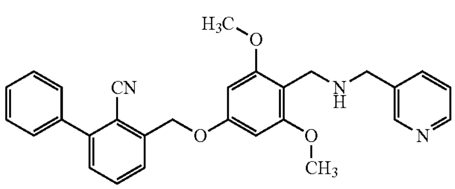 [SMILES: COc1cc(OCc2cccc(-c3ccccc3)c2C#N)cc(OC)c1CNCc1cccnc1] | 2-(3,5-dimethoxy-4-{[(pyridin-3-ylmethyl)amino]methyl}phenoxymethyl)-6-phenylbenzonitrile | 1.3 AT | 466.0 | |
| 130 | 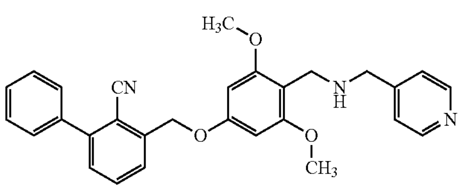 [SMILES: COc1cc(OCc2cccc(-c3ccccc3)c2C#N)cc(OC)c1CNCc1ccncc1] | 2-(3,5-dimethoxy-4-{[(pyridin-4-ylmethyl)amino]methyl}phenoxymethyl)-6-phenylbenzonitrile | 1.2 AT | 466.0 | |
| 131 | 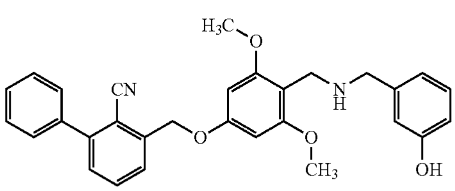 [SMILES: COc1cc(OCc2cccc(-c3ccccc3)c2C#N)cc(OC)c1CNCc1cccc(O)c1] | 2-[4-({[(3-hydroxyphenyl)methyl]amino}methyl)-3,5-dimethoxyphenoxymethyl]-6-phenylbenzonitrile | 1.5 AT | 481.0 | |

| Ex. No. | Structure | Name | HPLC Retention Time (minutes) (Method) | ESI-MS m/z MH+ | ESI-MS m/z MH− |
|---|---|---|---|---|---|
| 132 | 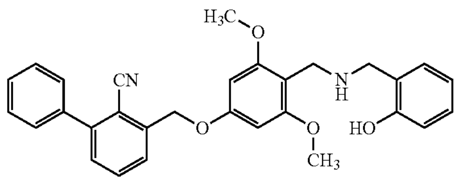 [SMILES: COc1cc(OCc2cccc(-c3ccccc3)c2C#N)cc(OC)c1CNCc1ccccc1O] | 2-[4-({[(2-hydroxyphenyl)methyl]amino}methyl)-3,5-dimethoxyphenoxymethyl]-6-phenylbenzonitrile | 1.6 AT | 481.0 | |
| 133 | 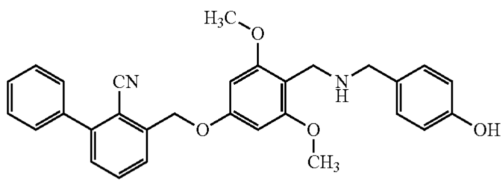 [SMILES: COc1cc(OCc2cccc(-c3ccccc3)c2C#N)cc(OC)c1CNCc1ccc(O)cc1] | 2-[4-({[(4-hydroxyphenyl)methyl]amino}methyl)-3,5-dimethoxyphenoxymethyl]-6-phenylbenzonitrile | 1.5 AT | 481.0 | |
| 134 | 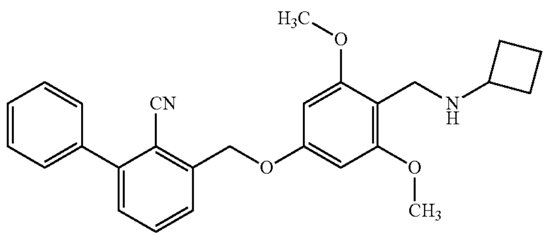 | 2-{4-[(cyclobutylamino)methyl]-3,5-dimethoxyphenoxymethyl}-6-phenylbenzonitrile | 1.6 AT | 429.0 | |
| 135 | 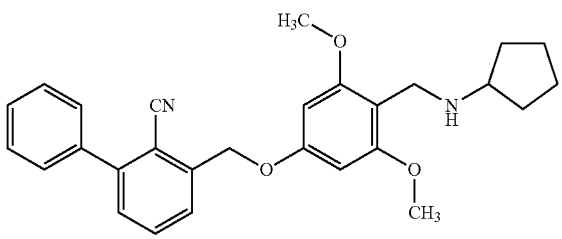 [SMILES: COc1cc(OCc2cccc(-c3ccccc3)c2C#N)cc(OC)c1CNC1CCCC1] | 2-{4-[(cyclopentylamino)methyl]-3,5-dimethoxyphenoxymethyl}-6-phenylbenzonitrile | 1.6 AT | 443.2 | |
| 136 | 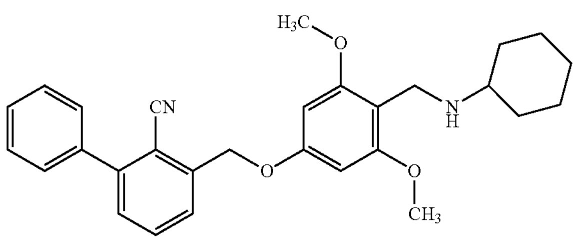 [SMILES: COc1cc(OCc2cccc(-c3ccccc3)c2C#N)cc(OC)c1CNC1CCCCC1] | 2-{4-[(cyclohexylamino)methyl]-3,5-dimethoxyphenoxymethyl}-6-phenylbenzonitrile | 1.7 AT | 457.2 | |
| 137 | 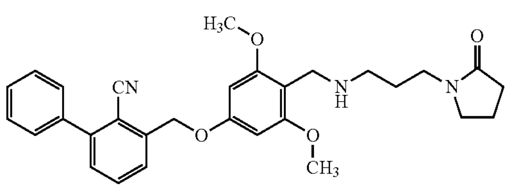 [SMILES: COc1cc(OCc2cccc(-c3ccccc3)c2C#N)cc(OC)c1CNCCCN1CCCC1=O] | 2-[3,5-dimethoxy-4-({[3-(2-oxopyrrolidin-1-yl)propyl]amino}methyl)phenoxymethyl]-6-phenylbenzonitrile | 1.4 AT | 500.2 | |
| 138 | 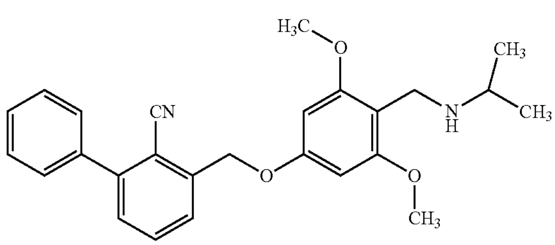 [SMILES: COc1cc(OCc2cccc(-c3ccccc3)c2C#N)cc(OC)c1CNC(C)C] | 2-(3,5-dimethoxy-4-({[(propan-2-yl)amino]methyl}phenoxymethyl)-6-phenylbenzonitrile | 1.5 AT | 417.0 | |

| Ex. No. | Structure | Name | HPLC Retention Time (minutes) (Method) | ESI-MS m/z MH+ | ESI-MS m/z MH− |
|---|---|---|---|---|---|
| 139 | 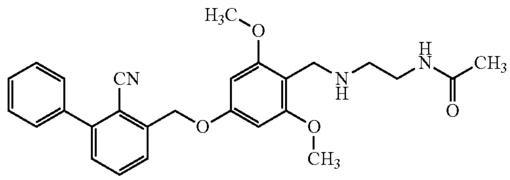 [SMILES: COc1cc(OCc2cccc(-c3ccccc3)c2C#N)cc(OC)c1CNCCNC(C)=O] | N-{2-[({4-[(2-cyano-3-phenylphenyl)methoxy]-2,6-dimethoxyphenyl}methyl)amino]ethyl}acetamide | | | |
| 140 | 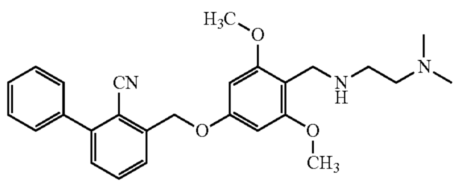 [SMILES: COc1cc(OCc2cccc(-c3ccccc3)c2C#N)cc(OC)c1CNCCN(C)C] | 2-[4-({[2-(dimethylamino)ethyl]amino}methyl)-3,5-dimethoxyphenoxymethyl]-6-phenylbenzonitrile | 1.2 AT | 446.2 | |
| 141 | 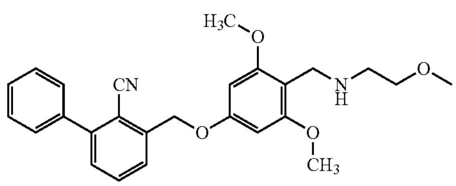 [SMILES: COCCNCc1c(OC)cc(OCc2cccc(-c3ccccc3)c2C#N)cc1OC] | 2-(3,5-dimethoxy-4-{[(2-methoxyethyl)amino]methyl}phenoxymethyl)-6-phenylbenzonitrile | 1.5 AT | 433.0 | |
| 142 | 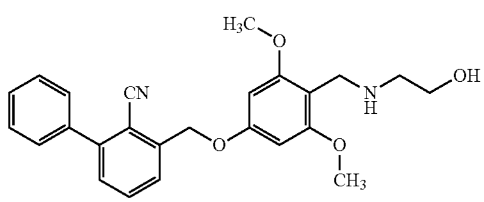 [SMILES: COc1cc(OCc2cccc(-c3ccccc3)c2C#N)cc(OC)c1CNCCO] | 2-(4-{[(2-hydroxyethyl)amino]methyl}-3,5-dimethoxyphenoxymethyl)-6-phenylbenzonitrile | 1.4 AT | 419.0 | |
| 143 | 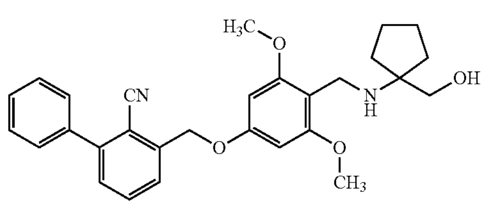 [SMILES: COc1cc(OCc2cccc(-c3ccccc3)c2C#N)cc(OC)c1CNC1(CO)CCCC1] | 2-[4-({[1-(hydroxymethyl)cyclopentyl]amino}methyl)-3,5-dimethoxyphenoxymethyl]-6-phenylbenzonitrile | 1.5 AT | 473.2 | |
| 144 | 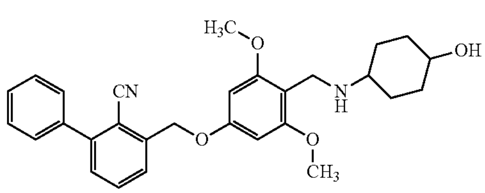 [SMILES: COc1cc(OCc2cccc(-c3ccccc3)c2C#N)cc(OC)c1CNC1CCC(O)CC1] | 2-(4-{[(4-hydroxycyclohexyl)amino]methyl}-3,5-dimethoxyphenoxymethyl)-6-phenylbenzonitrile | 1.4 AT | 473.2 | |
| 145 | 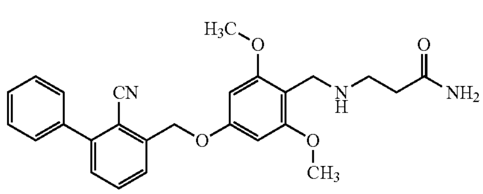 [SMILES: COc1cc(OCc2cccc(-c3ccccc3)c2C#N)cc(OC)c1CNCCC(N)=O] | 3-[({4-[(2-cyano-3-phenylphenyl)methoxy]-2,6-dimethoxyphenyl}methyl)amino]propanamide | 1.4 AT | 446.0 | |

-continued

| Ex. No. | Structure | Name | HPLC Retention Time (minutes) (Method) | ESI-MS m/z MH+ | ESI-MS m/z MH− |
|---|---|---|---|---|---|
| 146 | 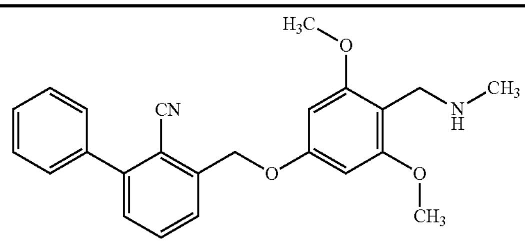 | 2-{3,5-dimethoxy-4-[(methylamino)methyl]phenoxymethyl}-6-phenylbenzonitrile | 1.4 AT | 389.0 | |
| 147 | 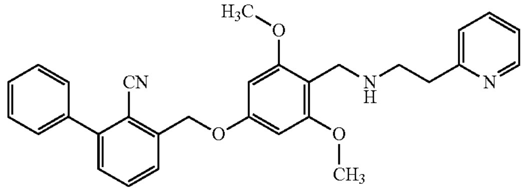 [SMILES: COc1cc(OCc2cccc(-c3ccccc3)c2C#N)cc(OC)c1CNCCc1ccccn1] | 2-[3,5-dimethoxy-4-({[2-(pyridin-2-yl)ethyl]amino}methyl)phenoxymethyl]-6-phenylbenzonitrile | 1.4 AT | 480.0 | |
| 148 | 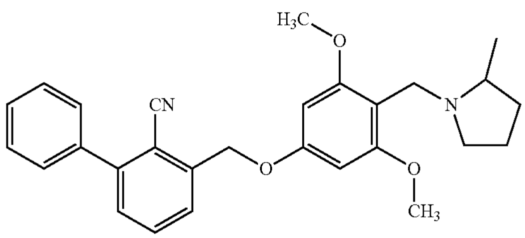 [SMILES: COc1cc(OCc2cccc(-c3ccccc3)c2C#N)cc(OC)c1CN1CCCC1C] | 2-{3,5-dimethoxy-4-[(2-methylpyrrolidin-1-yl)methyl]phenoxymethyl}-6-phenylbenzonitrile | 1.6 AT | 443.2 | |
| 149 | 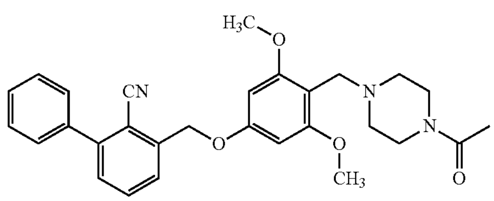 [SMILES: COc1cc(OCc2cccc(-c3ccccc3)c2C#N)cc(OC)c1CN1CCN(C(C)=O)CC1] | 2-{4-[(4-acetylpiperazin-1-yl)methyl]-3,5-dimethoxyphenoxymethyl}-6-phenylbenzonitrile | 1.4 AT | 486.2 | |
| 150 | 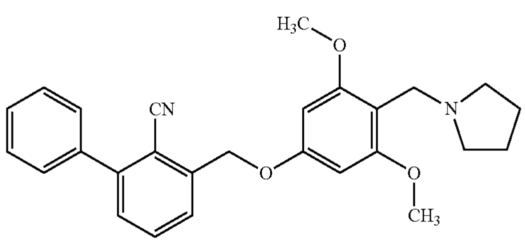 [SMILES: COc1cc(OCc2cccc(-c3ccccc3)c2C#N)cc(OC)c1CN1CCCC1] | 2-[3,5-dimethoxy-4-(pyrrolidin-1-ylmethyl)phenoxymethyl]-6-phenylbenzonitrile | 1.5 AT | 429.0 | |
| 151 | 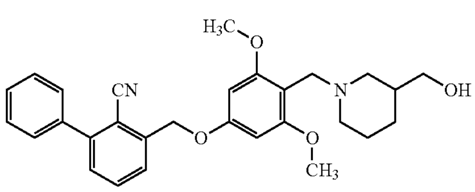 [SMILES: COc1cc(OCc2cccc(-c3ccccc3)c2C#N)cc(OC)c1CN1CCCC(CO)C1] | 2-(4-{[3-(hydroxymethyl)piperidin-1-yl]methyl}-3,5-dimethoxyphenoxymethyl)-6-phenylbenzonitrile | 1.5 AT | 473.2 | |
| 152 | 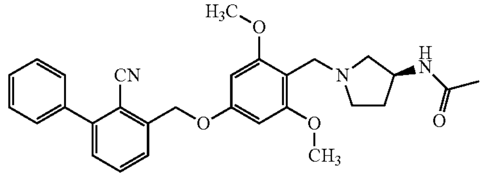 [SMILES: COc1cc(OCc2cccc(-c3ccccc3)c2C#N)cc(OC)c1CN1CC[C@H](NC(C)=O)C1] | N-[(3S)-1-({4-[(2-cyano-3-phenylphenyl)methoxy]-2,6-dimethoxyphenyl}methyl)pyrrolidin-3-yl]acetamide | 1.4 AT | 486.2 | |

| Ex. No. | Structure | Name | HPLC Retention Time (minutes) (Method) | ESI-MS m/z MH+ | ESI-MS m/z MH− |
|---|---|---|---|---|---|
| 153 | 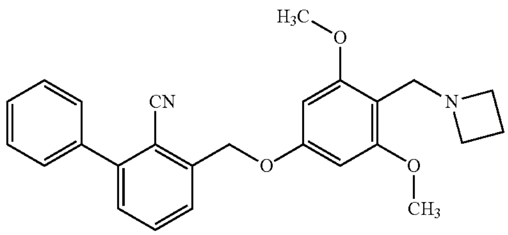 [SMILES: COc1cc(OCc2cccc(-c3ccccc3)c2C#N)cc(OC)c1CN1CCC1] | 2-[4-(azetidin-1-ylmethyl)-3,5-dimethoxyphenoxymethyl]-6-phenylbenzonitrile | 1.5 AT | 415.0 | |
| 154 | 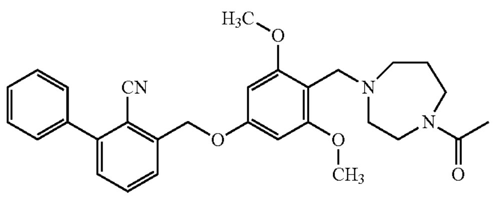 [SMILES: COc1cc(OCc2cccc(-c3ccccc3)c2C#N)cc(OC)c1CN1CCCN(C(C)=O)CC1] | 2-{4-[(4-acetyl-1,4-diazepan-1-yl)methyl]-3,5-dimethoxyphenoxymethyl}-6-phenylbenzonitrile | 1.4 AT | 500.2 | |
| 155 | 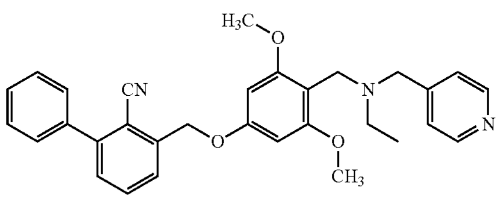 [SMILES: CCN(Cc1ccncc1)Cc1c(OC)cc(OCc2cccc(-c3ccccc3)c2C#N)cc1OC] | 2-(4-{[ethyl(pyridin-4-ylmethyl)amino]methyl}-3,5-dimethoxyphenoxymethyl)-6-phenylbenzonitrile | 1.3 AT | 494.2 | |
| 156 | 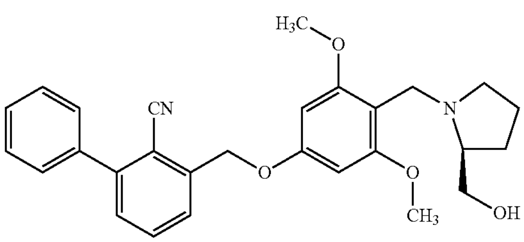 [SMILES: COc1cc(OCc2cccc(-c3ccccc3)c2C#N)cc(OC)c1CN1CCC[C@H]1CO] | 2-(4-{[(2S)-2-(hydroxymethyl)pyrrolidin-1-yl]methyl}-3,5-dimethoxyphenoxymethyl)-6-phenylbenzonitrile | 1.5 AT | 459.0 | |
| 157 | 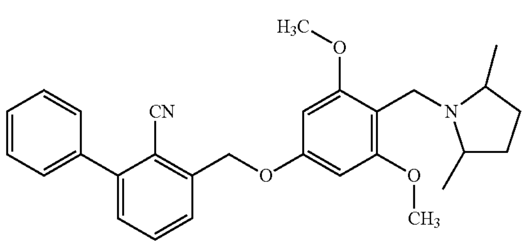 [SMILES: COc1cc(OCc2cccc(-c3ccccc3)c2C#N)cc(OC)c1CN1C(C)CCC1C] | 2-{4-[(2,5-dimethylpyrrolidin-1-yl)methyl]-3,5-dimethoxyphenoxymethyl}-6-phenylbenzonitrile | 1.6 AT | 457.2 | |
| 158 | 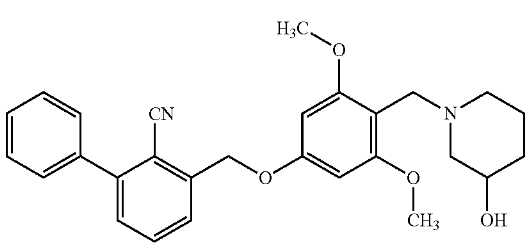 [SMILES: COc1cc(OCc2cccc(-c3ccccc3)c2C#N)cc(OC)c1CN1CCCC(O)C1] | 2-{4-[(3-hydroxypiperidin-1-yl)methyl]-3,5-dimethoxyphenoxymethyl}-6-phenylbenzonitrile | 1.4 AT | 459.2 | |

| Ex. No. | Structure | Name | HPLC Retention Time (minutes) (Method) | ESI-MS m/z MH+ | ESI-MS m/z MH− |
|---|---|---|---|---|---|
| 159 | 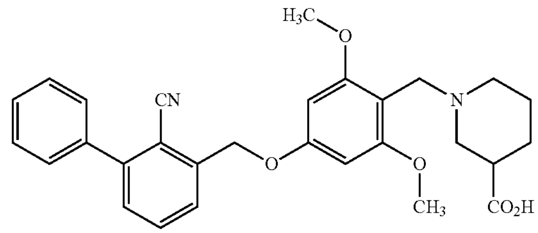 [SMILES: COc1cc(OCc2cccc(-c3ccccc3)c2C#N)cc(OC)c1CN1CCCC(C(=O)O)C1] | 1-({4-[(2-cyano-3-phenylphenyl)methoxy]-2,6-dimethoxyphenyl}methyl)piperidine-3-carboxylic acid | 1.5 | 487.0 | |
| 160 | 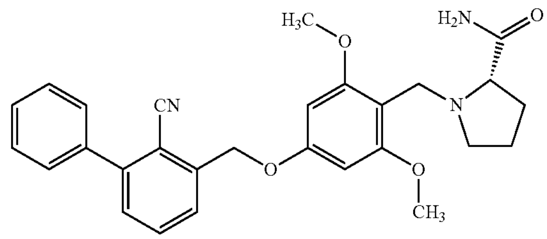 [SMILES: COc1cc(OCc2cccc(-c3ccccc3)c2C#N)cc(OC)c1CN1CCC[C@H]1C(N)=O] | (2S)-1-({4-[(2-cyano-3-phenylphenyl)methoxy]-2,6-dimethoxyphenyl}methyl)pyrrolidine-2-carboxamide | 1.5 AT | 472.0 | |
| 161 | 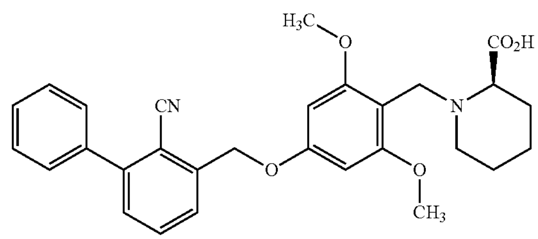 [SMILES: COc1cc(OCc2cccc(-c3ccccc3)c2C#N)cc(OC)c1CN1CCCC[C@@H]1C(=O)O] | (2S)-1-({4-[(2-cyano-3-phenylphenyl)methoxy]-2,6-dimethoxyphenyl}methyl)piperidine-2-carboxylic acid | 1.5 AT | 487.0 | |
| 162 | 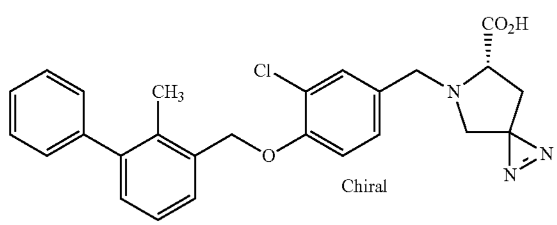 [SMILES: Cc1c(COc2ccc(CN3CC4(C[C@H]3C(=O)O)N=N4)cc2Cl)cccc1-c1ccccc1] | (6S)-5-({3-chloro-4-[(2-methyl-3-phenylphenyl)methoxy]phenyl}methyl)-1,2,5-triazaspiro[2.4]hept-1-ene-6-carboxylic acid | 2.9 A | 462.2 | 460.2 |
| 163 | 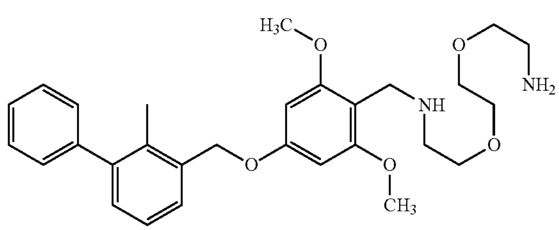 [SMILES: COc1cc(OCc2cccc(-c3ccccc3)c2C)cc(OC)c1CNCCOCCOCCN] | {2-[2-(2-aminoethoxy)ethoxy]ethyl}({2,6-dimethoxy-4-[(2-methyl-3-phenylphenyl)methoxy]phenyl}methyl)amine | 2.8 A | 495.3 | — |
| 164 | 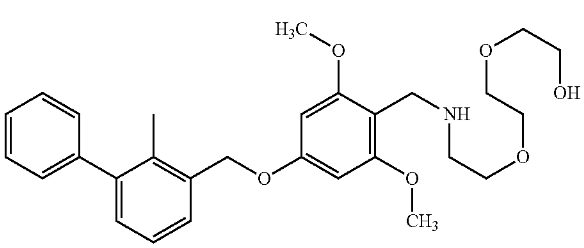 [SMILES: COc1cc(OCc2cccc(-c3ccccc3)c2C)cc(OC)c1CNCCOCCOCCO] | 2-(2-{2-[({2,6-dimethoxy-4-[(2-methyl-3-phenylphenyl)methoxy]phenyl}methyl)amino]ethoxy}ethoxy)ethan-1-ol | 2.9 A | 497.3 | — |

-continued

| Ex. No. | Structure | Name | HPLC Retention Time (minutes) (Method) | ESI-MS m/z MH+ | ESI-MS m/z MH− |
|---|---|---|---|---|---|
| 165 | 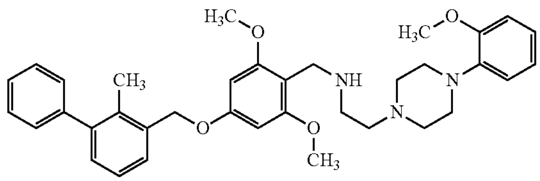 [SMILES: COc1ccccc1N1CCN(CCNCc2c(OC)cc(OCc3cccc(-c4ccccc4)c3C)cc2OC)CC1] | ({2,6-dimethoxy-4-[(2-methyl-3-phenylphenyl)methoxy]phenyl}methyl)({2-[4-(2-methoxyphenyl)piperazin-1-yl]ethyl})amine | 3.2 A | 582.4 | |
| 166 | 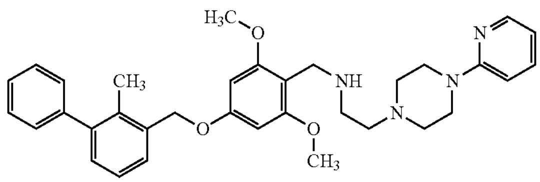 [SMILES: COc1cc(OCc2cccc(-c3ccccc3)c2C)cc(OC)c1CNCCN1CCN(c2ccccn2)CC1] | ({2,6-dimethoxy-4-[(2-methyl-3-phenylphenyl)methoxy]phenyl}methyl)({2-[4-(pyridin-2-yl)piperazin-1-yl]ethyl})amine | 3.2 A | 553.4 | |
| 167 | 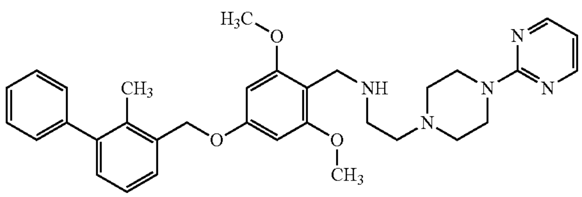 [SMILES: COc1cc(OCc2cccc(-c3ccccc3)c2C)cc(OC)c1CNCCN1CCN(c2ncccn2)CC1] | ({2,6-dimethoxy-4-[(2-methyl-3-phenylphenyl)methoxy]phenyl}methyl)({2-[4-(pyrimidin-2-yl)piperazin-1-yl]ethyl})amine | 3.0 A | 554.4 | |
| 168 | 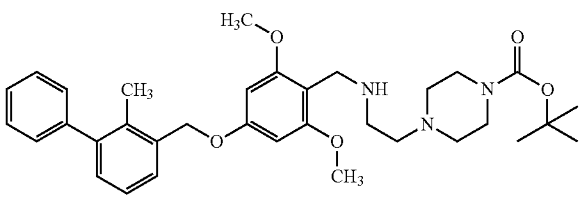 [SMILES: COc1cc(OCc2cccc(-c3ccccc3)c2C)cc(OC)c1CNCCN1CCN(C(=O)OC(C)(C)C)CC1] | tert-butyl 4-{2-[({2,6-dimethoxy-4-[(2-methyl-3-phenylphenyl)methoxy]phenyl}methyl)amino]ethyl}piperazine-1-carboxylate | 3.3 A | 576.4 | |
| 169 | 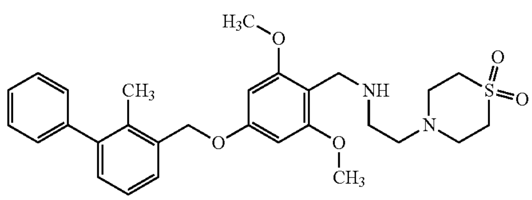 [SMILES: COc1cc(OCc2cccc(-c3ccccc3)c2C)cc(OC)c1CNCCN1CCS(=O)(=O)CC1] | 4-{2-[({2,6-dimethoxy-4-[(2-methyl-3-phenylphenyl)methoxy]phenyl}methylamino]ethyl}-1$\lambda^6$,4-thiomorpholine-1,1-dione | 2.8 A | 525.3 | |
| 170 | 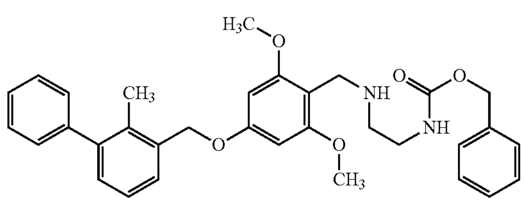 [SMILES: COc1cc(OCc2cccc(-c3ccccc3)c2C)cc(OC)c1CNCCNC(=O)OCc1ccccc1] | benzyl N-{2-[({2,6-dimethoxy-4-[(2-methyl-3-phenyl)methoxy]phenyl}methyl)amino]ethyl}carbamate | 3.2 A | 541.4 | |
| 171 | 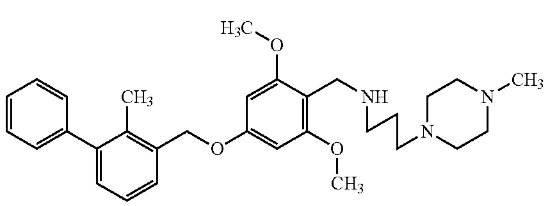 [SMILES: COc1cc(OCc2cccc(-c3ccccc3)c2C)cc(OC)c1CNCCCN1CCN(C)CC1] | ({2,6-dimethoxy-4-[(2-methyl-3-phenylphenyl)methoxy]phenyl}methyl)[3-(4-methylpiperazin-1-yl)propyl]amine | 2.6 A | 504.5 | |

-continued

| Ex. No. | Structure | Name | HPLC Retention Time (minutes) (Method) | ESI-MS m/z MH+ | ESI-MS m/z MH− |
|---|---|---|---|---|---|
| 172 | 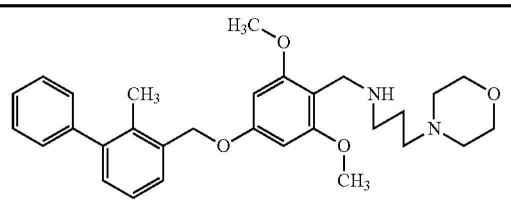 | ({2,6-dimethoxy-4-[(2-methyl-3-phenylphenyl)methoxy]phenyl}methyl)[3-(morpholin-4-yl)propyl]amine | 3.0 A | 491.5 | |
| 173 | 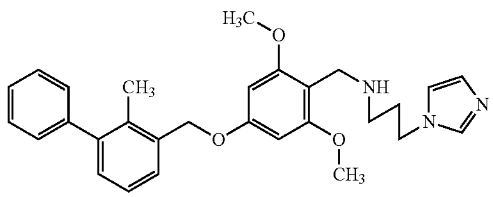 [SMILES: COc1cc(OCc2cccc(-c3ccccc3)c2C)cc(OC)c1CNCCCn1ccnc1] | ({2,6-dimethoxy-4-[(2-methyl-3-phenylphenyl)methoxy]phenyl}methyl)[3-(1H-imidazol-1-yl)propyl]amine | 2.7 A | 472.4 | |
| 174 | 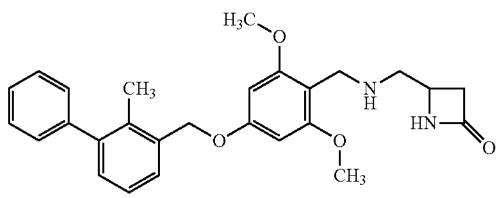 [SMILES: COc1cc(OCc2cccc(-c3ccccc3)c2C)cc(OC)c1CNCC1CC(=O)N1] | 4-{[({2,6-dimethoxy-4-[(2-methyl-3-phenylphenyl)methoxy]phenyl}methyl)amino]methyl}azetidin-2-one | 2.5 A | 347.3 | |
| 175 | 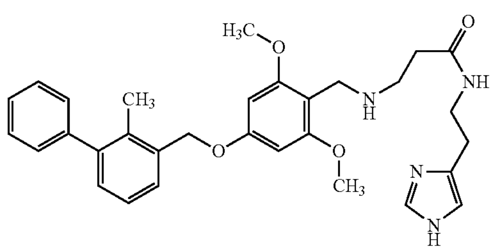 [SMILES: COc1cc(OCc2cccc(-c3ccccc3)c2C)cc(OC)c1CNCCC(=O)NCCc1c[nH]cn1] | 3-[({2,6-dimethoxy-4-[(2-methyl-3-phenylphenyl)methoxy]phenyl}methyl)amino]-N-[2-(1H-imidazol-4-yl)ethyl]propanamide | 2.9 A | 529.2 | 527.3 |
| 176 | 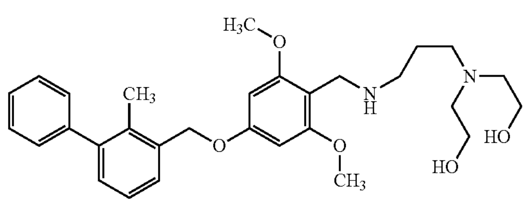 [SMILES: COc1cc(OCc2cccc(-c3ccccc3)c2C)cc(OC)c1CNCCCN(CCO)CCO] | 2-({3-[({2,6-dimethoxy-4-[(2-methyl-3-phenylphenyl)methoxy]phenyl}methyl)amino]propyl}(2-hydroxyethyl)amino)ethan-1-ol | 3.0 A | 509.4 | |
| 177 | 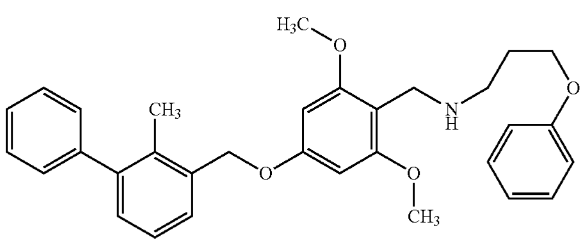 [SMILES: COc1cc(OCc2cccc(-c3ccccc3)c2C)cc(OC)c1CNCCCOc1ccccc1] | ({2,6-dimethoxy-4-[(2-methyl-3-phenylphenyl)methoxy]phenyl}methyl)(3-phenoxypropyl)amine | 4.2 M | 498.5 | |
| 178 | 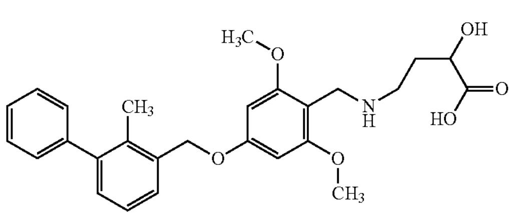 [SMILES: COc1cc(OCc2cccc(-c3ccccc3)c2C)cc(OC)c1CNCCC(O)C(=O)O] | 4-[({2,6-dimethoxy-4-[(2-methyl-3-phenylphenyl)methoxy(phenyl}methyl)amino]-2-hydroxybutanoic acid | 2.9 A | 466.3 | |

-continued

| Ex. No. | Structure | Name | HPLC Retention Time (minutes) (Method) | ESI-MS m/z MH+ | ESI-MS m/z MH− |
|---|---|---|---|---|---|
| 179 | 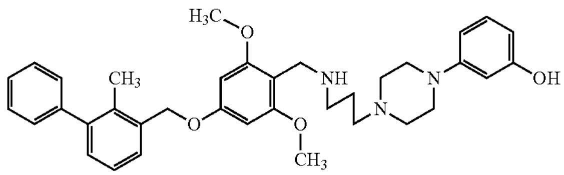 [SMILES: COc1cc(OCc2cccc(-c3ccccc3)c2C)cc(OC)c1CNCCCN1CCN(c2cccc(O)c2)CC1] | 3-(4-{3-[2-[(2,6-dimethoxy-4-[(2-methyl-3-phenylphenyl)methoxy]phenyl}methyl)amino]propyl}piperazin-1-yl)phenol | 4.4 M | 582.5 | |
| 180 | 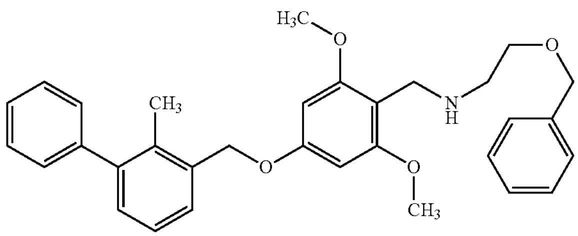 [SMILES: COc1cc(OCc2cccc(-c3ccccc3)c2C)cc(OC)c1CNCCOCc1ccccc1] | [2-(benzyloxy)ethyl]({2,6-dimethoxy-4-[(2-methyl-3-phenylphenyl)methoxy]phenyl}methyl)amine | 3.6 A | 498.3 | |
| 181 | 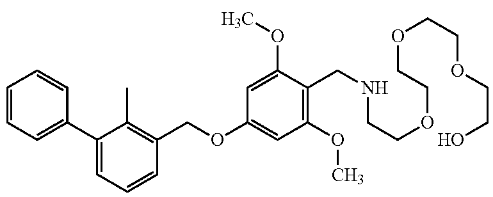 [SMILES: COc1cc(OCc2cccc(-c3ccccc3)c2C)cc(OC)c1CNCCOCCOCCOCCO] | 1-{2,6-dimethoxy-4-[(2-methyl-3-phenylphenyl)methoxy]phenyl}-5,8,11-trioxa-2-azatridecan-13-ol | 3.1 A | 541.4 | |
| 182 | 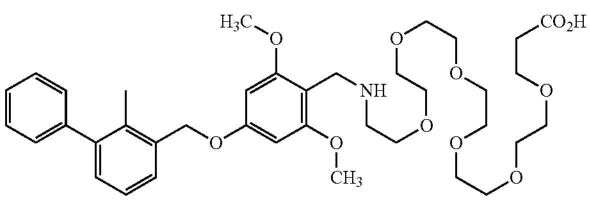 [SMILES: COc1cc(OCc2cccc(-c3ccccc3)c2C)cc(OC)c1CNCCOCCOCCOCCOCCOCCOCCC(=O)O] | 1-{2,6-dimethoxy-4-[(2-methyl-3-phenylphenyl)methoxy]phenyl}-5,8,11,14,17,20-hexaoxa-2-azatricosan-23-oic acid | 3.8 M | 700.4 | |
| 183 | 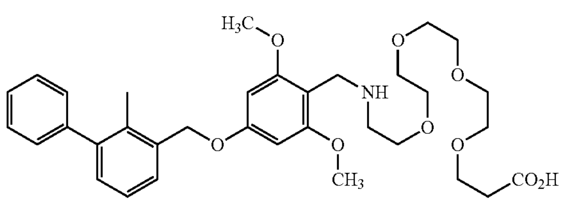 [SMILES: COc1cc(OCc2cccc(-c3ccccc3)c2C)cc(OC)c1CNCCOCCOCCOCCOCCC(=O)O] | 1-{2,6-dimethoxy-4-[(2-methyl-3-phenylphenyl)methoxy]phenyl}-5,8,11,14-tetraoxa-2-azaheptadecan-17-oic acid | 2.4 A | 612.4 | 610.5 |
| 184 | 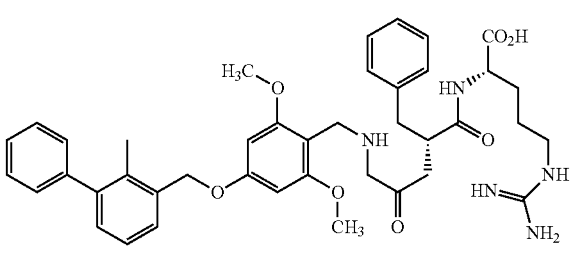 [SMILES: COc1cc(OCc2cccc(-c3ccccc3)c2C)cc(OC)c1CNCC(=O)C[C@H](Cc1ccccc1)C(=O)N[C@@H](CCCNC(=N)N)C(=O)O] | (2S)-5-carbamimidamido-2-[(2R)-2-{2-[({2,6-dimethoxy-4-[(2-methyl-3-phenylphenyl)methoxy]phenyl}methyl)amino]acetamido}-3-phenylpropanamido]pentanoic acid | 2.9 A | 725.5 | |
| 185 | 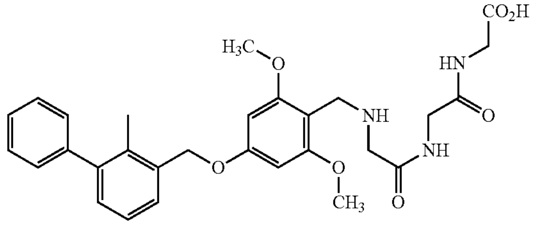 [SMILES: COc1cc(OCc2cccc(-c3ccccc3)c2C)cc(OC)c1CNCC(=O)NCC(=O)NCC(=O)O] | 2-(2-{2-[({2,6-dimethoxy-4-[(2-methyl-3-phenylphenyl)methoxy]phenyl}methyl)amino]acetamido}acetamido)acetic acid | 2.4 A | 536.2 | |

-continued

| Ex. No. | Structure | Name | HPLC Retention Time (minutes) (Method) | ESI-MS m/z MH+ | ESI-MS m/z MH− |
|---|---|---|---|---|---|
| 186 | 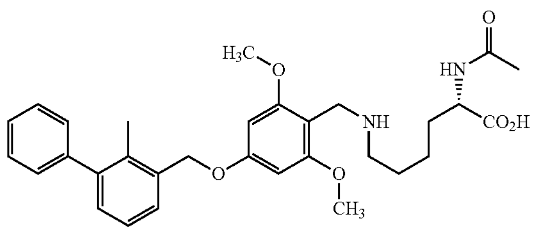 [SMILES: COc1cc(OCc2cccc(-c3ccccc3)c2C)cc(OC)c1CNCCCC[C@H](NC(C)=O)C(=O)O] | (2S)-5-[({2,6-dimethoxy-4-[(2-methyl-3-phenylphenyl)methoxy]phenyl}methyl)amino]-2-acetamidopentanoic acid | 2.8 A | 521.3 | 519.3 |
| 187 | 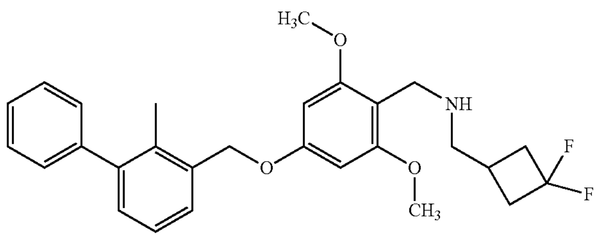 [SMILES: COc1cc(OCc2cccc(-c3ccccc3)c2C)cc(OC)c1CNCC1CC(F)(F)C1] | [(3,3-difluorocyclobutyl)methyl]({2,6-dimethoxy-4-[(2-methyl-3-phenylphenyl)methoxy]phenyl}methyl)amine | 3.1 A | 468.4 | |
| 188 | 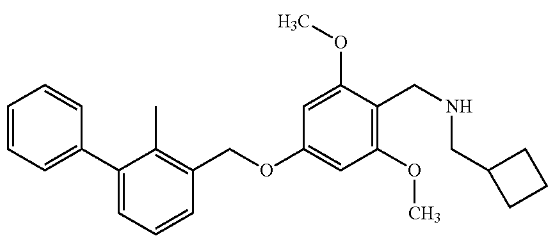 [SMILES: COc1cc(OCc2cccc(-c3ccccc3)c2C)cc(OC)c1CNCC1CCC1] | (cyclobutylmethyl)({2,6-dimethoxy-4-[(2-methyl-3-phenylphenyl)methoxy]phenyl}methyl)amine | 2.2 A | 432.4 | |
| 189 | 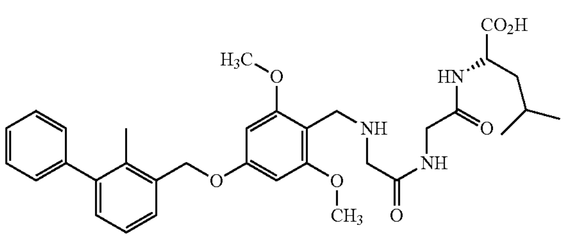 | (2S)-2-(2-{2-[({2,6-dimethoxy-4-[(2-methyl-3-phenylphenyl)methoxy]phenyl}methyl)amino]acetamido}acetamido)-4-methylpentanoic acid | 3.1 M | 592.5 | 590.5 |
| 190 | 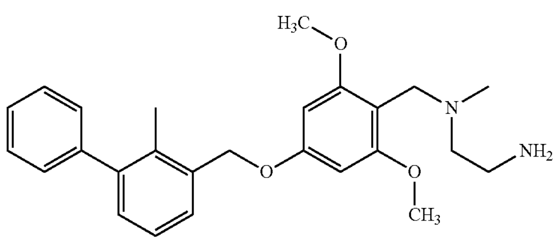 [SMILES: COc1cc(OCc2cccc(-c3ccccc3)c2C)cc(OC)c1CN(C)CCN] | (2-aminoethyl)({2,6-dimethoxy-4-[(2-methyl-3-phenylphenyl)methoxy]phenyl}methyl)methylamine | 1.9 A | 421.4 | — |
| 191 | 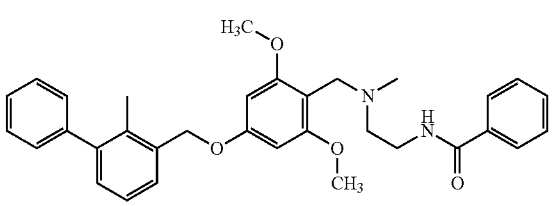 [SMILES: COc1cc(OCc2cccc(-c3ccccc3)c2C)cc(OC)c1CN(C)CCNC(=O)c1ccccc1] | 3-{2-[({2,6-dimethoxy-4-[(2-methyl-3-phenylphenyl)methoxy]phenyl}methyl)(methyl)amino]ethyl}-1-phenylurea | 2.1 A | 540.4 | 538.4 |

-continued

| Ex. No. | Structure | Name | HPLC Retention Time (minutes) (Method) | ESI-MS m/z MH+ | ESI-MS m/z MH− |
|---|---|---|---|---|---|
| 192 | 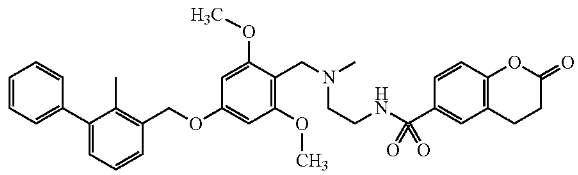 | N-{2-[({2,6-dimethoxy-4-[(2-methyl-3-phenylphenyl)methoxy]pheny}methyl)(methyl)amino]ethyl}-2-oxo-2H-chromene-6-sulfonamide | 2.2 A | 629.5 | 627.4 |
| 193 | 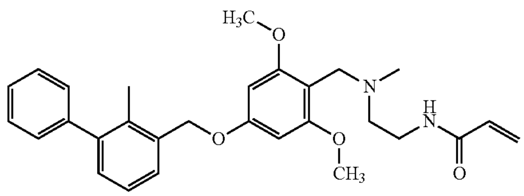 [SMILES: C=CC(=O)NCCN(C)Cc1c(OC)cc(OCc2cccc(-c3ccccc3)c2C)cc1OC] | N-{2-[({2,6-dimethoxy-4-[(2-methyl-3-phenylphenyl)methoxy]phenyl}methyl)(methyl)amino]ethyl}prop-2-enamide | 2.0 A | 475.4 | — |
| 194 | 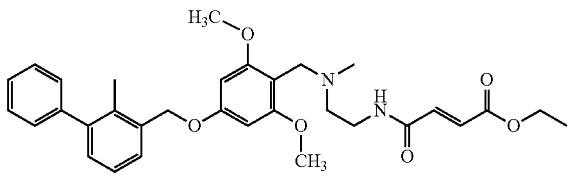 [SMILES: CCOC(=O)/C=C/C(=O)NCCN(C)Cc1c(OC)cc(OCc2cccc(-c3ccccc3)c2C)cc1OC] | ethyl (2E)-3-({2-[({2,6-dimethoxy-4-[(2-methyl-3-phenylphenyl)methoxy]phenyl}methyl)(methyl)amino]ethyl}carbamoyl)prop-2-enoate | 2.2 A | 547.5 | |
| 195 | 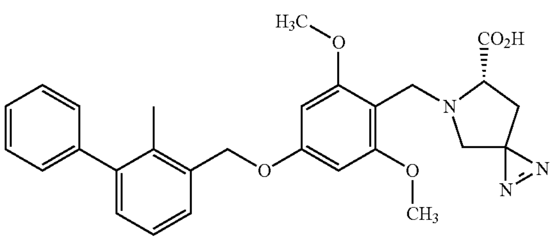 [SMILES: COc1cc(OCc2cccc(-c3ccccc3)c2C)cc(OC)c1CN1CC2(C[C@H]1C(=O)O)N=N2] | (6S)-5-({2,6-dimethoxy-4-[(2-methyl-3-phenylphenyl)methoxy]phenyl}methyl)-1,2,5-triazaspiro[2.4]hept-1-ene-6-carboxylic acid | 1.8 A | — | 486.6 |
| 196 | 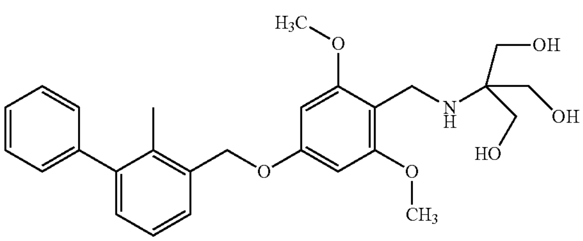 [SMILES: COc1cc(OCc2cccc(-c3ccccc3)c2C)cc(OC)c1CNC(CO)(CO)CO] | 2-[({2,6-dimethoxy-4-[(2-methyl-3-phenylphenyl)methoxy]phenyl}methyl)amino]-2-(hydroxymethyl)propane-1,3-diol | 1.9 A | 468.4 | — |
| 197 | 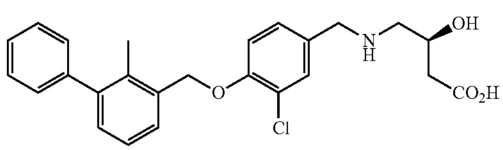 [SMILES: Cc1c(COc2ccc(CNC[C@@H](O)CC(=O)O)cc2Cl)cccc1-c1ccccc1] | (3S)-4-[({3-chloro-4-[(2-methyl-3-phenylphenyl)methoxy]phenyl}methyl)amino]-3-hydroxybutanoic acid | 1.6 A | 440.3 | 438.4 |
| 198 | 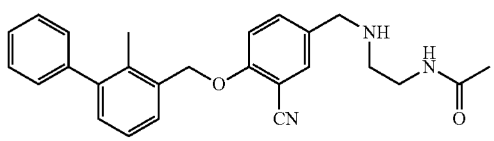 [SMILES: CC(=O)NCCNCc1ccc(OCc2cccc(-c3ccccc3)c2C)c(C#N)c1] | N-{2-[({3-cyano-4-[(2-methyl-3-phenylphenyl)methoxy]phenyl}methyl)amino]ethyl}acetamide | 1.8 A | 414.4 | |
| 199 | 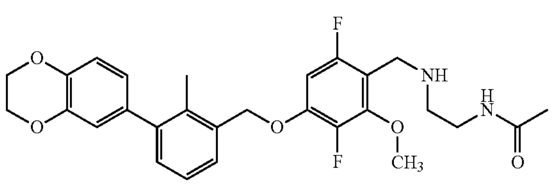 [SMILES: COc1c(F)c(OCc2cccc(-c3ccc4c(c3)OCCO4)c2C)cc(F)c1CNCCNC(C)=O] | N-(2-{[(4-{[3-(2,3-dihydro-1,4-benzodioxin-6-yl)-2-methylphenyl]methoxy}-2,5-difluorophenyl)methyl]amino}ethyl)acetamide | 1.8 A | 483.5 | 481.5 |

-continued

| Ex. No. | Structure | Name | HPLC Retention Time (minutes) (Method) | ESI-MS m/z MH+ | ESI-MS m/z MH− |
|---|---|---|---|---|---|
| 200 | 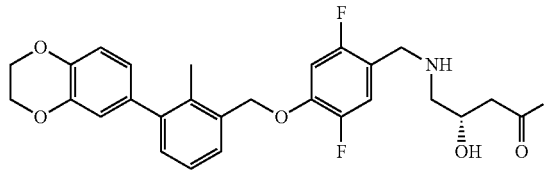 | (3S)-4-{[(4-{[3-(2,3-dihydro-1,4-benzodioxin-6-yl)-2-methylphenyl]methoxy}-2,5-difluorophenyl)methyl]amino}-3-hydroxybutanoic acid | 1.6 A | 500.3 | 498.3 |
| 201 | 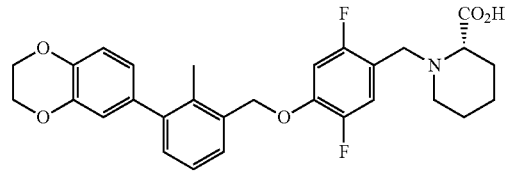 [SMILES: Cc1c(COc2cc(F)c(CN3CCCC[C@H]3C(=O)O)cc2F)cccc1-c1ccc2c(c1)OCCO2] | (2S)-1-[(4-{[3-(2,3-dihydro-1,4-benzodioxin-6-yl)-2-methylphenyl]methoxy}-2,5-difluorophenyl)methyl] piperidine-2-carboxylic acid | 1.7 A | 510.3 | — |
| 202 | 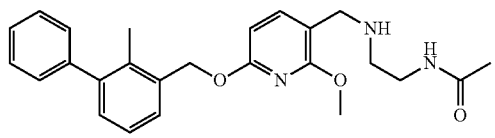 [SMILES: COc1nc(OCc2cccc(-c3ccccc3)c2C)ccc1CNCCNC(C)=O] | N-{2-[({2-methoxy-6-[(2-methyl-3-phenylphenyl)methoxy]pyridin-3-yl}methyl)amino]ethyl}acetamide | 1.9 A | 420.3 | 478.4 (+HOAc) |
| 203 | 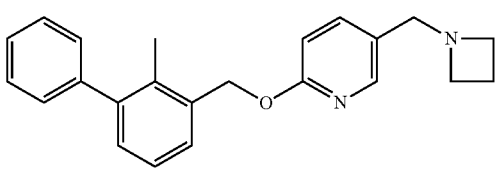 [SMILES: Cc1c(COc2ccc(CN3CCC3)cn2)cccc1-c1ccccc1] | 5-(azetidin-1-ylmethyl)-2-[(2-methyl-3-phenylphenyl)methoxy]pyridine | 4.1 M50 | 345.3 | |
| 204 | 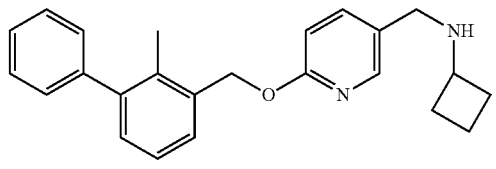 [SMILES: Cc1c(COc2ccc(CNC3CCC3)cn2)cccc1-c1ccccc1] | N-({6-[(2-methyl-3-phenylphenyl)methoxy]pyridin-3-yl}methyl)cyclobutanamine | 4.2 M50 | 359.2 | |
| 205 | 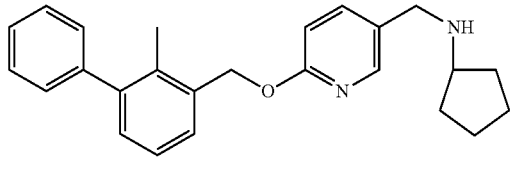 [SMILES: Cc1c(COc2ccc(CNC3CCCC3)cn2)cccc1-c1ccccc1] | N-({6-[(2-methyl-3-phenylphenyl)methoxy]pyridin-3-yl}methyl)cyclopentanamine | 2.8 A50 | 373.3 | |
| 206 | 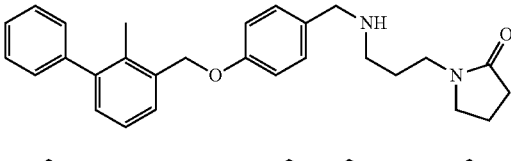 | 1-{3-[({6-[(2-methyl-3-phenylphenyl)methoxy]pyridin-3-yl[methyl]amino]propyl}pyrrolidin-2-one | 2.5 A50 | 430.4 | |
| 207 | 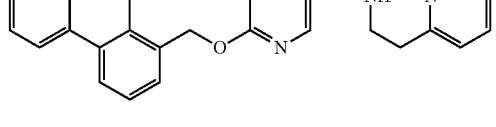 | ({6-[(2-methyl-3-phenylphenyl)methoxy]pyridin-3-yl}methyl)[2-(pyridin-2-yl)ethyl]amine | 2.8 A50 | 410.3 | |
| 208 | 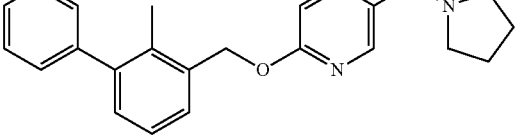 | 2-[(2-methyl-3-phenylphenyl)methoxy]-5-(pyrrolidin-1-ylmethyl)pyridine | 3.2 M50 | 359.3 | |

-continued

| Ex. No. | Structure | Name | HPLC Retention Time (minutes) (Method) | ESI-MS m/z MH+ | ESI-MS m/z MH− |
|---|---|---|---|---|---|
| 209 | 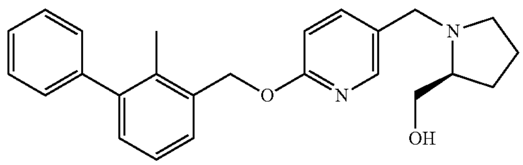 [SMILES: Cc1c(COc2ccc(CN3CCC[C@H]3CO)cn2)cccc1-c1ccccc1] | [(2S)-1-({6-[(2-methyl-3-phenylphenyl)methoxy]pyridin-3-yl}methyl)pyrrolidin-2-yl]methanol | 2.7 A50 | 389.3 | |
| 210 | 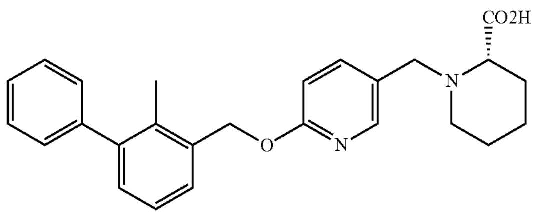 [SMILES: Cc1c(COc2ccc(CN3CCCC[C@H]3C(=O)O)cn2)cccc1-c1ccccc1] | (2S)-1-({6-[(2-methyl-3-phenylphenyl)methoxy]pyridin-3-yl}methyl)piperidine-2-carboxylic acid | 2.5 A50 | 417.3 | |
| 211 | 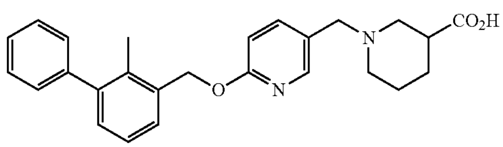 [SMILES: Cc1c(COc2ccc(CN3CCCC(C(=O)O)C3)cn2)cccc1-c1ccccc1] | 1-({6-[(2-methyl-3-phenylphenyl)methoxy]pyridin-3-yl}methyl)piperidine-3-carboxylic acid | 2.5 A50 | 417.3 | |
| 212 | 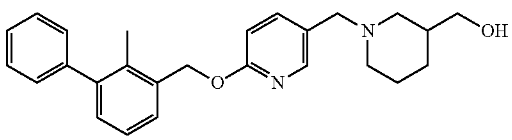 [SMILES: Cc1c(COc2ccc(CN3CCCC(CO)C3)cn2)cccc1-c1ccccc1] | [1-({6-[(2-methyl-3-phenylphenyl)methoxy]pyridin-3-yl}methyl)piperidin-3-yl]methanol | 4.4 M50 | 403.3 | |
| 213 | 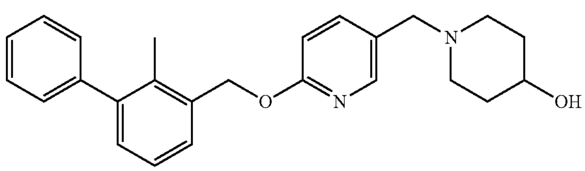 [SMILES: Cc1c(COc2ccc(CN3CCC(O)CC3)cn2)cccc1-c1ccccc1] | 1-({6-[(2-methyl-3-phenylphenyl)methoxy]pyridin-3-yl}methyl)piperidin-4-ol | 2.6 A50 | 389.3 | |
| 214 | 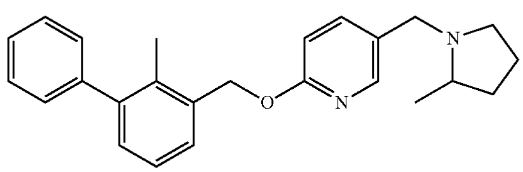 [SMILES: Cc1c(COc2ccc(CN3CCCC3C)cn2)cccc1-c1ccccc1] | 2-[(2-methyl-3-phenylphenyl)methoxy]-5-[(2-methylpyrrolidin-1-yl)methyl]pyridine | 2.8 A50 | 373.3 | |
| 215 | 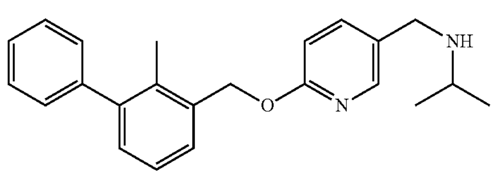 [SMILES: Cc1c(COc2ccc(CNC(C)C)cn2)cccc1-c1ccccc1] | ({6-[(2-methyl-3-phenylphenyl)methoxy]pyridin-3-yl}methyl)(propan-2-yl)amine | 2.6 A50 | 347.3 | |
| 216 | 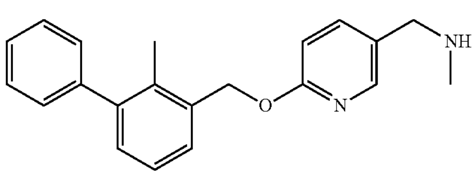 [SMILES: CNCc1ccc(OCc2cccc(-c3ccccc3)c2C)nc1] | methyl({6-[(2-methyl-3-phenylphenyl)methoxy]pyridin-3-yl}methyl)amine | 3.9 M50 | 319.3 | |

-continued

| Ex. No. | Structure | Name | HPLC Retention Time (minutes) (Method) | ESI-MS m/z MH+ | ESI-MS m/z MH− |
|---|---|---|---|---|---|
| 217 | 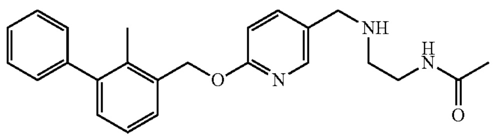 [SMILES: CC(=O)NCCNCc1ccc(OCc2cccc(-c3ccccc3)c2C)nc1] | N-{2-[({6-[(2-methyl-3-phenylphenyl)methoxy]pyridin-3-yl}methyl)amino]ethyl}acetamide | 4.0 M50 | 390.3 | |
| 218 | 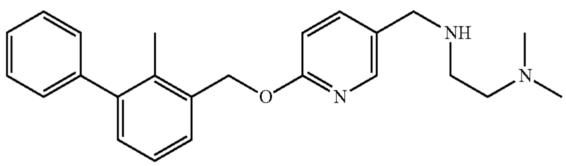 [SMILES: Cc1c(COc2ccc(CNCCN(C)C)cn2)cccc1-c1ccccc1] | [2-(dimethylamino)ethyl]({6-[(2-methyl-3-phenylphenyl)methoxy]pyridin-3-yl}methyl)amine | 4.0 M50 | 376.4 | |
| 219 | 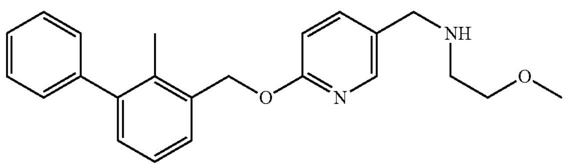 [SMILES: COCCNCc1ccc(OCc2cccc(-c3ccccc3)c2C)nc1] | (2-methoxyethyl)({6-[(2-methyl-3-phenylphenyl)methoxy]pyridin-3-yl[methyl)amine | 2.7 A50 | 363.3 | |
| 220 | 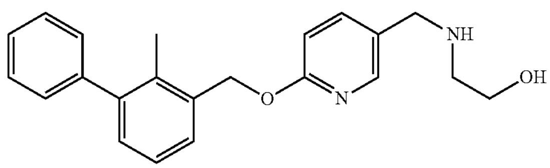 [SMILES: Cc1c(COc2ccc(CNCCO)cn2)cccc1-c1ccccc1] | 2-[({6-[(2-methyl-3-phenylphenyl)methoxy]pyridin-3-yl}methyl)amino]ethan-1-ol | 2.4 A50 | 349.3 | |
| 221 | 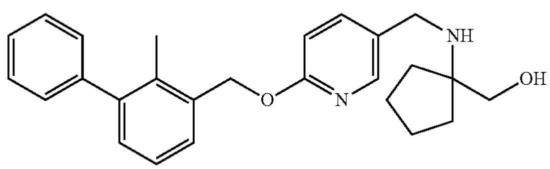 [SMILES: Cc1c(COc2ccc(CNC3(CO)CCCC3)cn2)cccc1-c1ccccc1] | {1-[({6-[(2-methyl-3-phenylphenyl)methoxy]pyridin-3-yl}methyl)amino]cyclopentyl}methanol | 4.1 M50 | 403.4 | |
| 222 | 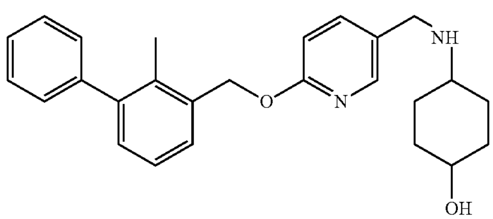 [SMILES: Cc1c(COc2ccc(CNC3CCC(O)CC3)cn2)cccc1-c1ccccc1] | 4-[({6-[(2-methyl-3-phenylphenyl)methoxy]pyridin-3-yl}methyl)amino]cyclohexan-1-ol | 3.9 M50 | 403.4 | |
| 223 | 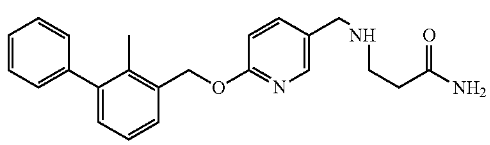 [SMILES: Cc1c(COc2ccc(CNCCC(N)=O)cn2)cccc1-c1ccccc1] | 3-[({6-[(2-methyl-3-phenylphenyl)methoxy]pyridin-3-yl}methyl)amino]propanamide | 2.4 A50 | 376.3 | |
| 224 | 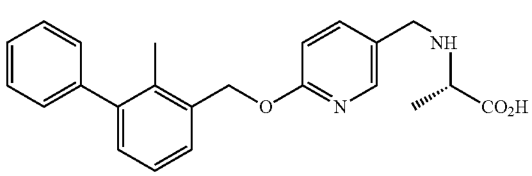 [SMILES: Cc1c(COc2ccc(CN[C@@H](C)C(=O)O)cn2)cccc1-c1ccccc1] | (2S)-2-[({6-[(2-methyl-3-phenylphenyl)methoxy]pyridin-3-yl[methyl)amino]propanoic acid | 2.2 A50 | 377.3 | |
| 225 | 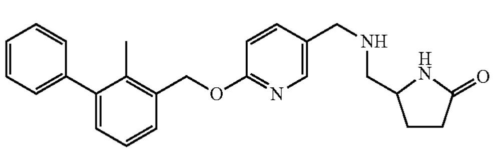 [SMILES: Cc1c(COc2ccc(CNCC3CCC(=O)N3)cn2)cccc1-c1ccccc1] | 5-{[({6-[(2-methyl-3-phenylphenyl)methoxy]pyridin-3-yl}methyl)amino]methyl}pyrrolidin-2-one | 2.7 A50 | 402.3 | |

| Ex. No. | Structure | Name | HPLC Retention Time (minutes) (Method) | ESI-MS m/z MH+ | ESI-MS m/z MH− |
|---|---|---|---|---|---|
| 226 | 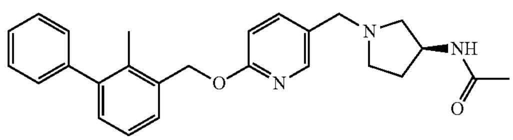 [SMILES: CC(=O)N[C@H]1CCN(Cc2ccc(OCc3cccc(-c4ccccc4)c3C)nc2)C1] | N-[(3S)-1-({6-[(2-methyl-3-phenylphenyl)methoxy]pyridin-3-yl}methyl)pyrrolidin-3-yl]acetamide | 4.3 M50 | 416.2 | |
| 227 | 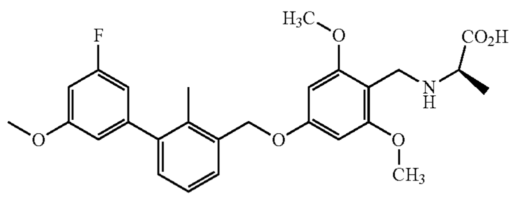 [SMILES: COc1cc(F)cc(-c2cccc(COc3cc(OC)c(CN[C@H](C)C(=O)O)c(OC)c3)c2C)c1] | (2R)-2-{[(4-{[3-(3-fluoro-5-methoxyphenyl)-2-methylphenyl]methoxy}-2,6-dimethoxyphenyl)methyl]amino}propanoic acid | 2.5 A50 | 484.5 | |
| 228 | 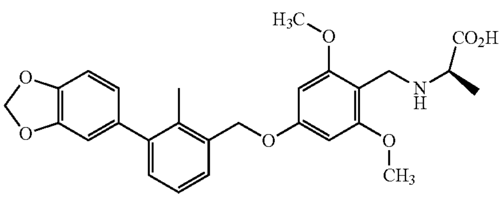 [SMILES: COc1cc(OCc2cccc(-c3ccc4c(c3)OCO4)c2C)cc(OC)c1CN[C@H](C)C(=O)O] | (2R)-2-{[(4-{[3-(2H-1,3-benzodioxol-5-yl)-2-methylphenyl]methoxy}-2,6-dimethoxyphenyl)methyl]amino}propanoic acid | 2.4 A50 | 502.4 | |
| 229 | 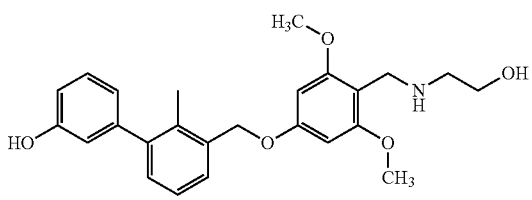 [SMILES: COc1cc(OCc2cccc(-c3cccc(O)c3)c2C)cc(OC)c1CNCCO] | 3-[3-(4-{[(2-hydroxyethyl)amino]methyl}-3,5-dimethoxyphenoxymethyl)-2-methylphenyl]phenol | 2.6 A50 | 424.3 | |
| 230 | 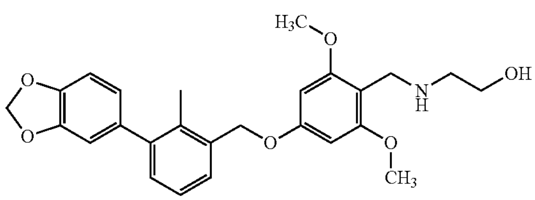 [SMILES: COc1cc(OCc2cccc(-c3ccc4c(c3)OCO4)c2C)cc(OC)c1CNCCO] | 2-{[(4-{[3-(2H-1,3-benzodioxol-5-yl)-2-methylphenyl]methoxy}-2,6-dimethoxyphenyl)methyl]amino}ethan-1-ol | 3.0 A50 | 452.2 | |
| 231 | 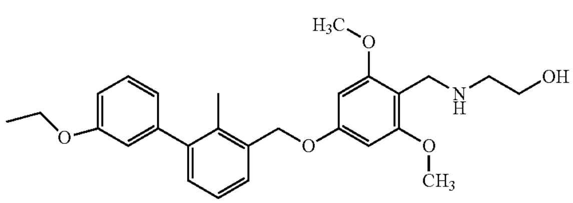 [SMILES: CCOc1cccc(-c2cccc(COc3cc(OC)c(CNCCO)c(OC)c3)c2C)c1] | 2-{[(4-{[3-(3-ethoxyphenyl)-2-methylphenyl]methoxy}-2,6-dimethoxyphenyl)methyl]amino}ethan-1-ol | 4.3 M50 | 452.2 | |
| 232 | 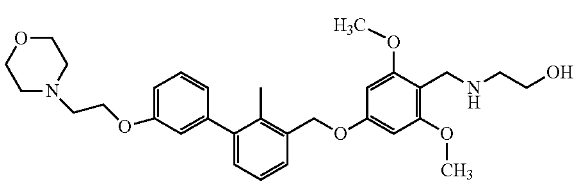 [SMILES: COc1cc(OCc2cccc(-c3cccc(OCCN4CCOCC4)c3)c2C)cc(OC)c1CNCCO] | 2-[({2,6-dimethoxy-4-[(2-methyl-3-{3-[2-(piperidin-1-yl)ethoxy]phenyl}phenyl)methoxy]phenyl}methyl)amino]ethan-1-ol | 2.6 A50 | 535.3 | |

-continued

| Ex. No. | Structure | Name | HPLC Retention Time (minutes) (Method) | ESI-MS m/z MH+ | ESI-MS m/z MH− |
|---|---|---|---|---|---|
| 233 | 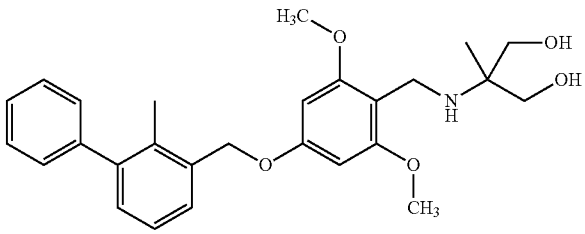 [SMILES: COc1cc(OCc2cccc(-c3ccccc3)c2C)cc(OC)c1CNC(C)(CO)CO] | 2-[({2,6-dimethoxy-4-[(2-methyl-3-phenylphenyl)methoxy]phenyl}methyl)amino]-2-methylpropane-1,3-diol | 2.9 A50 | 452.3 | |
| 234 | 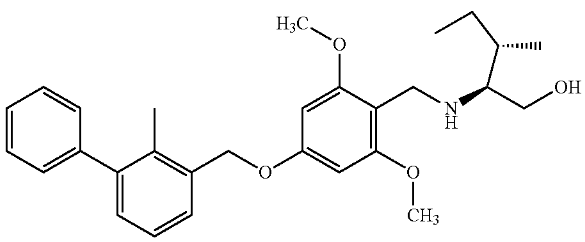 [SMILES: CC[C@H](C)[C@@H](CO)NCc1c(OC)cc(OCc2cccc(-c3ccccc3)c2C)cc1OC] | (2S,3S)-2-[({2,6-dimethoxy-4-[(2-methyl-3-phenylphenyl)methoxy]phenyl}methyl)amino]-3-methylpentan-1-ol | 3.3 A50 | 464.4 | |
| 235 | 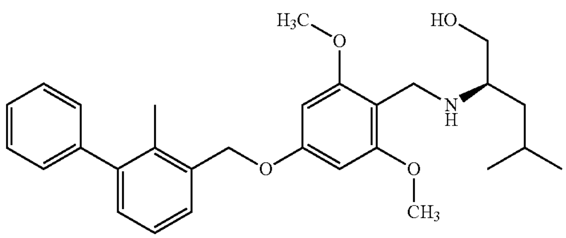 [SMILES: COc1cc(OCc2cccc(-c3ccccc3)c2C)cc(OC)c1CN[C@@H](CO)CC(C)C] | (2R)-2-[({2,6-dimethoxy-4-[(2-methyl-3-phenylphenyl)methoxy]phenyl}methyl)amino]-4-methylpentan-1-ol | 3.3 A50 | 464.4 | |
| 236 | 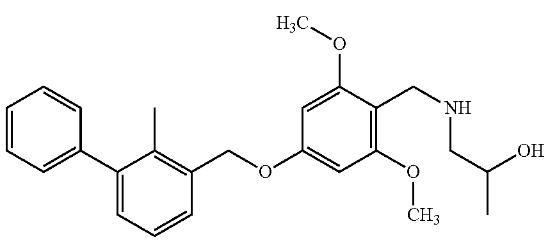 [SMILES: COc1cc(OCc2cccc(-c3ccccc3)c2C)cc(OC)c1CNCC(C)O] | 1-[({2,6-dimethoxy-4-[(2-methyl-3-phenylphenyl)methoxy]phenyl}methyl)amino]propan-2-ol | 3.0 A50 | 422.3 | |
| 237 | 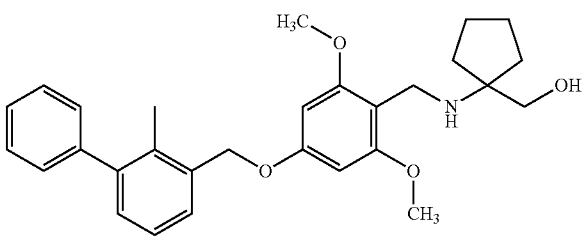 [SMILES: COc1cc(OCc2cccc(-c3ccccc3)c2C)cc(OC)c1CNC1(CO)CCCC1] | {1-[({2,6-dimethoxy-4-[(2-methyl-3-phenylphenyl)methoxy]phenyl}methyl)amino]cyclopentyl}methanol | 3.2 A50 | 462.3 | |
| 238 | 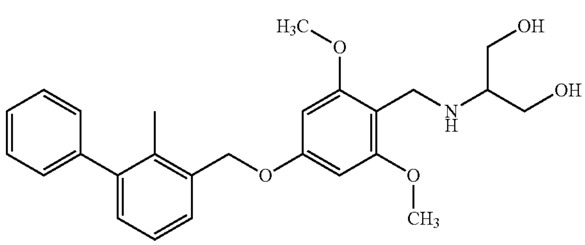 [SMILES: COc1cc(OCc2cccc(-c3ccccc3)c2C)cc(OC)c1CNC(CO)CO] | 2-[({2,6-dimethoxy-4-[(2-methyl-3-phenylphenyl)methoxy]phenyl}methyl)amino]propane-1,3-diol | 4.2 M50 | 438.3 | |

-continued

| Ex. No. | Structure | Name | HPLC Retention Time (minutes) (Method) | ESI-MS m/z MH+ | ESI-MS m/z MH− |
|---|---|---|---|---|---|
| 239 | 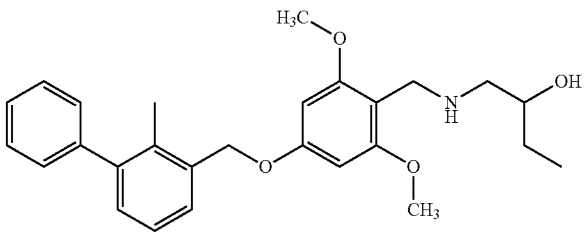 [SMILES: CCC(O)CNCc1c(OC)cc(OCc2cccc(-c3ccccc3)c2C)cc1OC] | 1-[({2,6-dimethoxy-4-[(2-methyl-3-phenylphenyl)methoxy]phenyl}methyl)amino]butan-2-ol | 3.1 A50 | 436.3 | |
| 240 | 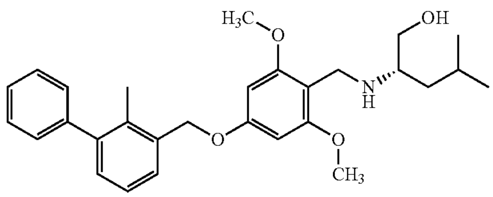 [SMILES: COc1cc(OCc2cccc(-c3ccccc3)c2C)cc(OC)c1CN[C@H](CO)CC(C)C] | (2S)-2-[({2,6-dimethoxy-4-[(2-methyl-3-phenylphenyl)methoxy]phenyl}methyl)amino]-4-methylpentan-1-ol | 3.2 A50 | 465.3 | |
| 241 | 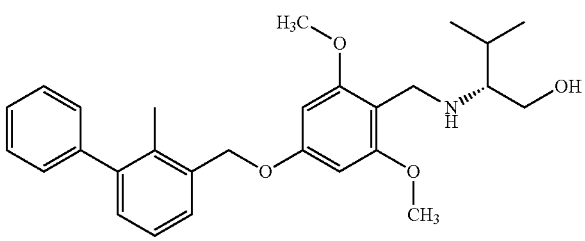 [SMILES: COc1cc(OCc2cccc(-c3ccccc3)c2C)cc(OC)c1CN[C@@H](CO)C(C)C] | (2R)-2-[({2,6-dimethoxy-4-[(2-methyl-3-phenylphenyl)methoxy]phenyl}methyl)amino]-3-methylbutan-1-ol | 4.0 M50 | 450.5 | |
| 242 | 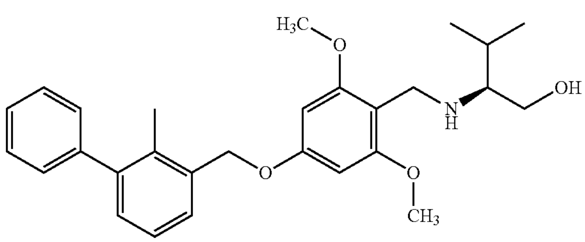 [SMILES: COc1cc(OCc2cccc(-c3ccccc3)c2C)cc(OC)c1CN[C@H](CO)C(C)C] | (2S)-2-[({2,6-dimethoxy-4-[(2-methyl-3-phenylphenyl)methoxy]phenyl}methyl)amino]-3-methylbutan-1-ol | 2.8 A50 | 450.5 | |
| 243 | 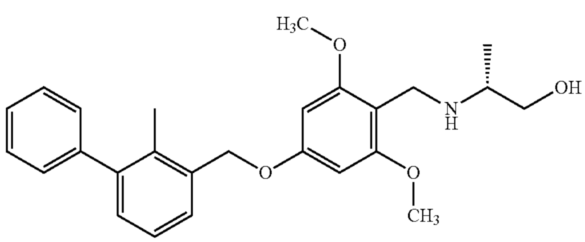 [SMILES: COc1cc(OCc2cccc(-c3ccccc3)c2C)cc(OC)c1CN[C@H](C)CO] | (2R)2-[({2,6-dimethoxy-4-[(2-methyl-3-phenylphenyl)methoxy]phenyl}methyl)amino]propan-1-ol | 3.8 M50 | 422.4 | |
| 244 | 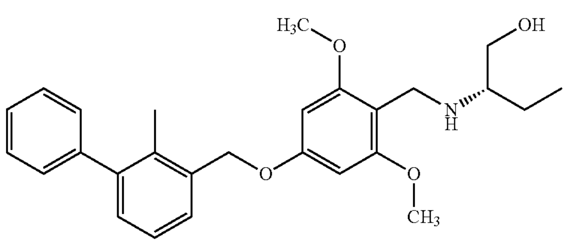 [SMILES: CC[C@@H](CO)NCc1c(OC)cc(OCc2cccc(-c3ccccc3)c2C)cc1OC] | (2S)-2-[({2,6-dimethoxy-4-[(2-methyl-3-phenylphenyl)methoxy]phenyl}methyl)amino]butan-1-ol | 3.9 M50 | 436.4 | |

-continued

| Ex. No. | Structure | Name | HPLC Retention Time (minutes) (Method) | ESI-MS m/z MH$^+$ | ESI-MS m/z MH$^-$ |
|---|---|---|---|---|---|
| 245 | 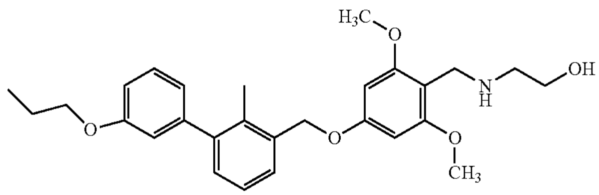 [SMILES: CCCOc1cccc(-c2cccc(COc3cc(OC)c(CNCCO)c(OC)c3)c2C)c1] | 2-{[(2,6-dimethoxy-4-{[2-methyl-3-(3-propoxyphenyl)phenyl]methoxy}phenyl)methyl]amino}ethan-1-ol | 4.2 M50 | 466.4 | |
| 246 | 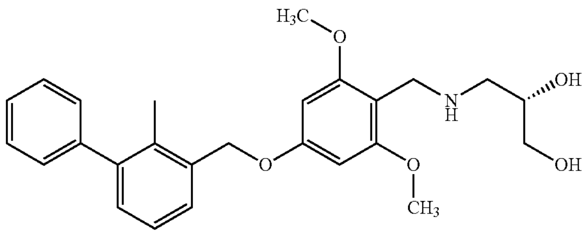 [SMILES: COc1cc(OCc2cccc(-c3ccccc3)c2C)cc(OC)c1CNC[C@H](O)CO] | (2S)-3-[({2,6-dimethoxy-4-[(2-methyl-3-phenylphenyl)methoxy]phenyl}methyl)amino]propane-1,2-diol | 2.9 A50 | 438.3 | |
| 247 | 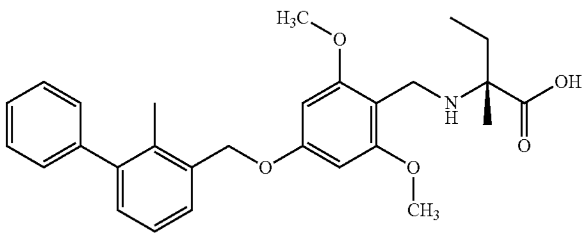 [SMILES: CC[C@@](C)(NCc1c(OC)cc(OCc2cccc(-c3ccccc3)c2C)cc1OC)C(=O)O] | (2R)-2-[({2,6-dimethoxy-4-[(2-methyl-3-phenylphenyl)methoxy]phenyl}methyl)amino]-2-methylbutanoic acid | 3.0 A50 | 464.3 | |
| 248 | 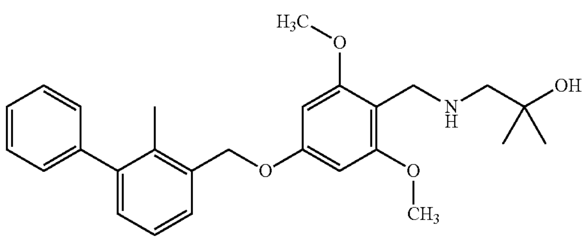 [SMILES: COc1cc(OCc2cccc(-c3ccccc3)c2C)cc(OC)c1CNCC(C)(C)O] | 1-[({2,6-dimethoxy-4-[(2-methyl-3-phenylphenyl)methoxy]phenyl}methyl)amino]-2-methylpropan-2-ol | 3.1 A50 | 436.3 | |
| 249 | 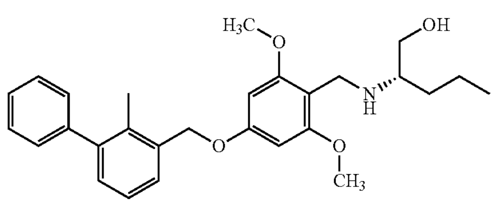 [SMILES: CCC[C@@H](CO)NCc1c(OC)cc(OCc2cccc(-c3ccccc3)c2C)cc1OC] | (2S)-2-[({2,6-dimethoxy-4-[(2-methyl-3-phenylphenyl)methoxy]phenyl}methyl)amino]pentan-1-ol | 4.4 M50 | 450.4 | |
| 250 | 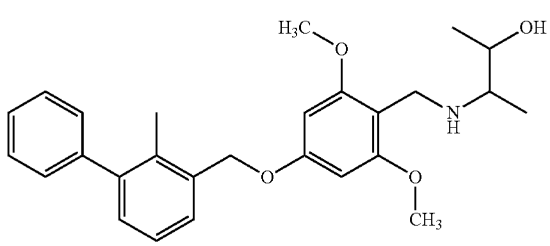 [SMILES: COc1cc(OCc2cccc(-c3ccccc3)c2C)cc(OC)c1CNC(C)C(C)O] | 3-[({2,6-dimethoxy-4-[(2-methyl-3-phenylphenyl)methoxy]phenyl}methyl)amino]butan-2-ol | 4.3 M50 | 436.3 | |

| Ex. No. | Structure | Name | HPLC Retention Time (minutes) (Method) | ESI-MS m/z MH+ | ESI-MS m/z MH− |
|---|---|---|---|---|---|
| 251 | 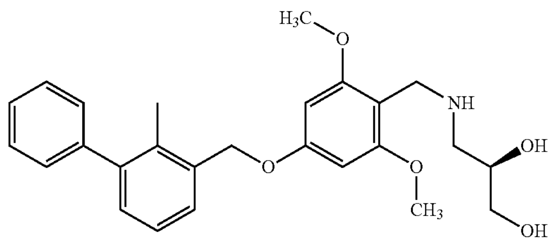 [SMILES: COc1cc(OCc2cccc(-c3ccccc3)c2C)cc(OC)c1CNC[C@@H](O)CO] | (2R)-3-[({2,6-dimethoxy-4-[(2-methyl-3-phenylphenyl)methoxy]phenyl}methyl)amino]propane-1,2-diol | 2.9 A50 | 438.3 | |
| 252 | 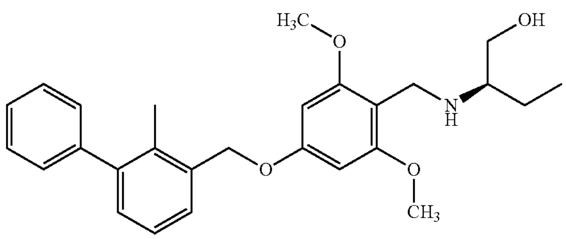 [SMILES: CC[C@H](CO)NCc1c(OC)cc(OCc2cccc(-c3ccccc3)c2C)cc1OC] | (2R)-2-[({2,6-dimethoxy-4-[(2-methyl-3-phenylphenyl)methoxy]phenyl}methyl)amino]butan-1-ol | 2.8 A50 | 436.4 | |
| 253 | 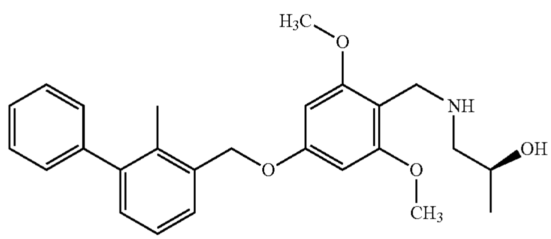 [SMILES: COc1cc(OCc2cccc(-c3ccccc3)c2C)cc(OC)c1CNC[C@H](C)O] | (2S)-1-[({2,6-dimethoxy-4-[(2-methyl-3-phenylphenyl)methoxy]phenyl}methyl)amino]propan-2-ol | 2.7 A50 | 422.4 | |
| 254 | 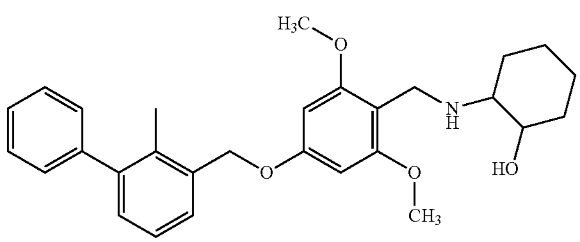 [SMILES: COc1cc(OCc2cccc(-c3ccccc3)c2C)cc(OC)c1CNC1CCCCC1O] | 2-[({2,6-dimethoxy-4-[(2-methyl-3-phenylphenyl)methoxy]phenyl}methyl)amino]cyclohexan-1-ol | 2.8 A50 | 462.5 | |
| 255 | 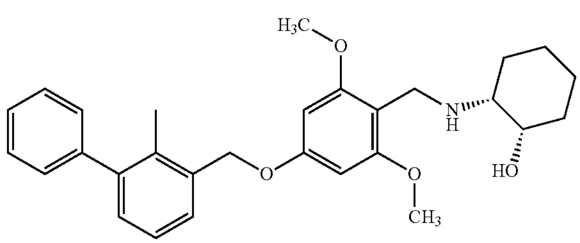 [SMILES: COc1cc(OCc2cccc(-c3ccccc3)c2C)cc(OC)c1CN[C@@H]1CCCC[C@@H]1O] | (1S,2R)-2-[({2,6-dimethoxy-4-[(2-methyl-3-phenylphenyl)methoxy]phenyl}methyl)amino]cyclohexan-1-ol | 2.89 A50 | 462.4 | |
| 256 | 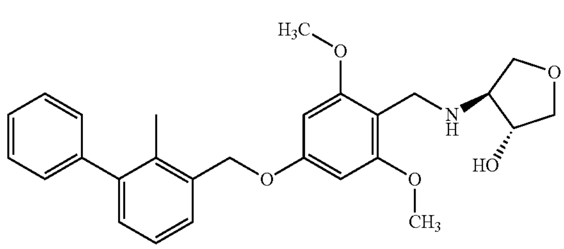 [SMILES: COc1cc(OCc2cccc(-c3ccccc3)c2C)cc(OC)c1CN[C@H]1COC[C@@H]1O] | (3R,4S)-4-[({2,6-dimethoxy-4-[(2-methyl-3-phenylphenyl)methoxy]phenyl}methyl)amino]oxolan-3-ol | 2.7 A50 | 450.3 | |

-continued

| Ex. No. | Structure | Name | HPLC Retention Time (minutes) (Method) | ESI-MS m/z MH+ | ESI-MS m/z MH− |
|---|---|---|---|---|---|
| 257 | 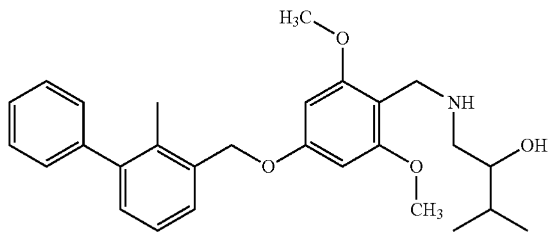 [SMILES: COc1cc(OCc2cccc(-c3ccccc3)c2C)cc(OC)c1CNCC(O)C(C)C] | 1-[({2,6-dimethoxy-4-[(2-methyl-3-phenylphenyl)methoxy]phenyl}methyl)amino]-3-methylbutan-2-ol | 2.9 A50 | 450.4 | |
| 258 | 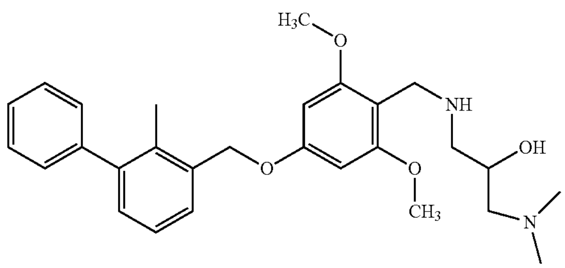 [SMILES: COc1cc(OCc2cccc(-c3ccccc3)c2C)cc(OC)c1CNCC(O)CN(C)C] | ({2,6-dimethoxy-4-[(2-methyl-3-phenylphenyl)methoxy]phenyl}methyl)[3-(dimethylamino)-2-hydroxypropyl]amine | 3.9 M50 | 465.5 | |
| 259 | 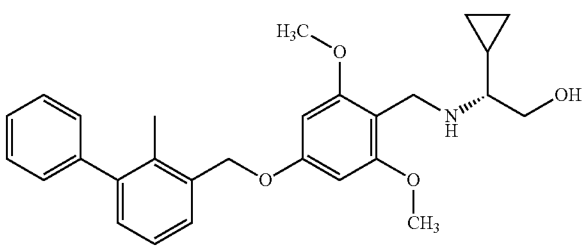 [SMILES: COc1cc(OCc2cccc(-c3ccccc3)c2C)cc(OC)c1CN[C@@H](CO)C1CC1] | (2R)-2-cyclopropyl-2-[({2,6-dimethoxy-4-[(2-methyl-3-phenylphenyl)methoxy]phenyl}methyl)amino]ethan-1-ol | 2.8 A50 | 448.4 | |
| 260 | 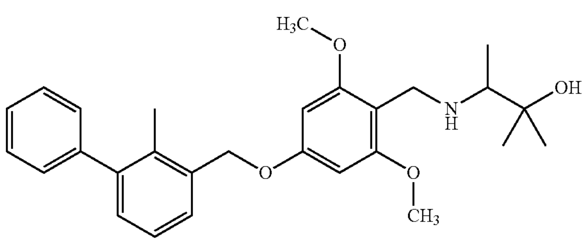 [SMILES: COc1cc(OCc2cccc(-c3ccccc3)c2C)cc(OC)c1CNC(C)C(C)(C)O] | 3-[({2,6-dimethoxy-4-[(2-methyl-3-phenylphenyl)methoxy]phenyl}methyl)amino]-2-methylbutan-2-ol | 2.8 A50 | 450.4 | |
| 261 | 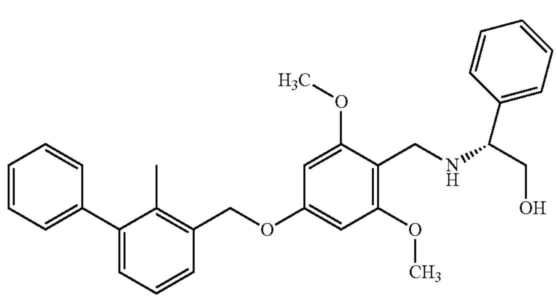 [SMILES: COc1cc(OCc2cccc(-c3ccccc3)c2C)cc(OC)c1CN[C@@H](CO)c1ccccc1] | (2R)-2-[({2,6-dimethoxy-4-[(2-methyl-3-phenylphenyl)methoxy]phenyl}methyl)amino]-2-phenylethan-1-ol | 3.0 A50 | 484.5 | |

-continued

| Ex. No. | Structure | Name | HPLC Retention Time (minutes) (Method) | ESI-MS m/z MH+ | ESI-MS m/z MH− |
|---|---|---|---|---|---|
| 262 | 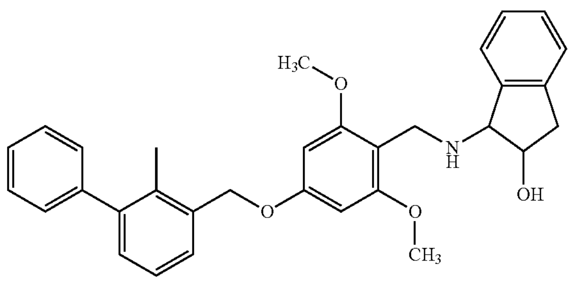 [SMILES: COc1cc(OCc2cccc(-c3ccccc3)c2C)cc(OC)c1CNC1c2ccccc2CC1O] | 1-[({2,6-dimethoxy-4-[(2-methyl-3-phenylphenyl)methoxy]phenyl}methyl)amino]-2.3-dihydro-1H-inden-2-ol | 3.1 A50 | 496.5 | |
| 263 | 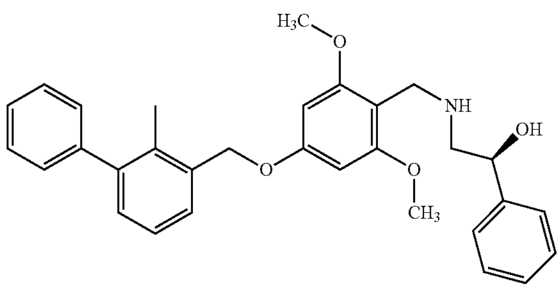 [SMILES: COc1cc(OCc2cccc(-c3ccccc3)c2C)cc(OC)c1CNC[C@@H](O)c1ccccc1] | (1S)-2-[({2,6-dimethoxy-4-[(2-methyl-3-phenylphenyl)methoxy]phenyl}methyl)amino]-1-phenylethan-1-ol | 3.0 A50 | 484.5 | |
| 264 | 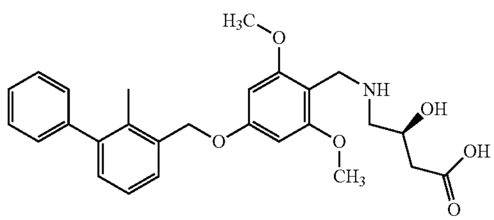 [SMILES: COc1cc(OCc2cccc(-c3ccccc3)c2C)cc(OC)c1CNC[C@@H](O)CC(=O)O] | (3S)-4-[({2,6-dimethoxy-4-[(2-methyl-3-phenylphenyl)methoxy]phenyl}methyl)amino]-3-hydroxybutanoic acid | 2.4 A50 | 466.4 | |
| 265 | 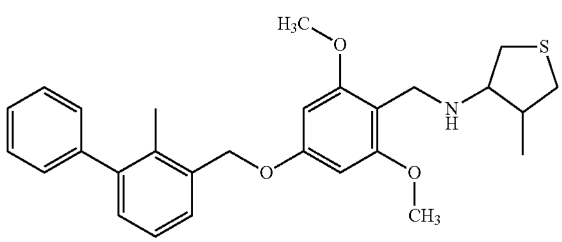 [SMILES: COc1cc(OCc2cccc(-c3ccccc3)c2C)cc(OC)c1CNC1CSCC1C] | 4-[((2,6-dimethoxy-4-[(2-methyl-3-phenylphenyl)methoxy]phenyl}methyl)amino]thiolan-3-ol | 2.9 A50 | 466.4 | |
| 266 | 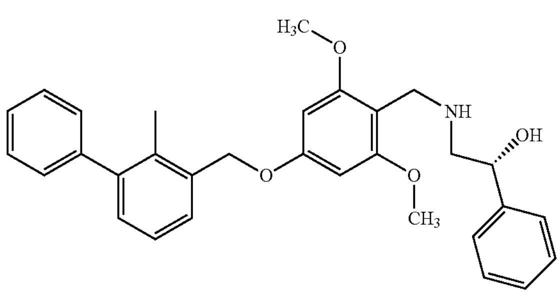 [SMILES: COc1cc(OCc2cccc(-c3ccccc3)c2C)cc(OC)c1CNC[C@H](O)c1ccccc1] | (1R)-2-[({2,6-dimethoxy-4-[(2-methyl-3-phenylphenyl)methoxy]phenyl}methyl)amino]-1-phenylethan-1-ol | 3.0 A50 | 484.5 | |

| Ex. No. | Structure | Name | HPLC Retention Time (minutes) (Method) | ESI-MS m/z MH+ | ESI-MS m/z MH− |
|---|---|---|---|---|---|
| 267 | 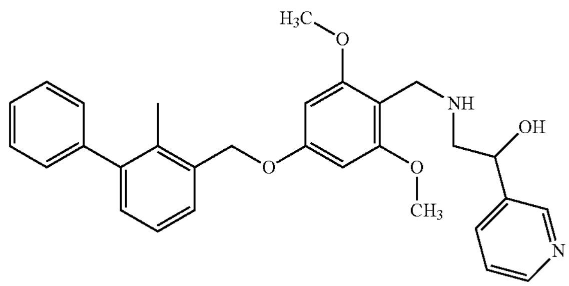 [SMILES: COc1cc(OCc2cccc(-c3ccccc3)c2C)cc(OC)c1CNCC(O)c1cccnc1] | 2-[({2,6-dimethoxy-4-[(2-methyl-3-phenylphenyl)methoxy]phenyl}methyl)amino]-1-(pyridin-3-yl)ethan-1-ol | 3.9 M50 | 485.4 | |
| 268 | 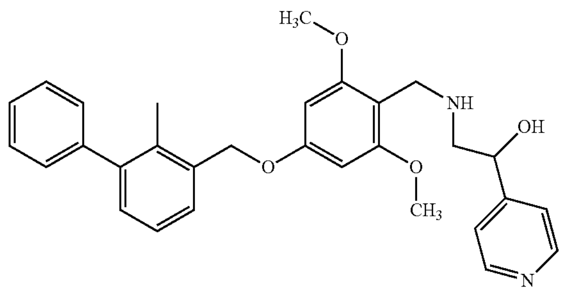 [SMILES: COc1cc(OCc2cccc(-c3ccccc3)c2C)cc(OC)c1CNCC(O)c1ccncc1] | 2-[({2,6-dimethoxy-4-[(2-methyl-3-phenylphenyl)methoxy]phenyl}methyl)amino]-1-(pyridin-4-yl)ethan-1-ol | 2.7 A50 | 485.5 | |
| 269 | 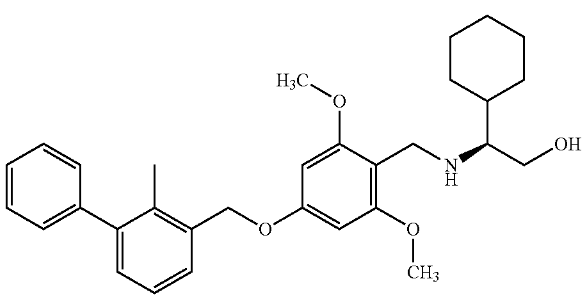 [SMILES: COc1cc(OCc2cccc(-c3ccccc3)c2C)cc(OC)c1CN[C@H](CO)C1CCCCC1] | (2S)-2-cyclohexyl-2-[({2,6-dimethoxy-4-[(2-methyl-3-phenylphenyl)methoxy]phenyl}methyl)amino]ethan-1-ol | 3.1 A50 | 490.5 | |
| 270 | 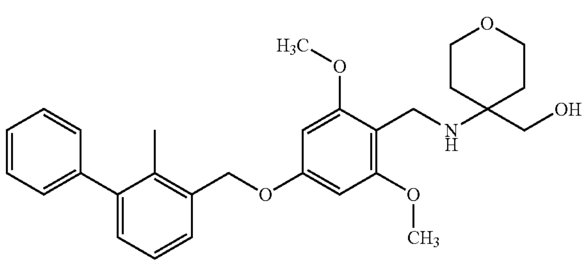 [SMILES: COc1cc(OCc2cccc(-c3ccccc3)c2C)cc(OC)c1CNC1(CO)CCOCC1] | {4-[({2,6-dimethoxy-4-[(2-methyl-3-phenylphenyl)methoxy]phenyl}methyl)amino]oxan-4-yl}methanol | 2.7 A50 | 478.4 | |
| 271 | 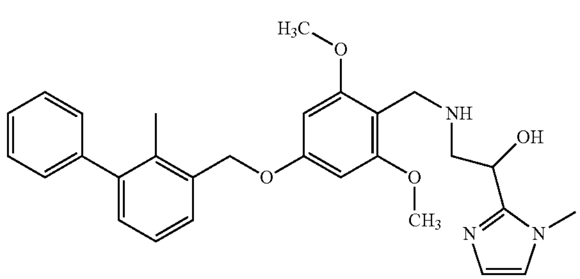 [SMILES: COc1cc(OCc2cccc(-c3ccccc3)c2C)cc(OC)c1CNCC(O)c1nccn1C] | 2-[({2,6-dimethoxy-4-[(2-methyl-3-phenylphenyl)methoxy]phenyl}methyl)amino]-1-(1-methyl-1H-imidazol-2-yl)ethan-1-ol | 2.8 A50 | 488.4 | |

-continued

| Ex. No. | Structure | Name | HPLC Retention Time (minutes) (Method) | ESI-MS m/z MH+ | ESI-MS m/z MH− |
|---|---|---|---|---|---|
| 272 | 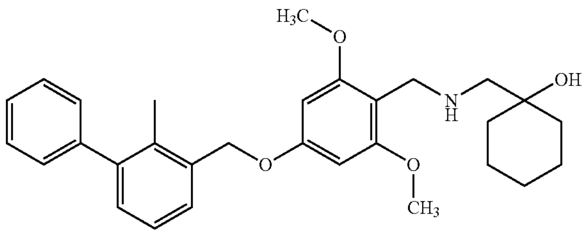 [SMILES: COc1cc(OCc2cccc(-c3ccccc3)c2C)cc(OC)c1CNCC1(O)CCCCC1] | 1-{[({2,6-dimethoxy-4-[(2-methyl-3-phenylphenyl)methoxy]phenyl}methyl)amino]methyl}cyclohexan-1-ol | 4.1 M50 | 476.5 | |
| 273 | 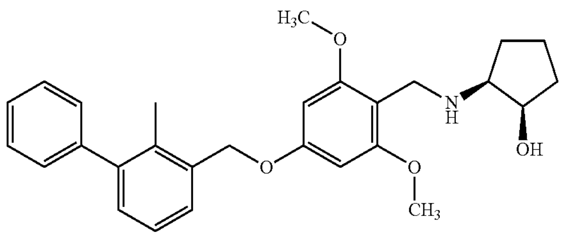 [SMILES: COc1cc(OCc2cccc(-c3ccccc3)c2C)cc(OC)c1CN[C@H]1CCC[C@H]1O] | (1R,2S)-2-[({2,6-dimethoxy-4-[(2-methyl-3-phenylphenyl)methoxy]phenyl}methyl)amino]cyclopentan-1-ol | 2.8 A50 | 448.4 | |
| 274 | 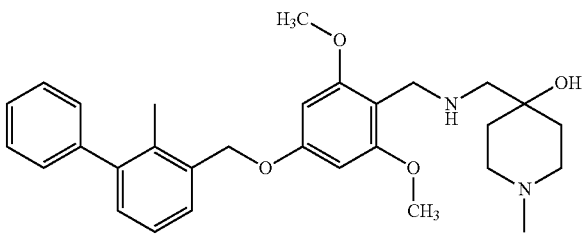 [SMILES: COc1cc(OCc2cccc(-c3ccccc3)c2C)cc(OC)c1CNCC1(O)CCN(C)CC1] | 4-{[({2,6-dimethoxy-4-[(2-methyl-3-phenylphenyl)methoxy]phenyl}methyl)amino]methyl}-1-methylpiperidin-4-ol | 3.9 M50 | 491.5 | |
| 275 | 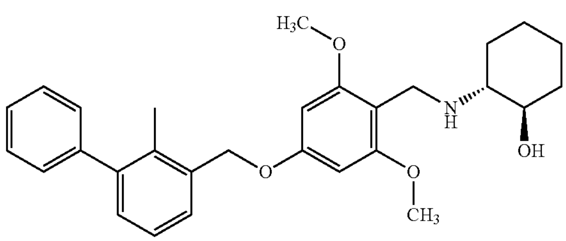 [SMILES: COc1cc(OCc2cccc(-c3ccccc3)c2C)cc(OC)c1CN[C@@H]1CCCC[C@H]1O] | (1R,2R)-2-[({2,6-dimethoxy-4-[(2-methyl-3-phenylphenyl)methoxy]phenyl}methyl)amino]cyclohexan-1-ol | 2.9 A50 | 462.4 | |
| 276 | 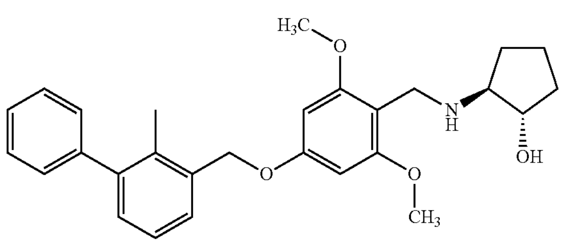 [SMILES: COc1cc(OCc2cccc(-c3ccccc3)c2C)cc(OC)c1CN[C@H]1CCC[C@@H]1O] | (1S,2S)-2-[({2,6-dimethoxy-4-[(2-methyl-3-phenylphenyl)methoxy]phenyl}methyl)amino]cyclopentan-1-ol | 2.7 A50 | 448.4 | |
| 277 | 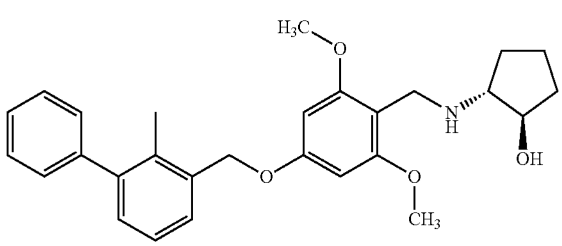 [SMILES: COc1cc(OCc2cccc(-c3ccccc3)c2C)cc(OC)c1CN[C@@H]1CCC[C@H]1O] | (1R,2R)-2-[({2,6-dimethoxy-4-[(2-methyl-3-phenylphenyl)methoxy]phenyl}methyl)amino]cyclopentan-1-ol | 2.7 A50 | 448.4 | |

-continued

| Ex. No. | Structure | Name | HPLC Retention Time (minutes) (Method) | ESI-MS m/z MH+ | ESI-MS m/z MH− |
|---|---|---|---|---|---|
| 278 | 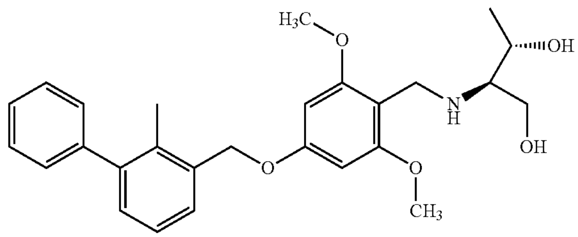 [SMILES: COc1cc(OCc2cccc(-c3ccccc3)c2C)cc(OC)c1CN[C@H](CO)[C@H](C)O] | (2R,3S)-2-[({2,6-dimethoxy-4-[(2-methyl-3-phenylphenyl)methoxy]phenyl}methyl)amino]butane-1,3-diol | 3.0 A50 | 452.3 | |
| 279 | 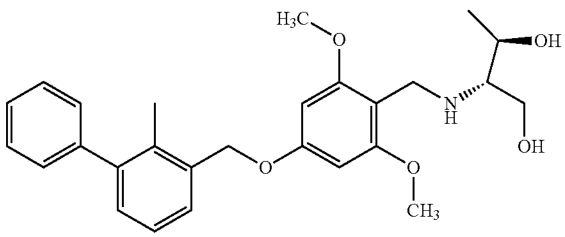 [SMILES: COc1cc(OCc2cccc(-c3ccccc3)c2C)cc(OC)c1CN[C@@H](CO)[C@@H](C)O] | (2S,3R)-2-[({2,6-dimethoxy-4-[(2-methyl-3-phenylphenyl)methoxy]phenyl}methyl)amino]butane-1,3-diol | 4.3 M50 | 452.3 | |
| 280 | 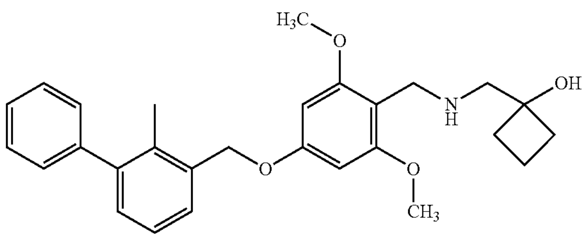 [SMILES: COc1cc(OCc2cccc(-c3ccccc3)c2C)cc(OC)c1CNCC1(O)CCC1] | 1-{[({2,6-dimethoxy-4-[(2-methyl-3-phenylphenyl)methoxy]phenyl}methyl)amino]methyl}cyclobutan-1-ol | 2.9 A50 | 448.4 | |
| 281 | 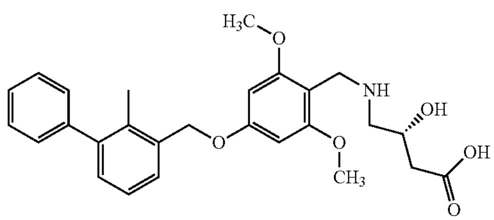 [SMILES: COc1cc(OCc2cccc(-c3ccccc3)c2C)cc(OC)c1CNC[C@H](O)CC(=O)O] | (3R)-4-[({2,6-dimethoxy-4-[(2-methyl-3-phenylphenyl)methoxy]phenyl}methyl)amino]-3-hydroxybutanoic acid | 3.8 M50 | 466.4 | |
| 282 | 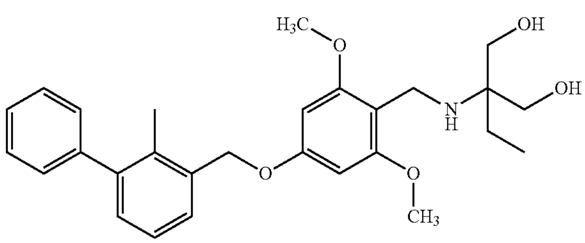 [SMILES: CCC(CO)(CO)NCc1c(OC)cc(OCc2cccc(-c3ccccc3)c2C)cc1OC] | 2-[({2,6-dimethoxy-4-[(2-methyl-3-phenylphenyl)methoxy]phenyl}methyl)amino]-2-ethylpropane-1,3-diol | 3.0 A50 | 466.4 | |
| 283 | 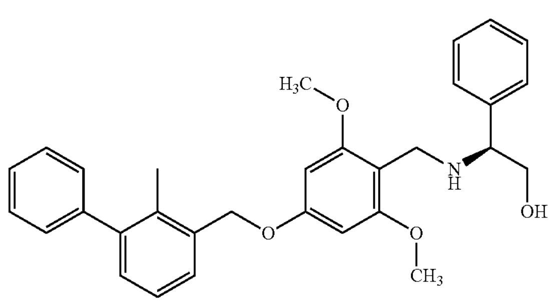 [SMILES: COc1cc(OCc2cccc(-c3ccccc3)c2C)cc(OC)c1CN[C@H](CO)c1ccccc1] | (2S)-2-[({2,6-dimethoxy-4-[(2-methyl-3-phenylphenyl)methoxy]phenyl}methyl)amino]-2-phenylethan-1-ol | 3.0 A50 | 484.4 | |

-continued

| Ex. No. | Name | HPLC Retention Time (minutes) (Method) | ESI-MS m/z MH+ | ESI-MS m/z MH− |
|---|---|---|---|---|
| 284 | 1-({2,6-dimethoxy-4-[(2-methyl-3-phenylphenyl)methoxy]phenyl}methyl)-4-hydroxypiperidine-4-carboxamide | 2.6 A50 | 491.6 | |
| 285 | N-(2-{[(2,6-dimethoxy-4-{[3-(3-methoxyphenyl)-2-methylphenyl]methoxy}phenyl)methyl]amino}ethyl)acetamide | 2.9 M50 | 479.4 | |
| 286 | N-(2-{[(4-{[3-(3-ethoxyphenyl)-2-methylphenyl]methoxy}-2,6-dimethoxyphenyl)methyl]amino}ethyl)acetamide | 1.9 A50 | 493.3 | |
| 287 | N-(2-{[(4-{[3-(2H-1,3-benzodioxol-5-yl)-2-methylphenyl]methoxy}-2,6-dimethoxyphenyl)methyl]amino}ethyl)acetamide | 1.7 A50 | 493.5 | |
| 288 | [(4-{[3-(2H-1,3-benzodioxol-5-yl)-2-methylphenyl]methoxy}-2,6-dimethoxyphenyl)methyl][2-methyl-1-(4-methylpiperazin-1-yl)propan-2-yl]amine | 1.9 A50 | 562.4 | |
| 289 | N-(2-{[(4-{[3-(2,3-dihydro-1,4-benzodioxin-6-yl)-2-methylphenyl]methoxy}-2,6-dimethoxyphenyl)methyl]amino}ethyl)acetamide | 1.7 A50 | 507.3 | |
| 290 | [(4-{[3-(3-ethoxyphenyl)-2-methylphenyl]methoxy}-2,6-dimethoxyphenyl)methyl][2-methyl-1-(4-methylpiperazin-2-yl)propan-2-yl]amine | 2.1 A50 | 562.5 | |

-continued

| Ex. No. | Structure | Name | HPLC Retention Time (minutes) (Method) | ESI-MS m/z MH+ | ESI-MS m/z MH− |
|---|---|---|---|---|---|
| 291 | 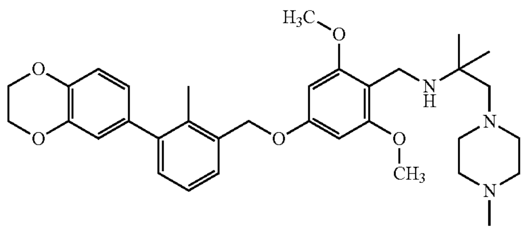 [SMILES: COc1cc(OCc2cccc(-c3ccc4c(c3)OCCO4)c2C)cc(OC)c1CNC(C)(C)CN1CCN(C)CC1] | [(4-{[3-(2,3-dihydro-1,4-benzodioxin-6-yl)-2-methylphenyl]methoxy}-2,6-dimethoxyphenyl)methyl][2-methyl-1-(4-methylpiperazin-1-yl)propan-2-yl]amine | 1.8 A50 | 576.5 | |
| 292 | 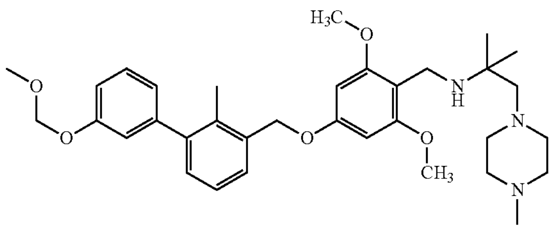 [SMILES: COCOc1cccc(-c2cccc(COc3cc(OC)c(CNC(C)(C)CN4CCN(C)CC4)c(OC)c3)c2C)c1] | {[2,6-dimethoxy-4-({3-[3-(methoxymethoxy)phenyl]-2-methylphenyl}methoxy)phenyl]methyl}[2-methyl-1-(4-methylpiperazin-1-yl)propan-2-yl]amine | 2.8 M50 | 578.6 | |
| 293 | 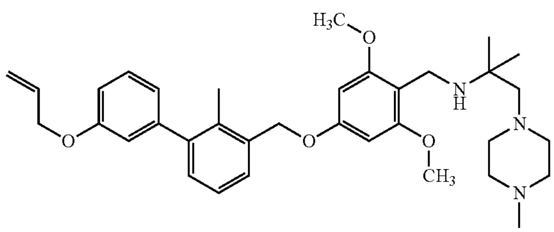 [SMILES: C=CCOc1cccc(-c2cccc(COc3cc(OC)c(CNC(C)(C)CN4CCN(C)CC4)c(OC)c3)c2C)c1] | {[2,6-dimethoxy-4-({2-methyl-3-[3-(prop-2-en-1-yloxy)phenyl]phenyl}methoxy)phenyl]methyl}[2-methyl-1-(4-methylpiperazin-1-yl)propan-2-yl]amine | 3.0 M50 | 574.6 | |
| 294 | 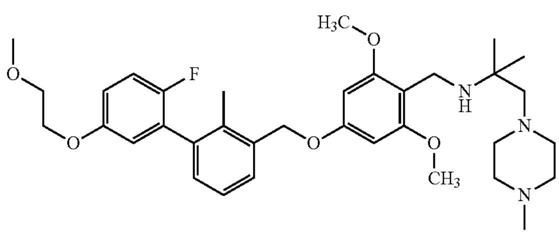 [SMILES: COCCOc1ccc(F)c(-c2cccc(COc3cc(OC)c(CNC(C)(C)CN4CCN(C)CC4)c(OC)c3)c2C)c1] | {[4-({3-[2-fluoro-5-(2-methoxyethoxy)phenyl]-2-methylphenyl}methoxy)-2,6-dimethoxyphenyl]methyl}[2-methyl-1-(4-methylpiperazin-1-yl)propan-2-yl]amine | 2.9 M50 | 610.4 | |
| 295 | 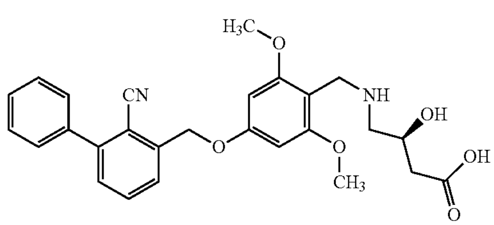 [SMILES: COc1cc(OCc2cccc(-c3ccccc3)c2C#N)cc(OC)c1CNC[C@@H](O)CC(=O)O] | (3S)-4-[({4-[(2-cyano-3-phenylphenyl)methoxy]-2,6-dimethoxyphenyl}methyl)amino]-3-hydroxybutanoic acid | 2.5 M50 | 477.5 | |
| 296 | 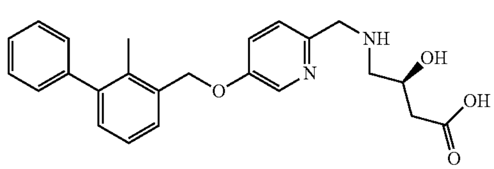 [SMILES: Cc1c(COc2ccc(CNC[C@@H](O)CC(=O)O)nc2)cccc1-c1ccccc1] | (3S)-3-hydroxy-4-[({5-[(2-methyl-3-phenylphenyl)methoxy]pyridin-2-yl}methyl)amino]butanoic acid | 1.7 A50 | 407.3 | |
| 297 | 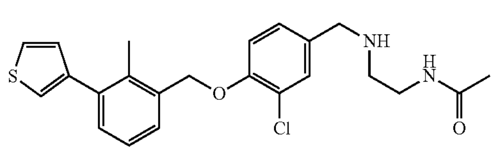 [SMILES: CC(=O)NCCNCc1ccc(OCc2cccc(-c3ccsc3)c2C)c(Cl)c1] | N-(2-{[(3-chloro-4-{[2-methyl-3-(thiophen-3-yl)phenyl]methoxy}phenyl)methyl]amino}ethyl)acetamide | 2.9 M50 | 429 | |

| Ex. No. | $^1$H NMR (500 MHz) δ ppm |
|---|---|
| 5 | $^1$H NMR (500 MHz, DMSO-d$_6$) δ 7.81 (br. s., 1H), 7.58 (d, J = 7.6 Hz, 1H), 7.51-7.44 (m, 2H), 7.40 (d, J = 7.0 Hz, 1H), 7.34-7.29 (m, 3H), 7.23 (d, J = 7.6 Hz, 1H), 6.83 (s, 1H), 5.29 (s, 2H), 3.88 (s, 3H), 3.77 (s, 3H), 3.71 (s, 2H), 3.14 (d, J = 6.1 Hz, 2H), 2.58 (t, J = 6.0 Hz, 2H), 2.26 (s, 3H), 1.79 (s, 3H) |
| 6 | $^1$H NMR (500 MHz, DMSO-d$_6$) δ 7.52-7.45 (m, 3H), 7.43-7.37 (m, 1H), 7.35-7.27 (m, 3H), 7.22 (d, J = 7.0 Hz, 1H), 6.38 (s, 2H), 5.17 (s, 2H), 3.79 (s, 6H), 3.61 (s, 2H), 2.31 (br. s., 3H), 2.23 (s, 5H), 2.15 (s, 3H), 1.89 (s, 5H, acetate), 1.04 (s, 6H) |
| 23 | $^1$H NMR (500 MHz, DMSO-d$_6$) δ 7.57-7.13 (m, 11H), 5.23 (br. s., 2H), 3.89 (d, J = 12.5 Hz, 3H), 3.52 (d, J = 13.7 Hz, 1H), 3.36 (br. s., 1H), 3.17 (br. s., 3H), 2.39 (d, J = 7.9 Hz, 1H), 2.22 (br. s., 3H), 2.03 (br. s., 2H) |
| 27 | $^1$H NMR (500 MHz, DMSO-d$_6$) δ 7.52-7.44 (m, 3H), 7.41-7.37 (m, 1H), 7.35-7.28 (m, 3H), 7.28-7.19 (m, 2H), 6.96 (d, J = 8.5 Hz, 1H), 5.15 (s, 2H), 3.93-3.88 (m, 1H), 3.70-3.64 (m, 4H), 3.19-3.14 (m, 2H), 2.94 (d, J = 11.3 Hz, 1H), 2.36 (d, J = 5.8 Hz, 1H), 2.12 (s, 3H), 1.91 (s, 3H), 1.86-1.70 (m, 2H), 1.56-1.32 (m, 3H) |
| 31 | $^1$H NMR (500 MHz, DMSO-d$_6$) δ 7.51 (d, J = 7.0 Hz, 1H), 7.49-7.44 (m, 2H), 7.42-7.36 (m, 2H), 7.34-7.23 (m, 5H), 7.21 (d, J = 7.6 Hz, 1H), 5.23 (s, 2H), 3.83 (d, J = 13.7 Hz, 1H), 3.75 (d, J = 3.4 Hz, 2H), 3.58-3.54 (m, 2H), 3.49 (d, J = 13.7 Hz, 1H), 3.19-3.15 (m, 1H), 2.90-2.85 (m, 1H), 2.22 (s, 4H) |
| 33 | $^1$H NMR (500 MHz, DMSO-d$_6$) δ 7.57-7.13 (m, 11H), 5.23 (br. s., 2H), 2.72 (d, J = 10.7 Hz, 2H), 2.29-2.11 (m, 4H), 2.02-1.85 (m, 4H), 1.77 (d, J = 10.1 Hz, 2H), 1.53 (d, J = 9.2 Hz, 2H) |
| 34 | $^1$H NMR (500 MHz, DMSO-d$_6$) δ 7.54-7.42 (m, 4H), 7.39 (d, J = 7.3 Hz, 1H), 7.34-7.25 (m, 5H), 7.21 (d, J = 7.3 Hz, 1H), 5.24 (br. s., 2H), 3.82 (d, J = 13.4 Hz, 1H), 3.45 (d, J = 12.2 Hz, 1H), 3.05 (br. s., 1H), 2.85 (br. s., 1H), 2.27-2.15 (m, 4H), 1.80 (br. s., 1H), 1.68 (br. s., 1H), 1.48 (br. s., 3H), 1.35 (br. s., 1H) |
| 35 | $^1$H NMR (500 MHz, DMSO-d$_6$) δ ppm 7.58-7.12 (m, 11H), 5.24 (br. s., 2H), 3.99-3.80 (m, 2H), 3.12-3.04 (m, 1H), 2.95-2.85 (m, 1H), 2.37-2.27 (m, 1H), 2.22 (s, 3H), 1.95-1.25 (m, 6H) |
| 37 | $^1$H NMR (500 MHz, DMSO-d$_6$) δ 7.94 (br. s., 1H), 7.45 (t, J = 7.3 Hz, 3H), 7.41-7.33 (m, 1H), 7.33-7.25 (m, 3H), 7.19 (d, J = 7.6 Hz, 1H), 6.35 (s, 2H), 5.15 (s, 2H), 3.15 (d, J = 4.9 Hz, 2H), 2.56 (br. s., 2H), 2.51 (br. s., 6H), 2.20 (s, 3H), 1.83 (s, 3H), 1.79 (s, 3H) |
| 40 | 1H NMR (500 MHz, DMSO-d$_6$) δ 7.56-7.01 (m, 11H), 5.14 (br. s., 2H), 3.98-3.84 (m, 2H), 3.56 (d, J = 13.4 Hz, 1H), 3.41-3.35 (m, 1H), 3.17 (s, 4H), 2.20 (d, J = 11.3 Hz, 6H), 2.11-1.98 (m, 2H) |
| 45 | $^1$H NMR (500 MHz, DMSO-d$_6$) δ 7.77 (br. s., 1H), 7.51 (d, J = 7.3 Hz, 1H), 7.49-7.43 (m, 2H), 7.43-7.35 (m, 2H), 7.35-7.24 (m, 5H), 7.21 (d, J = 7.6 Hz, 1H), 5.22 (s, 2H), 3.66 (d, J = 6.4 Hz, 1H), 3.14-2.99 (m, 2H), 2.42-2.28 (m, 2H), 2.23 (s, 3H), 1.77 (s, 3H), 1.26-1.18 (m, 3H) |
| 57 | $^1$H NMR (500 MHz, DMSO-d$_6$) δ 7.56-7.04 (m, 11H), 5.15 (br. s., 2H) 3.67 (d, J = 13.7 Hz, 2H), 3.13-2.90 (m, 2H), 2.42 (br. s., 1H), 2.20 (d, J = 9.5 Hz, 6H), 1.95-1.27 (m, 6H) |
| 58 | $^1$H NMR (500 MHz, DMSO-d$_6$) δ 7.51-7.43 (m, 3H), 7.39 (d, J = 6.7 Hz, 1H), 7.35-7.26 (m, 3H), 7.19 (d, J = 6.7 Hz, 1H), 7.10-7.00 (m, 3H), 5.13 (br. s., 2H), 2.72 (br. s., 2H), 2.20 (s, 7H), 1.99-1.88 (m, 3H), 1.76 (d, J = 12.5 Hz, 2H), 1.52 (d, J = 10.7 Hz, 2H) |
| 59 | $^1$H NMR (500 MHz, DMSO-d$_6$) δ 7.52-7.43 (m, 3H), 7.38 (br. s., 1H), 7.35-7.27 (m, 3H), 7.19 (br. s., 3H), 7.09 (d, J = 7.0 Hz, 1H), 5.15 (br. s., 2H), 3.97 (d, J = 13.1 Hz, 1H), 3.04 (br. s., 1H), 2.95 (br. s., 1H), 2.35 (br. s., 1H), 2.20 (d, J = 9.8 Hz, 6H), 1.85 (br. s., 1H), 1.68 (d, J = 8.9 Hz, 1H), 1.53 (br. s., 3H), 1.34 (br. s., 1H) |
| 60 | $^1$H NMR (500 MHz, DMSO-d$_6$) δ 7.52-7.44 (m, 3H), 7.41-7.36 (m, 1H), 7.33 (d, J = 7.3 Hz, 2H), 7.29 (t, J = 7.6 Hz, 1H), 7.20 (d, J = 7.6 Hz, 1H), 7.15-7.10 (m, 2H), 6.87 (d, J = 7.9 Hz, 1H), 5.16 (s, 2H), 3.96 (d, J = 13.1 Hz, 1H), 3.65 (d, J = 13.4 Hz, 1H), 3.08 (dd, J = 8.1, 3.8 Hz, 1H), 2.92 (br. s., 1H), 2.31 (br. s., 1H), 2.23 (s, 3H), 2.18 (s, 3H), 1.82 (br. s., 1H), 1.76-1.65 (m, 1H), 1.51 (br. s., 3H), 1.35 (br. s., 1H) |
| 65 | $^1$H NMR (500 MHz, DMSO-d$_6$) δ 7.64-7.12 (m, 11H), 5.27 (br. s., 2H), 3.84 (br. s., 2H), 2.22 (br. s., 3H), 1.38-1.23 (m, 6H) |
| 66 | $^1$H NMR (500 MHz, DMSO-d$_6$) δ 7.81 (br. s., 1H), 7.52 (d, J = 7.3 Hz, 1H), 7.50-7.45 (m, 2H), 7.44 (s, 1H), 7.42-7.37 (m, 1H), 7.35-7.25 (m, 5H), 7.22 (d, J = 6.7 Hz, 1H), 5.24 (s, 2H), 3.66 (s, 2H), 3.14 (q, J = 6.2 Hz, 2H), 2.57-2.49 (m, 2H), 2.24 (s, 3H), 1.80 (s, 3H) |
| 71 | $^1$H NMR (500 MHz, DMSO-d$_6$) δ 7.82 (br. s., 1H), 7.51-7.44 (m, 3H), 7.41-7.37 (m, 1H), 7.35-7.27 (m, 3H), 7.20 (d, J = 7.3 Hz, 1H), 7.18-7.12 (m, 2H), 7.06 (d, J = 8.2 Hz, 1H), 5.14 (s, 2H), 3.75 (br. s., 1H), 3.16-3.05 (m, 2H), 2.48-2.36 (m, 2H), 2.21 (d, J = 9.2 Hz, 6H), 1.91 (s, 3H, acetate), 1.78 (s, 3H) |
| 78 | $^1$H NMR (500 MHz, DMSO-d$_6$) δ 7.57 (br. s., 1H), 7.51-7.42 (m, 3H), 7.41-7.27 (m, 6H), 7.21 (d, J = 6.4 Hz, 1H), 5.26 (br. s., 2H), 3.99-3.82 (m, 2H), 3.15 (br. s., 1H), 2.22 (br. s., 3H), 1.27 (d, J = 6.4 Hz, 3H) |
| 79 | $^1$H NMR (500 MHz, DMSO-d$_6$) δ 7.67-7.10 (m, 11H), 5.27 (s, 2H), 4.08-3.88 (m, 2H), 2.22 (s, 3H), 1.46-1.05 (m, 3H) |
| 89 | $^1$H NMR (500 MHz, DMSO-d$_6$) δ 7.81 (br. s., 1H), 7.52 (d, J = 7.9 Hz, 1H), 7.49-7.43 (m, 2H), 7.42-7.36 (m, 1H), 7.36-7.27 (m, 3H), 7.21 (d, J = 7.3 Hz, 1H), 7.14-7.06 (m, 2H), 6.83 (d, J = 7.3 Hz, 1H), 5.14 (s, 2H), 3.68 (s, 2H), 3.18-3.10 (m, 2H), 2.54 (t, J = 6.4 Hz, 2H), 2.23 (s, 3H), 2.17 (s, 3H), 1.79 (s, 3H) |
| 93 | $^1$H NMR (500 MHz, DMSO-d$_6$) δ 7.66 (br. s., 1H), 7.45 (d, J = 6.7 Hz, 3H), 7.39 (d, J = 7.3 Hz, 1H), 7.34-7.24 (m, 5H), 7.19 (d, J = 7.3 Hz, 1H), 7.01 (d, J = 7.6 Hz, 2H), 5.12 (br. s., 2H), 3.69-3.57 (m, 4H), 2.49-2.45 (m, 2H), 2.20 (br. s., 3H), 2.14-2.05 (m, 3H), 1.91 (br. s., 3H, acetate), 1.66 (br. s., 1H) |

| Ex. No. | ¹H NMR (500 MHz) δ ppm |
|---|---|
| 97 | ¹H NMR (500 MHz, DMSO-d₆) δ 7.52-7.42 (m, 3H), 7.39 (d, J = 7.3 Hz, 1H), 7.36-7.26 (m, 3H), 7.19 (d, J = 7.6 Hz, 1H), 7.14 (br. s., 2H), 7.03 (d, J = 7.9 Hz, 1H), 5.13 (br. s., 2H), 3.68-3.52 (m, 2H), 2.85 (br. s., 1H), 2.20 (d, J = 11.0 Hz, 6H), 1.10 (br. s., 3H) |
| 101 | ¹H NMR (500 MHz, DMSO-d₆) δ 7.49-7.42 (m, 3H), 7.41-7.36 (m, 1H), 7.32 (d, J = 7.6 Hz, 2H), 7.28 (t, J = 7.6 Hz, 1H), 7.19 (d, J = 7.6 Hz, 1H), 6.98 (d, J = 8.5 Hz, 1H), 6.88-6.77 (m, 2H), 5.10 (s, 2H), 3.04-2.98 (m, 2H), 2.74 (t, J = 5.6 Hz, 2H), 2.19 (s, 3H), 1.90 (s, 2H). |
| 102 | ¹H NMR (500 MHz, DMSO-d₆) δ 7.51-7.44 (m, 3H), 7.41-7.37 (m, 1H), 7.35-7.27 (m, 3H), 7.20 (d, J = 7.6 Hz, 1H), 7.14-7.10 (m, 2H), 7.03 (d, J = 7.9 Hz, 1H), 5.13 (s, 2H), 3.62 (s, 2H), 3.47 (t, J = 5.6 Hz, 2H), 2.56 (t, J = 5.6 Hz, 2H), 2.21 (s, 3H), 2.20 (s, 3H), 1.89 (s, 1H, acetate) |
| 103 | ¹H NMR (500 MHz, DMSO-d₆) δ 7.51-7.45 (m, 3H), 7.41-7.37 (m, 1H), 7.35-7.27 (m, 3H), 7.21 (d, J = 7.0 Hz, 1H), 6.41-6.33 (m, 2H), 5.17 (s, 2H), 3.78 (s, 6H), 3.65 (s, 2H), 3.44 (t, J = 5.5 Hz, 2H), 2.55-2.51 (m, 2H), 2.23 (s, 3H), 1.87 (s, 2H, acetate) |
| 105 | ¹H NMR (500 MHz, DMSO-d₆) δ 7.48 (d, J = 8.2 Hz, 3H), 7.39 (br. s., 1H), 7.33 (d, J = 6.7 Hz, 3H), 7.23 (br. s., 1H), 6.45 (br. s., 2H), 5.21 (br. s., 2H), 3.97 (br. s., 2H), 3.83 (br. s., 6H), 3.06 (br. s., 1H), 2.22 (br. s., 3H), 1.27 (d, J = 5.8 Hz, 3H) |
| 106 | ¹H NMR (500 MHz, DMSO-d₆) δ 7.49 (d, J = 7.0 Hz, 1H), 7.38 (t, J = 7.9 Hz, 1H), 7.32-7.26 (m, 1H), 7.22 (d, J = 7.3 Hz, 1H), 6.96 (d, J = 8.2 Hz, 1H), 6.88 (d, J = 7.3 Hz, 1H), 6.85 (s, 1H), 6.44 (s, 2H), 5.20 (s, 2H), 3.97 (s, 2H), 3.83 (s, 6H), 3.80 (s, 3H), 3.05 (q, J = 7.2 Hz, 1H), 2.23 (s, 3H), 1.27 (d, J = 7.3 Hz, 3H) |
| 107 | ¹H NMR (500 MHz, DMSO-d₆) δ 7.52 (d, J = 7.9 Hz, 1H), 7.29 (d, J = 7.3 Hz, 1H), 7.24 (d, J = 7.9 Hz, 1H), 6.86 (d, J = 11.3 Hz, 1H), 6.74 (d, J = 9.8 Hz, 1H), 6.70 (br. s., 1H), 6.44 (s, 2H), 5.20 (s, 2H), 3.97 (br. s., 2H), 3.82 (d, J = 3.7 Hz, 9H), 3.05 (d, J = 6.7 Hz, 1H), 2.23 (s, 3H), 1.91 (s, 1H), 1.27 (d, J = 6.7 Hz, 3H) |
| 108 | ¹H NMR (500 MHz, DMSO-d₆) δ 7.46 (d, J = 7.6 Hz, 1H), 7.29-7.24 (m, 1H), 7.19 (d, J = 7.6 Hz, 1H), 6.99 (d, J = 7.9 Hz, 1H), 6.88 (s, 1H), 6.76 (d, J = 7.6 Hz, 1H), 6.44 (s, 2H), 6.07 (s, 2H), 5.18 (s, 2H), 3.99 (br. s., 2H), 3.83 (s, 6H), 3.11-3.05 (m, 1H), 2.23 (s, 3H), 1.29 (d, J = 6.7 Hz, 3H) |
| 163 | ¹H NMR (500 MHz, DMSO-d6) δ 7.52-7.44 (m, 3H), 7.42-7.36 (m, 1H), 7.35-7.27 (m, 3H), 7.21 (d, J = 7.3 Hz, 1H), 6.38 (s, 2H), 5.17 (s, 2H), 3.63 (s, 2H), 3.53-3.40 (m, 8H), 2.73 (t, J = 5.2 Hz, 2H), 2.61-2.54 (m, 2H), 2.22 (s, 3H) methoxy peaks hidden by residual water |
| 164 | ¹H NMR (500 MHz, DMSO-d6) δ 7.51-7.44 (m, 3H), 7.41-7.36 (m, 1H), 7.35-7.27 (m, 3H), 7.21 (d, J = 7.6 Hz, 1H), 6.38 (s, 2H), 5.17 (s, 2H), 3.77 (s, 6H), 3.63 (s, 2H), 3.50-3.37 (m, 10H), 2.58 (t, J = 5.3 Hz, 2H), 2.23 (s, 3H) |
| 174 | ¹H NMR (500 MHz, DMSO-d6) δ 7.94 (br. s., 1H), 7.52-7.44 (m, 3H), 7.42-7.37 (m, 1H), 7.35-7.27 (m, 3H), 7.21 (d, J = 7.6 Hz, 1H), 6.38 (s, 2H), 5.17 (s, 2H), 3.78 (s, 6H), 3.65 (s, 2H), 3.52 (br. s., 1H), 2.84 (dd, J = 14.6, 3.4 Hz, 1H), 2.61-2.54 (m, 1H), 2.44 (d, J = 15.0 Hz, 1H), 2.23 (s, 3H). A peak a 2.5 was partially hidden by the DMSO peak. |
| 175 | ¹H NMR (500 MHz, DMSO-d6) δ 8.07 (br. s., 1H), 7.51-7.43 (m, 4H), 7.40 (d, J = 7.3 Hz, 1H), 7.35-7.26 (m, 3H), 7.21 (d, J = 7.0 Hz, 1H), 6.76 (s, 1H), 6.39 (s, 2H), 5.17 (s, 2H), 3.78 (s, 6H), 3.66 (s, 2H), 3.24 (d, J = 6.4 Hz, 2H), 2.67 (t, J = 6.4 Hz, 2H), 2.60 (t, J = 7.5 Hz, 2H), 2.22 (m, 5H). |
| 176 | ¹H NMR (500 MHz, DMSO-d6) δ 7.53-7.44 (m, 3H), 7.40 (d, J = 7.6 Hz, 1H), 7.36-7.27 (m, 3H), 7.22 (d, J = 6.4 Hz, 1H), 6.39 (s, 2H), 5.18 (br. s., 2H), 3.79 (s, 6H), 3.69 (br. s., 2H), 3.42 (t, J = 5.8 Hz, 4H), 2.56 (d, J = 9.8 Hz, 2H), 2.23 (s, 2H), 1.86 (s, 5H), 1.56 (br. s., 2H) NMR signals hidden under residual DMSO and integrals off due to poor phasing. |
| 177 | ¹H NMR (500 MHz, DMSO-d6) δ 7.54-7.17 (m, 10H), 6.91 (br. s., 3H), 6.37 (br. s., 2H), 5.16 (br. s., 2H), 3.99 (br. s., 2H), 3.76 (br. s., 6H), 3.65 (br. s., 2H), 2.60 (br. s., 2H), 2.22 (br. s., 3H), 1.84 (d, J = 5.5 Hz, 2H). |
| 178 | ¹H NMR (500 MHz, DMSO-d6) δ 7.47 (br. s., 3H), 7.39 (br. s., 1H), 7.33 (d, J = 7.0 Hz, 3H), 7.23 (br. s., 1H), 6.45 (br. s., 2H), 5.21 (br. s., 2H), 3.91 (br. s., 2H), 3.83 (br. s., 6H), 3.50 (br. s., 1H), 2.95 (br. s., 2H), 2.23 (br. s., 3H), 1.83-1.65 (m, 2H). |
| 179 | ¹H NMR (500 MHz, DMSO-d6) δ 7.52-7.43 (m, 3H), 7.40 (d, J = 7.0 Hz, 1H), 7.35-7.26 (m, 3H), 7.21 (d, J = 7.0 Hz, 1H), 6.96 (t, J = 7.9 Hz, 1H), 6.42-6.33 (m, 3H), 6.29 (br. s., 1H), 6.20 (d, J = 6.1 Hz, 1H), 5.16 (br. s., 2H), 3.81-3.74 (m, 8H), 3.66 (br. s., 2H), 3.03 (br. s., 4H), 2.44 (br. s., 4H), 2.33 (br. s., 2H), 2.25-2.17 (m, 3H), 1.60 (br. s., 2H) unable to integrate signal at 2.5 ppm because of partial overlap with DMSO. |
| 180 | ¹H NMR (500 MHz, DMSO-d6) δ 7.53-7.43 (m, 3H), 7.42-7.25 (m, 9H), 7.21 (d, J = 7.0 Hz, 1H), 6.37 (s, 2H), 5.16 (br. s., 2H), 4.42 (s, 2H), 3.76 (s, 6H), 3.63 (br. s., 2H), 3.48 (br. s., 2H? partially hidden by water), 2.62 (br. s., 2H), 2.22 (br. s, 3H). |
| 181 | ¹H NMR (500 MHz, DMSO-d6) δ 7.52-7.43 (m, 3H), 7.39 (d, J = 7.0 Hz, 1H), 7.36-7.26 (m, 3H), 7.21 (d, J = 6.7 Hz, 1H), 6.37 (s, 2H), 5.16 (s, 2H), 3.77 (s, 6H), 3.62 (br. s., 2H), 3.52-3.47 (m, impossible to integrate due to a large water signal), 2.57 (br. s., 1H), 2.22 (s, 3H) |

| Ex. No. | ¹H NMR (500 MHz) δ ppm |
|---|---|
| 182 | ¹H NMR (500 MHz, DMSO-d6) δ 7.53-7.44 (m, 3H), 7.39 (d, J = 7.3 Hz, 1H), 7.36-7.25 (m, 3H), 7.21 (d, J = 7.6 Hz, 1H), 6.39 (s, 2H), 5.17 (s, 2H), 3.78 (s, 6H), 3.68 (br. s., 2H), 3.59 (t, J = 6.0 Hz, 2H), 3.50 (br. s., 22H), 2.63 (br. s., 2H), 2.39 (t, J = 5.8 Hz, 2H), 2.22 (s, 3H). Integrals for the region 3.4-3.9 imprecise due to the presence of a broad water peak centered at 3.75. |
| 183 | ¹H NMR (500 MHz, DMSO-d6) δ 7.52-7.44 (m, 3H), 7.42-7.36 (m, 1H), 7.35-7.27 (m, 3H), 7.21 (d, J = 7.6 Hz, 1H), 6.39 (s, 2H), 5.17 (s, 2H), 3.78 (s, 6H), 3.69 (s, 2H), 3.59 (t, J = 6.3 Hz, 2H), 3.52-3.44 (m, 14H), 2.63 (t, J = 5.5 Hz, 2H), 2.38 (t, J = 6.3 Hz, 2H), 2.23 (s, 3H). |
| 184 | ¹H NMR (500 MHz, DMSO-d6) δ 9.35-9.26 (m, 1H), 8.02 (d, J = 8.5 Hz, 1H), 7.72 (d, J = 6.7 Hz, 1H), 7.52-7.43 (m, 3H), 7.42-7.35 (m, 2H), 7.34-7.25 (m, 3H), 7.21 (d, J = 4.3 Hz, 5H), 7.16 (d, J = 4.6 Hz, 1H), 6.37 (s, 2H), 5.17 (s, 2H), 4.59 (d, J = 4.9 Hz, 1H), 3.93 (d, J = 6.4 Hz, 2H), 3.75 (s, 6H), 3.52 (br. s., 1H), 3.11-2.88 (m, 6H), 2.84 (d, J = 4.6 Hz, 1H), 2.22 (s, 3H), 1.71-1.32 (m, 4H). |
| 185 | ¹H NMR (400 MHz, METHANOL-d4) δ 7.44 (s, 3H), 7.40-7.34 (m, 1H), 7.32-7.25 (m, 3H), 7.24-7.19 (m, 1H), 6.42 (s, 2H), 5.22 (s, 2H), 4.20 (s, 2H), 3.96 (s, 2H), 3.90 (s, 6H), 3.78 (s, 2H), 3.69 (s, 2H), 2.26 (s, 3H) |
| 186 | ¹H NMR (500 MHz, DMSO-d6) δ 7.54-7.45 (m, 4H), 7.42-7.37 (m, 1H), 7.35-7.27 (m, 3H), 7.22 (d, J = 7.6 Hz, 1H), 6.42 (s, 2H), 5.20 (s, 2H), 3.90 (br. s., 3H), 3.81 (s, 6H), 3.17 (s, 1H), 2.72 (br. s., 2H), 2.22 (s, 3H), 1.84 (s, 3H), 1.62 (br. s., 4H). |
| 187 | ¹H NMR (500 MHz, DMSO-d6) δ 7.51-7.44 (m, 3H), 7.42-7.37 (m, 1H), 7.35-7.27 (m, 3H), 7.21 (d, J = 7.3 Hz, 1H), 6.38 (s, 2H), 5.17 (s, 2H), 3.78 (s, 6H), 3.62 (s, 2H), 2.61-2.53 (m, 2H(? partially obscured), 2.25-2.16 (m, 6H) |
| 188 | ¹H NMR (500 MHz, DMSO-d6) δ 7.51-7.44 (m, 3H), 7.42-7.37 (m, 1H), 7.35-7.27 (m, 3H), 7.21 (d, J = 7.6 Hz, 1H), 6.37 (s, 2H), 5.17 (s, 2H), 3.77 (s, 6H), 3.60 (s, 2H), 2.46 (d, J = 7.0 Hz, 2H), 2.40-2.32 (m, 1H), 2.23 (s, 3H), 1.95 (d, J = 8.5 Hz, 2H), 1.86-1.73 (m, 2H), 1.62-1.52 (m, 2H) |
| 189 | ¹H NMR (500 MHz, DMSO-d6) δ 8.16-7.98 (m, 2H), 7.51-7.44 (m, 3H), 7.42-7.36 (m, 1H), 7.35-7.27 (m, 3H), 7.21 (d, J = 7.3 Hz, 1H), 6.38 (s, 2H), 5.17 (s, 2H), 4.20 (q, J = 7.8 Hz, 2H), 3.77 (s, 8H), 3.64 (s, 2H), 3.09 (s, 2H), 2.22 (s, 3H), 1.67-1.57 (m, 1H), 1.50 (t, J = 7.2 Hz, 2H), 0.86 (dd, J = 18.0, 6.4 Hz, 6H). |
| 190 | ¹H NMR (400 MHz, CHLOROFORM-d) δ 7.47-7.41 (m, 3H), 7.38 (d, J = 7.1 Hz, 1H), 7.33 (d, J = 6.8 Hz, 2H), 7.30 (d, J = 3.2 Hz, 1H), 6.28 (s, 2H), 5.48 (br. s., 4H), 5.12 (s, 2H), 4.29 (q, J = 13.0 Hz, 2H), 3.92-3.77 (m, 6H), 3.70-3.39 (m, 5H), 2.86-2.73 (m, 3H), 2.29 (s, 3H). |
| 191 | ¹H NMR (500 MHz, DMSO-d6) δ 8.82 (br. s., 1H), 7.55-7.45 (m, 3H), 7.39 (d, J = 7.3 Hz, 3H), 7.37-7.28 (m, 3H), 7.25-7.16 (m, 3H), 6.88 (t, J = 7.2 Hz, 1H), 6.38 (s, 2H), 6.05 (br. s., 1H), 5.18 (s, 2H), 3.76 (s, 6H), 3.47 (br. s., 2H), 3.23 (d, J = 5.2 Hz, 2H), 2.48-2.42 (m, 2H), 2.24 (s, 3H), 2.13 (s, 3H). |
| 192 | ¹H NMR (500 MHz, DMSO-d6) δ 8.25 (s, 1H), 8.20 (d, J = 9.8 Hz, 1H), 7.97 (d, J = 8.2 Hz, 1H), 7.60 (d, J = 8.5 Hz, 1H), 7.53-7.45 (m, 3H), 7.43-7.37 (m, 1H), 7.36-7.27 (m, 3H), 7.22 (d, J = 7.3 Hz, 1H), 6.63 (d, J = 9.8 Hz, 1H), 6.36 (s, 2H), 5.17 (s, 2H), 3.73 (s, 6H), 3.36 (s, 2H), 2.91 (t, J = 6.7 Hz, 2H), 2.35 (t, J = 6.9 Hz, 2H), 2.23 (s, 3H), 1.99 (s, 3H). |
| 193 | ¹H NMR (500 MHz, DMSO-d6) δ 7.91-7.86 (m, 1H), 7.47 (s, 3H), 7.42-7.37 (m, 1H), 7.33 (d, J = 7.9 Hz, 3H), 7.24-7.19 (m, 1H), 6.37 (s, 2H), 6.27-6.16 (m, 1H), 6.13-5.97 (m, 1H), 5.61-5.52 (m, 1H), 5.17 (s, 2H), 3.75 (s, 6H), 3.30-3.22 (m, 2H), 2.44-2.37 (m, 2H), 2.23 (s, 3H), 2.10 (s, 3H) |
| 194 | ¹H NMR (500 MHz, DMSO-d6) δ 8.40 (br. s., 1H), 7.52-7.45 (m, 3H), 7.42-7.37 (m, 1H), 7.35-7.27 (m, 3H), 7.21 (d, J = 7.3 Hz, 1H), 7.02 (d, J = 15.3 Hz, 1H), 6.56 (d, J = 15.6 Hz, 1H), 6.37 (s, 2H), 5.16 (s, 2H), 4.18 (q, J = 7.2 Hz, 2H), 3.75 (s, 6H), 3.30 (d, J = 5.8 Hz, 2H), 2.43 (t, J = 6.6 Hz, 2H), 2.23 (s, 3H), 2.12 (s, 3H), 1.24 (t, J = 7.0 Hz, 3H). |
| 195 | ¹H NMR (500 MHz, DMSO-d6) δ 7.53-7.43 (m, 3H), 7.43-7.37 (m, 1H), 7.36-7.28 (m, 3H), 7.22 (d, J = 7.6 Hz, 1H), 6.50-6.34 (m, 2H), 5.25-5.13 (m, 2H), 3.94-3.69 (m, 8H), 3.42 (t, J = 7.3 Hz, 2H), 2.46 (d, J = 11.3 Hz, 1H), 2.29 (d, J = 11.6 Hz, 1H), 2.24 (s, 3H), 1.76 (dd, J = 14.0, 7.9 Hz, 1H), 1.50 (dd, J = 14.0, 7.0 Hz, 1H) |
| 196 | ¹H NMR (500 MHz, DMSO-d6) δ 7.52-7.45 (m, 3H), 7.42-7.37 (m, 1H), 7.35-7.27 (m, 3H), 7.22 (d, J = 7.3 Hz, 1H), 6.38 (s, 2H), 5.17 (s, 2H), 3.78 (s, 6H), 3.69 (s, 2H), 3.42 (s, 6H), 2.23 (s, 3H) |
| 198 | ¹H NMR (500 MHz, DMSO-d6) δ 7.80 (br. s., 1H), 7.69 (s, 1H), 7.63 (d, J = 8.4 Hz, 1H), 7.53-7.44 (m, 3H), 7.42-7.36 (m, 2H), 7.34-7.28 (m, 3H), 7.23 (d, J = 7.7 Hz, 1H), 5.33 (s, 2H), 3.66 (s, 2H), 3.38 (d, J = 11.7 Hz, 2H), 3.18-3.06 (m, 2H), 2.23 (s, 3H), 1.79 (s, 3H) |
| 199 | ¹H NMR (500 MHz, DMSO-d6) δ 7.79 (br. s., 1H), 7.42 (d, J = 7.7 Hz, 1H), 7.36-7.23 (m, 3H), 7.19 (d, J = 7.0 Hz, 1H), 6.93 (d, J = 8.1 Hz, 1H), 6.78 (s, 1H), 6.76 (d, J = 8.1 Hz, 1H), 5.21 (s, 2H), 4.29 (s, 4H), 3.12 (q, J = 6.1 Hz, 2H), 2.21 (s, 3H), 1.92 (br. s., 2H), 1.82-1.74 (m, 3H). 2 missing hydrogens are assumed to be under the DMSO or water peaks. |
| 200 | ¹H NMR (500 MHz, DMSO-d6) δ 7.42 (d, J = 7.3 Hz, 1H), 7.34 (dd, J = 11.7, 7.0 Hz, 1H), 7.31-7.23 (m, 2H), 7.18 (d, J = 7.7 Hz, 1H), 6.92 (d, J = 8.1 Hz, 1H), 6.78 (s, 1H), 6.75 (d, J = 8.1 Hz, 1H), 5.20 (s, 2H), 4.28 (s, 4H), 3.96-3.88 (m, 1H), 3.70 (br. s., 2H), 3.58 (br. s., 2H), 3.18 (s, 1H), 2.42 (dd, J = 15.2, 5.3 Hz, 1H), 2.27-2.22 (m, 1H), 2.21 (s, 3H). |

| Ex. No. | ¹H NMR (500 MHz) δ ppm |
|---|---|
| 201 | ¹H NMR (500 MHz, DMSO-d6) δ 7.43 (d, J = 7.3 Hz, 1H), 7.32-7.24 (m, 3H), 7.19 (d, J = 7.7 Hz, 1H), 6.93 (d, J = 8.1 Hz, 1H), 6.79 (s, 1H), 6.76 (dd, J = 8.1, 1.8 Hz, 1H), 5.21 (s, 2H), 4.29 (s, 4H), 3.76-3.65 (m, 1H), 3.52 (s, 1H), 3.09 (d, J = 3.7 Hz, 1H), 2.92-2.81 (m, 1H), 2.21 (s, 4H), 1.83-1.63 (m, 2H), 1.47 (br. s., 3H), 1.35 (br. s., 1H) |
| 202 | ¹H NMR (600 MHz, DMSO-d6) δ 7.80 (br. s., 1H), 7.62 (d, J = 8.1 Hz, 1H), 7.48-7.43 (m, 3H), 7.41-7.36 (m, 1H), 7.31 (d, J = 7.3 Hz, 2H), 7.26 (t, J = 7.5 Hz, 1H), 7.18 (d, J = 7.7 Hz, 1H), 6.42 (d, J = 7.7 Hz, 1H), 5.41 (s, 2H), 3.89 (s, 3H), 3.58 (s, 1H), 3.18-3.05 (m, 2H), 2.22 (s, 3H), 1.82-1.72 (m, 3H). The methylenes of the diamino acetamide were assumed to be under the DMSO peak at 2.5 ppm. |

Biological Assay

The ability of the compounds of Formula (I) to bind to PD-L1 was investigated using a PD-1/PD-L1 Homogenous Time-Resolved Fluorescence (HTRF) binding assay.

Homogenous Time-Resolved Fluorescence (HTRF) Binding Assay.

All binding studies were performed in an HTRF assay buffer consisting of dPBS supplemented with 0.1% (with v) bovine serum albumin and 0.05% (v/v) Tween-20. For the PD-1-Ig/PD-L1-His binding assay, inhibitors were pre-incubated with PD-L1-His (10 nM final) for 15 m in 4 µl of assay buffer, followed by addition of PD-1-Ig (20 nM final) in 1 µl of assay buffer and further incubation for 15 m. PD-L1 from either human, cyno, or mouse were used. HTRF detection was achieved using europium crypate-labeled anti-Ig (1 nM final) and allophycocyanin (APC) labeled anti-His (20 nM final). Antibodies were diluted in HTRF detection buffer and 5 µl was dispensed on top of binding reaction. The reaction mixture was allowed to equilibrate for 30 minutes and signal (665 nm/620 nm ratio) was obtained using an EnVision fluorometer. Additional binding assays were established between PD-1-Ig/PD-L2-His (20 & 5 nM, respectively), CD80-His/PD-L1-Ig (100 & 10 nM, respectively) and CD80-His/CTLA4-Ig (10 & 5 nM, respectively). Competition studies between biotinylated SEQ ID NO:71 and human PD-L1-His were performed as follows. Inhibitors were pre-incubated with PD-L1-His (10 nM final) for 60 m in 4 µl of assay buffer followed by addition of biotinylated SEQ ID NO:71 (0.5 nM final) in 1 µl of assay buffer. Binding was allowed to equilibrate for 30 m followed by addition of europium crypated labeled Strepatavidin (2.5 pM final) and APC-labeled anti-His (20 nM final) in 5 µl of HTRF buffer. The reaction was allowed to equilibrate for 30 m and signal (665 nm/620 nm ratio) was obtained using an EnVision fluorometer. The table below lists the IC$_{50}$ values for Examples 1-108 of this disclosure measured in the PD-1/PD-L1 Homogenous Time-Resolved Fluorescence (HTRF) binding assay. The compounds of the present disclosure, as exemplified by Examples 1-297, showed IC$_{50}$ values in the following ranges: A=0.006-0.10 µM; B=0.11-1.00 µM; C=1.01-10 µM.

| Example | PD1L1 HTRF IC$_{50}$, (µM) |
|---|---|
| 1 | A |
| 2 | B |
| 3 | A |
| 4 | C |
| 5 | B |
| 6 | A |
| 7 | B |
| 8 | 0.146 |
| 9 | B |
| 10 | B |
| 11 | B |
| 12 | B |
| 13 | B |
| 14 | B |
| 15 | B |
| 16 | 1.945 |
| 17 | B |
| 18 | B |
| 19 | B |
| 20 | B |
| 21 | B |
| 22 | B |
| 23 | B |
| 24 | B |
| 25 | B |
| 26 | B |
| 27 | B |
| 28 | B |
| 29 | B |
| 30 | C |
| 31 | B |
| 32 | B |
| 33 | B |
| 34 | B |
| 35 | A |
| 36 | B |
| 37 | A |
| 38 | B |
| 39 | 4.184 |
| 40 | A |
| 41 | B |
| 42 | B |
| 43 | B |
| 44 | B |
| 45 | B |
| 46 | B |
| 47 | B |
| 48 | B |
| 49 | 9.492 |
| 50 | B |
| 51 | B |
| 52 | B |
| 53 | A |
| 54 | B |
| 55 | B |
| 56 | B |
| 57 | A |
| 58 | B |
| 59 | B |
| 60 | B |
| 61 | C |
| 62 | B |
| 63 | C |
| 64 | C |

| Example | PD1L1 HTRF IC$_{50}$, (µM) |
|---|---|
| 65 | A |
| 66 | B |
| 67 | B |
| 68 | B |
| 69 | B |
| 70 | B |
| 71 | B |
| 72 | B |
| 73 | B |
| 74 | B |
| 75 | 0.953 |
| 76 | B |
| 77 | B |
| 78 | A |
| 79 | A |
| 80 | C |
| 81 | B |
| 82 | 3.186 |
| 83 | B |
| 84 | C |
| 85 | B |
| 86 | B |
| 87 | B |
| 88 | B |
| 89 | B |
| 90 | B |
| 91 | B |
| 92 | C |
| 93 | B |
| 94 | B |
| 95 | B |
| 96 | B |
| 97 | B |
| 98 | B |
| 99 | B |
| 100 | B |
| 101 | 1.076 |
| 102 | A |
| 103 | A |
| 104 | B |
| 105 | A |
| 106 | B |
| 107 | 0.329 |
| 108 | B |
| 109 | B |
| 110 | A |
| 111 | A |
| 112 | A |
| 113 | A |
| 114 | 0.043 |
| 115 | A |
| 116 | A |
| 117 | B |
| 118 | B |
| 119 | B |
| 120 | B |
| 121 | B |
| 122 | B |
| 123 | A |
| 124 | A |
| 125 | A |
| 126 | B |
| 127 | A |
| 128 | A |
| 129 | B |
| 130 | B |
| 131 | B |
| 132 | B |
| 133 | B |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |
| 149 | A |
| 150 | A |
| 151 | A |
| 152 | A |
| 153 | A |
| 154 | A |
| 155 | B |
| 156 | A |
| 157 | B |
| 158 | A |
| 159 | B |
| 160 | B |
| 161 | A |
| 162 | B |
| 163 | 0.093 |
| 164 | A |
| 165 | B |
| 166 | B |
| 167 | B |
| 168 | B |
| 169 | B |
| 170 | B |
| 171 | B |
| 172 | 0.107 |
| 173 | A |
| 174 | 0.022 |
| 175 | B |
| 176 | B |
| 177 | B |
| 178 | A |
| 179 | B |
| 180 | B |
| 181 | A |
| 182 | B |
| 183 | B |
| 184 | B |
| 185 | A |
| 186 | A |
| 187 | B |
| 188 | B |
| 189 | B |
| 190 | B |
| 191 | B |
| 192 | B |
| 193 | B |
| 194 | B |
| 195 | B |
| 196 | A |
| 197 | A |
| 198 | A |
| 199 | B |
| 200 | 0.080 |
| 201 | B |
| 202 | 0.018 |
| 203 | B |
| 204 | B |
| 205 | B |
| 206 | B |
| 207 | B |
| 208 | B |
| 209 | B |
| 210 | B |
| 211 | B |
| 212 | B |
| 213 | B |
| 214 | B |
| 215 | B |
| 216 | B |

| Example | PD1L1 HTRF IC$_{50}$, (µM) |
|---|---|
| 217 | B |
| 218 | B |
| 219 | B |
| 220 | A |
| 221 | B |
| 222 | B |
| 223 | B |
| 224 | B |
| 225 | B |
| 226 | B |
| 227 | B |
| 228 | B |
| 229 | B |
| 230 | A |
| 231 | B |
| 232 | B |
| 233 | A |
| 234 | A |
| 235 | B |
| 236 | A |
| 237 | A |
| 238 | A |
| 239 | A |
| 240 | A |
| 241 | A |
| 242 | A |
| 243 | A |
| 244 | A |
| 245 | B |
| 246 | A |
| 247 | A |
| 248 | A |
| 249 | A |
| 250 | A |
| 251 | A |
| 252 | A |
| 253 | A |
| 254 | A |
| 255 | A |
| 256 | A |
| 257 | A |
| 258 | A |
| 259 | A |
| 260 | B |
| 261 | B |
| 262 | B |
| 263 | B |
| 264 | A |
| 265 | A |
| 266 | B |
| 267 | A |
| 268 | A |
| 269 | A |
| 270 | A |
| 271 | A |
| 272 | B |
| 273 | A |
| 274 | A |
| 275 | A |
| 276 | A |
| 277 | A |
| 278 | A |
| 279 | A |
| 280 | B |
| 281 | A |
| 282 | A |
| 283 | A |
| 284 | A |
| 285 | B |
| 286 | B |
| 287 | B |
| 288 | B |
| 289 | A |
| 290 | B |
| 291 | A |
| 292 | B |
| 293 | B |
| 294 | B |
| 295 | A |
| 296 | B |
| 297 | B |

The compounds of Formula (I) possess activity as inhibitors of the PD-1/PD-L1 interaction, and therefore, may be used in the treatment of diseases associated with the PD-1/PD-L1 interaction. Via inhibition of the PD-1/PD-L1 interaction, the compounds of the present disclosure may be employed to treat infectious diseases such as Hepatitis C, and cancer.

What is claimed is:

1. A compound of Formula (I):

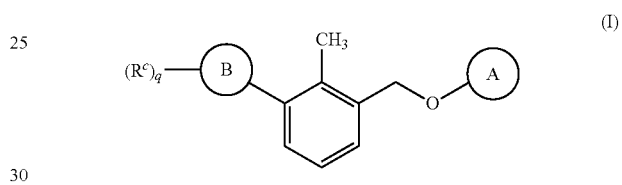

or salts thereof, wherein:
Ring B is phenyl or thienyl;
Ring A is:

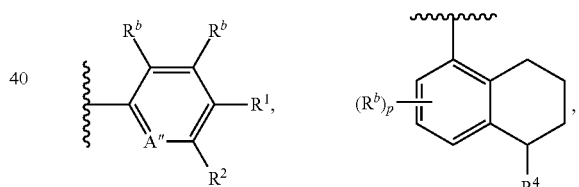

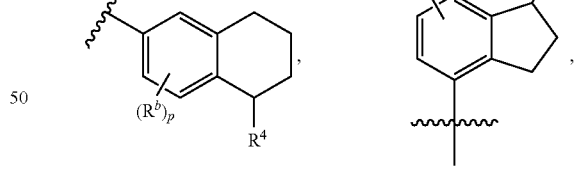

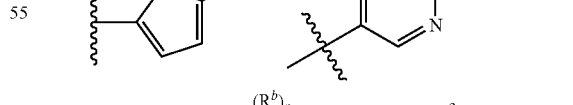

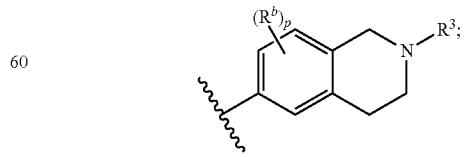

wherein A" is CH or N, and wherein one of $R^1$ and $R^2$ is Q and the other of $R^1$ and $R^2$ is $R^b$;

165

R³ is H or —CH₂C(O)OH;
R⁴ is —NHCH₂CH₂NHC(O)CH₃;
Q is:
(i)

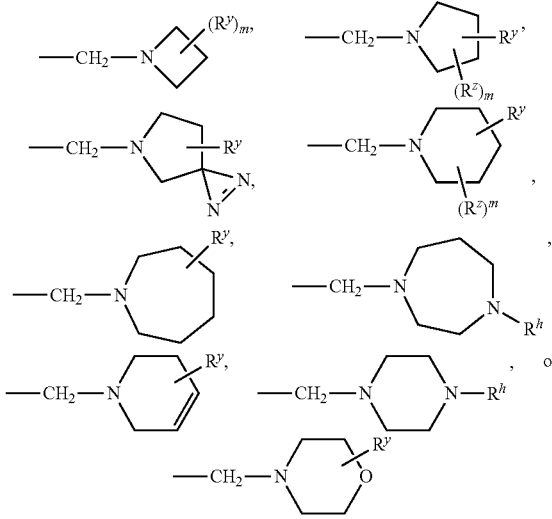

wherein R^y is —OH, —CH₃, —CH₂OH, —C(O)OH, —CH₂C(O)OH, or —C(O)NHCH₂CH₂OH, —C(O)NH₂, —NHC(O)CH₃, and R^z is —OH, —CH₃, —OCH₃, —OC(O)CH₃, or —CH₂CH=CH₂ and R^h is —CH₃ or —C(O)CH₃;

(ii) —CH₂NH—R^x wherein R^x is cyclobutyl, —(CH₂)cyclobutyl optionally substituted with two fluorine atoms, cyclopropyl, hydroxycyclopentyl, cyclopentyl, cyclohexyl, hydroxycyclohexyl, hydroxytetrahydrofuranyl, N-methyl piperidinyl, N-ethyl piperidinyl, hydroxytetrahydrothienyl, or

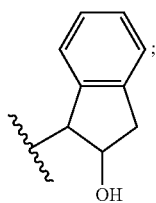 [SMILES: *C1c2ccccc2CC1O ; ";"]

(iii) —CH₂NR^a—CR^aR^a—(CH₂)ₙ—R^x wherein R^x is hydrogen, azetidinonyl, cyclohexyl, hydroxyphenyl, pyrrolidinonyl, piperidinonyl, piperazinonyl, morpholinyl, imidazolyl, N-methylimidazolyl, —C(O)(morpholinyl), piperazinyl optionally substituted with a methyl, phenyl, alkoxyphenyl, hydroxyphenyl, pyridinyl, pyrimidinyl, or —C(O)OC(CH₃)₃ group, pyrrolidinyl, pyridinyl, thiomorpholine dioxide, or methyl triazolyl; or (iv) —CHR^a—NR^a—CR^aR^a—(CHR^a)ₙ—R^x wherein R^x is —OH, —OCH₃, —C(O)OH, —OPh, —CH(CO₂H)—NHC(O)CH₃, —O(CH₂)₂O(CH₂)₂OH, —O(CH₂)₂O(CH₂)₂O(CH₂)₂OH, —O(CH₂)₂O(CH₂)₂O(CH₂)₂CO₂H—O(CH₂)₂O(CH₂)₂O(CH₂)₂O(CH₂)₂O(CH₂)₂O(CH₂)₂CO₂H, —C(O)CH₃, —C(O)NR^aR^a, —C(O)NR^qR^q, —N(CH₃)₂, —NHC(O)CH₃, —NHC(O)Ph, —C(O)NH(CH₂)₂-imidazolyl,

166

NHC(O)OCH₂Ph, —N(CH₃)S(O)₂CH₃, —NHC(O)CH=CH₂, —NHC(O)CH=CHC(O)CH₂CH₃, —NHS(O)₂CH₃, or

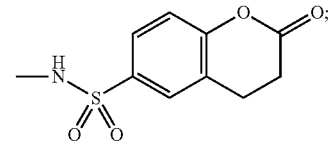 [SMILES: CNS(=O)(=O)c1ccc2c(c1)CCC(=O)O2]

each R^a is independently H, —CH(OH)CH₃, OH, —(CH₂)₂OH, —CH₂OH, —(CH₂)₂NH₂, —CH₂CH₃, or —CH₃; or, two R^a groups on the same carbon atom can form a four, five-, or six-membered carbocyclic ring, an N-methylpiperidinyl ring, or a pyranyl ring;

each R^b is independently H, F, Cl, Br, —CF₃, —CN, CH₃, or —OCH₃;

each R^c is independently —OCH₃, —OH, —OCH₂CH₃, —O(CH₂)OCH₃, —OCH₂CH=CH₂, —O(CH₂)₂CH₃, —O(CH₂)₂-morpholinyl, or F;

or two R^c attached to adjacent carbon atoms form —O—(CH₂)ᵥ—O—, wherein v is 1 or 2;

each R^q is selected from hydrogen, —CH₂C(O)NHCH₂CO₂H, —(CH₂)C(O)NHCH(CO₂H)CH₂CH(CH₃)₂, —CH(Bn)-C(O)NHCH(CO₂H)(CH₂)₃NHC(NH)NH₂;

m is zero or 1;
n is zero, 1, 2, or 3;
each p is independently zero or 1; and
q is zero, 1, or 2.

2. The compound according to claim 1 or salts thereof, wherein Ring A is:

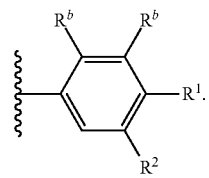

3. The compound according to claim 2 or salts thereof, wherein Q is:

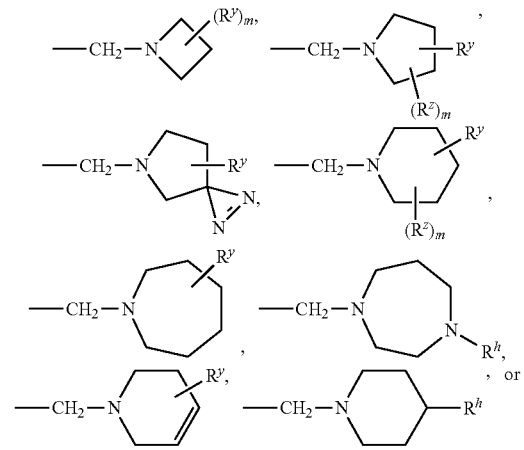

-continued

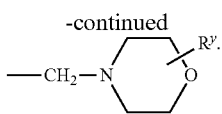

4. The compound according to claim 2 or salts thereof, wherein Q is: —CH₂NH—R$^x$ wherein R$^x$ is cyclobutyl, —(CH₂)cyclobutyl optionally substituted with two fluorine atoms, cyclopropyl, hydroxycyclopentyl, cyclopentyl, cyclohexyl, hydroxycyclohexyl, hydroxytetrahydrofuranyl, N-methyl piperidinyl, N-ethyl piperidinyl, hydroxytetrahydrothienyl, or

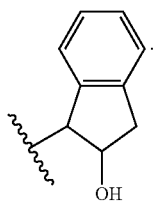

5. The compound according to claim 2 or salts thereof, wherein Q is: —CH₂NR$^a$—CR$^a$R$^a$—(CH₂)$_n$—R$^x$ wherein R$^x$ is hydrogen, azetidinonyl, cyclohexyl, hydroxyphenyl, pyrrolidinonyl, piperidinonyl, piperazinonyl, morpholinyl, imidazolyl, N-methylimidazolyl, —C(O)(morpholinyl), piperazinyl optionally substituted with a methyl, phenyl, alkoxyphenyl, hydroxyphenyl, pyridinyl, pyrimidinyl, or —C(O)OC(CH₃)₃ group, pyrrolidinyl, pyridinyl, thiomorpholine dioxide, or methyl triazolyl.

6. The compound according to claim 2 or salts thereof, wherein Q is —CHR$^a$—NR$^a$—CR$^a$R$^a$—(CHR$^a$)$_n$—R$^x$ wherein R$^x$ is —OH, —OCH₃, —C(O)OH, —OPh, —CH(CO₂H)—NHC(O)CH₃, —O(CH₂)₂O(CH₂)₂OH, —O(CH₂)₂O(CH₂)₂O(CH₂)₂OH, —O(CH₂)₂O(CH₂)₂O(CH₂)₂O(CH₂)₂CO₂H—O(CH₂)₂O(CH₂)₂O(CH₂)₂O(CH₂)₂O(CH₂)₂O(CH₂)₂CO₂H, —C(O)CH₃, —C(O)NR$^a$R$^a$, —C(O)NR$^q$R$^q$, —N(CH₃)₂, —NHC(O)CH₃, —NHC(O)Ph, —C(O)NH(CH2)2-imidazolyl, NHC(O)OCH₂Ph, —N(CH₃)S(O)₂CH₃, —NHC(O)CH=CH₂, —NHC(O)CH=CHC(O)CH₂CH₃, —NHS(O)₂CH₃, or

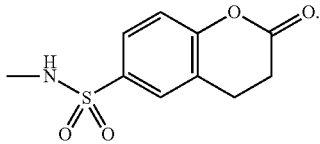 [SMILES: CNS(=O)(=O)c1ccc2c(c1)CCC(=O)O2]

7. The compound according to claim 1 selected from: (S)-1-(2,6-dimethoxy-4-((2-methylbiphenyl-3-yl)methoxy)benzyl)piperidine-2-carboxylic acid (1); 1-(4-((2'-fluoro-2-methylbiphenyl-3-yl)methoxy)benzyl)azetidine (3); N-{2-[({3-bromo-2,6-dimethoxy-4-[(2-methyl-3-phenylphenyl)methoxy]phenyl}methyl)amino]ethyl}acetamide (4); ({2,6-dimethoxy-4-[(2-methyl-3-phenylphenyl)methoxy]phenyl}methyl) [2-methyl-1-(4-methylpiperazin-1-yl)propan-2-yl]amine (5); N-{2-[({2,6-dimethoxy-4-[(2-methyl-3-phenylphenyl)methoxy]phenyl}methyl)amino]ethyl}-N-methylmethanesulfonamide (6); 1-({3-bromo-4-[(2-methyl-3-phenylphenyl)methoxy]phenyl}methyl)piperidine-2-carboxylic acid (7); 2-[({2,6-dimethoxy-4-[(2-methyl-3-phenylphenyl)methoxy]phenyl}methyl)amino]-1-(morpholin-4-yl)ethan-1-one (8); ({2,6-dimethoxy-4-[(2-methyl-3-phenylphenyl)methoxy]phenyl}methyl)[2-(4-methylpiperazin-1-yl)ethyl]amine (9); 1-{2-[({2,6-dimethoxy-4-[(2-methyl-3-phenylphenyl)methoxy]phenyl}methyl)amino]ethyl}piperidin-2-one (10); 1-{3-[({2,6-dimethoxy-4-[(2-methyl-3-phenylphenyl)methoxy]phenyl}methyl)amino]propyl}pyrrolidin-2-one (11); 4-{2-[({2,6-dimethoxy-4-[(2-methyl-3-phenylphenyl)methoxy]phenyl}methyl)amino]ethyl}piperazin-2-one (12); ({2,6-dimethoxy-4-[(2-methyl-3-phenylphenyl)methoxy]phenyl}methyl)[2-(morpholin-4-yl)ethyl]amine (13); 1-({2,6-dimethoxy-4-[(2-methyl-3-phenylphenyl)methoxy]phenyl}methyl)piperidine-2-carboxylic acid (14); 2-[methyl({3-[(2-methyl-3-phenylphenyl)methoxy]phenyl}methyl)amino]acetic acid (15); N-({2,6-dimethoxy-4-[(2-methyl-3-phenylphenyl)methoxy]phenyl}methyl)-1-ethylpiperidin-3-amine (16); 1-{2-[({2,6-dimethoxy-4-[(2-methyl-3-phenylphenyl)methoxy]phenyl}methyl)amino]ethyl}pyrrolidin-2-one (17); (2S,4R)-4-(acetyloxy)-1-({3-methyl-4-[(2-methyl-3-phenylphenyl)methoxy]phenyl}methyl)pyrrolidine-2-carboxylic acid (18); N-(2-hydroxyethyl)-1-({3-methyl-4-[(2-methyl-3-phenylphenyl)methoxy]phenyl}methyl) piperidine-4-carboxamide (19); ({2,6-dimethoxy-4-[(2-methyl-3-phenylphenyl)methoxy]phenyl}methyl)[1-(5-methyl-4H-1,2,4-triazol-3-yl)ethyl]amine (20); N-{2-[({3-bromo-4-[(2-methyl-3-phenylphenyl)methoxy]phenyl}methyl)amino]ethyl}acetamide (21); (2S,4R)-1-({3-chloro-4-[(2-methyl-3-phenylphenyl)methoxy]phenyl}methyl)-4-methoxypyrrolidine-2-carboxylic acid (22); N-{3-[({2,6-dimethoxy-4-[(2-methyl-3-phenylphenyl)methoxy]phenyl}methyl)amino]propyl}acetamide (23); (1R,2R)-2-[({2,6-dimethoxy-4-[(2-methyl-3-phenylphenyl)methoxy]phenyl}methyl)amino]cyclohexan-1-ol (24); N-({2,6-dimethoxy-4-[(2-methyl-3-phenylphenyl)methoxy]phenyl}methyl)-1-methylpiperidin-3-amine (25); (2S)-1-({2-methoxy-3-methyl-4-[(2-methyl-3-phenylphenyl)methoxy]phenyl}methyl)piperidine-2-carboxylic acid (26); (2S)-1-({3-methyl-4-[(2-methyl-3-phenylphenyl)methoxy]phenyl}methyl)-2-(prop-2-en-1-yl)pyrrolidine-2-carboxylic acid (27); 3-[({3-bromo-4-[(2-methyl-3-phenylphenyl) methoxy]phenyl}methyl)amino]propanamide (28); 3-[({3-[(2-methyl-3-phenylphenyl)methoxy]phenyl}methyl)amino]propanamide (29); 4-({3-chloro-4-[(2-methyl-3-phenylphenyl)methoxy]phenyl}methyl)morpholine-3-carboxylic acid (30); 3-[({2,6-dimethoxy-4-[(2-methyl-3-phenylphenyl)methoxy]phenyl}methyl)amino]butanoic acid (31); 1-({3-chloro-4-[(2-methyl-3-phenylphenyl)methoxy]phenyl}methyl)piperidine-4-carboxylic acid (32); (2R)-1-({3-chloro-4-[(2-methyl-3-phenylphenyl)methoxy]phenyl}methyl)piperidine-2-carboxylic acid (33); (2S)-1-({3-chloro-4-[(2-methyl-3-phenylphenyl)methoxy]phenyl}methyl)piperidine-2-carboxylic acid (34); 2-[({2,6-dimethoxy-4-[(2-methyl-3-phenylphenyl)methoxy]phenyl}methyl)amino]-N,N-dimethylacetamide (35); N-{2-[({2,6-dimethoxy-4-[(2-methyl-3-phenylphenyl)methoxy]phenyl}methyl)amino]ethyl}acetamide (36); 1-({2-methoxy-4-[(2-methyl-3-phenylphenyl)methoxy]phenyl}methyl)piperidine-2-carboxylic acid (37); 1-({3-[(2-methyl-3-phenylphenyl)methoxy]phenyl}methyl)azetidine (38); (2S,4R)-4-methoxy-1-({3-methyl-4-[(2-methyl-3-phenylphenyl)methoxy]phenyl}methyl) pyrrolidine-2-carboxylic acid (39); 1-({2,6-dimethyl-4-[(2-methyl-3-phenylphenyl)methoxy]phenyl}methyl)piperidine-2-carboxylic acid (40); 1-({3-methyl-4-[(2-methyl-3-phenylphenyl)methoxy]phenyl}methyl)azepane-2-carboxylic acid (41); 2-[1-({3-methyl-4-[(2-methyl-3-phenylphenyl)methoxy]phenyl}methyl)piperidin-2-yl]acetic acid (42); 1-{3-[({3-methyl-4-[(2-methyl-3-phenylphenyl)methoxy]phenyl}methyl)amino]propyl}pyrrolidin-2-one (43); N-{2-[(1-{3-chloro-4-[(2-methyl-3-phenylphenyl)methoxy]phenyl}ethyl)amino]ethyl}acetamide (44); 2-[({2,6- dimethoxy-4-[(2-methyl-3-phenylphenyl)methoxy]phenyl}methyl)(methyl)amino]acetic acid (45); 3-[({2,6-dimethoxy-4-[(2-methyl-3-phenylphenyl)methoxy]phenyl}methyl)amino]propanamide (46); (2S)-2-[({2,6-dimethoxy-4-[(2-methyl-3-phenylphenyl)methoxy]phenyl}methyl)amino]propanoic acid (47); 1-({3-[(2-methyl-3-phenylphenyl)methoxy]phenyl}methyl)piperidine-2-carboxylic acid (48); 1-({3-fluoro-4-[(2-methyl-3-phenylphenyl)methoxy]phenyl}methyl)piperidine-2-carboxylic acid (49); (2R,4R)-4-hydroxy-1-({3-methyl-4-[(2-methyl-3-phenylphenyl)methoxy]phenyl}methyl)pyrrolidine-2-carboxylic acid (50); (2R,4S)-4-hydroxy-1-({3-methyl-4-[(2-methyl-3-phenylphenyl)methoxy]phenyl}methyl) pyrrolidine-2-carboxylic acid (51); 1-({3-methyl-4-[(2-methyl-3-phenylphenyl)methoxy]phenyl}methyl)piperidine-2-carboxylic acid (52); 1-({3-methyl-4-[(2-methyl-3-phenylphenyl)methoxy]phenyl}methyl)piperidine-3-carboxylic acid (53); (3R)-1-({3-methyl-4-[(2-methyl-3-phenylphenyl)methoxy]phenyl}methyl)piperidine-3-carboxylic acid (54); (2R,4R)-4-methyl-1-({3-methyl-4-[(2-methyl-3-phenylphenyl)methoxy]phenyl}methyl)pyrrolidine-2-carboxylic acid (55); (2S)-1-({3-methyl-4-[(2-methyl-3-phenylphenyl)methoxy]phenyl}methyl)piperidine-2-carboxylic acid (56); 1-({3-methyl-4-[(2-methyl-3-phenylphenyl)methoxy]phenyl}methyl)piperidine-4-carboxylic acid (57); (2R)-1-({3-methyl-4-[(2-methyl-3-phenylphenyl)methoxy]phenyl}methyl)piperidine-2-carboxylic acid (58); (2S)-1-({4-methyl-3-[(2-methyl-3-phenylphenyl)methoxy]phenyl}methyl)piperidine-2-carboxylic acid (59); 1-{3-[({3-[(2-methyl-3-phenylphenyl) methoxy]phenyl}methyl)amino]propyl}pyrrolidin-2-one (60); 1-({3-methyl-4-[(2-methyl-3-phenylphenyl)methoxy]phenyl}methyl)-1,2,5,6-tetrahydropyridine-3-carboxylic acid (63); 2-[({3-chloro-4-[(2-methyl-3-phenylphenyl)methoxy]phenyl}methyl)amino]-2-methylpropanoic acid (64); N-{2-[({3-chloro-4-[(2-methyl-3-phenylphenyl)methoxy]phenyl}methyl)amino]ethyl}acetamide (65); 1-({3-bromo-4-[(2-methyl-3-phenylphenyl)methoxy]phenyl}methyl)azetidine (66); N-{2-[({2-methoxy-4-[(2-methyl-3-phenylphenyl)methoxy]phenyl}methyl)amino]ethyl}acetamide (67); N-({2,6-dimethoxy-4-[(2-methyl-3-phenylphenyl)methoxy]phenyl}methyl) cyclobutanamine (68); N-{2-[({2,6-dimethyl-4-[(2-methyl-3-phenylphenyl)methoxy]phenyl}methyl)amino]ethyl}acetamide (69); N-{2-[(1-{3-methyl-4-[(2-methyl-3-phenylphenyl)methoxy]phenyl}ethyl)amino]ethyl}acetamide (70); (2S)-1-({3-methyl-4-[(2-methyl-3-phenylphenyl)methoxy]phenyl}methyl)pyrrolidine-2-carboxylic acid (71); 1-({3-methyl-4-[(2-methyl-3-phenylphenyl)methoxy]phenyl}methyl)pyrrolidine-2-carboxylic acid (72); (1R,2R)-2-[({3-methyl-4-[(2-methyl-3-phenylphenyl)methoxy]phenyl}methyl)amino]cyclohexan-1-ol (73); 1-({4-[(2-methyl-3-phenylphenyl)methoxy]phenyl}methyl)piperidine-2-carboxylic acid (74); (2R)-1-({3-methyl-4-[(2-methyl-3-phenylphenyl)methoxy]phenyl}methyl) pyrrolidine-2-carboxylic acid (75); 5-{[({3-methyl-4-[(2-methyl-3-phenylphenyl)methoxy]phenyl}methyl)amino]methyl}pyrrolidin-2-one (76); (2S)-2-[({3-chloro-4-[(2-methyl-3-phenylphenyl)methoxy]phenyl}methyl)amino]propanoic acid (77); (2R)-2-[({3-chloro-4-[(2-methyl-3-phenylphenyl)methoxy]phenyl}methyl)amino]propanoic acid (78); N-{2-[({3-fluoro-4-[(2-methyl-3-phenylphenyl)methoxy]phenyl}methyl)amino]ethyl}acetamide (79); (2S)-2-[({2-methoxy-4-[(2-methyl-3-phenylphenyl)methoxy]phenyl}methyl)amino]propanoic acid (80); (2S)-2-[({3-[(2-methyl-3-phenylphenyl)methoxy]phenyl}methyl)amino]propanoic acid (81); 3-[({2-methoxy-4-[(2-methyl-3-phenylphenyl)methoxy]phenyl}methyl)amino]propanamide (82); 1-({2,6-dimethoxy-4-[(2-methyl-3-phenylphenyl)methoxy]phenyl}methyl)azetidine (83); 3-[({3-methyl-4-[(2-methyl-3-phenylphenyl)methoxy]phenyl}methyl)amino]butanoic acid (84); (2R)-2-[methyl({3-methyl-4-[(2-methyl-3-phenylphenyl)methoxy]phenyl}methyl)amino]propanoic acid (85); 3-[({2,6-dimethyl-4-[(2-methyl-3-phenylphenyl)methoxy]phenyl}methyl)amino]propanamide (86); N-{2-[({3-methyl-4-[(2-methyl-3-phenylphenyl)methoxy]phenyl}methyl)amino]ethyl}acetamide (87); N-{2-[({4-methyl-3-[(2-methyl-3-phenylphenyl)methoxy]phenyl}methyl)amino]ethyl}acetamide (88); [(2S)-1-({3-methyl-4-[(2-methyl-3-phenylphenyl) methoxy]phenyl}methyl)pyrrolidin-2-yl]methanol (89); (2S)-1-({3-methyl-4-[(2-methyl-3-phenylphenyl)methoxy]phenyl}methyl)azetidine-2-carboxylic acid (90); 5-{[({4-[(2-methyl-3-phenylphenyl)methoxy]phenyl}methyl)amino]methyl}pyrrolidin-2-one (91); 5-{[({4-[(2-methyl-3-phenylphenyl)methoxy]phenyl}methyl)amino]methyl}pyrrolidin-2-one (92); (2S)-2-[({3-methyl-4-[(2-methyl-3-phenylphenyl)methoxy]phenyl}methyl)amino]propanoic acid (93); 2-[methyl({3-methyl-4-[(2-methyl-3-phenylphenyl)methoxy]phenyl}methyl)amino]acetic acid (94); 3-[({3-methyl-4-[(2-methyl-3-phenylphenyl)methoxy]phenyl}methyl)amino]propanamide (95); (2R)-2-[({3-methyl-4-[(2-methyl-3-phenylphenyl)methoxy]phenyl}methyl)amino]propanoic acid (96); 1-({3-chloro-4-[(2-methyl-3-phenylphenyl)methoxy]phenyl}methyl)azetidine (97); 1-({2-methoxy-4-[(2-methyl-3-phenylphenyl)methoxy]phenyl}methyl)azetidine (98); 1-({3-methyl-4-[(2-methyl-3-phenylphenyl)methoxy]phenyl}methyl)azetidine (99); 1-({3-methyl-4-[(2-methyl-3-phenylphenyl)methoxy]phenyl}methyl)azetidine (100); 2-[({3-methyl-4-[(2-methyl-3-phenylphenyl)methoxy]phenyl}methyl)amino]ethan-1-ol (102); 2-[({2,6-dimethoxy-4-[(2-methyl-3-phenylphenyl)methoxy]phenyl}methyl)amino]ethan-1-ol (103); (2S)-2-[({3-bromo-4-[(2-methyl-3-phenylphenyl)methoxy]phenyl}methyl)amino]propanoic acid (104); (2R)-2-[({2,6-dimethoxy-4-[(2-methyl-3-phenylphenyl)methoxy]phenyl}methyl)amino]propanoic acid (105); (2R)-2-{[(2,6-dimethoxy-4-{[3-(3-methoxyphenyl)-2-methylphenyl]methoxy}phenyl)methyl]amino}propanoic acid (106); (2R)-2-{[(4-{[3-(3-fluoro-5-methoxyphenyl)-2-methylphenyl]methoxy}-2,6-dimethoxyphenyl)methyl]amino}propanoic acid (107); (2R)-2-{[(4-{[3-(2H-1,3-benzodioxol-5-yl)-2-methylphenyl]methoxy}-2,6-dimethoxyphenyl)methyl]amino}propanoic acid (108); 2-(6-((2-methyl-[1,1'-biphenyl]-3-yl)methoxy)-3,4-dihydroisoquinolin-2(1H)-yl)acetic acid (2); N-[2-({5-[(2-methyl-3-phenylphenyl)methoxy]-1,2,3,4-tetrahydronaphthalen-1-yl}amino)ethyl]acetamide (61); N-[2-({6-[(2-methyl-3-phenylphenyl)methoxy]-1,2,3,4-tetrahydronaphthalen-1-yl}amino)ethyl]acetamide (62); or 6-[(2-methyl-3-phenylphenyl) methoxy]-1,2,3,4-tetrahydroisoquinoline (101); or salts thereof.

8. The compound according to claim 1 or salts thereof, selected from

N-[2-({4-[(2-methyl-3-phenylphenyl)methoxy]-2,3-dihydro-1H-inden-1-yl}amino)ethyl]acetamide;

4-{[({3-methyl-4-[(2-methyl-3-phenylphenyl)methoxy]phenyl}methyl)amino]methyl}azetidin-2-one;

(3S)-4-[({2,6-dimethoxy-4-[(2-methyl-3-phenylphenyl)methoxy]phenyl}methyl)amino]-3-hydroxybutanoic acid;

(2S)-1-[(4-{[3-(2,3-dihydro-1,4-benzodioxin-6-yl)-2-methylphenyl]methoxy}-3-(trifluoromethyl)phenyl)methyl]piperidine-2-carboxylic acid;

N-(2-{[(4-{[3-(2,3-dihydro-1,4-benzodioxin-6-yl)-2-methylphenyl]methoxy}-3-(trifluoromethyl)phenyl)methyl]amino}ethyl)acetamide;

(3S)-4-{[(4-{[3-(2,3-dihydro-1,4-benzodioxin-6-yl)-2-methylphenyl]methoxy}-3-(trifluoromethyl)phenyl)methyl]amino}-3-hydroxybutanoic acid;

(2R,3S)-2-[({3-chloro-4-[(2-methyl-3-phenylphenyl)methoxy]phenyl}methyl)amino]-3-hydroxybutanoic acid;
(2R,3R)-2-[({3-chloro-4-[(2-methyl-3-phenylphenyl)methoxy]phenyl}methyl)amino]-3-hydroxybutanoic acid;
(2S,3S)-2-[({3-chloro-4-[(2-methyl-3-phenylphenyl)methoxy]phenyl}methyl)amino]-3-hydroxybutanoic acid;
2-[({5-[(2-methyl-3-phenylphenyl)methoxy]thiophen-2-yl}methyl)amino]ethan-1-ol;
2-[({5-[(2-methyl-3-phenylphenyl)methoxy]pyridin-2-yl}methyl)amino]ethan-1-ol;
{1-[({5-[(2-methyl-3-phenylphenyl)methoxy]pyridin-2-yl}methyl)amino]cyclopentyl}methanol;
methyl({5-[(2-methyl-3-phenylphenyl)methoxy]pyridin-2-yl}methyl)amine;
5-{[({5-[(2-methyl-3-phenylphenyl)methoxy]pyridin-2-yl}methyl)amino]methyl}pyrrolidin-2-one;
2-(3,5-dimethoxy-4-{[(pyridin-2-ylmethyl)amino]methyl}phenoxymethyl)-6-phenylbenzonitrile;
2-{4-[(cyclopropylamino)methyl]-3,5-dimethoxyphenoxymethyl}-6-phenylbenzonitrile;
2-{3,5-dimethoxy-4-[(3-methylpiperidin-1-yl)methyl]phenoxymethyl}-6-phenylbenzonitrile;
2-[3,5-dimethoxy-4-({[2-(pyrrolidin-1-yl)ethyl]amino}methyl)phenoxymethyl]-6-phenylbenzonitrile;
2-{4-[(4-hydroxypiperidin-1-yl)methyl]-3,5-dimethoxyphenoxymethyl}-6-phenylbenzonitrile;
2-[3,5-dimethoxy-4-(morpholin-4-ylmethyl)phenoxymethyl]-6-phenylbenzonitrile;
2-(3,5-dimethoxy-4-{[(pyridin-3-ylmethyl)amino]methyl}phenoxymethyl)-6-phenylbenzonitrile;
2-(3,5-dimethoxy-4-{[(pyridin-4-ylmethyl)amino]methyl}phenoxymethyl)-6-phenylbenzonitrile;
2-[4-({[(3-hydroxyphenyl)methyl]amino}methyl)-3,5-dimethoxyphenoxymethyl]-6-phenylbenzonitrile;
2-[4-({[(2-hydroxyphenyl)methyl]amino}methyl)-3,5-dimethoxyphenoxymethyl]-6-phenylbenzonitrile;
2-[4-({[(4-hydroxyphenyl)methyl]amino}methyl)-3,5-dimethoxyphenoxymethyl]-6-phenylbenzonitrile;
2-{4-[(cyclobutylamino)methyl]-3,5-dimethoxyphenoxymethyl}-6-phenylbenzonitrile;
2-{4-[(cyclopentylamino)methyl]-3,5-dimethoxyphenoxymethyl}-6-phenylbenzonitrile;
2-{4-[(cyclohexylamino)methyl]-3,5-dimethoxyphenoxymethyl}-6-phenylbenzonitrile;
2-[3,5-dimethoxy-4-({[3-(2-oxopyrrolidin-1-yl)propyl]amino}methyl)phenoxymethyl]-6-phenylbenzonitrile;
2-(3,5-dimethoxy-4-{[(propan-2-yl)amino]methyl}phenoxymethyl)-6-phenylbenzonitrile;
N-{2-[({4-[(2-cyano-3-phenylphenyl)methoxy]-2,6-dimethoxyphenyl}methyl)amino]ethyl}acetamide;
2-[4-({[2-(dimethylamino)ethyl]amino}methyl)-3,5-dimethoxyphenoxymethyl]-6-phenylbenzonitrile;
2-(3,5-dimethoxy-4-{[(2-methoxyethyl)amino]methyl}phenoxymethyl)-6-phenylbenzonitrile;
2-(4-{[(2-hydroxyethyl)amino]methyl}-3,5-dimethoxyphenoxymethyl)-6-phenylbenzonitrile;
2-[4-({[1-(hydroxymethyl)cyclopentyl]amino}methyl)-3,5-dimethoxyphenoxymethyl]-6-phenylbenzonitrile;
2-(4-{[(4-hydroxycyclohexyl)amino]methyl}-3,5-dimethoxyphenoxymethyl)-6-phenylbenzonitrile;
3-[({4-[(2-cyano-3-phenylphenyl)methoxy]-2,6-dimethoxyphenyl}methyl)amino]propanamide;
2-{3,5-dimethoxy-4-[(methylamino)methyl]phenoxymethyl}-6-phenylbenzonitrile;

2-[3,5-dimethoxy-4-({[2-(pyridin-2-yl)ethyl]amino}methyl)phenoxymethyl]-6-phenylbenzonitrile;
2-{3,5-dimethoxy-4-[(2-methylpyrrolidin-1-yl)methyl]phenoxymethyl}-6-phenylbenzonitrile;
2-{4-[(4-acetylpiperazin-1-yl)methyl]-3,5-dimethoxyphenoxymethyl}-6-phenylbenzonitrile;
2-[3,5-dimethoxy-4-(pyrrolidin-1-ylmethyl)phenoxymethyl]-6-phenylbenzonitrile;
2-(4-{[3-(hydroxymethyl)piperidin-1-yl]methyl}-3,5-dimethoxyphenoxymethyl)-6-phenylbenzonitrile;
N-[(3S)-1-({4-[(2-cyano-3-phenylphenyl)methoxy]-2,6-dimethoxyphenyl}methyl)pyrrolidin-3-yl]acetamide;
2-[4-(azetidin-1-ylmethyl)-3,5-dimethoxyphenoxymethyl]-6-phenylbenzonitrile;
2-{4-[(4-acetyl-1,4-diazepan-1-yl)methyl]-3,5-dimethoxyphenoxymethyl}-6-phenylbenzonitrile;
2-(4-{[ethyl(pyridin-4-ylmethyl)amino]methyl}-3,5-dimethoxyphenoxymethyl)-6-phenylbenzonitrile;
2-(4-{[(2S)-2-(hydroxymethyl)pyrrolidin-1-yl]methyl}-3,5-dimethoxyphenoxymethyl)-6-phenylbenzonitrile;
2-{4-[(2, 5-dimethylpyrrolidin-1-yl)methyl]-3,5-dimethoxyphenoxymethyl}-6-phenylbenzonitrile;
2-{4-[(3-hydroxypiperidin-1-yl)methyl]-3,5-dimethoxyphenoxymethyl}-6-phenylbenzonitrile;
1-({4-[(2-cyano-3-phenylphenyl)methoxy]-2,6-dimethoxyphenyl}methyl)piperidine-3-carboxylic acid;
(2S)-1-({4-[(2-cyano-3-phenylphenyl)methoxy]-2,6-dimethoxyphenyl}methyl)pyrrolidine-2-carboxamide;
(2S)-1-({4-[(2-cyano-3-phenylphenyl)methoxy]-2,6-dimethoxyphenyl}methyl)piperidine-2-carboxylic acid;
(6 S)-5-({3-chloro-4-[(2-methyl-3-phenylphenyl)methoxy]phenyl}methyl)-1,2,5-triazaspiro[2.4]hept-1-ene-6-carboxylic acid;
{2-[2-(2-aminoethoxy)ethoxy]ethyl}({2,6-dimethoxy-4-[(2-methyl-3-phenylphenyl)methoxy]phenyl}methyl)amine;
2-(2-{2-[({2,6-dimethoxy-4-[(2-methyl-3-phenylphenyl)methoxy]phenyl}methyl)amino]ethoxy}ethoxy)ethan-1-ol;
({2,6-dimethoxy-4-[(2-methyl-3-phenylphenyl)methoxy]phenyl}methyl)({2-[4-(2-methoxyphenyl)piperazin-1-yl]ethyl})amine;
({2,6-dimethoxy-4-[(2-methyl-3-phenylphenyl)methoxy]phenyl}methyl)({2-[4-(pyridin-2-yl)piperazin-1-yl]ethyl})amine;
({2,6-dimethoxy-4-[(2-methyl-3-phenylphenyl)methoxy]phenyl}methyl)({2-[4-(pyrimidin-2-yl)piperazin-1-yl]ethyl})amine;
tert-butyl 4-{2-[({2,6-dimethoxy-4-[(2-methyl-3-phenylphenyl)methoxy]phenyl}methyl)amino]ethyl}piperazine-1-carboxylate;
4-{2-[({2,6-dimethoxy-4-[(2-methyl-3-phenylphenyl)methoxy]phenyl}methyl)amino]ethyl}-1$\lambda^6$,4-thiomorpholine-1,1-dione;
benzyl N-{2-[({2,6-dimethoxy-4-[(2-methyl-3-phenylphenyl)methoxy]phenyl}methyl)amino]ethyl}carbamate;
({2,6-dimethoxy-4-[(2-methyl-3-phenylphenyl)methoxy]phenyl}methyl)[3-(4-methylpiperazin-1-yl)propyl]amine;
({2,6-dimethoxy-4-[(2-methyl-3-phenylphenyl)methoxy]phenyl}methyl)[3-(morpholin-4-yl)propyl]amine;
({2,6-dimethoxy-4-[(2-methyl-3-phenylphenyl)methoxy]phenyl}methyl)[3-(1H-imidazol-1-yl)propyl]amine;

4-{[({2,6-dimethoxy-4-[(2-methyl-3-phenylphenyl)methoxy]phenyl}methyl)amino]methyl}azetidin-2-one;
3-[({2,6-dimethoxy-4-[(2-methyl-3-phenylphenyl)methoxy]phenyl}methyl)amino]-N-[2-(1H-imidazol-4-yl)ethyl]propanamide;
2-({3-[({2,6-dimethoxy-4-[(2-methyl-3-phenylphenyl)methoxy]phenyl}methyl)amino]propyl}(2-hydroxyethyl)amino)ethan-1-ol;
({2,6-dimethoxy-4-[(2-methyl-3-phenylphenyl)methoxy]phenyl}methyl)(3-phenoxypropyl)amine;
4-[({2,6-dimethoxy-4-[(2-methyl-3-phenylphenyl)methoxy]phenyl}methyl)amino]-2-hydroxybutanoic acid;
3-(4-{3-[({2,6-dimethoxy-4-[(2-methyl-3-phenylphenyl)methoxy]phenyl}methyl)amino]propyl}piperazin-1-yl)phenol;
[2-(benzyloxy)ethyl]({2,6-dimethoxy-4-[(2-methyl-3-phenylphenyl)methoxy]phenyl}methyl)amine;
1-{2,6-dimethoxy-4-[(2-methyl-3-phenylphenyl)methoxy]phenyl}-5,8,11-trioxa-2-azatridecan-13-ol;
1-{2,6-dimethoxy-4-[(2-methyl-3-phenylphenyl)methoxy]phenyl}-5,8,11,14,17,20-hexaoxa-2-azatricosan-23-oic acid;
1-{2,6-dimethoxy-4-[(2-methyl-3-phenylphenyl)methoxy]phenyl}-5,8,11,14-tetraoxa-2-azaheptadecan-17-oic acid;
(2S)-5-carbamimidamido-2-[(2R)-2-{2-[({2,6-dimethoxy-4-[(2-methyl-3-phenylphenyl)methoxy]phenyl}methyl)amino]acetamido}-3-phenylpropanamido]pentanoic acid;
2-(2-{2-[({2,6-dimethoxy-4-[(2-methyl-3-phenylphenyl)methoxy]phenyl}methyl)amino]acetamido}acetamido)acetic acid;
(2S)-5-[({2,6-dimethoxy-4-[(2-methyl-3-phenylphenyl)methoxy]phenyl}methyl)amino]-2-acetamidopentanoic acid;
[(3,3-difluorocyclobutyl)methyl]({2,6-dimethoxy-4-[(2-methyl-3-phenylphenyl)methoxy]phenyl}methyl)amine;
(cyclobutylmethyl)({2,6-dimethoxy-4-[(2-methyl-3-phenylphenyl)methoxy]phenyl}methyl)amine;
(2S)-2-(2-{2-[({2,6-dimethoxy-4-[(2-methyl-3-phenylphenyl)methoxy]phenyl}methyl)amino]acetamido}acetamido)-4-methylpentanoic acid;
(2-aminoethyl)({2,6-dimethoxy-4-[(2-methyl-3-phenylphenyl)methoxy]phenyl}methyl)methylamine;
3-{2-[({2,6-dimethoxy-4-[(2-methyl-3-phenylphenyl)methoxy]phenyl}methyl)(methyl)amino]ethyl}-1-phenylurea;
N-{2-[({2,6-dimethoxy-4-[(2-methyl-3-phenylphenyl)methoxy]phenyl}methyl)(methyl)amino]ethyl}-2-oxo-2H-chromene-6-sulfonamide;
N-{2-[({2,6-dimethoxy-4-[(2-methyl-3-phenylphenyl)methoxy]phenyl}methyl)(methyl)amino]ethyl}prop-2-enamide;
ethyl (2E)-3-({2-[({2,6-dimethoxy-4-[(2-methyl-3-phenylphenyl)methoxy]phenyl}methyl)(methyl)amino]ethyl}carbamoyl)prop-2-enoate;
(6 S)-5-({2,6-dimethoxy-4-[(2-methyl-3-phenylphenyl)methoxy]phenyl}methyl)-1,2,5-triazaspiro[2.4]hept-1-ene-6-carboxylic acid;
2-[({2,6-dimethoxy-4-[(2-methyl-3-phenylphenyl)methoxy]phenyl}methyl)amino]-2-(hydroxymethyl)propane-1,3-diol;
(3S)-4-[({3-chloro-4-[(2-methyl-3-phenylphenyl)methoxy]phenyl}methyl)amino]-3-hydroxybutanoic acid;
N-{2-[({3-cyano-4-[(2-methyl-3-phenylphenyl)methoxy]phenyl}methyl)amino]ethyl}acetamide;
N-(2-{[(4-{[3-(2,3-dihydro-1,4-benzodioxin-6-yl)-2-methylphenyl]methoxy}-2,5-difluorophenyl)methyl]amino}ethyl)acetamide;
(3S)-4-{[(4-{[3-(2,3-dihydro-1,4-benzodioxin-6-yl)-2-methylphenyl]methoxy}-2, 5-difluorophenyl)methyl]amino}-3-hydroxybutanoic acid;
(2S)-1-[(4-{[3-(2,3-dihydro-1,4-benzodioxin-6-yl)-2-methylphenyl]methoxy}-2, 5-difluorophenyl)methyl]piperidine-2-carboxylic acid;
N-{2-[({2-methoxy-6-[(2-methyl-3-phenylphenyl)methoxy]pyridin-3-yl}methyl)amino]ethyl}acetamide;
5-(azetidin-1-ylmethyl)-2-[(2-methyl-3-phenylphenyl)methoxy]pyridine;
N-({6-[(2-methyl-3-phenylphenyl)methoxy]pyridin-3-yl}methyl)cyclobutanamine;
N-({6-[(2-methyl-3-phenylphenyl)methoxy]pyridin-3-yl}methyl)cyclopentanamine;
1-{3-[({6-[(2-methyl-3-phenylphenyl)methoxy]pyridin-3-yl}methyl)amino]propyl}pyrrolidin-2-one;
({6-[(2-methyl-3-phenylphenyl)methoxy]pyridin-3-yl}methyl)[2-(pyridin-2-yl)ethyl]amine;
2-[(2-methyl-3-phenylphenyl)methoxy]-5-(pyrrolidin-1-ylmethyl)pyridine;
[(2S)-1-({6-[(2-methyl-3-phenylphenyl)methoxy]pyridin-3-yl}methyl)pyrrolidin-2-yl]methanol;
(2S)-1-({6-[(2-methyl-3-phenylphenyl)methoxy]pyridin-3-yl}methyl)piperidine-2-carboxylic acid;
1-({6-[(2-methyl-3-phenylphenyl)methoxy]pyridin-3-yl}methyl)piperidine-3-carboxylic acid;
[1-({6-[(2-methyl-3-phenylphenyl)methoxy]pyridin-3-yl}methyl)piperidin-3-yl]methanol;
1-({6-[(2-methyl-3-phenylphenyl)methoxy]pyridin-3-yl}methyl)piperidin-4-ol;
2-[(2-methyl-3-phenylphenyl)methoxy]-5-[(2-methylpyrrolidin-1-yl)methyl]pyridine;
({6-[(2-methyl-3-phenylphenyl)methoxy]pyridin-3-yl}methyl)(propan-2-yl)amine;
methyl({6-[(2-methyl-3-phenylphenyl)methoxy]pyridin-3-yl}methyl)amine;
N-{2-[({6-[(2-methyl-3-phenylphenyl)methoxy]pyridin-3-yl}methyl)amino]ethyl}acetamide;
[2-(dimethylamino)ethyl]({6-[(2-methyl-3-phenylphenyl)methoxy]pyridin-3-yl}methyl)amine;
(2-methoxyethyl)({6-[(2-methyl-3-phenylphenyl)methoxy]pyridin-3-yl}methyl)amine;
2-[({6-[(2-methyl-3-phenylphenyl)methoxy]pyridin-3-yl}methyl)amino]ethan-1-ol;
{1-[({6-[(2-methyl-3-phenylphenyl)methoxy]pyridin-3-yl}methyl)amino]cyclopentyl}methanol;
4-[({6-[(2-methyl-3-phenylphenyl)methoxy]pyridin-3-yl}methyl)amino]cyclohexan-1-ol;
3-[({6-[(2-methyl-3-phenylphenyl)methoxy]pyridin-3-yl}methyl)amino]propanamide;
(2S)-2-[({6-[(2-methyl-3-phenylphenyl)methoxy]pyridin-3-yl}methyl)amino]propanoic acid;
5-{[({6-[(2-methyl-3-phenylphenyl)methoxy]pyridin-3-yl}methyl)amino]methyl}pyrrolidin-2-one;
N-[(3S)-1-({6-[(2-methyl-3-phenylphenyl)methoxy]pyridin-3-yl}methyl)pyrrolidin-3-yl]acetamide;
(2R)-2-{[(4-{[3-(3-fluoro-5-methoxyphenyl)-2-methylphenyl]methoxy}-2,6-dimethoxyphenyl)methyl]amino}propanoic acid;

(2R)-2-{[(4-{[3-(2H-1,3-benzodioxol-5-yl)-2-methyl-phenyl]methoxy}-2,6-dimethoxyphenyl)methyl]amino}propanoic acid;

3-[3-(4-{[(2-hydroxyethyl)amino]methyl}-3,5-dimethoxyphenoxymethyl)-2-methylphenyl]phenol;

2-{[(4-{[3-(2H-1,3-benzodioxol-5-yl)-2-methylphenyl]methoxy}-2,6-dimethoxyphenyl)methyl]amino}ethan-1-ol;

2-{[(4-{[3-(3-ethoxyphenyl)-2-methylphenyl]methoxy}-2,6-dimethoxyphenyl)methyl]amino}ethan-1-ol;

2-[({2,6-dimethoxy-4-[(2-methyl-3-{3-[2-(piperidin-1-yl)ethoxy]phenyl}phenyl)methoxy]phenyl}methyl)amino]ethan-1-ol;

2-[({2,6-dimethoxy-4-[(2-methyl-3-phenylphenyl)methoxy]phenyl}methyl)amino]-2-methylpropane-1,3-diol;

(2S,3S)-2-[({2,6-dimethoxy-4-[(2-methyl-3-phenylphenyl)methoxy]phenyl}methyl)amino]-3-methylpentan-1-ol;

(2R)-2-[({2,6-dimethoxy-4-[(2-methyl-3-phenylphenyl)methoxy]phenyl}methyl)amino]-4-methylpentan-1-ol;

1-[({2,6-dimethoxy-4-[(2-methyl-3-phenylphenyl)methoxy]phenyl}methyl)amino]propan-2-ol;

{1-[({2,6-dimethoxy-4-[(2-methyl-3-phenylphenyl)methoxy]phenyl}methyl)amino]cyclopentyl}methanol;

2-[({2,6-dimethoxy-4-[(2-methyl-3-phenylphenyl)methoxy]phenyl}methyl)amino]propane-1,3-diol;

1-[({2,6-dimethoxy-4-[(2-methyl-3-phenylphenyl)methoxy]phenyl}methyl)amino]butan-2-ol;

(2S)-2-[({2,6-dimethoxy-4-[(2-methyl-3-phenylphenyl)methoxy]phenyl}methyl)amino]-4-methylpentan-1-ol;

(2R)-2-[({2,6-dimethoxy-4-[(2-methyl-3-phenylphenyl)methoxy]phenyl}methyl)amino]-3-methylbutan-1-ol;

(2S)-2-[({2,6-dimethoxy-4-[(2-methyl-3-phenylphenyl)methoxy]phenyl}methyl)amino]-3-methylbutan-1-ol;

(2R)-2-[({2,6-dimethoxy-4-[(2-methyl-3-phenylphenyl)methoxy]phenyl}methyl)amino]propan-1-ol;

(2S)-2-[({2,6-dimethoxy-4-[(2-methyl-3-phenylphenyl)methoxy]phenyl}methyl)amino]butan-1-ol;

2-{[(2,6-dimethoxy-4-{[2-methyl-3-(3-propoxyphenyl)phenyl]methoxy}phenyl)methyl]amino}ethan-1-ol;

(2S)-3-[({2,6-dimethoxy-4-[(2-methyl-3-phenylphenyl)methoxy]phenyl}methyl)amino]propane-1,2-diol;

(2R)-2-[({2,6-dimethoxy-4-[(2-methyl-3-phenylphenyl)methoxy]phenyl}methyl)amino]-2-methylbutanoic acid;

1-[({2,6-dimethoxy-4-[(2-methyl-3-phenylphenyl)methoxy]phenyl}methyl)amino]-2-methylpropan-2-ol;

(2S)-2-[({2,6-dimethoxy-4-[(2-methyl-3-phenylphenyl)methoxy]phenyl}methyl)amino]pentan-1-ol;

3-[({2,6-dimethoxy-4-[(2-methyl-3-phenylphenyl)methoxy]phenyl}methyl)amino]butan-2-ol;

(2R)-3-[({2,6-dimethoxy-4-[(2-methyl-3-phenylphenyl)methoxy]phenyl}methyl)amino]propane-1,2-diol;

(2R)-2-[({2,6-dimethoxy-4-[(2-methyl-3-phenylphenyl)methoxy]phenyl}methyl)amino]butan-1-ol;

(2S)-1-[({2,6-dimethoxy-4-[(2-methyl-3-phenylphenyl)methoxy]phenyl}methyl)amino]propan-2-ol;

2-[({2,6-dimethoxy-4-[(2-methyl-3-phenylphenyl)methoxy]phenyl}methyl)amino]cyclohexan-1-ol;

(1S,2R)-2-[({2,6-dimethoxy-4-[(2-methyl-3-phenylphenyl)methoxy]phenyl}methyl)amino]cyclohexan-1-ol;

(3R,4S)-4-[({2,6-dimethoxy-4-[(2-methyl-3-phenylphenyl)methoxy]phenyl}methyl)amino]oxolan-3-ol;

1-[({2,6-dimethoxy-4-[(2-methyl-3-phenylphenyl)methoxy]phenyl}methyl)amino]-3-methylbutan-2-ol;

({2,6-dimethoxy-4-[(2-methyl-3-phenylphenyl)methoxy]phenyl}methyl)[3-(dimethylamino)-2-hydroxypropyl]amine;

(2R)-2-cyclopropyl-2-[({2,6-dimethoxy-4-[(2-methyl-3-phenylphenyl)methoxy]phenyl}methyl)amino]ethan-1-ol;

3-[({2,6-dimethoxy-4-[(2-methyl-3-phenylphenyl)methoxy]phenyl}methyl)amino]-2-methylbutan-2-ol;

(2R)-2-[({2,6-dimethoxy-4-[(2-methyl-3-phenylphenyl)methoxy]phenyl}methyl)amino]-2-phenylethan-1-ol;

1-[({2,6-dimethoxy-4-[(2-methyl-3-phenylphenyl)methoxy]phenyl}methyl)amino]-2,3-dihydro-1H-inden-2-ol;

(1S)-2-[({2,6-dimethoxy-4-[(2-methyl-3-phenylphenyl)methoxy]phenyl}methyl)amino]-1-phenylethan-1-ol;

(3S)-4-[({2,6-dimethoxy-4-[(2-methyl-3-phenylphenyl)methoxy]phenyl}methyl)amino]-3-hydroxybutanoic acid;

4-[({2,6-dimethoxy-4-[(2-methyl-3-phenylphenyl)methoxy]phenyl}methyl)amino]thiolan-3-ol;

(1R)-2-[({2,6-dimethoxy-4-[(2-methyl-3-phenylphenyl)methoxy]phenyl}methyl)amino]-1-phenylethan-1-ol;

2-[({2,6-dimethoxy-4-[(2-methyl-3-phenylphenyl)methoxy]phenyl}methyl)amino]-1-(pyridin-3-yl)ethan-1-ol;

2-[({2,6-dimethoxy-4-[(2-methyl-3-phenylphenyl)methoxy]phenyl}methyl)amino]-1-(pyridin-4-yl)ethan-1-ol;

(2S)-2-cyclohexyl-2-[({2,6-dimethoxy-4-[(2-methyl-3-phenylphenyl)methoxy]phenyl}methyl)amino]ethan-1-ol;

{4-[({2,6-dimethoxy-4-[(2-methyl-3-phenylphenyl)methoxy]phenyl}methyl)amino]oxan-4-yl}methanol;

2-[({2,6-dimethoxy-4-[(2-methyl-3-phenylphenyl)methoxy]phenyl}methyl)amino]-1-(1-methyl-1H-imidazol-2-yl)ethan-1-ol;

1-{[({2,6-dimethoxy-4-[(2-methyl-3-phenylphenyl)methoxy]phenyl}methyl)amino]methyl}cyclohexan-1-ol;

(1R,2S)-2-[({2,6-dimethoxy-4-[(2-methyl-3-phenylphenyl)methoxy]phenyl}methyl)amino]cyclopentan-1-ol;

4-{[({2,6-dimethoxy-4-[(2-methyl-3-phenylphenyl)methoxy]phenyl}methyl)amino]methyl}-1-methylpiperidin-4-ol;

(1R,2R)-2-[({2,6-dimethoxy-4-[(2-methyl-3-phenylphenyl)methoxy]phenyl}methyl)amino]cyclohexan-1-ol;

(1S,2S)-2-[({2,6-dimethoxy-4-[(2-methyl-3-phenylphenyl)methoxy]phenyl}methyl)amino]cyclopentan-1-ol;

(1R,2R)-2-[({2,6-dimethoxy-4-[(2-methyl-3-phenylphenyl)methoxy]phenyl}methyl)amino]cyclopentan-1-ol;

(2R,3S)-2-[({2,6-dimethoxy-4-[(2-methyl-3-phenylphenyl)methoxy]phenyl}methyl)amino]butane-1,3-diol;

(2S,3R)-2-[({2,6-dimethoxy-4-[(2-methyl-3-phenylphenyl)methoxy]phenyl}methyl)amino]butane-1,3-diol;

1-{[({2,6-dimethoxy-4-[(2-methyl-3-phenylphenyl)methoxy]phenyl}methyl)amino]methyl}cyclobutan-1-ol;

(3R)-4-[({2,6-dimethoxy-4-[(2-methyl-3-phenylphenyl)methoxy]phenyl}methyl)amino]-3-hydroxybutanoic acid;

2-[({2,6-dimethoxy-4-[(2-methyl-3-phenylphenyl)methoxy]phenyl}methyl)amino]-2-ethylpropane-1,3-diol;

(2S)-2-[({2,6-dimethoxy-4-[(2-methyl-3-phenylphenyl)methoxy]phenyl}methyl)amino]-2-phenylethan-1-ol;

1-({2,6-dimethoxy-4-[(2-methyl-3-phenylphenyl)
   methoxy]phenyl}methyl)-4-hydroxypiperidine-4-car-
   boxamide;
N-(2-{[(2,6-dimethoxy-4-{[3-(3-methoxyphenyl)-2-
   methylphenyl]methoxy}phenyl)methyl]amino}ethyl)
   acetamide;
N-(2-{[(4-{[3-(3-ethoxyphenyl)-2-methylphenyl]
   methoxy}-2,6-dimethoxyphenyl)methyl]amino}ethyl)
   acetamide;
N-(2-{[(4-{[3-(2H-1,3-benzodioxol-5-yl)-2-methylphe-
   nyl]methoxy}-2,6-dimethoxyphenyl)methyl]
   amino}ethyl)acetamide;
[(4-{[3-(2H-1,3-benzodioxol-5-yl)-2-methylphenyl]
   methoxy}-2,6-dimethoxyphenyl)methyl][2-methyl-1-
   (4-methylpiperazin-1-yl)propan-2-yl]amine;
N-(2-{[(4-{[3-(2,3-dihydro-1,4-benzodioxin-6-yl)-2-
   methylphenyl]methoxy}-2,6-dimethoxyphenyl)
   methyl]amino}ethyl)acetamide;
[(4-{[3-(3-ethoxyphenyl)-2-methylphenyl]methoxy}-2,6-
   dimethoxyphenyl)methyl][2-methyl-1-(4-methylpiper-
   azin-1-yl)propan-2-yl]amine;
[(4-{[3-(2,3-dihydro-1,4-benzodioxin-6-yl)-2-methyl-
   phenyl]methoxy}-2,6-dimethoxyphenyl)methyl][2-
   methyl-1-(4-methylpiperazin-1-yl)propan-2-yl]amine;
{[2,6-dimethoxy-4-({3-[3-(methoxymethoxy)phenyl]-2-
   methylphenyl}methoxy)phenyl]methyl}[2-methyl-1-
   (4-methylpiperazin-1-yl)propan-2-yl]amine;
{[2,6-dimethoxy-4-({2-methyl-3-[3-(prop-2-en-1-yloxy)
   phenyl]phenyl}methoxy)phenyl]methyl}[2-methyl-1-
   (4-methylpiperazin-1-yl)propan-2-yl]amine;
{[4-({3-[2-fluoro-5-(2-methoxyethoxy)phenyl]-2-
   methylphenyl}methoxy)-2,6-dimethoxyphenyl]
   methyl}[2-methyl-1-(4-methylpiperazin-1-yl)propan-
   2-yl]amine;
(3S)-4-[({4-[(2-cyano-3-phenylphenyl)methoxy]-2,6-
   dimethoxyphenyl}methyl)amino]-3-hydroxybutanoic
   acid;
(3S)-3-hydroxy-4-[({5-[(2-methyl-3-phenylphenyl)
   methoxy]pyridin-2-yl}methyl)amino]butanoic acid;
   and
N-(2-{[(3-chloro-4-{[2-methyl-3-(thiophen-3-yl)phenyl]
   methoxy}phenyl)methyl]amino}ethyl)acetamid.

9. The compound according to claim 1 or salts thereof, wherein Ring A is:

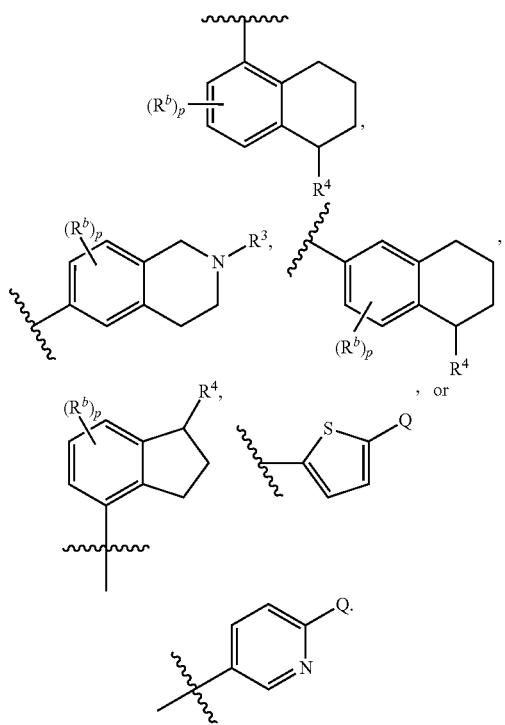

10. A pharmaceutical composition comprising a compound according to claim 1 or a pharmaceutically acceptable salt thereof, and a pharmaceutically acceptable carrier.

11. A method of treating a disease or disorder associated with the inhibition of the PD-1/PD-L1 interaction, wherein said disease or disorder is a cancer selected from the group consisting of melanoma, renal cancer, prostate cancer, breast cancer, colon cancer, lung cancer, bone cancer, pancreatic cancer, skin cancer, head and neck cancer, uterine cancer, bladder cancer, ovarian cancer, brain cancer, kidney cancer, colon cancer, rectal cancer, stomach cancer, testicular cancer, Hodgkin's lymphoma, acute myeloid leukemia, chronic myeloid leukemia, myeloma, small intestine cancer, squamous cell cancer; or a virological infection selected from the group consisting of HPV, HBV, HCV, KHSV and HIV infections, the method comprising administering to a mammalian patient a compound according to claim 1 or a pharmaceutically acceptable salt.

* * * * *

UNITED STATES PATENT AND TRADEMARK OFFICE
CERTIFICATE OF CORRECTION

PATENT NO. : 9,872,852 B2
APPLICATION NO. : 14/915782
DATED : January 23, 2018
INVENTOR(S) : Chupak et al.

Page 1 of 2

It is certified that error appears in the above-identified patent and that said Letters Patent is hereby corrected as shown below:

In the Claims

Claim 1, Column 65, Lines 10-15

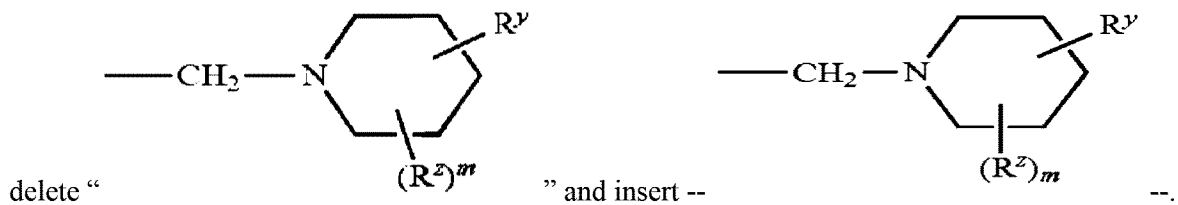

delete " " and insert -- --.

Claim 1, Column 166, Line 16 delete "four," and insert -- four-, --.

Claim 3, Column 166, Lines 64-67

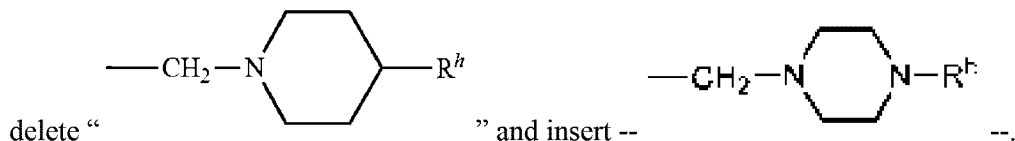

delete " " and insert -- --.

Claim 6, Column 167, Line 42 delete "(CH2)2-" and insert -- $(CH_2)_2$- --.

Claim 7, Column 168, Line 38 delete ") methoxy]" and insert -- )methoxy] --.

Claim 7, Column 168, Lines 39-40 delete ") methoxy]" and insert -- )methoxy] --.

Claim 7, Column 169, Line 30 delete ") methoxy]" and insert -- )methoxy] --.

Claim 7, Column 170, Line 10 delete ") methoxy]" and insert -- )methoxy] --.

Signed and Sealed this
Fourth Day of December, 2018

Andrei Iancu
*Director of the United States Patent and Trademark Office*

CERTIFICATE OF CORRECTION (continued)
U.S. Pat. No. 9,872,852 B2

Claim 7, Column 170, Lines 20-21 delete ") methoxy]" and insert -- )methoxy] --.

Claim 7, Column 170, Line 32 delete ") methoxy]" and insert -- )methoxy] --.

Claim 7, Column 170, Line 48 delete ") methoxy]" and insert -- )methoxy] --.

Claim 8, Column 172, Line 22 delete "[(2, 5-" and insert -- [(2,5- --.

Claim 8, Column 172, Line 34 delete "(6 S)" and insert -- (6S) --.

Claim 8, Column 173, Line 62 delete "(6 S)" and insert -- (6S) --.

Claim 8, Column 174, Line 10 delete "2, 5-" and insert -- 2,5- --.

Claim 8, Column 174, Line 13 delete "2, 5-" and insert -- 2,5- --.

Claim 8, Column 174, Lines 15-16 delete ") methoxy]" and insert -- )methoxy] --.

Claim 8, Column 177, Line 46 delete "acetamid." and insert -- acetamide. --.